United States Patent
Bailey et al.

(10) Patent No.: US 6,753,149 B2
(45) Date of Patent: Jun. 22, 2004

(54) STAPHYLOCOCCUS AUREUS GENES AND POLYPEPTIDES

(75) Inventors: Camella Bailey, Washington, DC (US); Gil H. Choi, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 82 days.

(21) Appl. No.: 10/138,701

(22) Filed: May 6, 2002

(65) Prior Publication Data

US 2003/0186364 A1 Oct. 2, 2003

Related U.S. Application Data

(60) Division of application No. 09/512,255, filed on Feb. 24, 2000, now Pat. No. 6,403,337, which is a continuation-in-part of application No. PCT/US99/19726, filed on Aug. 31, 1999, and a continuation-in-part of application No. 08/956,171, filed on Oct. 20, 1997, now Pat. No. 6,593,114, and a continuation-in-part of application No. 08/781,986, filed on Jan. 3, 1997, said application No. 08/956,171, is a continuation-in-part of application No. 08/781,986, filed on Jan. 3, 1997.

(60) Provisional application No. 60/098,964, filed on Sep. 1, 1998, and provisional application No. 60/009,861, filed on Jan. 5, 1996.

(51) Int. Cl.[7] .......................... C12Q 1/68; C12N 15/31
(52) U.S. Cl. .......................................... 435/6; 536/23.7
(58) Field of Search ............................. 435/6; 536/23.7

(56) References Cited

U.S. PATENT DOCUMENTS 6,037,123 A    3/2000   Benton et al.
6,150,340 A    11/2000  Black et al.

FOREIGN PATENT DOCUMENTS

| | | |
|---|---|---|
| EP | 786519 A2 | 7/1997 |
| EP | 0811696 A2 | 12/1997 |
| EP | 0826774 A2 | 3/1998 |
| EP | 0843016 A2 | 5/1998 |
| WO | 97/00524 A2 | 8/1997 |
| WO | 97/02318 | 8/1997 |

OTHER PUBLICATIONS

Kuroda et al., Staphylococcus aureus ygaE, yflG, orfX, yvqF, vraS, vraR genes, complete cds., NCBI Accession No. AB035448, National Center for Biotechnology Information, U.S.A. (Jul. 26, 2000).

*Primary Examiner*—John S. Brusca
(74) *Attorney, Agent, or Firm*—Human Genome Sciences, Inc.

(57) ABSTRACT

The present invention relates to novel genes from *S. aureus* and the polypeptides they encode. Also provided as are vectors, host cells, antibodies and recombinant methods for producing the same. The invention further relates to screening methods for identifying agonists and antagonists of *S. aureus* polypeptide activity. The invention additionally relates to diagnostic methods for detecting Staphylococcus nucleic acids, polypeptides and antibodies in a biological sample. The present invention further relates to novel vaccines for the prevention or attenuation of infection by Staphylococcus.

22 Claims, No Drawings

SEQUENCE LISTING

```
<160> NUMBER OF SEQ ID NOS: 61

<210> SEQ ID NO 1
<211> LENGTH: 1092
<212> TYPE: DNA
<213> ORGANISM: Staphylococcus aureus

<400> SEQUENCE: 1
attaactagt caatattcct acctctgact tgagtttaaa aagtaatcta tgttaaatta      60
atacctggta ttaaaaattt tattaagaag gtgttcaact atgaacgtgg gtattaaagg     120
ttttggtgca tatgcgccag aaaagattat tgacaatgcc tattttgagc aattttttaga    180
```

-continued

```
tacatctgat gaatggattt ctaagatgac tggaattaaa gaaagacatt gggcagatga      240
tgatcaagat acttcagatt tagcatatga agcaagttta aaagcaatcg ctgacgctgg      300
tattcagccc gaagatatag atatgataat tgttgccaca gcaactggag atatgccatt      360
tccaactgtc gcaaatatgt tgcaagaacg tttagggacg ggcaaagttg cctctatgga      420
tcaacttgca gcatgttctg gatttatgta ttcaatgatt acagctaaac aatatgttca      480
atctggagat tatcataaca ttttagttgt cggtgcagat aaattatcta aaataacaga      540
tttaactgac cgttctactg cagttctatt tggagatggt gcaggtgcgg ttatcatcgg      600
tgaagtttca gatggcagag gtattataag ttatgaaatg ggttctgatg gcacaggtgg      660
taaacattta tatttagata aagatactgg taaactgaaa atgaatggtc gagaagtatt      720
taaatttgct gttagaatta tgggtgatgc atcaacacgt gtagttgaaa aagcgaattt      780
aacatcagat gatatagatt tatttattcc tcatcaagct aatattagaa ttatggaatc      840
agctagagaa cgcttaggta tttcaaaaga caaaatgagt gtttctgtaa ataaatatgg      900
aaatacttca gctgcgtcaa tacctttaag tatcgatcaa gaattaaaaa atggtaaaat      960
caaagatgat gatacaattg ttcttgtcgg attcggtggc ggcctaactt ggggcgcaat     1020
gacaataaaa tggggaaaat aggaggataa cgaatgagtc aaaataaaag gtagttatt     1080 acaggtatgg ga                                                        1092
```

<210> SEQ ID NO 2
<211> LENGTH: 313
<212> TYPE: PRT
<213> ORGANISM: Staphylococcus aureus

<400> SEQUENCE: 2

```
Met Asn Val Gly Ile Lys Gly Phe Gly Ala Tyr Ala Pro Glu Lys Ile
1               5                   10                  15

Ile Asp Asn Ala Tyr Phe Glu Gln Phe Leu Asp Thr Ser Asp Glu Trp
            20                  25                  30

Ile Ser Lys Met Thr Gly Ile Lys Glu Arg His Trp Ala Asp Asp
        35                  40                  45

Gln Asp Thr Ser Asp Leu Ala Tyr Glu Ala Ser Leu Lys Ala Ile Ala
    50                  55                  60

Asp Ala Gly Ile Gln Pro Glu Asp Ile Asp Met Ile Ile Val Ala Thr
65                  70                  75                  80

Ala Thr Gly Asp Met Pro Phe Pro Thr Val Ala Asn Met Leu Gln Glu
                85                  90                  95

Arg Leu Gly Thr Gly Lys Val Ala Ser Met Asp Gln Leu Ala Ala Cys
            100                 105                 110

Ser Gly Phe Met Tyr Ser Met Ile Thr Ala Lys Gln Tyr Val Gln Ser
        115                 120                 125

Gly Asp Tyr His Asn Ile Leu Val Val Gly Ala Asp Lys Leu Ser Lys
    130                 135                 140

Ile Thr Asp Leu Thr Asp Arg Ser Thr Ala Val Leu Phe Gly Asp Gly
145                 150                 155                 160

Ala Gly Ala Val Ile Ile Gly Glu Val Ser Asp Gly Arg Gly Ile Ile
                165                 170                 175

Ser Tyr Glu Met Gly Ser Asp Gly Thr Gly Gly Lys His Leu Tyr Leu
            180                 185                 190

Asp Lys Asp Thr Gly Lys Leu Lys Met Asn Gly Arg Glu Val Phe Lys
        195                 200                 205
```

Phe Ala Val Arg Ile Met Gly Asp Ala Ser Thr Arg Val Val Glu Lys
210                 215                 220

Ala Asn Leu Thr Ser Asp Asp Ile Asp Leu Phe Ile Pro His Gln Ala
225                 230                 235                 240

Asn Ile Arg Ile Met Glu Ser Ala Arg Glu Arg Leu Gly Ile Ser Lys
                245                 250                 255

Asp Lys Met Ser Val Ser Val Asn Lys Tyr Gly Asn Thr Ser Ala Ala
            260                 265                 270

Ser Ile Pro Leu Ser Ile Asp Gln Glu Leu Lys Asn Gly Lys Ile Lys
        275                 280                 285

Asp Asp Asp Thr Ile Val Leu Val Gly Phe Gly Gly Leu Thr Trp
290                 295                 300

Gly Ala Met Thr Ile Lys Trp Gly Lys
305                 310

<210> SEQ ID NO 3
<211> LENGTH: 1074
<212> TYPE: DNA
<213> ORGANISM: Staphylococcus aureus

<400> SEQUENCE: 3
atactaattc taatactttc ttttcaattt tcgcaaatga attttaaaat tggtataata      60
ctatatgata ttaaagacat gagaaaggat gtactgagaa gtgataaata aagacatcta     120
tcaagcttta caacaactta tcccaaatga aaaattaaaa gttgatgaac ctttaaaacg     180
atacacttat actaaaacag gtggtaatgc cgacttttac attcccccta ctaaaaatga     240
agaagtacaa gcagttgtta aatatgccta tcaaatgag attcctgtta catatttagg      300
aaatggctca atattatta tccgtgaagg tggtattcgc ggtattgtaa ttagtttatt      360
atcactagat catatcgaag tatctgatga tgcgataata gccggtagcg gcgctgcaat     420
tattgatgtc tcacgtgttg ctcgtgatta cgcacttact ggccttgaat ttgcatgtgg     480
tattccaggt tcaattggtg gtgcagtgta tatgaatgct ggcgcttatg gtggcgaagt     540
taaagattgt atagactatg cgctttgcgt aaacgaacaa ggctcgttaa ttaaacttac     600
aacaaaagaa ttagagttag attatcgtaa tagcattatt caaaaagaac acttagttgt     660
attagaagct gcatttactt tagctcctgg taaaatgact gaaatacaag ctaaaatgga     720
tgatttaaca gaacgtagag aatctaaaca acctttagag tatccttcat gtggtagtgt     780
attccaaaga ccgcctggtc attttgcagg taaattgata caagattcta atttgcaagg     840
tcaccgtatt ggcggcgttg aagtttcaac caaacacgct ggttttatgg taaatgtaga     900
caatggaact gctacagatt atgaaaacct tattcattat gtacaaaaga ccgtcaaaga     960
aaaatttggc attgaattaa atcgtgaagt tcgcattatt ggtgaacatc caaggaatc    1020
gtaagttaag gagctttgtc tatgcctaaa gtttatggtt cattaatcga tact         1074

<210> SEQ ID NO 4
<211> LENGTH: 307
<212> TYPE: PRT
<213> ORGANISM: Staphylococcus aureus

<400> SEQUENCE: 4

Val Ile Asn Lys Asp Ile Tyr Gln Ala Leu Gln Gln Leu Ile Pro Asn
1               5                   10                  15

Glu Lys Ile Lys Val Asp Glu Pro Leu Lys Arg Tyr Thr Tyr Thr Lys
                20                  25                  30

Thr Gly Gly Asn Ala Asp Phe Tyr Ile Thr Pro Thr Lys Asn Glu Glu
         35                  40                  45

Val Gln Ala Val Val Lys Tyr Ala Tyr Gln Asn Glu Ile Pro Val Thr
 50                  55                  60

Tyr Leu Gly Asn Gly Ser Asn Ile Ile Ile Arg Glu Gly Gly Ile Arg
 65                  70                  75                  80

Gly Ile Val Ile Ser Leu Leu Ser Leu Asp His Ile Glu Val Ser Asp
                 85                  90                  95

Asp Ala Ile Ile Ala Gly Ser Gly Ala Ala Ile Ile Asp Val Ser Arg
                100                 105                 110

Val Ala Arg Asp Tyr Ala Leu Thr Gly Leu Glu Phe Ala Cys Gly Ile
        115                 120                 125

Pro Gly Ser Ile Gly Gly Ala Val Tyr Met Asn Ala Gly Ala Tyr Gly
        130                 135                 140

Gly Glu Val Lys Asp Cys Ile Asp Tyr Ala Leu Cys Val Asn Glu Gln
145                 150                 155                 160

Gly Ser Leu Ile Lys Leu Thr Thr Lys Glu Leu Glu Leu Asp Tyr Arg
                165                 170                 175

Asn Ser Ile Ile Gln Lys Glu His Leu Val Val Leu Glu Ala Ala Phe
                180                 185                 190

Thr Leu Ala Pro Gly Lys Met Thr Glu Ile Gln Ala Lys Met Asp Asp
        195                 200                 205

Leu Thr Glu Arg Arg Glu Ser Lys Gln Pro Leu Glu Tyr Pro Ser Cys
    210                 215                 220

Gly Ser Val Phe Gln Arg Pro Pro Gly His Phe Ala Gly Lys Leu Ile
225                 230                 235                 240

Gln Asp Ser Asn Leu Gln Gly His Arg Ile Gly Val Glu Val Ser
                245                 250                 255

Thr Lys His Ala Gly Phe Met Val Asn Val Asp Asn Gly Thr Ala Thr
                260                 265                 270

Asp Tyr Glu Asn Leu Ile His Tyr Val Gln Lys Thr Val Lys Glu Lys
        275                 280                 285

Phe Gly Ile Glu Leu Asn Arg Glu Val Arg Ile Ile Gly Glu His Pro
290                 295                 300

Lys Glu Ser
305

<210> SEQ ID NO 5
<211> LENGTH: 916
<212> TYPE: DNA
<213> ORGANISM: Staphylococcus aureus

<400> SEQUENCE: 5
aatagtgtta aaatgtattg acgaataaaa agttagttaa aactgggatt agatattcta      60
tccgttaaat taattattat aaggagttat cttacatgtt aaatcttgaa acaaaacat     120 atgtcatcat gggaatcgct aataagcgta gtattgcttt tggtgtcgct aaagttttag     180
atcaattagg tgctaaatta gtatttactt accgtaaaga acgtagccgt aaagagcttg     240
aaaaattatt agaacaatta aatcaaccag aagcgcactt atatcaaatt gatgttcaaa     300
gcgatgaaga ggttattaat ggttttgagc aaattggtaa agatgttggc aatattgatg     360
gtgtatatca ttcaatcgca tttgctaata tggaagactt acgcggacgc ttttctgaaa     420
cttcacgtga aggcttcttg ttagctcaag acattagttc ttactcatta acaattgtgg     480

-continued

```
ctcatgaagc taaaaaatta atgccagaag gtggtagcat tgttgcaaca acatatttag      540
gtggcgaatt cgcagttcaa actataatg tgatgggtgt tgctaaagcg agcttagaag       600
caaatgttaa atatttagca ttagacttag gtccagataa tattcgcgtt aatgcaattt      660
cagctagtcc aatccgtaca ttaagtgcaa aaggtgtggg tggtttcaat acaattctta     720
aagaaatcga agagcgtgca cctttaaaac gtaatgttga tcaagtagaa gtaggtaaaa      780
ctgcggctta cttattaagt gatttatcaa gtggcgttac aggtgaaaat attcatgtag      840
atagcggatt ccacgcaatt aaataatatc attcaacagc tttgttcacg ttattatata      900
tgtgagcaaa gctttt                                                      916
```

<210> SEQ ID NO 6
<211> LENGTH: 256
<212> TYPE: PRT
<213> ORGANISM: Staphylococcus aureus

<400> SEQUENCE: 6

```
Met Leu Asn Leu Glu Asn Lys Thr Tyr Val Ile Met Gly Ile Ala Asn
1               5                   10                  15

Lys Arg Ser Ile Ala Phe Gly Val Ala Lys Val Leu Asp Gln Leu Gly
            20                  25                  30

Ala Lys Leu Val Phe Thr Tyr Arg Lys Glu Arg Ser Arg Lys Glu Leu
        35                  40                  45

Glu Lys Leu Leu Glu Gln Leu Asn Gln Pro Glu Ala His Leu Tyr Gln
    50                  55                  60

Gly Lys Asp Val Gly Asn Ile Asp Gly Val Tyr His Ser Ile Ala Phe
65                  70                  75                  80

Ile Asp Val Gln Ser Asp Glu Glu Val Ile Asn Gly Phe Glu Gln Ile
                85                  90                  95

Ala Asn Met Glu Asp Leu Arg Gly Arg Phe Ser Glu Thr Ser Arg Glu
            100                 105                 110

Gly Phe Leu Leu Ala Gln Asp Ile Ser Ser Tyr Ser Leu Thr Ile Val
        115                 120                 125

Ala His Glu Ala Lys Lys Leu Met Pro Glu Gly Gly Ser Ile Val Ala
    130                 135                 140

Thr Thr Tyr Leu Gly Gly Glu Phe Ala Val Gln Asn Tyr Asn Val Met
145                 150                 155                 160

Gly Val Ala Lys Ala Ser Leu Glu Ala Asn Val Lys Tyr Leu Ala Leu
                165                 170                 175

Asp Leu Gly Pro Asp Asn Ile Arg Val Asn Ala Ile Ser Ala Ser Pro
            180                 185                 190

Ile Arg Thr Leu Ser Ala Lys Gly Val Gly Gly Phe Asn Thr Ile Leu
        195                 200                 205

Lys Glu Ile Glu Glu Arg Ala Pro Leu Lys Arg Asn Val Asp Gln Val
    210                 215                 220

Glu Val Gly Lys Thr Ala Ala Tyr Leu Leu Ser Asp Leu Ser Ser Gly
225                 230                 235                 240

Val Thr Gly Glu Asn Ile His Val Asp Ser Gly Phe His Ala Ile Lys
                245                 250                 255
```

<210> SEQ ID NO 7
<211> LENGTH: 1376
<212> TYPE: DNA
<213> ORGANISM: Staphylococcus aureus

<400> SEQUENCE: 7

```
taaaataatt ttaaaatagg gaaatgtaaa gtaataggag ttctaagtgg aggatttacg      60
atggataaaa tagtaatcaa aggtggaaat aaattaacgg gtgaagttaa agtagaaggt     120
gctaaaaatg cagtattacc aatattgaca gcatctttat tagcttctga taaaccgagc     180
aaattagtta atgttccagc tttaagtgat gtagaaacaa taaataatgt attaacaact     240
ttaaatgctg acgttacata caaaaaggac gaaaatgctg ttgtcgttga tgcaacaaag     300
actctaaatg aagaggcacc atatgaatat gttagtaaaa tgcgtgcaag tattttagtt     360
atgggacctc ttttagcaag actaggacat gctattgttg cattgcctgg tggttgtgca     420
attggaagta gaccgattga gcaacacatt aaaggttttg aagctttagg cgcagaaatt     480
catcttgaaa atggtaatat ttatgctaat gctaaagatg gattaaaagg tacatcaatt     540
catttagatt ttccaagtgt aggagcaaca caaatatta ttatggcagc atcattagct     600
aagggtaaga ctttaattga aaatgcagct aaagaacctg aaattgtcga tttagcaaac     660
tacattaatg aaatgggtgg tagaattact ggtgctggta cagacacaat tacaatcaat     720
ggtgtagaat cattacatgg tgtagaacat gctatcattc cagatagaat tgaagcaggc     780
acattactaa tcgctggtgc tataacgcgt ggtgatattt ttgtacgtgg tgcaatcaaa     840
gaacatatgg cgagtttagt ctataaacta aagaaatgg gcgttgaatt ggactatcaa     900
gaagatggta ttcgtgtacg tgctgaaggg gaattacaac ctgtagacat caaaactcta     960
ccacatcctg gattcccgac tgatatgcaa tcacaaatga tggcattgtt attaacggca    1020
aatggtcata aagtcgtaac cgaaactgtt tttgaaaacc gttttatgca tgttgcagag    1080
ttcaaacgta tgaatgctaa tatcaatgta gaaggtcgta gtgctaaact tgaaggtaaa    1140
agtcaattgc aaggtgcaca agttaaagcg actgatttaa gagcagcagc cgccttaatt    1200
ttagctggat tagttgctga tggtaaaaca agcgttactg aattaacgca cctagataga    1260
ggctatgttg acttacacgg taaattgaag caattaggtg cagacattga acgtattaac    1320
gattaattca gtaaattaat ataatggagg atttcaacca tggaaacaat ttttga        1376
```

<210> SEQ ID NO 8
<211> LENGTH: 421
<212> TYPE: PRT
<213> ORGANISM: Staphylococcus aureus

<400> SEQUENCE: 8

```
Met Asp Lys Ile Val Ile Lys Gly Gly Asn Lys Leu Thr Gly Glu Val
1               5                   10                  15

Lys Val Glu Gly Ala Lys Asn Ala Val Leu Pro Ile Leu Thr Ala Ser
            20                  25                  30

Leu Leu Ala Ser Asp Lys Pro Ser Lys Leu Val Asn Val Pro Ala Leu
        35                  40                  45

Ser Asp Val Glu Thr Ile Asn Asn Val Leu Thr Thr Leu Asn Ala Asp
    50                  55                  60

Val Thr Tyr Lys Lys Asp Glu Asn Ala Val Val Asp Ala Thr Lys
65                  70                  75                  80

Thr Leu Asn Glu Glu Ala Pro Tyr Glu Tyr Val Ser Lys Met Arg Ala
                85                  90                  95

Ser Ile Leu Val Met Gly Pro Leu Leu Ala Arg Leu Gly His Ala Ile
            100                 105                 110

Val Ala Leu Pro Gly Gly Cys Ala Ile Gly Ser Arg Pro Ile Glu Gln
        115                 120                 125
```

His Ile Lys Gly Phe Glu Ala Leu Gly Ala Glu Ile His Leu Glu Asn
            130                 135                 140
Gly Asn Ile Tyr Ala Asn Ala Lys Asp Gly Leu Lys Gly Thr Ser Ile
145                 150                 155                 160
His Leu Asp Phe Pro Ser Val Gly Ala Thr Gln Asn Ile Ile Met Ala
                165                 170                 175
Ala Ser Leu Ala Lys Gly Lys Thr Leu Ile Glu Asn Ala Ala Lys Glu
            180                 185                 190
Pro Glu Ile Val Asp Leu Ala Asn Tyr Ile Asn Glu Met Gly Gly Arg
        195                 200                 205
Ile Thr Gly Ala Gly Thr Asp Thr Ile Thr Ile Asn Gly Val Glu Ser
    210                 215                 220
Leu His Gly Val Glu His Ala Ile Ile Pro Asp Arg Ile Glu Ala Gly
225                 230                 235                 240
Thr Leu Leu Ile Ala Gly Ala Ile Thr Arg Gly Asp Ile Phe Val Arg
                245                 250                 255
Gly Ala Ile Lys Glu His Met Ala Ser Leu Val Tyr Lys Leu Glu Glu
            260                 265                 270
Met Gly Val Glu Leu Asp Tyr Gln Glu Asp Gly Ile Arg Val Arg Ala
        275                 280                 285
Glu Gly Glu Leu Gln Pro Val Asp Ile Lys Thr Leu Pro His Pro Gly
    290                 295                 300
Phe Pro Thr Asp Met Gln Ser Gln Met Met Ala Leu Leu Leu Thr Ala
305                 310                 315                 320
Asn Gly His Lys Val Val Thr Glu Thr Val Phe Glu Asn Arg Phe Met
                325                 330                 335
His Val Ala Glu Phe Lys Arg Met Asn Ala Asn Ile Asn Val Glu Gly
            340                 345                 350
Arg Ser Ala Lys Leu Glu Gly Lys Ser Gln Leu Gln Gly Ala Gln Val
        355                 360                 365
Lys Ala Thr Asp Leu Arg Ala Ala Ala Leu Ile Leu Ala Gly Leu
    370                 375                 380
Val Ala Asp Gly Lys Thr Ser Val Thr Glu Leu Thr His Leu Asp Arg
385                 390                 395                 400
Gly Tyr Val Asp Leu His Gly Lys Leu Lys Gln Leu Gly Ala Asp Ile
                405                 410                 415
Glu Arg Ile Asn Asp
            420

<210> SEQ ID NO 9
<211> LENGTH: 1537
<212> TYPE: DNA
<213> ORGANISM: Staphylococcus aureus

<400> SEQUENCE: 9
ttcatgtatt taaaggttg gggattagca taatgggatt gtgctagcac agttatttat      60
gcattgtcat gcctatctat tacttactaa ctaaaaaata atgaaatggg tgtaaactat     120
atgcctgaaa gagaacgtac atctcctcag tatgaatcat tccacgaatt gtacaagaac     180
tatactacca aggaactcac tcaaaaagct aaaactctta agttgacgaa ccatagtaaa     240
ttaaataaaa aagaacttgt tctagctatt atggaagcac aaatggaaaa agatggtaac     300
tattatatgg aaggtatctt agatgatata caaccaggtg ttatggtttt tttaagaaca     360
gtgaactatt ctaagggga aaaagatatt tatatatctg ctagccaaat tcgtcgtttt     420

-continued

```
gaaattaaac gtggggataa agtaactggg aaagttagaa aacctaaaga taacgaaaaa      480
tattatggct tattacaagt tgactttgtc aatgaccata acgcagaaga agtgaagaaa      540
cgtccgcatt tccaagcttt gacaccactt tatccagatg agcgtattaa attagagaca      600
gaaatacaaa attattcaac gcgcatcatg gatttagtaa caccgattgg tttaggtcaa      660
cgtggtttaa tagtggcgcc acctaaagca ggtaaaacat cgttattaaa agaaatagcg      720
aatgcaatca gtacgaacaa accagatgca aagctattta ttttgttagt tggcgagcgt      780
cctgaagagg taacagattt agaacgctca gtagaagctg ctgaagtcgt tcattcaacg      840
tttgacgaac caccagaaca ccatgttaaa gtagctgaat tattacttga acgtgcaaag      900
cgtttagtag aaattgggga agatgtcatt attttaatgg attctataac gagattagca      960
cgcgcttata acttagttat tccaccaagt ggtcgtacat tatcaggtgg tttagatcct     1020
gcatctttac acaaaccaaa agcattcttc ggtgcagcga gaaatattga agcgggtgga     1080
agtttaacaa tacttgcaac tgcattagtt gatacgggtt cacgtatgga cgatatgatt     1140
tacgaagaat ttaaaggaac aggtaacatg gagttacatt tagatcgtaa attgtctgaa     1200
cgtcgtatct tccctgcaat tgatattggc agaagttcaa cgcgtaaaga agaattgttg     1260
ataagtaaat ctgaattaga cacattatgg caattaagaa atctattcac tgactcaact     1320
gactttactg aaagatttat tcgcaaactt aaaaggtcta agaataatga agatttcttc     1380
aagcagctac aaaagtctgc agaagaaagt actaaaacgg gtcgacctat aatttaataa     1440
acattatata ggggcttgcg ttttgaatta attaccttta taattacaca gtattgggta     1500
aaaactcaca aataactctg ttccagatgg ttcaggg                              1537
```

```
<210> SEQ ID NO 10
<211> LENGTH: 438
<212> TYPE: PRT
<213> ORGANISM: Staphylococcus aureus

<400> SEQUENCE: 10
```

```
Met Pro Glu Arg Glu Arg Thr Ser Pro Gln Tyr Glu Ser Phe His Glu
1               5                   10                  15

Leu Tyr Lys Asn Tyr Thr Thr Lys Glu Leu Thr Gln Lys Ala Lys Thr
            20                  25                  30

Leu Lys Leu Thr Asn His Ser Lys Leu Asn Lys Lys Glu Leu Val Leu
        35                  40                  45

Ala Ile Met Glu Ala Gln Met Glu Lys Asp Gly Asn Tyr Tyr Met Glu
    50                  55                  60

Gly Ile Leu Asp Asp Ile Gln Pro Gly Gly Tyr Gly Phe Leu Arg Thr
65                  70                  75                  80

Val Asn Tyr Ser Lys Gly Glu Lys Asp Ile Tyr Ile Ser Ala Ser Gln
                85                  90                  95

Ile Arg Arg Phe Glu Ile Lys Arg Gly Asp Lys Val Thr Gly Lys Val
            100                 105                 110

Arg Lys Pro Lys Asp Asn Glu Lys Tyr Tyr Gly Leu Leu Gln Val Asp
        115                 120                 125

Phe Val Asn Asp His Asn Ala Glu Glu Val Lys Lys Arg Pro His Phe
    130                 135                 140

Gln Ala Leu Thr Pro Leu Tyr Pro Asp Glu Arg Ile Lys Leu Glu Thr
145                 150                 155                 160

Glu Ile Gln Asn Tyr Ser Thr Arg Ile Met Asp Leu Val Thr Pro Ile
                165                 170                 175
```

```
Gly Leu Gly Gln Arg Gly Leu Ile Val Ala Pro Pro Lys Ala Gly Lys
            180                 185                 190

Thr Ser Leu Leu Lys Glu Ile Ala Asn Ala Ile Ser Thr Asn Lys Pro
        195                 200                 205

Asp Ala Lys Leu Phe Ile Leu Leu Val Gly Glu Arg Pro Glu Glu Val
    210                 215                 220

Thr Asp Leu Glu Arg Ser Val Glu Ala Ala Glu Val Val His Ser Thr
225                 230                 235                 240

Phe Asp Glu Pro Pro Glu His His Val Lys Val Ala Glu Leu Leu Leu
                245                 250                 255

Glu Arg Ala Lys Arg Leu Val Glu Ile Gly Glu Asp Val Ile Ile Leu
            260                 265                 270

Met Asp Ser Ile Thr Arg Leu Ala Arg Ala Tyr Asn Leu Val Ile Pro
        275                 280                 285

Pro Ser Gly Arg Thr Leu Ser Gly Gly Leu Asp Pro Ala Ser Leu His
    290                 295                 300

Lys Pro Lys Ala Phe Phe Gly Ala Ala Arg Asn Ile Glu Ala Gly Gly
305                 310                 315                 320

Ser Leu Thr Ile Leu Ala Thr Ala Leu Val Asp Thr Gly Ser Arg Met
                325                 330                 335

Asp Asp Met Ile Tyr Glu Glu Phe Lys Gly Thr Gly Asn Met Glu Leu
            340                 345                 350

His Leu Asp Arg Lys Leu Ser Glu Arg Arg Ile Phe Pro Ala Ile Asp
        355                 360                 365

Ile Gly Arg Ser Ser Thr Arg Lys Glu Glu Leu Leu Ile Ser Lys Ser
    370                 375                 380

Glu Leu Asp Thr Leu Trp Gln Leu Arg Asn Leu Phe Thr Asp Ser Thr
385                 390                 395                 400

Asp Phe Thr Glu Arg Phe Ile Arg Lys Leu Lys Arg Ser Lys Asn Asn
                405                 410                 415

Glu Asp Phe Phe Lys Gln Leu Gln Lys Ser Ala Glu Glu Ser Thr Lys
            420                 425                 430

Thr Gly Arg Pro Ile Ile
        435

<210> SEQ ID NO 11
<211> LENGTH: 554
<212> TYPE: DNA
<213> ORGANISM: Staphylococcus aureus

<400> SEQUENCE: 11
gatctttttt ttcgtttaaa ttaagaataa atagaaattt atgttataag ctcaatagaa      60
gtttaaatat agcttcaata aaaacgataa taagcgagtg atgttattgg aaaaagctta     120
ccgaattaaa aagaatgcag attttcagag aatatataaa aaaggtcatt ctgtagccaa     180
cagacaattt gttgtataca cttgtaataa taaagaaata gaccattttc gcttaggtat     240
tagtgtttct aaaaaactag gtaatgcagt gttaagaaac aagattaaaa gagcaatacg     300
tgaaaatttc aaagtacata agtcgcatat attggccaaa gatattattg taatagcaag     360
acagccagct aaagatatga cgactttaca aatacgaat agtcttgagc acgtacttaa     420
aattgccaaa gttttaata aaaagattaa gtaaggatag ggtagggaa ggaaaacatt     480 aaccactcaa cacatcccga agtcttacct cagacaaacg taagactgac cttagggtta     540
taataactta cttt                                                      554
```

<210> SEQ ID NO 12
<211> LENGTH: 117
<212> TYPE: PRT
<213> ORGANISM: Staphylococcus aureus

<400> SEQUENCE: 12

```
Met Leu Leu Glu Lys Ala Tyr Arg Ile Lys Lys Asn Ala Asp Phe Gln
1               5                   10                  15

Arg Ile Tyr Lys Lys Gly His Ser Val Ala Asn Arg Gln Phe Val Val
            20                  25                  30

Tyr Thr Cys Asn Asn Lys Glu Ile Asp His Phe Arg Leu Gly Ile Ser
        35                  40                  45

Val Ser Lys Lys Leu Gly Asn Ala Val Leu Arg Asn Lys Ile Lys Arg
    50                  55                  60

Ala Ile Arg Glu Asn Phe Lys Val His Lys Ser His Ile Leu Ala Lys
65                  70                  75                  80

Asp Ile Ile Val Ile Ala Arg Gln Pro Ala Lys Asp Met Thr Thr Leu
                85                  90                  95

Gln Ile Gln Asn Ser Leu Glu His Val Leu Lys Ile Ala Lys Val Phe
            100                 105                 110

Asn Lys Lys Ile Lys
        115
```

<210> SEQ ID NO 13
<211> LENGTH: 1712
<212> TYPE: DNA
<213> ORGANISM: Staphylococcus aureus

<400> SEQUENCE: 13

| | | | | | |
|---|---|---|---|---|---|
| cagcaaaaac | tggtgaaggt | ggtaaattgt | ttgggtcagt | aagtacaaaa | caaattgccg | 60 |
| aagcactaaa | agcacaacat | gatattaaaa | ttgataaacg | taaatggat | ttaccaaatg | 120 |
| gaattcattc | cctaggatat | acgaatgtac | ctgttaaatt | agataaagaa | gttgaaggta | 180 |
| caattcgcgt | acacacagtt | gaacaataaa | gttggattga | aataagaggt | gtaaccattc | 240 |
| atggatagaa | tgtatgagca | aaatcaaatg | ccgcataaca | atgaagctga | acagtctgtc | 300 |
| ttaggttcaa | ttattataga | tccagaattg | attaatacta | ctcaggaagt | tttgcttcct | 360 |
| gagtcgtttt | ataggggtgc | ccatcaacat | attttccgtg | caatgatgca | cttaaatgaa | 420 |
| gataataaag | aaattgatgt | tgtaacattg | atggatcaat | tatcgacgga | aggtacgttg | 480 |
| aatgaagcgg | gtggcccgca | atatcttgca | gagttatcta | caaatgtacc | aacgacgcga | 540 |
| aatgttcagt | attatactga | tatcgtttct | aagcatgcat | taaaacgtag | attgattcaa | 600 |
| actgcagata | gtattgccaa | tgatggatat | aatgatgaac | ttgaactaga | tgcgatttta | 660 |
| agtgatgcag | aacgtcgaat | tttagagcta | tcatcttctc | gtgaaagcga | tggctttaaa | 720 |
| gacattcgag | acgtcttagg | acaagtgtat | gaaacagctg | aagagcttga | tcaaaatagt | 780 |
| ggtcaaacac | caggtatacc | tacaggatat | cgagatttag | accaaatgac | agcagggttc | 840 |
| aaccgaaatg | atttaattat | ccttgcagcg | cgtccatctg | taggtaagac | tgcgttcgca | 900 |
| cttaatattg | cacaaaaagt | tgcaacgcat | gaagatatgt | atacagttgg | tattttctcg | 960 |
| ctagagatgg | gtgctgatca | gttagccaca | cgtatgattt | gtagttctgg | aaatgttgac | 1020 |
| tcaaaccgct | taagaacggg | tactatgact | gaggaagatt | ggagtcgttt | tactatagcg | 1080 |
| gtaggtaaat | tatcacgtac | gaagattttt | attgatgata | caccgggtat | tcgaattaat | 1140 |
| gatttacgtt | ctaaatgtcg | tcgattaaag | caagaacatg | gcttagacat | gattgtgatt | 1200 |

```
gactacttac agttgattca aggtagtggt tcacgtgcgt ccgataacag acaacaggaa    1260
gtttctgaaa tctctcgtac attaaaagca ttagcccgtg aattaaaatg tccagttatc    1320
gcattaagtc agttatctcg tggtgttgaa caacgacaag ataaacgtcc aatgatgagt    1380
gatattcgtg aatctggttc gattgagcaa gatgccgata tcgttgcatt cttataccgt    1440
gatgattact ataaccgtgg cggcgatgaa gatgatgacg atgatggtgg tttcgagcca    1500
caaacgaatg atgaaaacgg tgaaattgaa attatcattg ctaagcaacg taacggtcca    1560
acaggcacag ttaagttaca ttttatgaaa caatataata aatttaccga tatcgattat    1620
gcacatgcag atatgatgta aaaaagtttt tccgtacaat aatcattaag atgataaaat    1680
tgtacggttt ttattttgtt ctgaacgggt tg                                  1712
```

<210> SEQ ID NO 14
<211> LENGTH: 466
<212> TYPE: PRT
<213> ORGANISM: Staphylococcus aureus

<400> SEQUENCE: 14

```
Met Asp Arg Met Tyr Glu Gln Asn Gln Met Pro His Asn Asn Glu Ala
1               5                   10                  15

Glu Gln Ser Val Leu Gly Ser Ile Ile Ile Asp Pro Glu Leu Ile Asn
            20                  25                  30

Thr Thr Gln Glu Val Leu Leu Pro Glu Ser Phe Tyr Arg Gly Ala His
        35                  40                  45

Gln His Ile Phe Arg Ala Met Met His Leu Asn Glu Asp Asn Lys Glu
    50                  55                  60

Ile Asp Val Val Thr Leu Met Asp Gln Leu Ser Thr Glu Gly Thr Leu
65                  70                  75                  80

Asn Glu Ala Gly Gly Pro Gln Tyr Leu Ala Glu Leu Ser Thr Asn Val
                85                  90                  95

Pro Thr Thr Arg Asn Val Gln Tyr Tyr Thr Asp Ile Val Ser Lys His
            100                 105                 110

Ala Leu Lys Arg Arg Leu Ile Gln Thr Ala Asp Ser Ile Ala Asn Asp
        115                 120                 125

Gly Tyr Asn Asp Glu Leu Glu Leu Asp Ala Ile Leu Ser Asp Ala Glu
    130                 135                 140

Arg Arg Ile Leu Glu Leu Ser Ser Ser Arg Glu Ser Asp Gly Phe Lys
145                 150                 155                 160

Asp Ile Arg Asp Val Leu Gly Gln Val Tyr Glu Thr Ala Glu Glu Leu
                165                 170                 175

Asp Gln Asn Ser Gly Gln Thr Pro Gly Ile Pro Thr Gly Tyr Arg Asp
            180                 185                 190

Leu Asp Gln Met Thr Ala Gly Phe Asn Arg Asn Asp Leu Ile Ile Leu
        195                 200                 205

Ala Ala Arg Pro Ser Val Gly Lys Thr Ala Phe Ala Leu Asn Ile Ala
    210                 215                 220

Gln Lys Val Ala Thr His Glu Asp Met Tyr Thr Val Gly Ile Phe Ser
225                 230                 235                 240

Leu Glu Met Gly Ala Asp Gln Leu Ala Thr Arg Met Ile Cys Ser Ser
                245                 250                 255

Gly Asn Val Asp Ser Asn Arg Leu Arg Thr Gly Thr Met Thr Glu Glu
            260                 265                 270

Asp Trp Ser Arg Phe Thr Ile Ala Val Gly Lys Leu Ser Arg Thr Lys
```

```
                275                 280                 285
Ile Phe Ile Asp Asp Thr Pro Gly Ile Arg Ile Asn Asp Leu Arg Ser
            290                 295                 300
Lys Cys Arg Arg Leu Lys Gln Glu His Gly Leu Asp Met Ile Val Ile
305                 310                 315                 320
Asp Tyr Leu Gln Leu Ile Gln Gly Ser Gly Ser Arg Ala Ser Asp Asn
                325                 330                 335
Arg Gln Gln Glu Val Ser Glu Ile Ser Arg Thr Leu Lys Ala Leu Ala
            340                 345                 350
Arg Glu Leu Lys Cys Pro Val Ile Ala Leu Ser Gln Leu Ser Arg Gly
            355                 360                 365
Val Glu Gln Arg Gln Asp Lys Arg Pro Met Met Ser Asp Ile Arg Glu
370                 375                 380
Ser Gly Ser Ile Glu Gln Asp Ala Asp Ile Val Ala Phe Leu Tyr Arg
385                 390                 395                 400
Asp Asp Tyr Tyr Asn Arg Gly Gly Asp Glu Asp Asp Asp Asp Asp Gly
                405                 410                 415
Gly Phe Glu Pro Gln Thr Asn Asp Glu Asn Gly Glu Ile Glu Ile Ile
            420                 425                 430
Ile Ala Lys Gln Arg Asn Gly Pro Thr Gly Thr Val Lys Leu His Phe
            435                 440                 445
Met Lys Gln Tyr Asn Lys Phe Thr Asp Ile Asp Tyr Ala His Ala Asp
    450                 455                 460
Met Met
465

<210> SEQ ID NO 15
<211> LENGTH: 1170
<212> TYPE: DNA
<213> ORGANISM: Staphylococcus aureus

<400> SEQUENCE: 15
gtggttccgt attattagga ttggaaggta ctgtagttaa agcacacggt agttcaaatg     60
ctaaagcttt ttattctgca attagacaag cgaaaatcgc aggagaacaa aatattgtac    120
aaacaatgaa agagactgta ggtgaatcaa atgagtaaaa cagcaattat ttttccggga    180
caaggtgccc aaaaagttgg tatggcgcaa gatttgttta caacaatga tcaagcaact    240
gaaattttaa cttcagcagc gaacacatta gactttgata ttttagagac aatgttttact   300
gatgaagaag gtaaattggg tgaaactgaa acacacaac cagctttatt gacgcatagt    360
tcggcattat tagcagcgct aaaaaatttg aatcctgatt ttactatggg gcatagttta    420
ggtgaatatt caagtttagt tgcagctgac gtattatcat ttgaagatgc agttaaaatt    480
gttagaaaac gtggtcaatt aatggcgcaa gcatttccta ctggtgtagg aagcatggct    540
gcagtattgg gattagattt tgataaagtc gatgaaattt gtaagtcatt atcatctgat    600
gacaaaataa ttgaaccagc aaacattaat tgcccaggtc aaattgttgt tcaggtcac     660
aaagcttttaa ttgatgagct agtagaaaaa ggtaaatcat taggtgcaaa acgtgtcatg    720
cctttagcag tatctggacc attccattca tcgctaatga agtgattga agaagatttt    780
tcaagttaca ttaatcaatt tgaatggcgt gatgctaagt ttcctgtagt tcaaaatgta    840
aatgcgcaag gtgaaactga caaagaagta attaaatcta atatggtcaa gcaattatat    900
tcaccagtac aattcattaa ctcaacagaa tggctaatag accaaggtgt tgatcatttt    960
attgaaattg gtcctggaaa agttttatct ggcttaatta aaaaaataaa tagagatgtt   1020
```

```
aagttaacat caattcaaac tttagaagat gtgaaaggat ggaatgaaaa tgactaagag     1080
tgctttagta acaggtgcat caagaggaat tggacgtagt attgcgttac aattagcaga     1140
agaaggatat aatgtagcag taaactatgc                                      1170
```

<210> SEQ ID NO 16
<211> LENGTH: 308
<212> TYPE: PRT
<213> ORGANISM: Staphylococcus aureus

<400> SEQUENCE: 16

```
Met Ser Lys Thr Ala Ile Ile Phe Pro Gly Gln Gly Ala Gln Lys Val
1               5                   10                  15

Gly Met Ala Gln Asp Leu Phe Asn Asn Asn Asp Gln Ala Thr Glu Ile
            20                  25                  30

Leu Thr Ser Ala Ala Asn Thr Leu Asp Phe Asp Ile Leu Glu Thr Met
        35                  40                  45

Phe Thr Asp Glu Glu Gly Lys Leu Gly Glu Thr Glu Asn Thr Gln Pro
    50                  55                  60

Ala Leu Leu Thr His Ser Ser Ala Leu Leu Ala Leu Lys Asn Leu
65                  70                  75                  80

Asn Pro Asp Phe Thr Met Gly His Ser Leu Gly Glu Tyr Ser Ser Leu
                85                  90                  95

Val Ala Ala Asp Val Leu Ser Phe Glu Asp Ala Val Lys Ile Val Arg
            100                 105                 110

Lys Arg Gly Gln Leu Met Ala Gln Ala Phe Pro Thr Gly Val Gly Ser
        115                 120                 125

Met Ala Ala Val Leu Gly Leu Asp Phe Asp Lys Val Asp Glu Ile Cys
    130                 135                 140

Lys Ser Leu Ser Ser Asp Asp Lys Ile Ile Glu Pro Ala Asn Ile Asn
145                 150                 155                 160

Cys Pro Gly Gln Ile Val Val Ser Gly His Lys Ala Leu Ile Asp Glu
                165                 170                 175

Leu Val Glu Lys Gly Lys Ser Leu Gly Ala Lys Arg Val Met Pro Leu
            180                 185                 190

Ala Val Ser Gly Pro Phe His Ser Ser Leu Met Lys Val Ile Glu Glu
        195                 200                 205

Asp Phe Ser Ser Tyr Ile Asn Gln Phe Glu Trp Arg Asp Ala Lys Phe
    210                 215                 220

Pro Val Val Gln Asn Val Asn Ala Gln Gly Glu Thr Asp Lys Glu Val
225                 230                 235                 240

Ile Lys Ser Asn Met Val Lys Gln Leu Tyr Ser Pro Val Gln Phe Ile
                245                 250                 255

Asn Ser Thr Glu Trp Leu Ile Asp Gln Gly Val Asp His Phe Ile Glu
            260                 265                 270

Ile Gly Pro Gly Lys Val Leu Ser Gly Leu Ile Lys Lys Ile Asn Arg
        275                 280                 285

Asp Val Lys Leu Thr Ser Ile Gln Thr Leu Glu Asp Val Lys Gly Trp
    290                 295                 300

Asn Glu Asn Asp
305
```

<210> SEQ ID NO 17
<211> LENGTH: 1080
<212> TYPE: DNA

<213> ORGANISM: Staphylococcus aureus

<400> SEQUENCE: 17

```
aaatacacat ttaatctgca gtatttcaat gcattgacgc tatttttttg atataattac      60
tttgaaaaat acgtgcgtaa gcactcaagg aggaactttc atgcctttag tttcaatgaa     120
agaaatgtta attgatgcaa agaaaatgg ttatgcggta ggtcaataca atattaataa      180
cctagaattc actcaagcaa ttttagaagc gtcacaagaa gaaaatgcac ctgtaatttt     240
aggtgtttct gaaggtgctg ctcgttacat gagcggtttc tacacaattg ttaaaatggt     300
tgaagggtta atgcatgact aaacatcac tattcctgta gcaatccatt tagaccatgg      360
ttcaagcttt gaaaaatgta agaagctat cgatgctggt ttcacatcag taatgatcga      420
tgcttcacac agcccattcg aagaaaacgt agcaacaact aaaaaagttg ttgaatacgc     480
tcatgaaaaa ggtgtttctg tagaagctga attaggtact gttggtggac aagaagatga     540
tgttgtagca gacggcatca tttatgctga tcctaaagaa tgtcaagaac tagttgaaaa     600
aactggtatt gatgcattag cgccagcatt aggttcagtt catggtccat acaaaggtga     660
accaaaatta ggatttaaag aaatggaaga atcggttta tctacaggtt taccattagt      720
attacacggt ggtactggta tcccgactaa agatatccaa aaagcaattc catttggtac     780
agctaaaatt aacgtaaaca ctgaaaacca atcgcttca gcaaaagcag ttcgtgacgt      840
tttaaataac gacaaagaag tttacgatcc tcgtaaatac ttaggacctg cacgtgaagc     900
catcaaagaa acagttaaag gtaaaattaa agagttcggt acttctaacc gcgctaaata     960
attaatattt agtctttaag ttattaataa cgtagggata ttaatttaa aagaagcaga    1020
caaaatggtg tttgcttctt ttttatgtcg tataagtaat aaataaaaca gtttgatttt    1080
```

<210> SEQ ID NO 18
<211> LENGTH: 286
<212> TYPE: PRT
<213> ORGANISM: Staphylococcus aureus

<400> SEQUENCE: 18

```
Met Pro Leu Val Ser Met Lys Glu Met Leu Ile Asp Ala Lys Glu Asn
  1               5                  10                  15

Gly Tyr Ala Val Gly Gln Tyr Asn Ile Asn Asn Leu Glu Phe Thr Gln
             20                  25                  30

Ala Ile Leu Glu Ala Ser Gln Glu Glu Asn Ala Pro Val Ile Leu Gly
         35                  40                  45

Val Ser Glu Gly Ala Ala Arg Tyr Met Ser Gly Phe Tyr Thr Ile Val
     50                  55                  60

Lys Met Val Glu Gly Leu Met His Asp Leu Asn Ile Thr Ile Pro Val
 65                  70                  75                  80

Ala Ile His Leu Asp His Gly Ser Ser Phe Glu Lys Cys Lys Glu Ala
                 85                  90                  95

Ile Asp Ala Gly Phe Thr Ser Val Met Ile Asp Ala Ser His Ser Pro
            100                 105                 110

Phe Glu Glu Asn Val Ala Thr Thr Lys Lys Val Glu Tyr Ala His
        115                 120                 125

Glu Lys Gly Val Ser Val Glu Ala Glu Leu Gly Thr Val Gly Gly Gln
    130                 135                 140

Glu Asp Asp Val Val Ala Asp Gly Ile Ile Tyr Ala Asp Pro Lys Glu
145                 150                 155                 160

Cys Gln Glu Leu Val Glu Lys Thr Gly Ile Asp Ala Leu Ala Pro Ala
```

```
                    165                 170                 175
Leu Gly Ser Val His Gly Pro Tyr Lys Gly Glu Pro Lys Leu Gly Phe
                180                 185                 190
Lys Glu Met Glu Glu Ile Gly Leu Ser Thr Gly Leu Pro Leu Val Leu
            195                 200                 205
His Gly Thr Gly Ile Pro Thr Lys Asp Ile Gln Lys Ala Ile Pro
        210                 215                 220
Phe Gly Thr Ala Lys Ile Asn Val Asn Thr Glu Asn Gln Ile Ala Ser
225                 230                 235                 240
Ala Lys Ala Val Arg Asp Val Leu Asn Asn Asp Lys Glu Val Tyr Asp
                245                 250                 255
Pro Arg Lys Tyr Leu Gly Pro Ala Arg Glu Ala Ile Lys Glu Thr Val
            260                 265                 270
Lys Gly Lys Ile Lys Glu Phe Gly Thr Ser Asn Arg Ala Lys
        275                 280                 285

<210> SEQ ID NO 19
<211> LENGTH: 1340
<212> TYPE: DNA
<213> ORGANISM: Staphylococcus aureus

<400> SEQUENCE: 19
gctataatag gcatggttac aatgagcttg ctcatacata ttaatataat tacaaaaaca      60
cgtcggaggt acgacatgat taaaaataca attaaaaaat tgatagaaca tagtatatat    120
acgactttta aattactatc aaaattgcca acaagaatct taatttattt tgaaagcttt    180
catggtaaac aatacagcga caccccaaa gcattatatg aatacttaac tgaacatagc    240
gatgcccaat aatatggggg tgtgaaaaaa ggatatgaac acatattcca acagcacaat    300
gtaccatatg ttacaaagtt ttcaatgaaa tggttttag cgatgccaag agcgaaagcg    360
tggatgatta acacacgtac accagattgg ttatataaat caccgcgaac gacgtactta    420
caaacatggc atggcacgcc attaaaaaag attggtttgg atattagtaa cgttaaaatg    480
ctaggaacaa atactcaaaa ttaccaagat ggctttaaaa agaaagcca acggtgggat    540
tatctagtgt cacctaatcc atattcgaca tcgatatttc aaaatgcatt tcatgttagt    600
cgagataaga ttttggaaac aggttatcca agaaatgata aattatcaca taacgcaat     660
gatactgaat atattaatgg tattaagaca agattaaata ttccattaga taaaaaagtg    720
attatgtacg cgccaacttg gcgtgacgat gaagcgattc gagaaggttc atatcaattt    780
aatgttaact tgatataga agctttgcgt caagcgctgg atgatgatta tgttatttta    840
ttacgcatgc attatttagt tgtgacacgt attgatgaac atgatgattt tgtgaaagac    900
gtttcagatt atgaagacat ttcggattta tacttaatca gcgatgcgtt agttaccgac    960
tactcatctg tcatgttcga cttcggtgta ttaaagcgtc cgcaaatttt ctatgcatat   1020
gacttagata aatatggcga tgagcttaga ggttttttaca tggattataa aaaagagttg   1080
ccaggtccaa ttgttgaaaa tcaaacagca ctcattgatg cattaaaaca aatcgatgag   1140
actgcaaatg agtatattga agcacgaacg gtatttttatc aaaaattctg ttcattagaa   1200
gatggacaag cgtcacaacg aatttgccaa acgattttta agtgataact aaaaacaat    1260
aaaaaattat aaattaatta gttaagtgat ataaataata aacgaaatgt ttgcttgtat   1320
gttattattt gtgtatgaaa                                               1340

<210> SEQ ID NO 20
```

```
<211> LENGTH: 389
<212> TYPE: PRT
<213> ORGANISM: Staphylococcus aureus

<400> SEQUENCE: 20

Met Ile Lys Asn Thr Ile Lys Lys Leu Ile Glu His Ser Ile Tyr Thr
1               5                   10                  15

Thr Phe Lys Leu Leu Ser Lys Leu Pro Asn Lys Asn Leu Ile Tyr Phe
            20                  25                  30

Glu Ser Phe His Gly Lys Gln Tyr Ser Asp Asn Pro Lys Ala Leu Tyr
        35                  40                  45

Glu Tyr Leu Thr Glu His Ser Asp Ala Gln Leu Ile Trp Gly Val Lys
    50                  55                  60

Lys Gly Tyr Glu His Ile Phe Gln Gln His Asn Val Pro Tyr Val Thr
65                  70                  75                  80

Lys Phe Ser Met Lys Trp Phe Leu Ala Met Pro Arg Ala Lys Ala Trp
                85                  90                  95

Met Ile Asn Thr Arg Thr Pro Asp Trp Leu Tyr Lys Ser Pro Arg Thr
            100                 105                 110

Thr Tyr Leu Gln Thr Trp His Gly Thr Pro Leu Lys Lys Ile Gly Leu
        115                 120                 125

Asp Ile Ser Asn Val Lys Met Leu Gly Thr Asn Thr Gln Asn Tyr Gln
130                 135                 140

Asp Gly Phe Lys Lys Glu Ser Gln Arg Trp Asp Tyr Leu Val Ser Pro
145                 150                 155                 160

Asn Pro Tyr Ser Thr Ser Ile Phe Gln Asn Ala Phe His Val Ser Arg
                165                 170                 175

Asp Lys Ile Leu Glu Thr Gly Tyr Pro Arg Asn Asp Lys Leu Ser His
            180                 185                 190

Lys Arg Asn Asp Thr Glu Tyr Ile Asn Gly Ile Lys Thr Arg Leu Asn
        195                 200                 205

Ile Pro Leu Asp Lys Lys Val Ile Met Tyr Ala Pro Thr Trp Arg Asp
210                 215                 220

Asp Glu Ala Ile Arg Glu Gly Ser Tyr Gln Phe Asn Val Asn Phe Asp
225                 230                 235                 240

Ile Glu Ala Leu Arg Gln Ala Leu Asp Asp Tyr Val Ile Leu Leu
                245                 250                 255

Arg Met His Tyr Leu Val Val Thr Arg Ile Asp Glu His Asp Asp Phe
            260                 265                 270

Val Lys Asp Val Ser Asp Tyr Glu Asp Ile Ser Asp Leu Tyr Leu Ile
        275                 280                 285

Ser Asp Ala Leu Val Thr Asp Tyr Ser Ser Val Met Phe Asp Phe Gly
    290                 295                 300

Val Leu Lys Arg Pro Gln Ile Phe Tyr Ala Tyr Asp Leu Asp Lys Tyr
305                 310                 315                 320

Gly Asp Glu Leu Arg Gly Phe Tyr Met Asp Tyr Lys Lys Glu Leu Pro
                325                 330                 335

Gly Pro Ile Val Glu Asn Gln Thr Leu Ile Asp Ala Leu Lys Gln
            340                 345                 350

Ile Asp Glu Thr Ala Asn Glu Tyr Ile Glu Ala Arg Thr Val Phe Tyr
        355                 360                 365

Gln Lys Phe Cys Ser Leu Glu Asp Gly Gln Ala Ser Gln Arg Ile Cys
    370                 375                 380

Gln Thr Ile Phe Lys
```

-continued

<210> SEQ ID NO 21
<211> LENGTH: 1430
<212> TYPE: DNA
<213> ORGANISM: Staphylococcus aureus

<400> SEQUENCE: 21

```
tgatttgtaa tcaaaactag atataattaa ataatgactt aaaataattt taaaataggg      60
aaatgtaaag taataggagt tctaagtgga ggatttacga tggataaaat agtaatcaaa     120
ggtggaaata aattaacggg tgaagttaaa gtagaaggtg ctaaaaatgc agtattacca     180
atattgacag catctttatt agcttctgat aaaccgagca aattagttaa tgttccagct     240
ttaagtgatg tagaaacaat aaataatgta ttaacaactt aaatgctga cgttacatac      300
aaaaaggacg aaaatgctgt tgtcgttgat gcaacaaaga ctctaaatga gaggcacca     360
tatgaatatg ttagtaaaat gcgtgcaagt attttagtta tgggacctct tttagcaaga     420
ctaggacatg ctattgttgc attgcctggt ggttgtgcaa ttggaagtag accgattgag     480
caacacatta aaggtttttga agctttaggc gcagaaattc atcttgaaaa tggtaatatt     540
tatgctaatg ctaaagatgg attaaaaggt acatcaattc atttagattt tccaagtgta     600
ggagcaacac aaaatattat tatggcagca tcattagcta agggtaagac tttaattgaa     660
aatgcagcta agaacctga aattgtcgat ttagcaaact acattaatga aatgggtggt      720
agaattactg gtgctggtac agacacaatt acaatcaatg gtgtagaatc attacatggt     780
gtagaacatg ctatcattcc agatagaatt gaagcaggca cattactaat cgctggtgct     840
ataacgcgtg gtgatatttt tgtacgtggt gcaatcaaag aacatatggc gagtttagtc     900
tataaactag aagaaatggg cgttgaattg gactatcaag aagatggtat tcgtgtacgt     960
gctgaagggg aattacaacc tgtagacatc aaaactctac cacatcctgg attcccgact    1020
gatatgcaat cacaaatgat ggcattgtta ttaacggcaa atggtcataa agtcgtaacc    1080
gaaactgttt ttgaaaaccg ttttatgcat gttgcagagt tcaaacgtat gaatgctaat    1140
atcaatgtag aaggtcgtag tgctaaactt gaaggtaaaa gtcaattgca aggtgcacaa    1200
gttaaagcga ctgatttaag agcagcagcc gccttaattt tagctggatt agttgctgat    1260
ggtaaaacaa gcgttactga attaacgcac ctagatagag ctatgttga cttacacggt    1320
aaattgaagc aattaggtgc agacattgaa cgtattaacg attaattcag taaattaata    1380
taatggagga tttcaaccat ggaaacaatt tttgattata accaaattaa                1430
```

<210> SEQ ID NO 22
<211> LENGTH: 421
<212> TYPE: PRT
<213> ORGANISM: Staphylococcus aureus

<400> SEQUENCE: 22

```
Met Asp Lys Ile Val Ile Lys Gly Gly Asn Lys Leu Thr Gly Glu Val
1               5                   10                  15

Lys Val Glu Gly Ala Lys Asn Ala Val Leu Pro Ile Leu Thr Ala Ser
            20                  25                  30

Leu Leu Ala Ser Asp Lys Pro Ser Lys Leu Val Asn Val Pro Ala Leu
        35                  40                  45

Ser Asp Val Glu Thr Ile Asn Asn Val Leu Thr Thr Leu Asn Ala Asp
    50                  55                  60

Val Thr Tyr Lys Lys Asp Glu Asn Ala Val Val Val Asp Ala Thr Lys
```

```
               65                  70                  75                  80
Thr Leu Asn Glu Glu Ala Pro Tyr Glu Tyr Val Ser Lys Met Arg Ala
                    85                  90                  95
Ser Ile Leu Val Met Gly Pro Leu Leu Ala Arg Leu Gly His Ala Ile
                100                 105                 110
Val Ala Leu Pro Gly Gly Cys Ala Ile Gly Ser Arg Pro Ile Glu Gln
            115                 120                 125
His Ile Lys Gly Phe Glu Ala Leu Gly Ala Glu Ile His Leu Glu Asn
        130                 135                 140
Gly Asn Ile Tyr Ala Asn Ala Lys Asp Gly Leu Lys Gly Thr Ser Ile
145                 150                 155                 160
His Leu Asp Phe Pro Ser Val Gly Ala Thr Gln Asn Ile Ile Met Ala
                165                 170                 175
Ala Ser Leu Ala Lys Gly Lys Thr Leu Ile Glu Asn Ala Ala Lys Glu
            180                 185                 190
Pro Glu Ile Val Asp Leu Ala Asn Tyr Ile Asn Glu Met Gly Gly Arg
        195                 200                 205
Ile Thr Gly Ala Gly Thr Asp Thr Ile Thr Ile Asn Gly Val Glu Ser
    210                 215                 220
Leu His Gly Val Glu His Ala Ile Ile Pro Asp Arg Ile Glu Ala Gly
225                 230                 235                 240
Thr Leu Leu Ile Ala Gly Ala Ile Thr Arg Gly Asp Ile Phe Val Arg
                245                 250                 255
Gly Ala Ile Lys Glu His Met Ala Ser Leu Val Tyr Lys Leu Glu Glu
            260                 265                 270
Met Gly Val Glu Leu Asp Tyr Gln Glu Asp Gly Ile Arg Val Arg Ala
        275                 280                 285
Glu Gly Glu Leu Gln Pro Val Asp Ile Lys Thr Leu Pro His Pro Gly
    290                 295                 300
Phe Pro Thr Asp Met Gln Ser Gln Met Met Ala Leu Leu Leu Thr Ala
305                 310                 315                 320
Asn Gly His Lys Val Val Thr Glu Thr Val Phe Glu Asn Arg Phe Met
                325                 330                 335
His Val Ala Glu Phe Lys Arg Met Asn Ala Asn Ile Asn Val Glu Gly
            340                 345                 350
Arg Ser Ala Lys Leu Glu Gly Lys Ser Gln Leu Gln Gly Ala Gln Val
        355                 360                 365
Lys Ala Thr Asp Leu Arg Ala Ala Ala Leu Ile Leu Ala Gly Leu
    370                 375                 380
Val Ala Asp Gly Lys Thr Ser Val Thr Glu Leu Thr His Leu Asp Arg
385                 390                 395                 400
Gly Tyr Val Asp Leu His Gly Lys Leu Lys Gln Leu Gly Ala Asp Ile
                405                 410                 415
Glu Arg Ile Asn Asp
            420

<210> SEQ ID NO 23
<211> LENGTH: 2204
<212> TYPE: DNA
<213> ORGANISM: Staphylococcus aureus

<400> SEQUENCE: 23
agaaaaatgg ctcaatcgaa ctagatatta tctttaaatc acaagggcca aaacgtttgt       60
tagcgcaatt tgcaccaatt gaaaaaagga ggattaaggg atggctgatt tatcgtctcg      120
```

```
tgtgaacgag ttacatgatt tattaaatca atacagttat gaatactatg tagaggataa      180
tccatctgta ccagatagtg aatatgacaa attacttcat gaactgatta aaatagaaga      240
ggagcatcct gagtataaga ctgtagattc tccaacagtt agagttggcg gtgaagccca      300
agcctctttc aataaagtca accatgacac gccaatgtta agtttaggga atgcatttaa      360
tgaggatgat ttgagaaaat tcgaccaacg catacgtgaa caaattggca acgttgaata      420
tatgtgcgaa ttaaaaattg atggcttagc agtatcattg aaatatgttg atggatactt      480
cgttcaaggt ttaacacgtg gtgatggaac aacaggtgaa gatattaccg aaaatttaaa      540
aacaattcat gcgataccct tgaaaatgaa agaaccatta aatgtagaag ttcgtggtga      600
agcatatatg ccgagacgtt catttttacg attaaatgaa gaaaagaaa aaaatgatga      660 gcagttattt gcaaatccaa gaaacgctgc tgcgggatca ttaagacagt tagattctaa      720
attaacggca aaacgaaagc taagcgtatt tatatatagt gtcaatgatt tcactgattt      780
caatgcgcgt tcgcaaagtg aagcattaga tgagttagat aaattaggtt ttacaacgaa      840
taaaaataga gcgcgtgtaa ataatatcga tggtgtttta gagtatattg aaaaatggac      900
aagccaaaga gagtcattac cttatgatat tgatgggatt gttattaagg ttaatgattt      960
agatcaacag gatgagatgg gattcacaca aaaatctcct agatgggcca ttgcttataa     1020
atttccagct gaggaagtag taactaaatt attagatatt gaattaagta ttggacgaac     1080
aggtgtagtc acacctactg ctatttttaga accagtaaaa gtrgctggta caactgtatc     1140
aagagcatct ttgcacaatg aggatttaat tcatgacaga gatattcgaa ttggtgatag     1200
tgttgtagtg aaaaaagcag gtgacatcat acctgaagtt gtacgtagta ttccagaacg     1260
tagacctgag gatgctgtca catatcatat gccaacccat tgtccaagtt gtggacatga     1320
attagtacgt attgaaggcg aagtagcact tcgttgcatt aatccaaaat gccaagcaca     1380
acttgttgaa ggattgattc actttgtatc aagacaagcc atgaatattg atggtttagg     1440
cactaaaatt attcaacagc tttatcaaag cgaattaatt aaagatgttg ctgatatttt     1500
ctatttaaca gaagaagatt tattaccttt agacagaatg gggcagaaaa agttgataa      1560 tttattagct gccattcaac aagctaagga caactcttta gaaaatttat tatttggtct     1620
aggtattagg catttaggtg ttaaagcgag ccaagtgtta gcagaaaaat atgaaacgat     1680
agatcgatta ctaacggtaa ctgaagcgga attagtagaa attcatgata taggtgataa     1740
agtagcacaa tctgtagtta cttatttaga aaatgaagat attcgtgctt taattcaaaa     1800
attaaaagat aaacatgtta atatgattta taaggtatc aaaacatcag atattgaagg      1860
acatcctgaa tttagtggta aaacgatagt actgactggt aagytacatc aaatgacacg     1920
caatgaagca tctaaatggc ttgcatcaca aggtgctaaa gttacaagta gcgttactaa     1980
aaatacagat gtcgttattg ctggtgaaga tgcaggttca aaattaacaa agcacaaag      2040 tttaggtatt gaaatttgga cagagcaaca atttgtagat aagcaaaatg aattaaatag     2100
ttagaggggt atgtcgatga agcgtacatt agtattattg attacagcta tctttatact     2160
cgctgcttgt ggtaaccata aggatgacca ggctggaaaa gata                      2204
```

<210> SEQ ID NO 24
<211> LENGTH: 667
<212> TYPE: PRT
<213> ORGANISM: Staphylococcus aureus

<400> SEQUENCE: 24

-continued

```
Met Ala Asp Leu Ser Ser Arg Val Asn Glu Leu His Asp Leu Leu Asn
1               5                   10                  15

Gln Tyr Ser Tyr Glu Tyr Tyr Val Glu Asp Asn Pro Ser Val Pro Asp
            20                  25                  30

Ser Glu Tyr Asp Lys Leu Leu His Glu Leu Ile Lys Ile Glu Glu Glu
        35                  40                  45

His Pro Glu Tyr Lys Thr Val Asp Ser Pro Thr Val Arg Val Gly Gly
    50                  55                  60

Glu Ala Gln Ala Ser Phe Asn Lys Val Asn His Asp Thr Pro Met Leu
65                  70                  75                  80

Ser Leu Gly Asn Ala Phe Asn Glu Asp Asp Leu Arg Lys Phe Asp Gln
                85                  90                  95

Arg Ile Arg Glu Gln Ile Gly Asn Val Glu Tyr Met Cys Glu Leu Lys
            100                 105                 110

Ile Asp Gly Leu Ala Val Ser Leu Lys Tyr Val Asp Gly Tyr Phe Val
        115                 120                 125

Gln Gly Leu Thr Arg Gly Asp Gly Thr Thr Gly Glu Asp Ile Thr Glu
    130                 135                 140

Asn Leu Lys Thr Ile His Ala Ile Pro Leu Lys Met Lys Glu Pro Leu
145                 150                 155                 160

Asn Val Glu Val Arg Gly Glu Ala Tyr Met Pro Arg Arg Ser Phe Leu
                165                 170                 175

Arg Leu Asn Glu Glu Lys Glu Lys Asn Asp Glu Gln Leu Phe Ala Asn
            180                 185                 190

Pro Arg Asn Ala Ala Ala Gly Ser Leu Arg Gln Leu Asp Ser Lys Leu
        195                 200                 205

Thr Ala Lys Arg Lys Leu Ser Val Phe Ile Tyr Ser Val Asn Asp Phe
210                 215                 220

Thr Asp Phe Asn Ala Arg Ser Gln Ser Glu Ala Leu Asp Glu Leu Asp
225                 230                 235                 240

Lys Leu Gly Phe Thr Thr Asn Lys Asn Arg Ala Arg Val Asn Asn Ile
                245                 250                 255

Asp Gly Val Leu Glu Tyr Ile Glu Lys Trp Thr Ser Gln Arg Glu Ser
            260                 265                 270

Leu Pro Tyr Asp Ile Asp Gly Ile Val Ile Lys Val Asn Asp Leu Asp
        275                 280                 285

Gln Gln Asp Glu Met Gly Phe Thr Gln Lys Ser Pro Arg Trp Ala Ile
290                 295                 300

Ala Tyr Lys Phe Pro Ala Glu Glu Val Val Thr Lys Leu Leu Asp Ile
305                 310                 315                 320

Glu Leu Ser Ile Gly Arg Thr Gly Val Val Thr Pro Thr Ala Ile Leu
                325                 330                 335

Glu Pro Val Lys Val Ala Gly Thr Thr Val Ser Arg Ala Ser Leu His
            340                 345                 350

Asn Glu Asp Leu Ile His Asp Arg Asp Ile Arg Ile Gly Asp Ser Val
        355                 360                 365

Val Val Lys Lys Ala Gly Asp Ile Ile Pro Glu Val Val Arg Ser Ile
        370                 375                 380

Pro Glu Arg Arg Pro Glu Asp Ala Val Thr Tyr His Met Pro Thr His
385                 390                 395                 400

Cys Pro Ser Cys Gly His Glu Leu Val Arg Ile Glu Gly Glu Val Ala
                405                 410                 415

Leu Arg Cys Ile Asn Pro Lys Cys Gln Ala Gln Leu Val Glu Gly Leu
```

```
                   420                 425                 430
Ile His Phe Val Ser Arg Gln Ala Met Asn Ile Asp Gly Leu Gly Thr
            435                 440                 445
Lys Ile Ile Gln Gln Leu Tyr Gln Ser Glu Leu Ile Lys Asp Val Ala
450                 455                 460
Asp Ile Phe Tyr Leu Thr Glu Glu Asp Leu Leu Pro Leu Asp Arg Met
465                 470                 475                 480
Gly Gln Lys Lys Val Asp Asn Leu Leu Ala Ile Gln Gln Ala Lys
                485                 490                 495
Asp Asn Ser Leu Glu Asn Leu Leu Phe Gly Leu Gly Ile Arg His Leu
            500                 505                 510
Gly Val Lys Ala Ser Gln Val Leu Ala Glu Lys Tyr Glu Thr Ile Asp
            515                 520                 525
Arg Leu Leu Thr Val Thr Glu Ala Glu Leu Val Glu Ile His Asp Ile
            530                 535                 540
Gly Asp Lys Val Ala Gln Ser Val Val Thr Tyr Leu Glu Asn Glu Asp
545                 550                 555                 560
Ile Arg Ala Leu Ile Gln Lys Leu Lys Asp Lys His Val Asn Met Ile
                565                 570                 575
Tyr Lys Gly Ile Lys Thr Ser Asp Ile Glu Gly His Pro Glu Phe Ser
            580                 585                 590
Gly Lys Thr Ile Val Leu Thr Gly Lys Leu His Gln Met Thr Arg Asn
            595                 600                 605
Glu Ala Ser Lys Trp Leu Ala Ser Gln Gly Ala Lys Val Thr Ser Ser
            610                 615                 620
Val Thr Lys Asn Thr Asp Val Val Ile Ala Gly Glu Asp Ala Gly Ser
625                 630                 635                 640
Lys Leu Thr Lys Ala Gln Ser Leu Gly Ile Glu Ile Trp Thr Glu Gln
                645                 650                 655
Gln Phe Val Asp Lys Gln Asn Glu Leu Asn Ser
                660                 665

<210> SEQ ID NO 25
<211> LENGTH: 959
<212> TYPE: DNA
<213> ORGANISM: Staphylococcus aureus

<400> SEQUENCE: 25
tgtctcactc actttccaaa atactaaagt aacatcttta gtatatcaaa gaattttttgc      60 tataataagt tataattata taaaaaagga acgggataaa atgattgtaa aaacagaaga     120
agaattacaa gcgttaaaag aaattggata catatgcgct aaagtgcgca atacaatgca     180
agctgcaacc aaaccaggta tcactacgaa agagcttgat aatattgcga aagagttatt     240
tgaagaatac ggtgctattt ctgcgccaat tcatgatgaa aatttttcctg gtcaaacgtg     300 tattagtgtc aatgaagagg tggcacatgg gattccaagt aagcgtgtca ttcgtgaagg     360
agatttagta atattgatg tatcggcttt gaagaatggc tattatgcag atacaggcat     420
ttcatttgtc gttggagaat cagatgatcc aatgaaacaa aaagtatgtg acgtagcaac     480
gatggcattt gagaatgcaa ttgcaaaagt aaaaccgggt actaagttaa gtaacattgg     540
taaagcggtg cataatacag ctagacaaaa tgatttgaaa gtcattaaaa acttaacagg     600
tcatggtgtt ggtttatcat tacatgaagc accagcacat gtacttaatt actttgatcc     660
aaaagacaaa acattattaa ctgaaggtat ggtattagct attgaaccgt ttatctcatc     720
```

-continued

```
aaatgcatca tttgttacag aaggtaaaaa tgaatgggct tttgaaacga gcgataaaag    780
ttttgttgct caaattgagc atacggttat cgtgactaag gatggtccga ttttaacgac    840
aaagattgaa gaagaatagt tcaacatata ctaagactaa agtatgaaca tcatttagtt    900
ccggagccta ttcatattgg tttcggaact gttttataat aattaagaac acaatcaat     959
```

<210> SEQ ID NO 26
<211> LENGTH: 252
<212> TYPE: PRT
<213> ORGANISM: Staphylococcus aureus

<400> SEQUENCE: 26

```
Met Ile Val Lys Thr Glu Glu Leu Gln Ala Leu Lys Glu Ile Gly
1               5                   10                  15

Tyr Ile Cys Ala Lys Val Arg Asn Thr Met Gln Ala Ala Thr Lys Pro
                20                  25                  30

Gly Ile Thr Thr Lys Glu Leu Asp Asn Ile Ala Lys Glu Leu Phe Glu
            35                  40                  45

Glu Tyr Gly Ala Ile Ser Ala Pro Ile His Asp Glu Asn Phe Pro Gly
        50                  55                  60

Gln Thr Cys Ile Ser Val Asn Glu Glu Val Ala His Gly Ile Pro Ser
65                  70                  75                  80

Lys Arg Val Ile Arg Glu Gly Asp Leu Val Asn Ile Asp Val Ser Ala
                85                  90                  95

Leu Lys Asn Gly Tyr Tyr Ala Asp Thr Gly Ile Ser Phe Val Val Gly
                100                 105                 110

Glu Ser Asp Asp Pro Met Lys Gln Lys Val Cys Asp Val Ala Thr Met
            115                 120                 125

Ala Phe Glu Asn Ala Ile Ala Lys Val Lys Pro Gly Thr Lys Leu Ser
        130                 135                 140

Asn Ile Gly Lys Ala Val His Asn Thr Ala Arg Gln Asn Asp Leu Lys
145                 150                 155                 160

Val Ile Lys Asn Leu Thr Gly His Gly Val Gly Leu Ser Leu His Glu
                165                 170                 175

Ala Pro Ala His Val Leu Asn Tyr Phe Asp Pro Lys Asp Lys Thr Leu
                180                 185                 190

Leu Thr Glu Gly Met Val Leu Ala Ile Glu Pro Phe Ile Ser Ser Asn
            195                 200                 205

Ala Ser Phe Val Thr Glu Gly Lys Asn Glu Trp Ala Phe Glu Thr Ser
        210                 215                 220

Asp Lys Ser Phe Val Ala Gln Ile Glu His Thr Val Ile Val Thr Lys
225                 230                 235                 240

Asp Gly Pro Ile Leu Thr Thr Lys Ile Glu Glu Glu
                245                 250
```

<210> SEQ ID NO 27
<211> LENGTH: 3400
<212> TYPE: DNA
<213> ORGANISM: Staphylococcus aureus

<400> SEQUENCE: 27

```
tatacagttt atatgaaatt aaagtagcac ctcataaata cttagatttt taattggaaa     60
tttgatacaa tttagtgatg aatgacttaa aggaggcttt tattaatgac aaaagtaaca    120
cgtgaagaag ttgagcatat cgcgaatctt gcaagacttc aaatttctcc tgaagaaacg    180
gaagaaatgg ccaacacatt agaaagcatt ttagattttg caaaacaaaa tgatagcgct    240
```

-continued

```
gatacagaag gcgttgaacc tacatatcac gttttagatt tacaaaacgt tttacgtgaa      300
gataaagcaa ttaaaggtat tccacaagaa ttagctttga aaaatgccaa agaaacagaa      360
gatggacaat ttaaagtgcc tacaatcatg aatgaggagg acgcgtaaga tgagcattcg      420
ctacgaatcg gttgagaatt tattaacttt aataaaagac aaaaaaatca aaccatctga      480
tgttgttaaa gatatatatg atgcaattga agagactgat ccaacaatta agtcttttct      540
agcgctggat aaagaaaatg caatcaaaaa agcgcaagaa ttggatgaat acaagcaaa       600 agatcaaatg gatggcaaat tatttggtat tccaatgggt ataaaagata acattattac      660
aaacggatta gaaacaacat gtgcaagtaa aatgttagaa ggttttgtgc caatttacga      720
atctactgta atggaaaaac tacataatga aaatgccgtt ttaatcggta aattaaatat      780
ggatgagttt gcaatgggtg gttcaacaga acatcttat ttcaaaaaaa cagttaaccc       840
atttgaccat aaagcagtgc caggtggttc atcaggtgga tctgcagcag cagttgcagc      900
tggcttagta ccatttagct taggttcaga cacaggtggt tcaattagac aaccggctgc      960
atattgtggc gttgtcggta tgaaaccaac atacggtcgt gtatctcgat ttggattagt     1020
tgcttttgca tcttcattag accaaattgg tccattgact cgaaatgtaa aagataatgc     1080
aatcgtatta gaagctattt ctggtgcaga tgttaatgac tctacaagtg caccagttga     1140
tgatgtagac tttacatctg aaattggtaa agatattaaa ggattaaaag ttgcattacc     1200
taaagaatac ttaggtgaag gtgtagctga tgacgtaaaa gaagcagttc aaaacgctgt     1260
agaaacttta aaatctttag gtgctgtcgt tgaggaagta tcattgccaa atactaaatt     1320
tggtattcca tcatattacg tgattgcatc atcagaagct tcgtcaaacc tttctcgttt     1380
tgacggaatt cgttatggtt atcattctaa agaagctcat tcattagaag aattatataa     1440
aatgtcaaga tctgaaggtt tcggtaaaga agtaaaacgt cgtattttct taggtacatt     1500
tgcattaagt tcaggttact atgatgctta ctataaaaaa tctcaaaaag ttagaacatt     1560
gattaaaaat gactttgata agtattcga aaattatgat gtagtagttg gtccaacagc     1620
gcctacaact gcgtttaatt taggtgaaga aattgatgat ccattaacaa tgtatgccaa     1680
tgatttatta acaacaccag taaacttagc tggattacct ggtatttctg ttccttgtgg     1740
acaatcaaat ggccgaccaa tcggtttaca gttcattggt aaaccattcg atgaaaaaac     1800
gttatatcgt gtcgcttatc aatatgaaac acaatacaat ttacatgacg tttatgaaaa     1860
attataagga gtggaaatca tgcattttga aacagttata ggacttgaag ttcacgtaga     1920
gttaaaaacg gactcaaaaa tgttttctcc atcaccagcg cattttggag cagaacctaa     1980
ctcaaataca aatgttatcg acttagcata tccaggtgtc ttaccagttg ttaataagcg     2040
tgcagtagac tgggcaatgc gtgctgcaat ggcactaaat atggaaatcg caacagaatc     2100
taagtttgac cgtaagaact atttctatcc agataatcca aaagcatatc aaatttctca     2160
atttgatcaa ccaattggtg aaaatggata tatcgatatc gaagtcgacg gtgaaacaaa     2220
acgaatcggt attactcgtc ttcacatgga agaagatgct ggtaagtcaa cacataaagg     2280
tgagtattca ttagttgact tgaaccgtca aggtacaccg ctaattgaaa tcgtatctga     2340
accagatatt cgttcaccta agaagcata tgcatattta gaaaaattgc gttcaattat     2400
tcaatacact ggtgtatcag acgttaagat ggaagaggga tctttacgtt gtgatgctaa     2460
catctcttta cgtccatatg gtcaagaaaa atttggtact aaagccgaat tgaaaaactt     2520
aaactcattt aactatgtac gtaaaggttt agaatatgaa gaaaacgcc aagaagaaga     2580
```

-continued

```
attgttaaat ggtggagaaa tcggacaaga aacacgtcga tttgatgaat ctacaggtaa    2640
aacaatttta atgcgtgtta agaaggttc tgatgattac cgttacttcc cagagcctga    2700
cattgtacct ttatatattg atgatgcttg gaaagagcgt gttcgtcaga caattcctga   2760
attaccagat gaacgtaaag ctaagtatgt aaatgaatta ggtttacctg catacgatgc   2820
acacgtatta acattgacta agaaatgtc agatttcttt gaatcaacaa ttgaacacgg    2880
tgcagatgtt aaattaacat ctaactggtt aatgggtggc gtaaacgaat atttaaataa   2940
aaatcaagta gaattattag atactaaatt aacaccagaa aatttagcag gtatgattaa   3000
acttatcgaa gacggaacaa tgagcagtaa aattgcgaag aaagtcttcc cagagttagc   3060
agctaaaggt ggtaatgcta acagattat ggaagataat ggcttagttc aaatttctga    3120
tgaagcaaca cttctaaaat ttgtaaatga agcattagac aataacgaac aatcagttga   3180
agattacaaa aatggtaaag caaagctat gggcttctta gttggtcaaa ttatgaaagc    3240
gtctaaaggt caagctaatc cacaattagt aaatcaacta ttaaaacaag aattagataa   3300
aagataattt aaatcatcaa actatgaaga tttaaaaaat aaaccttga ttgctgactt    3360
agatgcaatc gagggtttat ttatatctat agaagtcaaa                         3400
```

<210> SEQ ID NO 28
<211> LENGTH: 485
<212> TYPE: PRT
<213> ORGANISM: Staphylococcus aureus

<400> SEQUENCE: 28

```
Met Ser Ile Arg Tyr Glu Ser Val Glu Asn Leu Leu Thr Leu Ile Lys
1               5                   10                  15

Asp Lys Lys Ile Lys Pro Ser Asp Val Val Lys Asp Ile Tyr Asp Ala
            20                  25                  30

Ile Glu Glu Thr Asp Pro Thr Ile Lys Ser Phe Leu Ala Leu Asp Lys
        35                  40                  45

Glu Asn Ala Ile Lys Lys Ala Gln Glu Leu Asp Glu Leu Gln Ala Lys
    50                  55                  60

Asp Gln Met Asp Gly Lys Leu Phe Gly Ile Pro Met Gly Ile Lys Asp
65                  70                  75                  80

Asn Ile Ile Thr Asn Gly Leu Glu Thr Thr Cys Ala Ser Lys Met Leu
                85                  90                  95

Glu Gly Phe Val Pro Ile Tyr Glu Ser Thr Val Met Glu Lys Leu His
            100                 105                 110

Asn Glu Asn Ala Val Leu Ile Gly Lys Leu Asn Met Asp Glu Phe Ala
        115                 120                 125

Met Gly Gly Ser Thr Glu Thr Ser Tyr Phe Lys Lys Thr Val Asn Pro
    130                 135                 140

Phe Asp His Lys Ala Val Pro Gly Gly Ser Gly Gly Ser Ala Ala
145                 150                 155                 160

Ala Val Ala Ala Gly Leu Val Pro Phe Ser Leu Gly Ser Asp Thr Gly
                165                 170                 175

Gly Ser Ile Arg Gln Pro Ala Ala Tyr Cys Gly Val Val Gly Met Lys
            180                 185                 190

Pro Thr Tyr Gly Arg Val Ser Arg Phe Gly Leu Val Ala Phe Ala Ser
        195                 200                 205

Ser Leu Asp Gln Ile Gly Pro Leu Thr Arg Asn Val Lys Asp Asn Ala
    210                 215                 220

Ile Val Leu Glu Ala Ile Ser Gly Ala Asp Val Asn Asp Ser Thr Ser
```

```
                225                 230                 235                 240
Ala Pro Val Asp Asp Val Asp Phe Thr Ser Glu Ile Gly Lys Asp Ile
                    245                 250                 255
Lys Gly Leu Lys Val Ala Leu Pro Lys Glu Tyr Leu Gly Glu Gly Val
                260                 265                 270
Ala Asp Asp Val Lys Glu Ala Val Gln Asn Ala Val Glu Thr Leu Lys
                275                 280                 285
Ser Leu Gly Ala Val Val Glu Glu Val Ser Leu Pro Asn Thr Lys Phe
            290                 295                 300
Gly Ile Pro Ser Tyr Tyr Val Ile Ala Ser Ser Glu Ala Ser Ser Asn
305                 310                 315                 320
Leu Ser Arg Phe Asp Gly Ile Arg Tyr Gly Tyr His Ser Lys Glu Ala
                    325                 330                 335
His Ser Leu Glu Glu Leu Tyr Lys Met Ser Arg Ser Glu Gly Phe Gly
                340                 345                 350
Lys Glu Val Lys Arg Arg Ile Phe Leu Gly Thr Phe Ala Leu Ser Ser
                355                 360                 365
Gly Tyr Tyr Asp Ala Tyr Tyr Lys Lys Ser Gln Lys Val Arg Thr Leu
370                 375                 380
Ile Lys Asn Asp Phe Asp Lys Val Phe Glu Asn Tyr Asp Val Val Val
385                 390                 395                 400
Gly Pro Thr Ala Pro Thr Thr Ala Phe Asn Leu Gly Glu Glu Ile Asp
                    405                 410                 415
Asp Pro Leu Thr Met Tyr Ala Asn Asp Leu Leu Thr Thr Pro Val Asn
                420                 425                 430
Leu Ala Gly Leu Pro Gly Ile Ser Val Pro Cys Gly Gln Ser Asn Gly
                435                 440                 445
Arg Pro Ile Gly Leu Gln Phe Ile Gly Lys Pro Phe Asp Glu Lys Thr
            450                 455                 460
Leu Tyr Arg Val Ala Tyr Gln Tyr Glu Thr Gln Tyr Asn Leu His Asp
465                 470                 475                 480
Val Tyr Glu Lys Leu
                485

<210> SEQ ID NO 29
<211> LENGTH: 475
<212> TYPE: PRT
<213> ORGANISM: Staphylococcus aureus

<400> SEQUENCE: 29

Met His Phe Glu Thr Val Ile Gly Leu Glu Val His Val Glu Leu Lys
1               5                   10                  15
Thr Asp Ser Lys Met Phe Ser Pro Ser Pro Ala His Phe Gly Ala Glu
                20                  25                  30
Pro Asn Ser Asn Thr Asn Val Ile Asp Leu Ala Tyr Pro Gly Val Leu
            35                  40                  45
Pro Val Val Asn Lys Arg Ala Val Asp Trp Ala Met Arg Ala Ala Met
        50                  55                  60
Ala Leu Asn Met Glu Ile Ala Thr Glu Ser Lys Phe Asp Arg Lys Asn
65                  70                  75                  80
Tyr Phe Tyr Pro Asp Asn Pro Lys Ala Tyr Gln Ile Ser Gln Phe Asp
                85                  90                  95
Gln Pro Ile Gly Glu Asn Gly Tyr Ile Asp Ile Glu Val Asp Gly Glu
            100                 105                 110
```

```
Thr Lys Arg Ile Gly Ile Thr Arg Leu His Met Glu Glu Asp Ala Gly
        115                 120                 125

Lys Ser Thr His Lys Gly Glu Tyr Ser Leu Val Asp Leu Asn Arg Gln
    130                 135                 140

Gly Thr Pro Leu Ile Glu Ile Val Ser Glu Pro Asp Ile Arg Ser Pro
145                 150                 155                 160

Lys Glu Ala Tyr Ala Tyr Leu Glu Lys Leu Arg Ser Ile Ile Gln Tyr
                165                 170                 175

Thr Gly Val Ser Asp Val Lys Met Glu Glu Gly Ser Leu Arg Cys Asp
            180                 185                 190

Ala Asn Ile Ser Leu Arg Pro Tyr Gly Gln Glu Lys Phe Gly Thr Lys
        195                 200                 205

Ala Glu Leu Lys Asn Leu Asn Ser Phe Asn Tyr Val Arg Lys Gly Leu
    210                 215                 220

Glu Tyr Glu Glu Lys Arg Gln Glu Glu Leu Leu Asn Gly Gly Glu
225                 230                 235                 240

Ile Gly Gln Glu Thr Arg Arg Phe Asp Glu Ser Thr Gly Lys Thr Ile
                245                 250                 255

Leu Met Arg Val Lys Glu Gly Ser Asp Asp Tyr Arg Tyr Phe Pro Glu
            260                 265                 270

Pro Asp Ile Val Pro Leu Tyr Ile Asp Ala Trp Lys Glu Arg Val
        275                 280                 285

Arg Gln Thr Ile Pro Glu Leu Pro Asp Glu Arg Lys Ala Lys Tyr Val
    290                 295                 300

Asn Glu Leu Gly Leu Pro Ala Tyr Asp Ala His Val Leu Thr Leu Thr
305                 310                 315                 320

Lys Glu Met Ser Asp Phe Phe Glu Ser Thr Ile Glu His Gly Ala Asp
                325                 330                 335

Val Lys Leu Thr Ser Asn Trp Leu Met Gly Val Asn Glu Tyr Leu
            340                 345                 350

Asn Lys Asn Gln Val Glu Leu Leu Asp Thr Lys Leu Thr Pro Glu Asn
        355                 360                 365

Leu Ala Gly Met Ile Lys Leu Ile Glu Asp Gly Thr Met Ser Ser Lys
    370                 375                 380

Ile Ala Lys Lys Val Phe Pro Glu Leu Ala Ala Lys Gly Gly Asn Ala
385                 390                 395                 400

Lys Gln Ile Met Glu Asp Asn Gly Leu Val Gln Ile Ser Asp Glu Ala
                405                 410                 415

Thr Leu Leu Lys Phe Val Asn Glu Ala Leu Asp Asn Asn Glu Gln Ser
            420                 425                 430

Val Glu Asp Tyr Lys Asn Gly Lys Gly Lys Ala Met Gly Phe Leu Val
        435                 440                 445

Gly Gln Ile Met Lys Ala Ser Lys Gly Gln Ala Asn Pro Gln Leu Val
    450                 455                 460

Asn Gln Leu Leu Lys Gln Glu Leu Asp Lys Arg
465                 470                 475

<210> SEQ ID NO 30
<211> LENGTH: 100
<212> TYPE: PRT
<213> ORGANISM: Staphylococcus aureus

<400> SEQUENCE: 30

Met Thr Lys Val Thr Arg Glu Glu Val Glu His Ile Ala Asn Leu Ala
1               5                   10                  15
```

```
Arg Leu Gln Ile Ser Pro Glu Glu Thr Glu Glu Met Ala Asn Thr Leu
             20                  25                  30

Glu Ser Ile Leu Asp Phe Ala Lys Gln Asn Asp Ser Ala Asp Thr Glu
         35                  40                  45

Gly Val Glu Pro Thr Tyr His Val Leu Asp Leu Gln Asn Val Leu Arg
     50                  55                  60

Glu Asp Lys Ala Ile Lys Gly Ile Pro Gln Leu Ala Leu Lys Asn
 65                  70                  75                  80

Ala Lys Glu Thr Glu Asp Gly Gln Phe Lys Val Pro Thr Ile Met Asn
                 85                  90                  95

Glu Glu Asp Ala
            100

<210> SEQ ID NO 31
<211> LENGTH: 772
<212> TYPE: DNA
<213> ORGANISM: Staphylococcus aureus

<400> SEQUENCE: 31
cttactaagc taaagaataa tgataattga tggcaatggc ggaaaatgga tgttgtcatt      60
ataataataa atgaaacaat tatgttggag gtaaacacgc atgaaatgta ttgtaggtct     120
aggtaatata ggtaaacgtt ttgaacttac aagacataat atcggctttg aagtcgttga     180
ttatatttta gagaaaaata attttttcatt agataaacaa agtttaaaag gtgcatatac     240
aattgaacga atgaacggcg ataaagtgtt atttatcgaa ccaatgacaa tgatgaattt     300
gtcaggtgaa gcagttgcac cgattatgga ttattacaat gttaatccag aagatttaat     360
tgtcttatat gatgatttag atttagaaca aggacaagtt cgcttaagac aaaaaggaag     420
tgcgggcggt cacaatggta tgaaatcaat tattaaaatg cttggtacag accaatttaa     480
acgtattcgt attggtgtgg aagaccaacg aatggtatg acggtacctg attatgtttt     540
acaacgcttt tcaaatgatg aaatggtaac gatggaaaaa gttatcgaac acgcagcacg     600
cgcaattgaa aagtttgttg aaacatcacg atttgaccat gttatgaatg aatttaatgg     660
tgaagtgaaa aatgacaat attgacaacg cttataaaag aagataatca ttttcaagac     720
cttaatcagg tatttggaca agcaaacaca ctagtaactg gtctttcccc gt             772

<210> SEQ ID NO 32
<211> LENGTH: 190
<212> TYPE: PRT
<213> ORGANISM: Staphylococcus aureus

<400> SEQUENCE: 32

Met Lys Cys Ile Val Gly Leu Gly Asn Ile Gly Lys Arg Phe Glu Leu
 1               5                  10                  15

Thr Arg His Asn Ile Gly Phe Glu Val Val Asp Tyr Ile Leu Glu Lys
             20                  25                  30

Asn Asn Phe Ser Leu Asp Lys Gln Lys Phe Lys Gly Ala Tyr Thr Ile
         35                  40                  45

Glu Arg Met Asn Gly Asp Lys Val Leu Phe Ile Glu Pro Met Thr Met
     50                  55                  60

Met Asn Leu Ser Gly Glu Ala Val Ala Pro Ile Met Asp Tyr Tyr Asn
 65                  70                  75                  80

Val Asn Pro Glu Asp Leu Ile Val Leu Tyr Asp Asp Leu Asp Leu Glu
                 85                  90                  95
```

-continued

```
Gln Gly Gln Val Arg Leu Arg Gln Lys Gly Ser Ala Gly Gly His Asn
                100                 105                 110
Gly Met Lys Ser Ile Ile Lys Met Leu Gly Thr Asp Gln Phe Lys Arg
            115                 120                 125
Ile Arg Ile Gly Val Gly Arg Pro Thr Asn Gly Met Thr Val Pro Asp
        130                 135                 140
Tyr Val Leu Gln Arg Phe Ser Asn Asp Glu Met Val Thr Met Glu Lys
145                 150                 155                 160
Val Ile Glu His Ala Ala Arg Ala Ile Glu Lys Phe Val Glu Thr Ser
                165                 170                 175
Arg Phe Asp His Val Met Asn Glu Phe Asn Gly Glu Val Lys
            180                 185                 190

<210> SEQ ID NO 33
<211> LENGTH: 1277
<212> TYPE: DNA
<213> ORGANISM: Staphylococcus aureus

<400> SEQUENCE: 33
tgatccgatt atcttagtag gtgccaatga aagttatgag ccacgttgtc gcgcgcacca      60
tatcgtagca cctagtgata ataataagga ggaattataa gtgtttgatc aattagatat     120
tgtagaagaa agatacgaac agttaaatga actgttaagt gacccagatg ttgtaaatga     180
ttcagataaa ttacgtaaat attctaaaga gcaagctgat ttacaaaaaa ctgtagatgt     240
ttatcgtaac tataaagcta aaaagaaga ttagctgat attgaagaaa tgttaagtga     300
gactgatgat aaagaagaag tagaaatgtt aaaagaggag agtaatggta ttaaagctga     360
acttccaaat cttgaagaag agcttaaaat attattgatt cctaaagatc ctaatgatga     420
caaagacgtt attgtagaaa taagagcagc agcaggtggt gatgaggctg cgattttttgc    480
tggtgattta atgcgtatgt attcaaagta tgctgaatca caaggattca aaactgaaat     540
agtagaagcg tctgaaagtg accatggtgg ttacaaagaa attagtttct cagtttctgg     600
taatggcgcg tatagtaaat tgaaatttga aaatggtgcg caccgcgttc aacgtgtgcc     660
tgaaacagaa tcaggtggac gtattcatac ttcaacagct acagtggcag ttttaccaga     720
agttgaagat gtagaaattg aaattagaaa tgaagattta aaaatcgaca cgtatcgttc     780
aagtggtgca ggtggtcagc acgtaaacac aactgactct gcagtacgta ttacccattt     840
accaactggt gtcattgcaa catcttctga gaagtctcaa attcaaaacc gtgaaaaagc     900
aatgaaagtg ttaaaagcac gtttatacga tatgaaagtt caagaagaac aacaaaagta     960
tgcgtcacaa cgtaaatcag cagtcggtac tggtgatcgt tcagaacgta ttcgaactta    1020
taattatcca caaagccgtg taacagacca tcgtataggt ctaacgcttc aaaaattagg    1080
gcaaattatg gaaggccatt tagaagaaat tatagatgca ctgactttat cagagcagac    1140
agataaattg aaagaactta ataatggtga attataaaga aagttagat gaagcaattc    1200
atttaacaca acaaaaggg tttgaacaaa cacgagctga atggttaatg ttagatgtat    1260
ttcaatggac gcgtacg                                                    1277
```

<210> SEQ ID NO 34
<211> LENGTH: 358
<212> TYPE: PRT
<213> ORGANISM: Staphylococcus aureus

<400> SEQUENCE: 34

Val Phe Asp Gln Leu Asp Ile Val Glu Glu Arg Tyr Glu Gln Leu Asn

```
              1               5                  10                 15
        Glu Leu Leu Ser Asp Pro Asp Val Val Asn Asp Ser Asp Lys Leu Arg
                     20                 25                 30

Lys Tyr Ser Lys Glu Gln Ala Asp Leu Gln Lys Thr Val Asp Val Tyr
                     35                 40                 45

Arg Asn Tyr Lys Ala Lys Lys Glu Glu Leu Ala Asp Ile Glu Glu Met
                     50                 55                 60

Leu Ser Glu Thr Asp Asp Lys Glu Glu Val Glu Met Leu Lys Glu Glu
        65                  70                 75                 80

Ser Asn Gly Ile Lys Ala Glu Leu Pro Asn Leu Glu Glu Glu Leu Lys
                         85                 90                 95

Ile Leu Leu Ile Pro Lys Asp Pro Asn Asp Lys Asp Val Ile Val
                        100                105                110

Glu Ile Arg Ala Ala Ala Gly Gly Asp Glu Ala Ala Ile Phe Ala Gly
                        115                120                125

Asp Leu Met Arg Met Tyr Ser Lys Tyr Ala Glu Ser Gln Gly Phe Lys
                        130                135                140

Thr Glu Ile Val Glu Ala Ser Glu Ser Asp His Gly Gly Tyr Lys Glu
        145                150                155                160

Ile Ser Phe Ser Val Ser Gly Asn Gly Ala Tyr Ser Lys Leu Lys Phe
                        165                170                175

Glu Asn Gly Ala His Arg Val Gln Arg Val Pro Glu Thr Glu Ser Gly
                        180                185                190

Gly Arg Ile His Thr Ser Thr Ala Thr Val Ala Val Leu Pro Glu Val
                        195                200                205

Glu Asp Val Glu Ile Glu Ile Arg Asn Glu Asp Leu Lys Ile Asp Thr
        210                215                220

Tyr Arg Ser Ser Gly Ala Gly Gly Gln His Val Asn Thr Thr Asp Ser
        225                230                235                240

Ala Val Arg Ile Thr His Leu Pro Thr Gly Val Ile Ala Thr Ser Ser
                        245                250                255

Glu Lys Ser Gln Ile Gln Asn Arg Glu Lys Ala Met Lys Val Leu Lys
                        260                265                270

Ala Arg Leu Tyr Asp Met Lys Val Gln Glu Glu Gln Gln Lys Tyr Ala
                        275                280                285

Ser Gln Arg Lys Ser Ala Val Gly Thr Gly Asp Arg Ser Glu Arg Ile
                        290                295                300

Arg Thr Tyr Asn Tyr Pro Gln Ser Arg Val Thr Asp His Arg Ile Gly
        305                310                315                320

Leu Thr Leu Gln Lys Leu Gly Gln Ile Met Glu Gly His Leu Glu Glu
                        325                330                335

Ile Ile Asp Ala Leu Thr Leu Ser Glu Gln Thr Asp Lys Leu Lys Glu
                        340                345                350

Leu Asn Asn Gly Glu Leu
                        355

<210> SEQ ID NO 35
<211> LENGTH: 1315
<212> TYPE: DNA
<213> ORGANISM: Staphylococcus aureus

<400> SEQUENCE: 35
atttcttaac attgttattt aacaaaatta tgttaaaatt tagcattata aaagatgcaa      60
atcaatgact tgaattgaaa tataaatagg agcgaatgct atggaattat cagaaatcaa     120
```

-continued

```
acgaaatata gataagtata atcaagattt aacacaaatt aggggggtctc ttgacttaga    180 gaacaaagaa actaatattc aagaatatga agaaatgatg gcagaaccta atttttggga    240
taaccaaacg aaagcgcaag atattataga taaaaataat gcgttaaaag caatagttaa    300
tggttataaa acactacaag cagaagtaga tgacatggat gctacttggg atttattaca    360
agaagaattt gatgaagaaa tgaagaaga cttagagcaa gaggtcatta attttaaggc    420
taaagtggat gaatacgaat tgcaattatt attagatggg cctcacgatg ccaataacgc    480
aattctagag ttcatcctg gtgcaggtgg cacggagtct caagattggg ctaatatgct    540
atttagaatg tatcaacgtt attgtgagaa gaaaggcttt aaagttgaaa ctgttgatta    600
tctacctggg gatgaagcgg ggattaaaag tgtaacattg ctcatcaaag ggcataatgc    660
ttatggttat ttaaaagctg aaaaaggtgt acaccgacta gtacgaattt ctccatttga    720
ttcatcagga cgtcgtcata catcatttgc atcatgcgac gttattccag atttttaataa    780 tgatgaaata gagattgaaa tcaatccgga tgatattaca gttgatacat tcagagcttc    840
tggtgcaggt ggtcagcata ttaacaaaac tgaatcggca atacgaatta ccccaccacc    900
ctcaggtata gttgttaata accaaaatga acgttctcaa attaaaaacc gtgaagcagc    960
tatgaaaatg ttaaagtcta aattatatca attaaaattg gaagagcagg cacgtgaaat   1020
ggctgaaatt cgtggcgaac aaaaagaaat cggctgggga agccaaatta gatcatatgt   1080
tttccatcca tactcaatgg tgaaagatca tcgtacgaac gaagaaacag gtaaggttga   1140
tgcagtgatg gatggagaca ttggaccatt tatcgaatca tatttaagac agacaatgtc   1200
gcacgattaa tatatatttt aaaaccgagg ctctaaaagg gcgtcggttt ttggtttttt   1260
taaaggtagc taaataaatt gtaaattaga ttttggaata tgatttgttt atgaa        1315
```

<210> SEQ ID NO 36
<211> LENGTH: 369
<212> TYPE: PRT
<213> ORGANISM: Staphylococcus aureus

<400> SEQUENCE: 36

```
Met Glu Leu Ser Glu Ile Lys Arg Asn Ile Asp Lys Tyr Asn Gln Asp
1               5                   10                  15

Leu Thr Gln Ile Arg Gly Ser Leu Asp Leu Glu Asn Lys Glu Thr Asn
            20                  25                  30

Ile Gln Glu Tyr Glu Glu Met Met Ala Glu Pro Asn Phe Trp Asp Asn
        35                  40                  45

Gln Thr Lys Ala Gln Asp Ile Ile Asp Lys Asn Asn Ala Leu Lys Ala
    50                  55                  60

Ile Val Asn Gly Tyr Lys Thr Leu Gln Ala Glu Val Asp Asp Met Asp
65                  70                  75                  80

Ala Thr Trp Asp Leu Leu Gln Glu Glu Phe Asp Glu Glu Met Lys Glu
                85                  90                  95

Asp Leu Glu Gln Glu Val Ile Asn Phe Lys Ala Lys Val Asp Glu Tyr
            100                 105                 110

Glu Leu Gln Leu Leu Asp Gly Pro His Asp Ala Asn Asn Ala Ile
        115                 120                 125

Leu Glu Leu His Pro Gly Ala Gly Gly Thr Glu Ser Gln Asp Trp Ala
    130                 135                 140

Asn Met Leu Phe Arg Met Tyr Gln Arg Tyr Cys Glu Lys Lys Gly Phe
145                 150                 155                 160
```

```
Lys Val Glu Thr Val Asp Tyr Leu Pro Gly Asp Ala Gly Ile Lys
                165                 170                 175

Ser Val Thr Leu Leu Ile Lys Gly His Asn Ala Tyr Gly Tyr Leu Lys
                180                 185                 190

Ala Glu Lys Gly Val His Arg Leu Val Arg Ile Ser Pro Phe Asp Ser
            195                 200                 205

Ser Gly Arg Arg His Thr Ser Phe Ala Ser Cys Asp Val Ile Pro Asp
        210                 215                 220

Phe Asn Asn Asp Glu Ile Glu Ile Glu Ile Asn Pro Asp Asp Ile Thr
225                 230                 235                 240

Val Asp Thr Phe Arg Ala Ser Gly Ala Gly Gln His Ile Asn Lys
                245                 250                 255

Thr Glu Ser Ala Ile Arg Ile Thr His His Pro Ser Gly Ile Val Val
                260                 265                 270

Asn Asn Gln Asn Glu Arg Ser Gln Ile Lys Asn Arg Glu Ala Ala Met
            275                 280                 285

Lys Met Leu Lys Ser Lys Leu Tyr Gln Leu Lys Leu Glu Glu Gln Ala
        290                 295                 300

Arg Glu Met Ala Glu Ile Arg Gly Glu Gln Lys Glu Ile Gly Trp Gly
305                 310                 315                 320

Ser Gln Ile Arg Ser Tyr Val Phe His Pro Tyr Ser Met Val Lys Asp
                325                 330                 335

His Arg Thr Asn Glu Glu Thr Gly Lys Val Asp Ala Val Met Asp Gly
            340                 345                 350

Asp Ile Gly Pro Phe Ile Glu Ser Tyr Leu Arg Gln Thr Met Ser His
        355                 360                 365

Asp
```

<210> SEQ ID NO 37
<211> LENGTH: 840
<212> TYPE: DNA
<213> ORGANISM: Staphylococcus aureus

<400> SEQUENCE: 37

```
ataactgaa aatatgatag aattggtaaa tgaatatctg gaaactggaa tgatagttga      60
aggaattaaa aataataaaa ttttagttga ggatgaataa aatgtcagct tttataactt    120
ttgagggccc agaaggctct ggaaaaacaa ctgtaattaa tgaagtttac catagattag    180
taaaagatta tgatgtcatt atgactagag aaccaggtgg tgttcctact ggtgaagaaa    240
tacgtaaaat tgtattagaa ggcaatgata tggacattag aactgaagca atgttatttg    300
ctgcatctag aagagaacat cttgtattaa aggtcatacc agctttaaaa gaaggtaagg    360
ttgtgttgtg tgatcgctat atcgatagtt cattagctta tcaaggttat gctagaggga    420
ttggcgttga agaagtaaga gcattaaacg aatttgcaat aaatggatta tatccagact    480
tgacgattta tttaaatgtt agtgctgaag taggtcgcga acgtattatt aaaaattcaa    540
gagatcaaaa tagattagat caagaagatt taaagtttca cgaaaaagta attgaaggtt    600
accaagaaat cattcataat gaatcacaac ggttcaaaag cgttaatgca gatcaacctc    660
ttgaaaatgt tgttgaagac acgtatcaaa ctatcatcaa atatttagaa aagatatgat    720
ataattgtta gaagaggtgt tataaaatga aatgattat agcgatcgta caagatcaag    780
atagtcagga acttgcagat caacttgtta aaaataactt tagagcaaca aaattggcaa    840
```

<210> SEQ ID NO 38

<211> LENGTH: 205
<212> TYPE: PRT
<213> ORGANISM: Staphylococcus aureus

<400> SEQUENCE: 38

```
Met Ser Ala Phe Ile Thr Phe Glu Gly Pro Glu Gly Ser Gly Lys Thr
  1               5                  10                  15
Thr Val Ile Asn Glu Val Tyr His Arg Leu Val Lys Asp Tyr Asp Val
             20                  25                  30
Ile Met Thr Arg Glu Pro Gly Gly Val Pro Thr Gly Glu Glu Ile Arg
         35                  40                  45
Lys Ile Val Leu Glu Gly Asn Asp Met Asp Ile Arg Thr Glu Ala Met
     50                  55                  60
Leu Phe Ala Ala Ser Arg Arg Glu His Leu Val Leu Lys Val Ile Pro
 65                  70                  75                  80
Ala Leu Lys Glu Gly Lys Val Val Leu Cys Asp Arg Tyr Ile Asp Ser
                 85                  90                  95
Ser Leu Ala Tyr Gln Gly Tyr Ala Arg Gly Ile Gly Val Glu Glu Val
            100                 105                 110
Arg Ala Leu Asn Glu Phe Ala Ile Asn Gly Leu Tyr Pro Asp Leu Thr
        115                 120                 125
Ile Tyr Leu Asn Val Ser Ala Glu Val Gly Arg Glu Arg Ile Ile Lys
    130                 135                 140
Asn Ser Arg Asp Gln Asn Arg Leu Asp Gln Glu Asp Leu Lys Phe His
145                 150                 155                 160
Glu Lys Val Ile Glu Gly Tyr Gln Glu Ile Ile His Asn Glu Ser Gln
                165                 170                 175
Arg Phe Lys Ser Val Asn Ala Asp Gln Pro Leu Glu Asn Val Val Glu
            180                 185                 190
Asp Thr Tyr Gln Thr Ile Ile Lys Tyr Leu Glu Lys Ile
        195                 200                 205
```

<210> SEQ ID NO 39
<211> LENGTH: 923
<212> TYPE: DNA
<213> ORGANISM: Staphylococcus aureus

<400> SEQUENCE: 39

| | | |
|---|---|---|
| aatgttgctt tattaaaatg taaatcattc taataaaacg acaactgtgt cttctttact | 60 |
| tgtatatgtt acatatattc acgatagaga ggataagaaa atggctcaaa tttctaaata | 120 |
| taaacgtgta gttttgaaac taagtggtga agcgttagct ggagaaaaag gatttggcat | 180 |
| aaatccagta attattaaaa gtgttgctga gcaagtggct gaagttgcta aaatggactg | 240 |
| tgaaatcgca gtaatcgttg gtggcggaaa catttggaga ggtaaaacag gtagtgactt | 300 |
| aggtatggac cgtggaactg ctgattacat gggtatgctt gcaactgtaa tgaatgcctt | 360 |
| agcattacaa gatagtttag aacaattgga ttgtgataca cgagtattaa catctattga | 420 |
| aatgaagcaa gtggctgaac ttatattcg tcgtcgtgca attagacact tagaaaagaa | 480 |
| acgcgtagtt atttttgctg caggtattgg aaacccatac ttctctacag atactacagc | 540 |
| ggcattacgt gctgcagaag ttgaagcaga tgttattta tgggcaaaa ataatgtaga | 600 |
| tggtgtatat tctgcagatc ctaaagtaaa caaagatgcg gtaaaatatg aacatttaac | 660 |
| gcatattcaa atgcttcaag aaggtttaca agtaatggat tcaacagcat cctcattctg | 720 |
| tatggataat aacattccgt taactgtttt ctctattatg gaagaaggaa atattaaacg | 780 |

```
tgctgttatg ggtgaaaaga taggtacgtt aattacaaaa taaatttaga ggtgtaaaat      840
aatgagtgac attattaatg aaactaaatc aagaatgcaa aaatcaatcg aaagcttatc      900
acgtgaatta gctaacatca gtg                                              923
```

<210> SEQ ID NO 40
<211> LENGTH: 240
<212> TYPE: PRT
<213> ORGANISM: Staphylococcus aureus

<400> SEQUENCE: 40

```
Met Ala Gln Ile Ser Lys Tyr Lys Arg Val Val Leu Lys Leu Ser Gly
1               5                   10                  15

Glu Ala Leu Ala Gly Glu Lys Gly Phe Gly Ile Asn Pro Val Ile Ile
            20                  25                  30

Lys Ser Val Ala Glu Gln Val Ala Glu Val Ala Lys Met Asp Cys Glu
        35                  40                  45

Ile Ala Val Ile Val Gly Gly Gly Asn Ile Trp Arg Gly Lys Thr Gly
    50                  55                  60

Ser Asp Leu Gly Met Asp Arg Gly Thr Ala Asp Tyr Met Gly Met Leu
65                  70                  75                  80

Ala Thr Val Met Asn Ala Leu Ala Leu Gln Asp Ser Leu Glu Gln Leu
                85                  90                  95

Asp Cys Asp Thr Arg Val Leu Thr Ser Ile Glu Met Lys Gln Val Ala
            100                 105                 110

Glu Pro Tyr Ile Arg Arg Arg Ala Ile Arg His Leu Glu Lys Lys Arg
        115                 120                 125

Val Val Ile Phe Ala Ala Gly Ile Gly Asn Pro Tyr Phe Ser Thr Asp
    130                 135                 140

Thr Thr Ala Ala Leu Arg Ala Ala Glu Val Glu Ala Asp Val Ile Leu
145                 150                 155                 160

Met Gly Lys Asn Asn Val Asp Gly Val Tyr Ser Ala Asp Pro Lys Val
                165                 170                 175

Asn Lys Asp Ala Val Lys Tyr Glu His Leu Thr His Ile Gln Met Leu
            180                 185                 190

Gln Glu Gly Leu Gln Val Met Asp Ser Thr Ala Ser Ser Phe Cys Met
        195                 200                 205

Asp Asn Asn Ile Pro Leu Thr Val Phe Ser Ile Met Glu Glu Gly Asn
    210                 215                 220

Ile Lys Arg Ala Val Met Gly Glu Lys Ile Gly Thr Leu Ile Thr Lys
225                 230                 235                 240
```

<210> SEQ ID NO 41
<211> LENGTH: 1013
<212> TYPE: DNA
<213> ORGANISM: Staphylococcus aureus

<400> SEQUENCE: 41

```
gatagcatcc atgtatagtg atagtattta caacaattat tataatacta tttagttaag       60
tagagaaata gttaaacatt tgaaagtgtg gtttaatgga atgtcagcaa taggaacagt      120 tttttaaagaa catgtaaaga acttttattt aattcaaaga ctggctcagt ttcaagttaa     180
aattatcaat catagtaact atttaggtgt ggcttgggaa ttaattaacc ctgttatgca      240
aattatggtt tactggatgg tttttggatt aggaataaga agtaatgcac caattcatgg      300 tgtaccttttt gtttattggt tattggttgg tatcagtatg tggttcttca tcaaccaagg    360
```

-continued

```
tattttagaa ggtactaaag caattacaca aaagtttaat caagtatcga aaatgaactt      420
cccgttatcg ataataccga catatattgt gacaagtaga ttttatggac atttaggctt      480
acttttactt gtgataattg catgtatgtt tactggtatt tatccatcaa tacatatcat      540
tcaattattg atatatgtac cgttttgttt tttcttaact gcctcggtga cgttattaac      600
atcaacactc ggtgtgttag ttagagatac acaaatgtta atgcaagcaa tattaagaat      660
attattttac ttttcaccaa ttttgtggct accaaagaac catggtatca gtggtttaat      720
tcatgaaatg atgaaatata atccagttta ctttattgct gaatcatacc gtgcagcaat      780
tttatatcac gaatggtatt tcatggatca ttggaaatta atgttataca atttcggtat      840
tgttgccatt ttctttgcaa ttggtgcgta cttacacatg aaatatagag atcaatttgc      900
agacttcttg taatatattt tatgacgaa accccgctaa ccattaataa atggaagtgg      960
ggttcatttt tgtttataat ttaagtaaat aacatattaa gttggtgtat tat           1013
```

<210> SEQ ID NO 42
<211> LENGTH: 270
<212> TYPE: PRT
<213> ORGANISM: Staphylococcus aureus

<400> SEQUENCE: 42

```
Met Ser Ala Ile Gly Thr Val Phe Lys Glu His Val Lys Asn Phe Tyr
1               5                   10                  15

Leu Ile Gln Arg Leu Ala Gln Phe Gln Val Lys Ile Ile Asn His Ser
                20                  25                  30

Asn Tyr Leu Gly Val Ala Trp Glu Leu Ile Asn Pro Val Met Gln Ile
            35                  40                  45

Met Val Tyr Trp Met Val Phe Gly Leu Gly Ile Arg Ser Asn Ala Pro
        50                  55                  60

Ile His Gly Val Pro Phe Val Tyr Trp Leu Leu Val Gly Ile Ser Met
65                  70                  75                  80

Trp Phe Phe Ile Asn Gln Gly Ile Leu Glu Gly Thr Lys Ala Ile Thr
                85                  90                  95

Gln Lys Phe Asn Gln Val Ser Lys Met Asn Phe Pro Leu Ser Ile Ile
                100                 105                 110

Pro Thr Tyr Ile Val Thr Ser Arg Phe Tyr Gly His Leu Gly Leu Leu
            115                 120                 125

Leu Leu Val Ile Ile Ala Cys Met Phe Thr Gly Ile Tyr Pro Ser Ile
        130                 135                 140

His Ile Ile Gln Leu Leu Ile Tyr Val Pro Phe Cys Phe Phe Leu Thr
145                 150                 155                 160

Ala Ser Val Thr Leu Leu Thr Ser Thr Leu Gly Val Leu Val Arg Asp
                165                 170                 175

Thr Gln Met Leu Met Gln Ala Ile Leu Arg Ile Leu Phe Tyr Phe Ser
                180                 185                 190

Pro Ile Leu Trp Leu Pro Lys Asn His Gly Ile Ser Gly Leu Ile His
            195                 200                 205

Glu Met Met Lys Tyr Asn Pro Val Tyr Phe Ile Ala Glu Ser Tyr Arg
        210                 215                 220

Ala Ala Ile Leu Tyr His Glu Trp Tyr Phe Met Asp His Trp Lys Leu
225                 230                 235                 240

Met Leu Tyr Asn Phe Gly Ile Val Ala Ile Phe Ala Ile Gly Ala
                245                 250                 255

Tyr Leu His Met Lys Tyr Arg Asp Gln Phe Ala Asp Phe Leu
```

<210> SEQ ID NO 43
<211> LENGTH: 995
<212> TYPE: DNA
<213> ORGANISM: Staphylococcus aureus

<400> SEQUENCE: 43

```
taacaaaatc ttctatacac tttcaacag gttttaaaat ttaacaactg ttgagtagta      60
tattataatc tagataaatg tgaataagga aggtctacaa atgaacgttt cggtaaacat    120
taaaaatgta acaaagaat atcgtattta tcgtacaaat aaagaacgta tgaaagatgc    180
gctcattccc aaacataaaa acaaaacatt tttcgcttta gatgacatta gtttaaaagc    240
atatgaaggt gacgtcatag ggcttgttgg catcaatggt tccggcaaat caacgttgag    300
caatatcatt ggcggttctt tgtcgcctac tgttggcaaa gtggatcgta atggtgaagt    360
cagcgttatc gcaattagtg ctggcttgag tggacaactt acagggattg aaaatatcga    420
atttaaaatg ttatgtatgg gctttaagcg aaaagaaatt aaagcgatga cacctaagat    480
tattgaattt agtgaacttg gtgagtttat ttatcaacca gttaaaaagt attcaagtgg    540
tatgcgtgca aaacttggtt tttcaattaa tatcacagtt aatccagata tcttagtcat    600
tgacgaagct ttatctgtag gtgaccaaac ttttgcacaa aaatgtttag ataaaattta    660
cgagtttaaa gagcaaaaca aaccatctt tttcgttagt cataacttag acaagtgag     720
acaattttgt actaagattg cttggattga aggcggaaag ttaaaagatt acggtgaact    780
tgatgatgta ttacctaaat atgaagcttt ccttaacgat tttaaaaaga aatccaaagc    840
cgaacaaaaa gaatttagaa acaaactcga tgagtcccgc ttcgttatta ataaaccga    900
aaaaaccgag aatctccatt taaggatttc ctcggtttta tttttgtcat catgattatt    960
tcgccttttt tattttttctt tttgctttgg ctatt                              995
```

<210> SEQ ID NO 44
<211> LENGTH: 264
<212> TYPE: PRT
<213> ORGANISM: Staphylococcus aureus

<400> SEQUENCE: 44

```
Met Asn Val Ser Val Asn Ile Lys Asn Val Thr Lys Glu Tyr Arg Ile
 1               5                  10                  15

Tyr Arg Thr Asn Lys Glu Arg Met Lys Asp Ala Leu Ile Pro Lys His
                20                  25                  30

Lys Asn Lys Thr Phe Phe Ala Leu Asp Asp Ile Ser Leu Lys Ala Tyr
            35                  40                  45

Glu Gly Asp Val Ile Gly Leu Val Gly Ile Asn Gly Ser Gly Lys Ser
        50                  55                  60

Thr Leu Ser Asn Ile Ile Gly Gly Ser Leu Ser Pro Thr Val Gly Lys
    65                  70                  75                  80

Val Asp Arg Asn Gly Glu Val Ser Val Ile Ala Ile Ser Ala Gly Leu
                85                  90                  95

Ser Gly Gln Leu Thr Gly Ile Glu Asn Ile Glu Phe Lys Met Leu Cys
            100                 105                 110

Met Gly Phe Lys Arg Lys Glu Ile Lys Ala Met Thr Pro Lys Ile Ile
        115                 120                 125

Glu Phe Ser Glu Leu Gly Glu Phe Ile Tyr Gln Pro Val Lys Lys Tyr
    130                 135                 140
```

-continued

```
Ser Ser Gly Met Arg Ala Lys Leu Gly Phe Ser Ile Asn Ile Thr Val
145                 150                 155                 160

Asn Pro Asp Ile Leu Val Ile Asp Glu Ala Leu Ser Val Gly Asp Gln
                165                 170                 175

Thr Phe Ala Gln Lys Cys Leu Asp Lys Ile Tyr Glu Phe Lys Glu Gln
            180                 185                 190

Asn Lys Thr Ile Phe Phe Val Ser His Asn Leu Gly Gln Val Arg Gln
        195                 200                 205

Phe Cys Thr Lys Ile Ala Trp Ile Glu Gly Lys Leu Lys Asp Tyr
    210                 215                 220

Gly Glu Leu Asp Asp Val Leu Pro Lys Tyr Glu Ala Phe Leu Asn Asp
225                 230                 235                 240

Phe Lys Lys Lys Ser Lys Ala Glu Gln Lys Glu Phe Arg Asn Lys Leu
                245                 250                 255

Asp Glu Ser Arg Phe Val Ile Lys
            260
```

<210> SEQ ID NO 45
<211> LENGTH: 738
<212> TYPE: DNA
<213> ORGANISM: Staphylococcus aureus

<400> SEQUENCE: 45

```
ataaggtgaa gacacataaa acaatatatc ttagtaagca tgcaacactc ttttttgttt      60
attcataaca acaaaaaaga attaaaggag gagtcttatt atggctcgat tcagaggttc     120
aaactggaaa aaatctcgtc gtttaggtat ctctttaagc ggtactggta agaattaga      180
aaaacgtcct tacgcaccag acaacatgg tccaaaccaa cgtaaaaaat tatcagaata     240
tggtttacaa ttacgtgaaa aacaaaaatt acgttactta tatggaatga ctgaaagaca     300
attccgtaac acatttgaca tcgctggtaa aaaattcggt gtacacggtg aaaacttcat     360
gatcttatta gcaagtcgtt tagacgctgt tgtttattca ttaggtttag ctcgtactcg     420
tcgtcaagca cgtcaattag ttaaccacgg tcatatctta gtagatggta aacgtgttga     480
tattccatct tattctgtta aacctggtca aacaatttca gttcgtgaaa aatctcaaaa     540
attaaacatc atcgttgaat cagttgaaat caacaatttc gtacctgagt acttaaactt     600
tgatgctgac agcttaactg gtactttcgt acgtttacca gaacgtagcg aattacctgc     660
tgaaattaac gaacaattaa tccgttgagt actactcaag ataatacggt caataccaac     720
acccacaatt gtgggtgt                                                   738
```

<210> SEQ ID NO 46
<211> LENGTH: 195
<212> TYPE: PRT
<213> ORGANISM: Staphylococcus aureus

<400> SEQUENCE: 46

```
Met Ala Arg Phe Arg Gly Ser Asn Trp Lys Lys Ser Arg Arg Leu Gly
1               5                   10                  15

Ile Ser Leu Ser Gly Thr Gly Lys Glu Leu Glu Lys Arg Pro Tyr Ala
                20                  25                  30

Pro Gly Gln His Gly Pro Asn Gln Arg Lys Lys Leu Ser Glu Tyr Gly
            35                  40                  45

Leu Gln Leu Arg Glu Lys Gln Lys Leu Arg Tyr Leu Tyr Gly Met Thr
        50                  55                  60

Glu Arg Gln Phe Arg Asn Thr Phe Asp Ile Ala Gly Lys Lys Phe Gly
```

```
                65                  70                  75                  80
            Val His Gly Glu Asn Phe Met Ile Leu Leu Ala Ser Arg Leu Asp Ala
                            85                  90                  95

Val Val Tyr Ser Leu Gly Leu Ala Arg Thr Arg Gln Ala Arg Gln
                        100                 105                 110

Leu Val Asn His Gly His Ile Leu Val Asp Gly Lys Arg Val Asp Ile
                        115                 120                 125

Pro Ser Tyr Ser Val Lys Pro Gly Gln Thr Ile Ser Val Arg Glu Lys
                        130                 135                 140

Ser Gln Lys Leu Asn Ile Ile Val Glu Ser Val Glu Ile Asn Asn Phe
            145                 150                 155                 160

Val Pro Glu Tyr Leu Asn Phe Asp Ala Asp Ser Leu Thr Gly Thr Phe
                            165                 170                 175

Val Arg Leu Pro Glu Arg Ser Glu Leu Pro Ala Glu Ile Asn Glu Gln
                        180                 185                 190

Leu Ile Arg
                        195

<210> SEQ ID NO 47
<211> LENGTH: 980
<212> TYPE: DNA
<213> ORGANISM: Staphylococcus aureus

<400> SEQUENCE: 47
tgttgattgc acctgcttca gtcattgcta taactatttt aatttttaat ttaaccggtg      60
atgcactaag agatagattg ctgaaacaac ggggtgaata tgatgagtct cattgatata     120
caaaatttaa caataaagaa tactagtgag aaatctctta ttaaagggat tgatttgaaa     180
atttttagtc aacagattaa tgccttgatt ggagagagcg gcgctggaaa aagtttgatt     240
gctaaagctt tacttgaata tttaccattt gatttaagct gcacgtatga ttcgtaccaa     300
tttgatgggg aaaatgttag tagattgagt caatattatg gtcatacaat ggctatatt     360 tctcaaaatt atgcagaaag ttttaacgac catactaaat taggtaaaca gttaactgcg     420
atttatcgta agcattataa aggtagtaaa gaagaggctt tgtccaaagt tgataaggct     480
ttgtcgtggg ttaatttaca aagcaaagat atattaaata aatatagttt ccaactttct     540
gggggccaac ttgaacgcgt atacatagca agcgttctca tgttggagcc taaattaatc     600
attgcagacg aaccagttgc atcattggat gctttgaacg gtaatcaagt gatggattta     660
ttacagcata ttgtattaga acatggtcaa acattattta ttatcacaca taacttaagt     720
catgtattga atattgtcaa gtacatttat gttttaaaag aaggtcaaat cattgaacga     780
ggtaatatta atcatttcaa gtatgagcat ttgcatccgt atactgaacg tctaattaaa     840
tatagaacac aattaaagag ggattactat gattgagtta aaacatgtga cttttggtta     900
taataaaaag cagatggtgc tacaagatat caatattact atacctgatg gagaaaatgt     960
tggtatttta ggcgaaagtg                                                 980

<210> SEQ ID NO 48
<211> LENGTH: 258
<212> TYPE: PRT
<213> ORGANISM: Staphylococcus aureus

<400> SEQUENCE: 48

Met Met Ser Leu Ile Asp Ile Gln Asn Leu Thr Ile Lys Asn Thr Ser
1               5                   10                  15
```

| | | | | | | | | | | | |
|---|---|---|---|---|---|---|---|---|---|---|---|
|Glu|Lys|Ser|Leu|Ile|Lys|Gly|Ile|Asp|Leu|Lys|Ile|Phe|Ser|Gln|Gln|

```
            Glu Lys Ser Leu Ile Lys Gly Ile Asp Leu Lys Ile Phe Ser Gln Gln
                             20                  25                  30

Ile Asn Ala Leu Ile Gly Glu Ser Gly Ala Gly Lys Ser Leu Ile Ala
                         35                  40                  45

Lys Ala Leu Leu Glu Tyr Leu Pro Phe Asp Leu Ser Cys Thr Tyr Asp
                     50                  55                  60

Ser Tyr Gln Phe Asp Gly Glu Asn Val Ser Arg Leu Ser Gln Tyr Tyr
            65                  70                  75                  80

Gly His Thr Ile Gly Tyr Ile Ser Gln Asn Tyr Ala Glu Ser Phe Asn
                                 85                  90                  95

Asp His Thr Lys Leu Gly Lys Gln Leu Thr Ala Ile Tyr Arg Lys His
                            100                 105                 110

Tyr Lys Gly Ser Lys Glu Glu Ala Leu Ser Lys Val Asp Lys Ala Leu
                        115                 120                 125

Ser Trp Val Asn Leu Gln Ser Lys Asp Ile Leu Asn Lys Tyr Ser Phe
                    130                 135                 140

Gln Leu Ser Gly Gly Gln Leu Glu Arg Val Tyr Ile Ala Ser Val Leu
            145                 150                 155                 160

Met Leu Glu Pro Lys Leu Ile Ile Ala Asp Glu Pro Val Ala Ser Leu
                            165                 170                 175

Asp Ala Leu Asn Gly Asn Gln Val Met Asp Leu Leu Gln His Ile Val
                        180                 185                 190

Leu Glu His Gly Gln Thr Leu Phe Ile Ile Thr His Asn Leu Ser His
                    195                 200                 205

Val Leu Lys Tyr Cys Gln Tyr Ile Tyr Val Leu Lys Glu Gly Gln Ile
                210                 215                 220

Ile Glu Arg Gly Asn Ile Asn His Phe Lys Tyr Glu His Leu His Pro
            225                 230                 235                 240

Tyr Thr Glu Arg Leu Ile Lys Tyr Arg Thr Gln Leu Lys Arg Asp Tyr
                            245                 250                 255

Tyr Asp

<210> SEQ ID NO 49
<211> LENGTH: 760
<212> TYPE: DNA
<213> ORGANISM: Staphylococcus aureus
<220> FEATURE:
<221> NAME/KEY: misc_feature
<222> LOCATION: (712)..(712)
<223> OTHER INFORMATION: n equal a, t, c, or g

<400> SEQUENCE: 49
gatgatattt taattacaga aaatggttgt caagtcttta ctaaatgcac aaaagacctt       60
atagttttaa cataagcgtg taaaatgagg aggaaactga atgatttcgg ttaatgattt      120
taaaacaggt ttaacaattt ctgttgataa cgctatttgg aaagttatag acttccaaca      180
tgtaaagcct ggtaaaggtt cagcattcgt tcgttcaaaa ttacgtaatt taagaactgg      240
tgcaattcaa gagaaaacgt ttagagctgg tgaaaaagtt gaaccagcaa tgattgaaaa      300
tcgtcgcatg caatatttat atgctgacgg rgataatcat gtatttatgg ataatgaaag      360
ctttgaacaa acagaacttt caagtgatta cttaaaagaa gaattgaatt acttaaaaga      420
aggtatggaa gtacaaattc aaacatacga aggtgaaact atcggtgttg aattacctaa      480
aactgttgaa ttaacagtaa ctgaaacaga acctggtatt aaaggtgata ctgcaactgg      540
tgccactaaa tcggcaactg ttgaaactgg ttatacatta aatgtacctt tatttgtaaa      600
```

```
cgaaggtgac gttttaatta tcaacactgg tgatggaagc tacatttcaa gaggataatc    660
tctaatttgt taacaaatag cttgtattca ctatactgat ttaacgtaag anattctaaa    720
taagtctcat aaagctattg cctaaaatga ttataggtta                          760
```

<210> SEQ ID NO 50
<211> LENGTH: 185
<212> TYPE: PRT
<213> ORGANISM: Staphylococcus aureus

<400> SEQUENCE: 50

```
Met Ile Ser Val Asn Asp Phe Lys Thr Gly Leu Thr Ile Ser Val Asp
1               5                   10                  15

Asn Ala Ile Trp Lys Val Ile Asp Phe Gln His Val Lys Pro Gly Lys
            20                  25                  30

Gly Ser Ala Phe Val Arg Ser Lys Leu Arg Asn Leu Arg Thr Gly Ala
        35                  40                  45

Ile Gln Glu Lys Thr Phe Arg Ala Gly Glu Lys Val Glu Pro Ala Met
    50                  55                  60

Ile Glu Asn Arg Arg Met Gln Tyr Leu Tyr Ala Asp Gly Asp Asn His
65                  70                  75                  80

Val Phe Met Asp Asn Glu Ser Phe Glu Gln Thr Glu Leu Ser Ser Asp
                85                  90                  95

Tyr Leu Lys Glu Glu Leu Asn Tyr Leu Lys Glu Gly Met Glu Val Gln
            100                 105                 110

Ile Gln Thr Tyr Glu Gly Glu Thr Ile Gly Val Glu Leu Pro Lys Thr
        115                 120                 125

Val Glu Leu Thr Val Thr Glu Thr Pro Gly Ile Lys Gly Asp Thr
    130                 135                 140

Ala Thr Gly Ala Thr Lys Ser Ala Thr Val Glu Thr Gly Tyr Thr Leu
145                 150                 155                 160

Asn Val Pro Leu Phe Val Asn Glu Gly Asp Val Leu Ile Ile Asn Thr
                165                 170                 175

Gly Asp Gly Ser Tyr Ile Ser Arg Gly
            180                 185
```

<210> SEQ ID NO 51
<211> LENGTH: 9326
<212> TYPE: DNA
<213> ORGANISM: Staphylococcus aureus

<400> SEQUENCE: 51

```
ttaggatgta agaaagttcc agtgcaagaa atccatgaaa cacaatattc aattagtaca    60 tgcaacata aagttccatt tggtgtgtgg tgggaaacgt tacaacaaga acatcgcttg    120
ccatggacta ctgagacaag acaagaagcg ccatttatta caatgtgtca tggtgataca    180
gaacaatatt tgtatacaaa agatttaggc gaagcacatt ttcaagtatg ggaaaaggtt    240
gtcgcaagtt atagtggttg ttgttctgta gagagaattg cacaaggtac atatccttgt    300 cttttctcaac aagatgtact catgaagtat cagccattga gttataagga aattgaagcg    360
gttgttcata aggggaaac tgtgccagca ggtgtgacac gctttaatat ttcaggacga    420
tgtcttaatc ttcaagtacc actggcatta cttaaacaag atgatgatgt tgaacaatgc    480
gcaattggaa gcagttttta gcagataagt ttgccaatat gagatgctat actgaaaaag    540
tatacttggt ggagcaatag ttttactgtg atgttgaggg aaatatgatg atttagcgta    600
ttgatagcga aaatataata aaacaatata gtgtggagaa cttttgatat tttataaata    660
```

-continued

```
ttgaagttct ccatttttgt attttgcata taaaaattaa ataaaataag gtatattaag      720
gtaaagtata aattttaaat aaatggggaa tgagtatgag ctcaattata ggaaaaatag      780
caatttggat aggcatcgta gctcaaatat attttagtgt cgttttttgtt aggatgatat    840
ctattaatat tgctggagga tctgattacg aaacaatttt tttattagga ttaatattgg      900
ctcttttcac tgttttacca accatcttta ctgcgattta tatggaaagt tactctgtaa    960
tcggaggtgc acttttttatt gtttatgcta ttattgcact gtgtttatat aatttccttt   1020
cgtcaatttt atggctgatt ggtggtatttt tgctgatttg gaataaatac tcaaaagatg   1080
aatcgacaga cgaaaatgaa aaagttgata ttgaaagtac agagaatcaa tttgaatcta    1140
aagataaaat cactaaagaa taaagagaat attttaaggta aagtataaat tttaaataaa    1200
tggggaatag acatggaaaa aaatgtagaa aaatcattca taaagatagg tttatatttt    1260
caaatagctt atatagtact catggctata actttatgtg ggtttgtaat ttgctatgga    1320
ctaattttcg gccttttcta tttattatca ggtagcagag ctgattattt aatagtaaca    1380
atagttatat cggcaataat ttctatatttt gtaattatac tttcaatcgt acctgtcatc    1440
gtattggcat ctgacttatt taaagaaagg atttcaaaag gtgtcatatt aattgtattg    1500
gctattatcg ctttagtatt atgcaacttt gtatctgcaa tactctggtt tgtttcagcc    1560
atatctatttt taggtagaaa aaaattagta gctgcagcag atactaccac tattcaaaaa    1620
agtaaaggga acgcaaatca agcatcacat aaagacacgt gtaaaaagga acttgatagt    1680
caagacatga tggaacatcc tgaggttaaa aatcccacga ctaaaaaccct tgaaggatttt    1740
aacgaagaaa tacataaaga tgaagctaca actaaagttg tcagtgataa cacggaaccg    1800
cctattgaat caaaagacca tgtctcgaaa aaagattgat gacaaactaa tcgagagact    1860
taaaaaaata atattcaaca taagaacttt taaaacgaca tttaaacgca ttgccaatca    1920
ctaatggtag tgcgtttaac tataccttaa atatctgaat attttgttaa atggagctac    1980
ctttgttgta ctattcaaat gaagaggagt aaaatgtaat taaaggaaag aaatttgagg    2040
agtgatcttt atgacaaaca acaaagtagc attagtaact ggcggagcac aagggattgg    2100
tttttaaaatt gcagaacgtt tagtggaaga tggtttcaaa gtagcagttg ttgatttcaa    2160
tgaagaaggg gcaaaagcag ctgcacttaa attatcaagt gatggtacaa aagctattgc    2220
tatcaaagca gatgtatcaa accgtgatga tgtatttaac gcataagaca aactgccgcg    2280
caatttggcg atttccatgt catggttaac aatgccggcc ttggaccaac aacaccaatc    2340
gatacaatta ctgaagaaca gtttaaaaca gtatatggcg tgaacgttgc aggtgtgcta    2400
tggggtattc aagccgcaca tgaacaattt aaaaaattca atcatggcgg taaaattatc    2460
aatgcaacat ctcaagcagg cgttgagggt aacccaggct tgtctttata ttgcagtaca    2520
aaattcgcag tgcgaggttt aacacaagta gccgcacaag atttagcgtc tgaaggtatt    2580
actgtgaatg cattcgcacc tggtatcgtt caaacaccaa tgatggaaag tatcgcagtg    2640
gcaacagccg aagaagcagg taaacctgaa gcatggggtt gggaacaatt tacaagtcag    2700
attgctttgg gcagagtttc tcaaccagaa gatgtttcaa atgtagtgag cttcttagct    2760
ggtaaagact ctgattacat tactggacaa acaattattg tagatggtgg tatgagattc    2820
cgttaataat catccactaa tgataaataa atccttattg ttaagtttaa tcacttagca    2880
gtaaggatttt tttagtgcac ttagaaggga gtgtattggt agaaaattaa taagcgaagt    2940
tcttaagtga gttatgatgt cacagtctaa tgcatcagtt gaaagcatta ttagtattaa    3000
```

```
cacacccaag atattataaa acatcacaaa aacaccacta tctaatttat ctcaataaaa    3060
attcacaaag ttatctcatt ttatttttat aaataaaaaa tatcgataaa aagcttacaa    3120
tactttatgt ttttatgata tattttttaat gtataaatga ggtggaagat ttggaaagag   3180
ttttgataac tggtggggct ggttttattg ggtcgcattt agtagatgat ttacaacaag    3240
attatgatgt ttatgttcta gataactata gaacaggtaa acgagaaaat attaaaagtt    3300
tggctgacga tcatgtgttt gaattagata ttcgtgaata tgatgcagtt gaacaaatca    3360
tgaagacata tcaatttgat tatgttattc atttagcagc attagttagt gttgctgagt    3420
cggttgagaa acctatctta tctcaagaaa taaacgtcgt agcaacatta agattgttag    3480
aaatcattaa aaaatataat aatcatataa aacgttttat ctttgcttcg tcagcagctg    3540
tttatggtga tcttcctgat ttgcctaaaa gtgatcaatc attaatctta ccattatcac    3600
catatgcaat agataaatat tacggcgaac ggacgacatt aaattattgt tcgttatata    3660
acataccaac agcggttgtt aaattttttta atgtatttgg gccaagacag gatcctaagt    3720
cacaatattc aggtgtgatt tcaaagatgt tcgattcatt tgagcataac aagccattta    3780
cattttttgg tgacggactg caaactagag attttgtata tgtatatgat gttgttcaat    3840
ctgtacgctt aattatggaa cacaaagatg caattggaca cggttataac attggtacag    3900
gcacttttac taatttatta gaggtttatc gtattattgg tgaattatat ggaaaatcag    3960
tcgagcatga atttaaagaa gcacgaaaag gagatattaa gcattcttat gcagatattt    4020
ctaacttaaa ggcattagga tttgttccta aatatacagt agaaacaggt ttaaaggatt    4080
actttaattt tgaggtagat aatattgaag aagttacagc taaagaagtg gaaatgtcgt    4140
gaaaatgaca ttgaagctgt ccataataat aagggttatg cctatcaaag aaaattagac    4200
aaactagaag aagtgagaaa aagctattac ccaattaaac gtgcgattga cttaatttta    4260
agcattgttt tattattttt aactttaccg attatggtta tattcgccat tgctatcgtc    4320
atagattcgc caggaaaccc tatttatagt caggttagag ttgggaagat gggtaaatta    4380
attaaaatat acaaattacg ttcgatgtgc aaaaacgcag agaaaaacgg tgcgcaatgg    4440
gctgataaag atgatgatcg tataacaaat gtcgggaagt ttattcgtaa aacacgcatt    4500
gatgaattac cacaactaat taatgttgtt aaagggaaaa tgagtttttat tggaccacgc    4560
ccggaacgtc cggaatttgt agaattattt agttcagaag tgataggttt cgagcaaaga    4620
tgtcttgtta caccagggtt aacaggactt gcgcaaattc aaggtggata tgacttaaca    4680
ccgcaacaaa aactgaaata tgacatgaaa tatatacata aaggtagttt aatgatggaa    4740
ctatatatat caattagaac attgatggtt gttattacag gggaaggctc aaggtagtct    4800
taatttactt aataagttca aataaaagtt atattttaaa gattgtgacc aattgttaca    4860
gtataacgag gaatccctg agacagtatc aaatggcatt aagaaatatg tgccatcatt    4920
gatttgcatg gctataaata ctattcatct gatgagatag ccatgttaag aaattgaaag    4980
tatagcatta aaggggtttg taacagttga aaattatata ttgtattact aaagcagaca    5040
atggtggtgc acaaacacat ctcattcaac tcgccaacca tttttgcgta cacaatgatg    5100
tttatgtcat tgtaggcaat catggaccaa tgattgaaca actagatgca agagttaatg    5160
taattattat cgaacattta gtaggtccaa ttgactttaa acaagatatt ttagctgtca    5220
aagtgttagc acagttattc tcgaaaatta aacctgatgt tatccattta cattcttcca    5280
aagctggaac ggtcggacga attgcgaagt tcatttcgaa atcgaaagac acacgtatag    5340
tttttactgc acatggatgg gcttttacag agggtgttaa accagctaaa aaatttctat    5400
```

-continued

```
atttagttat cgaaaaatta atgtcactta ttacagatag cattatttgt gtttcagatt    5460
tcgataaaca gttagcgtta aaatatcgat ttaatcgatt gaaattaacc acaatacata    5520
atggtattgc agatgttccc gctgttaagc aaacgctaaa aagccaatca cataacaata    5580
ttggcgaagt agttggaatg ttgcctaata acaagattt acagattaat gccccgacaa     5640
agcatcaatt tgttatgatt gcaagatttg cttatccaaa attgccacaa aatctaatcg    5700
cggcaataga gatattgaaa ttacataaca gtaatcatgc gcatttaca tttataggcg     5760 atggacctac attaaatgat tgtcagcaac aagttgtaca agctgggtta gaaaatgatg    5820
tcacattttt gggcaatgtc attaatgcga gtcatttatt atcacaatac gatacgttta    5880
ttttaataag taagcatgaa ggtttgccaa ttagcattat agaagctatg gctacaggtt    5940
tgcctgttat agccagtcat gttggcggta tttcagaatt agtagctgat aatggtatat    6000
gtatgatgaa caaccaaccc gaaactattg ctaaagtcct ggaaaaatat ttaatagaca    6060
gtgattacat caaaatgagt aatcaatcta gaaaacgtta tttagaatgt tttactgagg    6120
agaaaatgat taaagaagtg gaagacgttt ataatggaaa atcaacacaa tagtaaatta    6180
ctaacattgt tacttatcgg tttagcggtt tttattcagc aatcttcggt tattgccggt    6240
gtgaatgttt ctatagctga ctttatcaca ttactaatat tagtttattt actgttttc     6300 gctaaccatt tattaaaggc aaatcatttt ttacagtttt tcattatttt gtatacatat    6360
cgtatgatta ttacgctttg tttgctattt tttgatgatt tgatatttat tacggttaag    6420
gaagttcttg catctacagt taaatatgca tttgtagtca tttatttcta tttagggatg    6480
atcatcttta agttaggtaa tagcaaaaaa gtgatcgtta cctcttatat tataagcagt    6540
gtgactatag gtctatttttg tattatagct ggtttgaaca gtcccctttt actaatgaaa    6600
ttgttatatt ttgatgaaat acgttcaaaa ggattaatga atgaccctaa ctatttcgcg    6660
atgacacaga ttattacatt ggtacttgct tacaagtata ttcataatta catattcaag    6720
gtccttgcat gtggtatttt gctatggtct ttaactacaa cggggtctaa gactgcgttt    6780
atcatattaa tcgtcttagc catttatttc tttattaaaa agttatttag tagaaatgcg    6840
gtaagtgttg tgagtatgtc agtgattatg ctgatattac tttgtttac cttttataat     6900 atcaactact atttattcca attaagcgac cttgatgcct taccgtcatt agatcgaatg    6960
gcgtctattt ttgaagaggg ctttgcatca ttaaatgata gtgggtctga gcgaagtgtt    7020
gtatggataa atgccatttc agtaattaaa tatacactag gttttggtgt cggattagtg    7080
gattatgtac atattggctc gcaaattaat ggtatttac ttgttgccca taatacatat      7140
ttgcagatct ttgcggaatg gggcatttta ttcggtgcat tatttatcat atttatgctt    7200
tatttactgt ttgaattatt tagatttaac atttctggga aaaatgtaac agcaattgtt    7260
gtaatgttga cgatgctgat ttactttta acagtatcat ttaataactc aagatatgtc     7320
gcttttattt taggaattat cgtctttatt gttcaatatg aaaagatgga aagggatcgt    7380
aatgaagagt gattcactaa aagaaaatat tatttatcaa gggctatacc aattgattag    7440
aacgatgaca ccactgatta caatacccat tatttcacgt gcatttggtc ccagtggtgt    7500
gggtattgtt tcattttctt tcaatatcgt gcaatacttt tgatgattg caagtgttgg      7560 cgttcagtta tattttaata gagttatcgc gaagtccgtt aacgacaaac ggcaattgtc    7620
acagcagttt tgggatatct ttgtcagtaa attattttta gcgttaacag tttttgcgat    7680
gtatatggtc gtaattacta tatttattga tgattactat cttattttcc tactacaagg    7740
```

-continued

| | |
|---|---|
| aatctatatt ataggtgcag cactcgatat ttcatggttt tatgctggaa ctgaaaagtt | 7800 |
| taaaattcct agcctcagta atattgttgc gtctggtatt gtattaagtg tagttgttat | 7860 |
| ttttgtcaaa gatcaatcag atttatcatt gtatgtattt actattgcta ttgtgacggt | 7920 |
| attaaaccaa ttacctttgt ttatctattt aaaacgatac attagctttg tttcggttaa | 7980 |
| ttggatacac gtctggcaat tgtttcgttc gtcattagca tacttattac caaatggaca | 8040 |
| gctcaactta tatactagta tttcttgcgt tgttcttggt ttagtaggta cataccaaca | 8100 |
| agttggtatc ttttctaacg catttaatat tttaacggtc gcaatcataa tgattaatac | 8160 |
| atttgatctt gtaatgattc cgcgtattac caaaatgtct atccagcaat cacatagttt | 8220 |
| aactaaaacg ttagctaata atatgaatat tcaattgata ttaacaatac ctatggtctt | 8280 |
| tggtttaatt gcaattatgc catcatttta tttatggttc tttggtgagg aattcgcatc | 8340 |
| aactgtccca ttgatgacca ttttagcgat acttgtatta atcattcctt taaatatgtt | 8400 |
| gataagcagg caatatttat taatagtgaa taaaataaga ttatataatg cgtcaattac | 8460 |
| tattggtgca gtgataaacc tagtattatg tattattttg atatatttt atggaattta | 8520 |
| cggtgctgct attgcgcgtt taattacaga gttttcttg ctcatttggc gatttattga | 8580 |
| tattactaaa atcaatgtga agttgaatat tgtaagtacg attcaatgtg tcattgctgc | 8640 |
| tgttatgatg tttattgtgc ttggtgtggt caatcattat ttgcccccta caatgtacgc | 8700 |
| tacgctgcta ttaattgcga ttggtatagt agtttatctt ttattaatga tgactatgaa | 8760 |
| aaatcaatac gtatggcaaa tattgaggca tcttcgacat aaaacaattt aagtaccggt | 8820 |
| aatgctatac tttagaaaat taagattaag aagaaaaggc aatttcttat tgaaaaatgg | 8880 |
| aagttgtctt ttttaattct ctttaaaagc gggaaacaaa agcagttaaa tgcctttttg | 8940 |
| cattcaatat taaatattat atcaatttcg aatatttaaa ttttatataa ttggatataa | 9000 |
| caaataaata ataattattg caaaacacac ccaaaattaa ttattataaa agtatattca | 9060 |
| taaaaggagg aatatactta tggcattta attaccaaat ttaccatatg catatgatgc | 9120 |
| attggaacca tatatagatc aaagaacaat ggagtttcat cacgacaaac atcacaatac | 9180 |
| gtacgtgacg aaattaaacg caacagttga aggaacagag ttagagcatc aatcactagc | 9240 |
| ggatatgatt gctaacttag acaaggtacc ggaagcgatg gggtaccgag ctcgaattcg | 9300 |
| taatcatgtc atagctgttt cctgtg | 9326 |

<210> SEQ ID NO 52
<211> LENGTH: 981
<212> TYPE: DNA
<213> ORGANISM: Staphylococcus aureus

<400> SEQUENCE: 52

| | |
|---|---|
| gtggaagatt tggaaagagt tttgataact ggtggggctg gttttattgg gtcgcattta | 60 |
| gtagatgatt tacaacaaga ttatgatgtt tatgttctag ataactatag aacaggtaaa | 120 |
| cgagaaaata ttaaaagttt ggctgacgat catgtgtttg aattagatat tcgtgaatat | 180 |
| gatgcagttg aacaaatcat gaagacatat caatttgatt atgttattca tttagcagca | 240 |
| ttagttagtg ttgctgagtc ggttgagaaa cctatcttat ctcaagaaat aaacgtcgta | 300 |
| gcaacattaa gattgttaga atcattaaaa aatataata atcatataaa acgttttatc | 360 |
| tttgcttcgt cagcagctgt ttatggtgat cttcctgatt tgcctaaaag tgatcaatca | 420 |
| ttaatcttac cattatcacc atatgcaata gataaatatt acggcgaacg gacgacatta | 480 |
| aattattgtt cgttatataa cataccaaca gcggttgtta aatttttaa tgtatttggg | 540 |

```
ccaagacagg atcctaagtc acaatattca ggtgtgattt caaagatgtt cgattcattt      600
gagcataaca agccatttac attttttggt gacggactgc aaactagaga ttttgtatat      660
gtatatgatg ttgttcaatc tgtacgctta attatggaac acaaagatgc aattggacac      720
ggttataaca ttggtacagg cacttttact aatttattag aggtttatcg tattattggt      780
gaattatatg gaaatcagt cgagcatgaa tttaaagaag cacgaaaagg agatattaag       840
cattcttatg cagatatttc taacttaaag gcattaggat ttgttcctaa atatacagta      900
gaaacaggtt taaaggatta ctttaatttt gaggtagata atattgaaga agttacagct      960
aaagaagtgg aaatgtcgtg a                                                981
```

<210> SEQ ID NO 53
<211> LENGTH: 326
<212> TYPE: PRT
<213> ORGANISM: Staphylococcus aureus

<400> SEQUENCE: 53

```
Val Glu Asp Leu Glu Arg Val Leu Ile Thr Gly Gly Ala Gly Phe Ile
1               5                   10                  15

Gly Ser His Leu Val Asp Asp Leu Gln Gln Asp Tyr Asp Val Tyr Val
            20                  25                  30

Leu Asp Asn Tyr Arg Thr Gly Lys Arg Glu Asn Ile Lys Ser Leu Ala
        35                  40                  45

Asp Asp His Val Phe Glu Leu Asp Ile Arg Glu Tyr Asp Ala Val Glu
    50                  55                  60

Gln Ile Met Lys Thr Tyr Gln Phe Asp Tyr Val Ile His Leu Ala Ala
65                  70                  75                  80

Leu Val Ser Val Ala Glu Ser Val Glu Lys Pro Ile Leu Ser Gln Glu
                85                  90                  95

Ile Asn Val Val Ala Thr Leu Arg Leu Leu Glu Ile Ile Lys Lys Tyr
            100                 105                 110

Asn Asn His Ile Lys Arg Phe Ile Phe Ala Ser Ser Ala Ala Val Tyr
        115                 120                 125

Gly Asp Leu Pro Asp Leu Pro Lys Ser Asp Gln Ser Leu Ile Leu Pro
    130                 135                 140

Leu Ser Pro Tyr Ala Ile Asp Lys Tyr Tyr Gly Glu Arg Thr Thr Leu
145                 150                 155                 160

Asn Tyr Cys Ser Leu Tyr Asn Ile Pro Thr Ala Val Val Lys Phe Phe
                165                 170                 175

Asn Val Phe Gly Pro Arg Gln Asp Pro Lys Ser Gln Tyr Ser Gly Val
            180                 185                 190

Ile Ser Lys Met Phe Asp Ser Phe Glu His Asn Lys Pro Phe Thr Phe
        195                 200                 205

Phe Gly Asp Gly Leu Gln Thr Arg Asp Phe Val Tyr Val Tyr Asp Val
    210                 215                 220

Val Gln Ser Val Arg Leu Ile Met Glu His Lys Asp Ala Ile Gly His
225                 230                 235                 240

Gly Tyr Asn Ile Gly Thr Gly Thr Phe Thr Asn Leu Leu Glu Val Tyr
                245                 250                 255

Arg Ile Ile Gly Glu Leu Tyr Gly Lys Ser Val Glu His Glu Phe Lys
            260                 265                 270

Glu Ala Arg Lys Gly Asp Ile Lys His Ser Tyr Ala Asp Ile Ser Asn
        275                 280                 285
```

Leu Lys Ala Leu Gly Phe Val Pro Lys Tyr Thr Val Glu Thr Gly Leu
    290                 295                 300

Lys Asp Tyr Phe Asn Phe Glu Val Asp Asn Ile Glu Glu Val Thr Ala
305                 310                 315                 320

Lys Glu Val Glu Met Ser
                325

<210> SEQ ID NO 54
<211> LENGTH: 504
<212> TYPE: DNA
<213> ORGANISM: Staphylococcus aureus

<400> SEQUENCE: 54
atggttatat tcgccattgc tatcgtcata gattcgccag gaaaccctat ttatagtcag    60
gttagagttg ggaagatggg taaattaatt aaaatataca aattacgttc gatgtgcaaa   120
aacgcagaga aaaacggtgc gcaatgggct gataaagatg atgatcgtat aacaaatgtc   180
gggaagttta ttcgtaaaac acgcattgat gaattaccac aactaattaa tgttgttaaa   240
ggggaaatga gttttattgg accacgcccg gaacgtccgg aatttgtaga attatttagt   300
tcagaagtga taggtttcga gcaaagatgt cttgttacac agggttaac aggacttgcg    360 caaattcaag gtggatatga cttaacaccg caacaaaaac tgaaatatga catgaaatat   420
atacataaag gtagtttaat gatggaacta tatatatcaa ttagaacatt gatggttgtt   480
attacagggg aaggctcaag gtag                                           504

<210> SEQ ID NO 55
<211> LENGTH: 200
<212> TYPE: PRT
<213> ORGANISM: Staphylococcus aureus

<400> SEQUENCE: 55

Leu Asp Lys Leu Glu Glu Val Arg Lys Ser Tyr Tyr Pro Ile Lys Arg
1               5                   10                  15

Ala Ile Asp Leu Ile Leu Ser Ile Val Leu Leu Phe Leu Thr Leu Pro
            20                  25                  30

Ile Met Val Ile Phe Ala Ile Ala Ile Val Ile Asp Ser Pro Gly Asn
        35                  40                  45

Pro Ile Tyr Ser Gln Val Arg Val Gly Lys Met Gly Lys Leu Ile Lys
    50                  55                  60

Ile Tyr Lys Leu Arg Ser Met Cys Lys Asn Ala Glu Lys Asn Gly Ala
65                  70                  75                  80

Gln Trp Ala Asp Lys Asp Asp Arg Ile Thr Asn Val Gly Lys Phe
                85                  90                  95

Ile Arg Lys Thr Arg Ile Asp Glu Leu Pro Gln Leu Ile Asn Val Val
                100                 105                 110

Lys Gly Glu Met Ser Phe Ile Gly Pro Arg Pro Glu Arg Pro Glu Phe
            115                 120                 125

Val Glu Leu Phe Ser Ser Glu Val Ile Gly Phe Glu Gln Arg Cys Leu
    130                 135                 140

Val Thr Pro Gly Leu Thr Gly Leu Ala Gln Ile Gln Gly Gly Tyr Asp
145                 150                 155                 160

Leu Thr Pro Gln Gln Lys Leu Lys Tyr Asp Met Lys Tyr Ile His Lys
                165                 170                 175

Gly Ser Leu Met Met Glu Leu Tyr Ile Ser Ile Arg Thr Leu Met Val
            180                 185                 190

-continued

```
Val Ile Thr Gly Glu Gly Ser Arg
        195                 200

<210> SEQ ID NO 56
<211> LENGTH: 1044
<212> TYPE: DNA
<213> ORGANISM: Staphylococcus aureus

<400> SEQUENCE: 56
atgattgaac aactagatgc aagagttaat gtaattatta tcgaacattt agtaggtcca      60
attgacttta acaagatat tttagctgtc aaagtgttag cacagttatt ctcgaaaatt     120
aaacctgatg ttatccattt acattcttcc aaagctggaa cggtcggacg aattgcgaag     180
ttcatttcga aatcgaaaga cacacgtata gtttttactg cacatggatg ggcttttaca     240
gagggtgtta aaccagctaa aaaatttcta tatttagtta tcgaaaaatt aatgtcactt     300
attacagata gcattatttg tgtttcagat ttcgataaac agttagcgtt aaaatatcga     360
tttaatcgat tgaaattaac cacaatacat aatggtattg cagatgttcc cgctgttaag     420
caaacgctaa aaagccaatc acataacaat attggcgaag tagttggaat gttgcctaat     480
aaacaagatt tacagattaa tgccccgaca aagcatcaat ttgttatgat tgcaagattt     540
gcttatccaa aattgccaca aaatctaatc gcggcaatag agatattgaa attacataac     600
agtaatcatg cgcattttac atttataggc gatggaccta cattaaatga ttgtcagcaa     660
caagttgtac aagctgggtt agaaaatgat gtcacatttt tgggcaatgt cattaatgcg     720
agtcatttat tatcacaata cgatacgttt attttaataa gtaagcatga aggtttgcca     780
attagcatta tagaagctat ggctacaggt ttgcctgtta tagccagtca tgttggcggt     840
atttcagaat tagtagctga taatggtata tgtatgatga caaccaacc cgaaactatt     900 gctaaagtcc tggaaaaata tttaatagac agtgattaca tcaaaatgag taatcaatct     960
agaaaacgtt atttagaatg ttttactgag gagaaaatga ttaagaagt ggaagacgtt    1020 tataatggaa aatcaacaca atag                                          1044

<210> SEQ ID NO 57
<211> LENGTH: 388
<212> TYPE: PRT
<213> ORGANISM: Staphylococcus aureus

<400> SEQUENCE: 57

Leu Lys Ile Ile Tyr Cys Ile Thr Lys Ala Asp Asn Gly Gly Ala Gln
1               5                   10                  15

Thr His Leu Ile Gln Leu Ala Asn His Phe Cys Val His Asn Asp Val
            20                  25                  30

Tyr Val Ile Val Gly Asn His Gly Pro Met Ile Glu Gln Leu Asp Ala
        35                  40                  45

Arg Val Asn Val Ile Ile Glu His Leu Val Gly Pro Ile Asp Phe
    50                  55                  60

Lys Gln Asp Ile Leu Ala Val Lys Val Leu Ala Gln Leu Phe Ser Lys
65                  70                  75                  80

Ile Lys Pro Asp Val Ile His Leu His Ser Ser Lys Ala Gly Thr Val
                85                  90                  95

Gly Arg Ile Ala Lys Phe Ile Ser Lys Ser Lys Asp Thr Arg Ile Val
            100                 105                 110

Phe Thr Ala His Gly Trp Ala Phe Thr Glu Gly Val Lys Pro Ala Lys
        115                 120                 125
```

| Lys | Phe | Leu | Tyr | Leu | Val | Ile | Glu | Lys | Leu | Met | Ser | Leu | Ile | Thr | Asp |
| | 130 | | | | 135 | | | | | 140 | | | | | |

| Ser | Ile | Ile | Cys | Val | Ser | Asp | Phe | Asp | Lys | Gln | Leu | Ala | Leu | Lys | Tyr |
| 145 | | | | | 150 | | | | | 155 | | | | | 160 |

| Arg | Phe | Asn | Arg | Leu | Lys | Leu | Thr | Thr | Ile | His | Asn | Gly | Ile | Ala | Asp |
| | | | 165 | | | | | 170 | | | | | 175 | | |

| Val | Pro | Ala | Val | Lys | Gln | Thr | Leu | Lys | Ser | Gln | Ser | His | Asn | Asn | Ile |
| | | | 180 | | | | | 185 | | | | | 190 | | |

| Gly | Glu | Val | Val | Gly | Met | Leu | Pro | Asn | Lys | Gln | Asp | Leu | Gln | Ile | Asn |
| | | 195 | | | | | 200 | | | | | 205 | | | |

| Ala | Pro | Thr | Lys | His | Gln | Phe | Val | Met | Ile | Ala | Arg | Phe | Ala | Tyr | Pro |
| | 210 | | | | | 215 | | | | | 220 | | | | |

| Lys | Leu | Pro | Gln | Asn | Leu | Ile | Ala | Ala | Ile | Glu | Ile | Leu | Lys | Leu | His |
| 225 | | | | | 230 | | | | | 235 | | | | | 240 |

| Asn | Ser | Asn | His | Ala | His | Phe | Thr | Phe | Ile | Gly | Asp | Gly | Pro | Thr | Leu |
| | | | | 245 | | | | | 250 | | | | | 255 | |

| Asn | Asp | Cys | Gln | Gln | Gln | Val | Val | Gln | Ala | Gly | Leu | Glu | Asn | Asp | Val |
| | | | 260 | | | | | 265 | | | | | 270 | | |

| Thr | Phe | Leu | Gly | Asn | Val | Ile | Asn | Ala | Ser | His | Leu | Leu | Ser | Gln | Tyr |
| | | 275 | | | | | 280 | | | | | 285 | | | |

| Asp | Thr | Phe | Ile | Leu | Ile | Ser | Lys | His | Glu | Gly | Leu | Pro | Ile | Ser | Ile |
| | 290 | | | | | 295 | | | | | 300 | | | | |

| Ile | Glu | Ala | Met | Ala | Thr | Gly | Leu | Pro | Val | Ile | Ala | Ser | His | Val | Gly |
| 305 | | | | | 310 | | | | | 315 | | | | | 320 |

| Gly | Ile | Ser | Glu | Leu | Val | Ala | Asp | Asn | Gly | Ile | Cys | Met | Met | Asn | Asn |
| | | | | 325 | | | | | 330 | | | | | 335 | |

| Gln | Pro | Glu | Thr | Ile | Ala | Lys | Val | Leu | Glu | Lys | Tyr | Leu | Ile | Asp | Ser |
| | | | 340 | | | | | 345 | | | | | 350 | | |

| Asp | Tyr | Ile | Lys | Met | Ser | Asn | Gln | Ser | Arg | Lys | Arg | Tyr | Leu | Glu | Cys |
| | | 355 | | | | | 360 | | | | | 365 | | | |

| Phe | Thr | Glu | Glu | Lys | Met | Ile | Lys | Glu | Val | Glu | Asp | Val | Tyr | Asn | Gly |
| | 370 | | | | | 375 | | | | | 380 | | | | |

| Lys | Ser | Thr | Gln |
| 385 | | | |

<210> SEQ ID NO 58
<211> LENGTH: 1239
<212> TYPE: DNA
<213> ORGANISM: Staphylococcus aureus

<400> SEQUENCE: 58

| atggaaaatc aacacaatag taaattacta acattgttac ttatcggttt agcggttttt | 60 |
| attcagcaat cttcggttat tgccggtgtg aatgtttcta tagctgactt tatcacatta | 120 |
| ctaatattag tttatttact gttttttcgct aaccatttat taaaggcaaa tcattttta | 180 |
| cagttttttca ttatttgta tacatatcgt atgattatta cgctttgttt gctattttt | 240 |
| gatgatttga tatttattac ggttaaggaa gttcttgcat ctacagttaa atatgcattt | 300 |
| gtagtcattt atttctattt agggatgatc atctttaagt taggtaatag caaaaaagtg | 360 |
| atcgttaccct cttatattat aagcagtgtg actataggtc tattttgtat tatagctggt | 420 |
| ttgaacaagt ccccttttact aatgaaattg ttatattttg atgaaatacg ttcaaaagga | 480 |
| ttaatgaatg accctaacta tttcgcgatg acacagatta ttcacattggt acttgcttac | 540 |
| aagtatattc ataattacat attcaaggtc cttgcatgtg gtattttgct atggtcttta | 600 |

-continued

```
actacaacgg ggtctaagac tgcgtttatc atattaatcg tcttagccat ttatttcttt        660
attaaaaagt tatttagtag aaatgcggta agtgttgtga gtatgtcagt gattatgctg        720
atattacttt gttttacctt ttataatatc aactactatt tattccaatt aagcgacctt        780
gatgccttac cgtcattaga tcgaatggcg tctattttg  aagagggctt tgcatcatta        840
aatgatagtg ggtctgagcg aagtgttgta tggataaatg ccatttcagt aattaaatat        900
acactaggtt ttggtgtcgg attagtggat tatgtacata ttggctcgca aattaatggt        960
attttacttg ttgcccataa tacatatttg cagatctttg cggaatgggg catttttattc       1020 ggtgcattat ttatcatatt tatgctttat ttactgtttg aattatttag atttaacatt       1080
tctgggaaaa atgtaacagc aattgttgta atgttgacga tgctgattta cttttttaaca     1140 gtatcattta ataactcaag atatgtcgct tttattttag gaattatcgt ctttattgtt       1200
caatatgaaa agatggaaag ggatcgtaat gaagagtga                              1239
```

<210> SEQ ID NO 59
<211> LENGTH: 412
<212> TYPE: PRT
<213> ORGANISM: Staphylococcus aureus

<400> SEQUENCE: 59

```
Met Glu Asn Gln His Asn Ser Lys Leu Leu Thr Leu Leu Ile Gly
  1               5                  10                  15

Leu Ala Val Phe Ile Gln Gln Ser Ser Val Ile Ala Gly Val Asn Val
                 20                  25                  30

Ser Ile Ala Asp Phe Ile Thr Leu Leu Ile Leu Val Tyr Leu Leu Phe
             35                  40                  45

Phe Ala Asn His Leu Leu Lys Ala Asn His Phe Leu Gln Phe Phe Ile
         50                  55                  60

Ile Leu Tyr Thr Tyr Arg Met Ile Ile Thr Leu Cys Leu Leu Phe Phe
 65                  70                  75                  80

Asp Asp Leu Ile Phe Ile Thr Val Lys Glu Val Leu Ala Ser Thr Val
                 85                  90                  95

Lys Tyr Ala Phe Val Val Ile Tyr Phe Tyr Leu Gly Met Ile Ile Phe
                100                 105                 110

Lys Leu Gly Asn Ser Lys Lys Val Ile Val Thr Ser Tyr Ile Ile Ser
            115                 120                 125

Ser Val Thr Ile Gly Leu Phe Cys Ile Ile Ala Gly Leu Asn Lys Ser
        130                 135                 140

Pro Leu Leu Met Lys Leu Leu Tyr Phe Asp Glu Ile Arg Ser Lys Gly
145                 150                 155                 160

Leu Met Asn Asp Pro Asn Tyr Phe Ala Met Thr Gln Ile Ile Thr Leu
                165                 170                 175

Val Leu Ala Tyr Lys Tyr Ile His Asn Tyr Ile Phe Lys Val Leu Ala
            180                 185                 190

Cys Gly Ile Leu Leu Trp Ser Leu Thr Thr Thr Gly Ser Lys Thr Ala
        195                 200                 205

Phe Ile Ile Leu Ile Val Leu Ala Ile Tyr Phe Phe Ile Lys Lys Leu
    210                 215                 220

Phe Ser Arg Asn Ala Val Ser Val Val Ser Met Ser Val Ile Met Leu
225                 230                 235                 240

Ile Leu Leu Cys Phe Thr Phe Tyr Asn Ile Asn Tyr Tyr Leu Phe Gln
                245                 250                 255

Leu Ser Asp Leu Asp Ala Leu Pro Ser Leu Asp Arg Met Ala Ser Ile
```

-continued

```
                    260                 265                 270
Phe Glu Glu Gly Phe Ala Ser Leu Asn Asp Ser Gly Ser Glu Arg Ser
                275                 280                 285
Val Val Trp Ile Asn Ala Ile Ser Val Ile Lys Tyr Thr Leu Gly Phe
            290                 295                 300
Gly Val Gly Leu Val Asp Tyr Val His Ile Gly Ser Gln Ile Asn Gly
305                 310                 315                 320
Ile Leu Leu Val Ala His Asn Thr Tyr Leu Gln Ile Phe Ala Glu Trp
                325                 330                 335
Gly Ile Leu Phe Gly Ala Leu Phe Ile Ile Phe Met Leu Tyr Leu Leu
            340                 345                 350
Phe Glu Leu Phe Arg Phe Asn Ile Ser Gly Lys Asn Val Thr Ala Ile
                355                 360                 365
Val Val Met Leu Thr Met Leu Ile Tyr Phe Leu Thr Val Ser Phe Asn
            370                 375                 380
Asn Ser Arg Tyr Val Ala Phe Ile Leu Gly Ile Ile Val Phe Ile Val
385                 390                 395                 400
Gln Tyr Glu Lys Met Glu Arg Asp Arg Asn Glu Glu
                405                 410
```

<210> SEQ ID NO 60
<211> LENGTH: 1455
<212> TYPE: DNA
<213> ORGANISM: Staphylococcus aureus

<400> SEQUENCE: 60

```
atgaaaagat ggaaagggat cgtaatgaag agtgattcac taaaagaaaa tattatttat      60
caagggctat accaattgat tagaacgatg acaccactga ttacaatacc cattatttca     120
cgtgcatttg gtcccagtgg tgtgggtatt gtttcatttt ctttcaatat cgtgcaatac     180
ttttttgatga ttgcaagtgt tggcgttcag ttatatttta atagagttat cgcgaagtcc     240
gttaacgaca aacggcaatt gtcacagcag ttttgggata tctttgtcag taaattattt     300
ttagcgttaa cagttttttgc gatgtatatg gtcgtaatta ctatatttat tgatgattac     360
tatcttattt tcctactaca aggaatctat attataggtg cagcactcga tatttcatgg     420
ttttatgctg gaactgaaaa gtttaaaatt cctagcctca gtaatattgt tgcgtctggt     480
attgtattaa gtgtagttgt tattttttgtc aaagatcaat cagatttatc attgtatgta     540
tttactattg ctattgtgac ggtattaaac caattacctt tgtttatcta tttaaaacga     600
tacattagct tgtttcggt taattggata cacgtctggc aattgtttcg ttcgtcatta     660
gcatacttat taccaaatgg acagctcaac ttatatacta gtatttcttg cgttgttctt     720
ggtttagtag gtacataccaa caagttggt atctttttcta acgcatttaa tattttaacg     780
gtcgcaatca taatgattaa tacatttgat cttgtaatga ttccgcgtat taccaaaatg     840
tctatccagc aatcacatag tttaactaaa acgttagcta ataatatgaa tattcaattg     900
atattaacaa tacctatggt ctttggttta attgcaatta tgccatcatt ttatttatgg     960
ttctttggtg aggaattcgc atcaactgtc ccattgatga ccattttagc gatacttgta    1020
ttaatcattc ctttaaatat gttgataagc aggcaatatt tattaatagt gaataaaata    1080
agattatata atgcgtcaat tactattggt gcagtgataa acctagtatt atgtattatt    1140
ttgatatatt tttatggaat ttacggtgct gctattgcgc gtttaattac agagttttttc    1200
ttgctcattt ggcgatttat tgatattact aaaatcaatg tgaagttgaa tattgtaagt    1260
```

```
acgattcaat gtgtcattgc tgctgttatg atgtttattg tgcttggtgt ggtcaatcat    1320
tatttgcccc ctacaatgta cgctacgctg ctattaattg cgattggtat agtagtttat    1380 ctttttattaa tgatgactat gaaaaatcaa tacgtatggc aaatattgag gcatcttcga    1440
cataaaacaa tttaa                                                     1455
```

<210> SEQ ID NO 61
<211> LENGTH: 476
<212> TYPE: PRT
<213> ORGANISM: Staphylococcus aureus

<400> SEQUENCE: 61

```
Met Lys Ser Asp Ser Leu Lys Glu Asn Ile Ile Tyr Gln Gly Leu Tyr
1               5                   10                  15

Gln Leu Ile Arg Thr Met Thr Pro Leu Ile Thr Ile Pro Ile Ile Ser
            20                  25                  30

Arg Ala Phe Gly Pro Ser Gly Val Gly Ile Val Ser Phe Ser Phe Asn
        35                  40                  45

Ile Val Gln Tyr Phe Leu Met Ile Ala Ser Val Gly Val Gln Leu Tyr
    50                  55                  60

Phe Asn Arg Val Ile Ala Lys Ser Val Asn Asp Lys Arg Gln Leu Ser
65                  70                  75                  80

Gln Gln Phe Trp Asp Ile Phe Val Ser Lys Leu Phe Ala Leu Thr
                85                  90                  95

Val Phe Ala Met Tyr Met Val Val Ile Thr Ile Phe Ile Asp Asp Tyr
            100                 105                 110

Tyr Leu Ile Phe Leu Leu Gln Gly Ile Tyr Ile Ile Gly Ala Ala Leu
        115                 120                 125

Asp Ile Ser Trp Phe Tyr Ala Gly Thr Glu Lys Phe Lys Ile Pro Ser
    130                 135                 140

Leu Ser Asn Ile Val Ala Ser Gly Ile Val Leu Ser Val Val Ile
145                 150                 155                 160

Phe Val Lys Asp Gln Ser Asp Leu Ser Leu Tyr Val Phe Thr Ile Ala
                165                 170                 175

Ile Val Thr Val Leu Asn Gln Leu Pro Leu Phe Ile Tyr Leu Lys Arg
            180                 185                 190

Tyr Ile Ser Phe Val Ser Val Asn Trp Ile His Val Trp Gln Leu Phe
        195                 200                 205

Arg Ser Ser Leu Ala Tyr Leu Leu Pro Asn Gly Gln Leu Asn Leu Tyr
    210                 215                 220

Thr Ser Ile Ser Cys Val Val Leu Gly Leu Val Gly Thr Tyr Gln Gln
225                 230                 235                 240

Val Gly Ile Phe Ser Asn Ala Phe Asn Ile Leu Thr Val Ala Ile Ile
                245                 250                 255

Met Ile Asn Thr Phe Asp Leu Val Met Ile Pro Arg Ile Thr Lys Met
            260                 265                 270

Ser Ile Gln Gln Ser His Ser Leu Thr Lys Thr Leu Ala Asn Asn Met
        275                 280                 285

Asn Ile Gln Leu Ile Leu Thr Ile Pro Met Val Phe Gly Leu Ile Ala
    290                 295                 300

Ile Met Pro Ser Phe Tyr Leu Trp Phe Phe Gly Glu Glu Phe Ala Ser
305                 310                 315                 320

Thr Val Pro Leu Met Thr Ile Leu Ala Ile Leu Val Leu Ile Ile Pro
                325                 330                 335
```

-continued

```
Leu Asn Met Leu Ile Ser Arg Gln Tyr Leu Leu Ile Val Asn Lys Ile
            340             345             350

Arg Leu Tyr Asn Ala Ser Ile Thr Ile Gly Ala Val Ile Asn Leu Val
        355             360             365

Leu Cys Ile Ile Leu Ile Tyr Phe Tyr Gly Ile Tyr Gly Ala Ala Ile
    370             375             380

Ala Arg Leu Ile Thr Glu Phe Phe Leu Leu Ile Trp Arg Phe Ile Asp
385             390             395             400

Ile Thr Lys Ile Asn Val Lys Leu Asn Ile Val Ser Thr Ile Gln Cys
            405             410             415

Val Ile Ala Ala Val Met Met Phe Ile Val Leu Gly Val Val Asn His
            420             425             430

Tyr Leu Pro Pro Thr Met Tyr Ala Thr Leu Leu Leu Ile Ala Ile Gly
        435             440             445

Ile Val Val Tyr Leu Leu Leu Met Met Thr Met Lys Asn Gln Tyr Val
    450             455             460

Trp Gln Ile Leu Arg His Leu Arg His Lys Thr Ile
465             470             475
```

STAPHYLOCOCCUS AUREUS GENES AND POLYPEPTIDES

This application is a divisional of and claims priority under 35 U.S.C. § 120 to U.S. application Ser. No. 09/512,255, filed Feb. 24, 2000, now U.S. Pat. No. 6,403,337 which is a continuation-in-part of and claims priority under 35 U.S.C. § 120 to U.S. application Ser. No. 08/781,986, filed Jan. 3, 1997, which is a non-provisional of and claims benefit under 35 U.S.C. § 119(e) of U.S. Provisional Application No. 60/009,861, filed Jan. 5, 1996; U.S. application Ser. No. 09/512,255 is also a continuation-in-part of and claims priority under 35 U.S.C. § 120 to U.S. patent application Ser. No. 08/956,171, filed Oct. 20, 1997 now U.S. Pat. No. 6,593,114, which is a continuation-in-part of and claims priority under 35 U.S.C. § 120 to U.S. patent application Ser. No. 08/781,986, filed Jan. 3, 1997, which is a non-provisional of and claims benefit under 35 U.S.C. § 119(e) of U.S. Provisional Application No. 60/009,861, filed Jan. 5, 1996; U.S. application Ser. No. 09/512,255 is also a continuation-in-part of and claims priority under 35 U.S.C. § 120 to International Application No. PCT/US99/19726, filed Aug. 31, 1999, which claims benefit under 35 U.S.C. § 119(e) of U.S. Provisional Application No. 60/098,964, filed Sep. 1, 1998. Each of the above-listed priority applications is incorporated herein by reference in its entirety.

FIELD OF THE INVENTION

The present invention relates to novel *Staphylococcus aureus* genes (*S. aureus*) nucleic acids and polypeptides. Also provided are vectors, host cells and recombinant methods for producing the same. Further provided are diagnostic methods for detecting *S. aureus* using probes, primers, and antibodies to the *S. aureus* nucleic acids and polypeptides of the present invention. The invention further relates to screening methods for identifying agonists and antagonists of *S. aureus* polypeptide activity and to vaccines using *S. aureus* nucleic acids and polypeptides.

BACKGROUND OF THE INVENTION

The genus Staphylococcus includes at least 20 distinct species. (For a review see Novick, R. P., The Staphylococcus as a Molecular Genetic System in MOLECULAR BIOLOGY OF THE STAPHYLOCOCCI, 1–37 (R. Novick, Ed., VCH Publishers, New York (1990)). Species differ from one another by 80% or more, by hybridization kinetics, whereas strains within a species are at least 90% identical by the same measure.

The species *S. aureus*, a gram-positive, facultatively aerobic, clump-forming cocci, is among the most important etiological agents of bacterial infection in humans, as discussed briefly below.

Human Health and *S. aureus*

*Staphylococcus aureus* is a ubiquitous pathogen. See, e.g., Mims et al., MEDICAL MICROBIOLOGY (Mosby-Year Book Europe Limited, London, UK 1993). It is an etiological agent of a variety of conditions, ranging in severity from mild to fatal. A few of the more common conditions caused by *S. aureus* infection are burns, cellulitis, eyelid infections, food poisoning, joint infections, neonatal conjunctivitis, osteomyelitis, skin infections, surgical wound infection, scalded skin syndrome and toxic shock syndrome, some of which are described further below.

Burns: Burn wounds generally are sterile initially. However, they generally compromise physical and immune barriers to infection, cause loss of fluid and electrolytes and result in local or general physiological dysfunction. After cooling, contact with viable bacteria results in mixed colonization at the injury site. Infection may be restricted to the non-viable debris on the burn surface ("eschar"), it may progress into full skin infection and invade viable tissue below the eschar and it may reach below the skin, enter the lymphatic and blood circulation and develop into septicemia. *S. aureus* is among the most important pathogens typically found in burn wound infections. It can destroy granulation tissue and produce severe septicemia.

Cellulitis: Cellulitis, an acute infection of the skin that expands from a typically superficial origin to spread below the cutaneous layer, most commonly is caused by *S. aureus* in conjunction with *S. pyrogenes*. Cellulitis can lead to systemic infection. In fact, cellulitis can be one aspect of synergistic bacterial gangrene. This condition typically is caused by a mixture of *S. aureus* and microaerophilic Streptococci. It causes necrosis and treatment is limited to excision of the necrotic tissue. The condition often is fatal.

Eyelid infections: *S. aureus* is the cause of styes and of "sticky eye" in neonates, among other eye infections. Typically such infections are limited to the surface of the eye, and may occasionally penetrate the surface with more severe consequences.

Food poisoning: Some strains of *S. aureus* produce one or more of five serologically distinct, heat and acid stable enterotoxins that are not destroyed by digestive process of the stomach and small intestine (enterotoxins A-E). Ingestion of the toxin, in sufficient quantities, typically results in severe vomiting, but not diarrhea. The effect does not require viable bacteria. Although the toxins are known, their mechanism of action is not understood.

Joint infections: *S. aureus* infects bone joints causing diseases such osteomyelitis. See, e.g., R. Cunningham et al., (1996) J. Med. Microbiol. 44:157–164.

Osteomyelitis: *S. aureus* is the most common causative agent of haematogenous osteomyelitis. The disease tends to occur in children and adolescents more than adults and it is associated with non-penetrating injuries to bones. Infection typically occurs in the long end of growing bone, hence its occurrence in physically immature populations. Most often, infection is localized in the vicinity of sprouting capillary loops adjacent to epiphysis growth plates in the end of long, growing bones.

Skin infections: *S. aureus* is the most common pathogen of such minor skin infections as abscesses and boils. Such infections often are resolved by normal host response mechanisms, but they also can develop into severe internal infections. Recurrent infections of the nasal passages plague nasal carriers of *S. aureus*.

Surgical Wound Infections: Surgical wounds often penetrate far into the body. Infection of such wound thus poses a grave risk to the patient. *S. aureus* is the most important causative agent of infections in surgical wounds. *S. aureus* is unusually adept at invading surgical wounds; sutured wounds can be infected by far fewer *S. aureus* cells then are necessary to cause infection in normal skin. Invasion of surgical wound can lead to severe *S. aureus* septicemia. Invasion of the blood stream by *S. aureus* can lead to seeding and infection of internal organs, particularly heart valves and bone, causing systemic diseases, such as endocarditis and osteomyelitis.

Scalded Skin Syndrome: *S. aureus* is responsible for "scalded skin syndrome" (also called toxic epidermal necrosis, Ritter's disease and Lyell's disease). This diseases occurs in older children, typically in outbreaks caused by flowering of *S. aureus* strains produce exfoliation (also called scalded skin syndrome toxin). Although the bacteria initially may infect only a minor lesion, the toxin destroys intercellular connections, spreads epidermal layers and allows the infection to penetrate the outer layer of the skin, producing the desquamation that typifies the diseases. Shedding of the outer layer of skin generally reveals normal skin below, but fluid lost in the process can produce severe injury in young children if it is not treated properly.

Toxic Shock Syndrome: Toxic shock syndrome is caused by strains of *S. aureus* that produce the so-called toxic shock syndrome toxin. The disease can be caused by *S. aureus* infection at any site, but it is too often erroneously viewed exclusively as a disease solely of women who use tampons. The disease involves toxemia and septicemia, and can be fatal.

Nocosomial Infections: In the 1984 National Nocosomial Infection Surveillance Study ("NNIS") *S. aureus* was the most prevalent agent of surgical wound infections in many hospital services, including medicine, surgery, obstetrics, pediatrics and newborns. Other Infections: Other types of infections, risk factors, etc. involving *S. aureus* are discussed in: A. Trilla (1995) J. Chemotherapy 3:37–43; F. Espersen (1995) J. Chemotherapy 3:11–17; D. E. Craven (1995) J. Chemotherapy 3:19–28; J. D. Breen et al. (1995) Infect. Dis. Clin. North Am. 9(1):11–24 (each incorporated herein in their entireties).

Resistance to Drugs of *S. aureus* Strains

Prior to the introduction of penicillin the prognosis for patients seriously infected with *S. aureus* was unfavorable. Following the introduction of penicillin in the early 1940s even the worst *S. aureus* infections generally could be treated successfully. The emergence of penicillin-resistant strains of *S. aureus* did not take long, however. Most strains of *S. aureus* encountered in hospital infections today do not respond to penicillin; although, fortunately, this is not the case for *S. aureus* encountered in community infections.

It is well known now that penicillin-resistant strains of *S. aureus* produce a lactamase which converts penicillin to pencillinoic acid, and thereby destroys antibiotic activity. Furthermore, the lactamase gene often is propagated episomally, typically on a plasmid, and often is only one of several genes on an episomal element that, together, confer multidrug resistance.

Methicillins, introduced in the 1960s, largely overcame the problem of penicillin resistance in *S. aureus*. These compounds conserve the portions of penicillin responsible for antibiotic activity and modify or alter other portions that make penicillin a good substrate for inactivating lactamases. However, methicillin resistance has emerged in *S. aureus*, along with resistance to many other antibiotics effective against this organism, including aminoglycosides, tetracycline, chloramphenicol, macrolides and lincosamides. In fact, methicillin-resistant strains of *S. aureus* generally are multiply drug resistant.

Methicillian-resistant *S. aureus* (MRSA) has become one of the most important nosocomial pathogens worldwide and poses serious infection control problems. Today, many strains are multiresistant against virtually all antibiotics with the exception of vancomycin-type glycopeptide antibiotics.

Recent reports that transfer of vancomycin resistance genes from enterococci to *S. aureus* has been observed in the laboratory sustain the fear that MRSA might become resistant against vancomycin, too, a situation generally considered to result in a public health disaster. MRSA owe their resistance against virtually all β-lactam antibiotics to the expression of an extra penicillin binding protein (PBP) 2a, encoded by the mecA gene. This additional very low affinity pbp, which is found exclusively in resistant strains, appears to be the only pbp still functioning in cell wall peptidoglycan synthesis at β-lactam concentrations high enough to saturate the normal set of *S. aureus* pbp 1–4. In 1983 it was shown by insertion mutagenesis using transposon Tn551 that several additional genes independent of mecA are needed to sustain the high level of methicillin resistance of MRSA. Interruption of these genes did not influence the resistance level by interfering with PBP2a expression, and were therefore called fem (factor essential for expression of methicillin resistance) or aux (auxiliary genes).

Six fem genes (femA-through F) have been described and the minimal number of additional aux genes has been estimated to be more than 10. Interference with femA and femB results in a strong reduction of methicillin resistance, back to sensitivity of strains without PBP2a. The fem genes are involved in specific steps of cell wall synthesis. Consequently, inactivation of fem encoded factors induce β-lactam hypersensitivity in already sensitive strains. Both femA and femB have been shown to be involved in peptidoglycan pentaglycine interpeptide bridge formation. FemA is responsible for the formation of glycines 2 and 3, and FemB is responsible for formation of glycines 4 and 5. *S. aureus* may be involved in the formation of a monoglycine muropeptide precursors. FemC-F influence amidation of the iso-D-glutamic acid residue of the peptidoglycan stem peptide, formation of a minor muropeptide with L-alanine instead of glycine at position 1 of the interpeptide bridge, perform a yet unknown function, or are involved in an early step of peptidoglycan precursors biosynthesis (addition of L-lysine), respectively.

SUMMARY OF THE INVENTION

The present invention provides isolated *S. aureus* polynucleotides and polypeptides shown in Table 1 and SEQ ID NO:1 through SEQ ID NO:61. One aspect of the invention provides isolated nucleic acid molecules comprising or alternatively consisting of polynucleotides having a nucleotide sequence selected from the group consisting of: (a) a nucleotide sequence shown in Table 1; (b) a nucleotide sequence encoding any of the amino acid sequences of the polypeptides shown in Table 1; and (c) a nucleotide sequence complementary to any of the nucleotide sequences in (a) or (b). The invention further provides for fragments of the nucleic acid molecules of (a), (b) & (c) above.

Further embodiments of the invention include isolated nucleic acid molecules that comprise, or alternatively consist of, a polynucleotide having a nucleotide sequence at least 90% identical, and more preferably at least 95%, 96%, 97%, 98% or 99% identical, to any of the nucleotide sequences in (a), (b) or (c) above, or a polynucleotide which hybridizes under stringent hybridization conditions to a polynucleotide in (a), (b) or (c) above. Additional nucleic acid embodiments of the invention relate to isolated nucleic acid molecules comprising polynucleotides which encode the amino acid sequences of epitope-bearing portions of a *S. aureus* polypeptide having an amino acid sequence in Table 1, and including but not limited to those epitope-bearing portions shown in Table 4.

The present invention also relates to recombinant vectors, which include the isolated nucleic acid molecules of the present invention, and to host cells containing the recombinant vectors, as well as to methods of making such vectors and host cells. The present invention further relates to the use of these vectors in the production of *S. aureus* polypeptides or peptides by recombinant techniques.

The invention further provides isolated *S. aureus* polypeptides having an amino acid sequence selected from the group consisting of an amino acid sequence of any of the polypeptides described in Table 1 or fragments thereof.

The polypeptides of the present invention also include polypeptides having an amino acid sequence with at least 70% similarity, and more preferably at least 75%, 80%, 85%, 90%, 95%, 96%, 97%, 98%, or 99% similarity to those described in Table 1, as well as polypeptides having an amino acid sequence at least 70% identical, more preferably at least 75% identical, and still more preferably 80%, 85%, 90%, 95%, 96%, 97%, 98%, or 99% identical to an amino acid sequence of any of the polypeptides described in Table 1 or fragments thereof. Polynucleotides encoding these polypeptides are also encompassed by the invention.

The present invention further provides a vaccine, preferably a multi-component vaccine comprising one or more of the S. aureus polynucleotides or polypeptides described in Table 1, or fragments thereof, together with a pharmaceutically acceptable diluent, carrier, or excipient, wherein the S. aureus polypeptide(s) are present in an amount effective to elicit an immune response to members of the Staphylococcus genus, or at least S. aureus, in an animal. The S. aureus polypeptides of the present invention may further be combined with one or more immunogens of one or more other staphylococcal or non-staphylococcal organisms to produce a multi-component vaccine intended to elicit an immunological response against members of the Staphylococcus genus and, optionally, one or more non-staphylococcal organisms.

The vaccines of the present invention can be administered in a DNA form, e.g., "naked" DNA, wherein the DNA encodes one or more staphylococcal polypeptides and, optionally, one or more polypeptides of a non-staphylococcal organism. The DNA encoding one or more polypeptides may be constructed such that these polypeptides are expressed as fusion proteins.

The vaccines of the present invention may also be administered as a component of a genetically engineered organism or host cell. Thus, a genetically engineered organism or host cell which expresses one or more S. aureus polypeptides may be administered to an animal. For example, such a genetically engineered organism or host cell may contain one or more S. aureus polypeptides of the present invention intracellularly, on its cell surface, or in its periplasmic space. Further, such a genetically engineered organism or host cell may secrete one or more S. aureus polypeptides. The vaccines of the present invention may also be co-administered to an animal with an immune system modulator (e.g., CD86 and GM-CSF).

The invention also provides a method of inducing an immunological response in an animal to one or more members of the Staphylococcus genus, preferably one or more isolates of the S. aureus species, comprising administering to the animal a vaccine as described above.

The invention further provides a method of inducing a protective immune response in an animal, sufficient to prevent, attenuate, or control an infection by members of the Staphylococcus genus, preferably at least S. aureus species, comprising administering to the animal a composition comprising one or more of the polynucleotides or polypeptides described in Table 1, or fragments thereof (e.g., including, but not limited to, fragments which comprise the epitopes shown in Table 4). Further, these polypeptides, or fragments thereof, may be conjugated to another immunogen and/or administered in admixture with an adjuvant.

The invention further relates to antibodies elicited in an animal by the administration of one or more S. aureus polypeptides of the present invention and to methods for producing such antibodies and fragments thereof. The invention further relates to recombinant antibodies and fragments thereof and to methods for producing such antibodies and fragments thereof.

The invention also provides diagnostic methods for detecting the expression of the polynucleotides and polypeptides of Table 1 by members of the Staphylococcus genus in a biological or environmental sample. One such method involves assaying for the expression of a polynucleotide encoding S. aureus polypeptides in a sample from an animal. This expression may be assayed either directly (e.g., by assaying polypeptide levels using antibodies elicited in response to amino acid sequences described in Table 1 or fragments thereof) or indirectly (e.g., by assaying for antibodies having specificity for amino acid sequences described in Table 1 or fragments thereof). The expression of polynucleotides can also be assayed by detecting the nucleic acids of Table 1. An example of such a method involves the use of the polymerase chain reaction (PCR) to amplify and detect Staphylococcus nucleic acid sequences in a biological or environmental sample.

The invention also includes a kit for analyzing samples for the presence of members of the Staphylococcus genus in a biological or environmental sample. In a general embodiment, the kit includes at least one polynucleotide probe containing a nucleotide sequence that will specifically hybridize with a S. aureus nucleic acid molecule of Table 1 and a suitable container. In a specific embodiment, the kit includes two polynucleotide probes defining an internal region of the S. aureus nucleic acid molecule of Table 1, where each probe has one strand containing a 31'mer-end internal to the region. In a further embodiment, the probes may be useful as primers for polymerase chain reaction amplification.

The present invention also relates to nucleic acid probes having all or part of a nucleotide sequence described in Table 1 which are capable of hybridizing under stringent conditions to Staphylococcus nucleic acids. The invention further relates to a method of detecting one or more Staphylococcus nucleic acids in a biological sample obtained from an animal, said one or more nucleic acids encoding Staphylococcus polypeptides, comprising: (a) contacting the sample with one or more of the above-described nucleic acid probes, under conditions such that hybridization occurs, and (b) detecting hybridization of said one or more probes to the Staphylococcus nucleic acid present in the biological sample.

By "biological sample" is intended any biological sample obtained from an individual, body fluid, cell line, tissue culture, or other source which contains S. aureus polypeptides or polynucleotides of the invention. As indicated, biological samples include body fluids (such as semen, lymph, sera, plasma, urine, synovial fluid and spinal fluid) which contain the S. aureus polypeptides or polynucleotides of the invention, and tissue sources found to contain the expressed S. aureus polypeptides shown in Table 1. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which S. aureus polynucleotides and/or polypeptides of the invention are attached to a solid support. In one exemplary method, the support may be a "gene chip" or a "biological chip" as described in U.S. Pat. Nos. 5,837,832, 5,874,219, and 5,856, 174. Further, such a gene chip with *S. aureus* polynucleotides of Table 1 attached may be used to diagnose *S. aureus* infection in a mammal, preferably a human. The US Patents referenced above are incorporated herein by reference in their entirety.

DETAILED DESCRIPTION

The present invention relates to recombinant antigenic *S. aureus* polypeptides and fragments thereof. The invention also relates to methods for using these polypeptides to produce immunological responses and to confer immunological protection to disease caused by members of the genus Staphylococcus. The invention further relates to nucleic acid sequences which encode antigenic *S. aureus* polypeptides and to methods for detecting Staphylococcus nucleic acids and polypeptides in biological samples. The invention also relates to Staphylococcus specific antibodies and methods for detecting such antibodies produced in a host animal.

Definitions

The following definitions are provided to clarify the subject matter which the inventors consider to be the present invention.

As used herein, the phrase "pathogenic agent" means an agent which causes a disease state or affliction in an animal. Included within this definition, for examples, are bacteria, protozoans, fungi, viruses and metazoan parasites which either produce a disease state or render an animal infected with such an organism susceptible to a disease state (e.g., a secondary infection). Further included are species and strains of the genus Staphylococcus which produce disease states in animals.

As used herein, the term "organism" means any living biological system, including viruses, regardless of whether it is a pathogenic agent.

As used herein, the term "Staphylococcus" means any species or strain of bacteria which is members of the genus Staphylococcus regardless of whether they are known pathogenic agents.

As used herein, the phrase "one or more *S. aureus* polypeptides of the present invention" means the amino acid sequence of one or more of the *S. aureus* polypeptides disclosed in Table 1. These polypeptides may be expressed as fusion proteins wherein the *S. aureus* polypeptides of the present invention are linked to additional amino acid sequences which may be of Staphylococcal or non-Staphylococcal origin. This phrase further includes fragments of the *S. aureus* polypeptides of the present invention.

As used herein, the phrase "full-length amino acid sequence" and "full-length polypeptide" refer to an amino acid sequence or polypeptide encoded by a full-length open reading frame (ORF). For purposes of the present invention, polynucleotide ORFs in Table 1 are defined by the corresponding polypeptide sequences of Table 1 encoded by said polynucleotide. Therefore, a polynucleotide ORF is defined at the 5' end by the first base coding for the initiation codon of the corresponding polypeptide sequence of Table 1 and is defined at the 3' end by the last base of the last codon of said polypeptide sequence. As is well known in the art, initiation codons for bacterial species may include, but are not limited to, those encoding Methionine, Valine, or Leucine. As discussed below for polynucleotide fragments, the ORFs of the present invention may be claimed by a 5' and 3' position of a polynucleotide sequence of the present invention wherein the first base of said sequence is position 1.

As used herein, the phrase "truncated amino acid sequence" and "truncated polypeptide" refer to a subsequence of a full-length amino acid sequence or polypeptide. Several criteria may also be used to define the truncated amino acid sequence or polypeptide. For example, a truncated polypeptide may be defined as a mature polypeptide (e.g., a polypeptide which lacks a leader sequence). A truncated polypeptide may also be defined as an amino acid sequence which is a portion of a longer sequence that has been selected for ease of expression in a heterologous system but retains regions which render the polypeptide useful for use in vaccines (e.g., antigenic regions which are expected to elicit a protective immune response).

Additional definitions are provided throughout the specification.

Explanation of Table 1

Table 1 lists the full length *S. aureus* polynucleotide and polypeptide sequences of the present invention. Each polynucleotide and polypeptide sequence is proceeded by a gene identifier. Each polynucleotide sequence is followed by at least one polypeptide sequence encoded by said polynucleotide. For some of the sequences of Table 1, a known biological activity and the name of the homolog with similar activity is listed after the gene sequence identifier.

Explanation of Table 2

Table 2 lists accession numbers for the closest matching sequences between the polypeptides of the present invention and those available through GenBank and GeneSeq databases. These reference numbers are the database entry numbers commonly used by those of skill in the art, who will be familar with their denominations. The descriptions of the nomenclature for GenBank are available from the National Center for Biotechnology Information. Column 1 lists the polynucleotide sequence of the present invention. Column 2 lists the accession number of a "match" gene sequence in GenBank or GeneSeq databases. Column 3 lists the description of the "match" gene sequence. Columns 4 and 5 are the high score and smallest sum probability, respectively, calculated by BLAST. Polypeptides of the present invention that do not share significant identity/similarity with any polypeptide sequences of GenBank and GeneSeq are not represented in Table 2. Polypeptides of the present invention that share significant identity/similarity with more than one of the polypeptides of GenBank and GeneSeq may be represented more than once.

Explanation of Table 3.

The *S. aureus* polypeptides of the present invention may include one or more conservative amino acid substitutions from natural mutations or human manipulation as indicated in Table 3. Changes are preferably of a minor nature, such as conservative amino acid substitutions that do not significantly affect the folding or activity of the protein. Residues from the following groups, as indicated in Table 3, may be substituted for one another: Aromatic, Hydrophobic, Polar, Basic, Acidic, and Small, Explanation of Table 4

Table 4 lists residues comprising antigenic epitopes of antigenic epitope-bearing fragments present in each of the *S. aureus* polypeptides described in Table 1 as predicted by the inventors using the algorithm of Jameson and Wolf, (1988) Comp. Appl. Biosci. 4:181–186. The Jameson-Wolf antigenic analysis was performed using the computer program PROTEAN (Version 3.11 for the Power MacIntosh, DNASTAR, Inc., 1228 South Park Street Madison, Wis.). *S. aureus* polypeptides shown in Table 1 may possess one or more antigenic epitopes comprising residues described in Table 4. It will be appreciated that depending on the analytical criteria used to predict antigenic determinants, the exact address of the determinant may vary slightly. The residues and locations shown and described in Table 4 correspond to the amino acid sequences for each polypeptide sequence shown in Table 1 and in the Sequence Listing. Polypeptides of the present invention that do not have antigenic epitopes recognized by the Jameson-Wolf algorithm are not represented in Table 2.

Nucleic Acid Molecules

Sequenced S. aureus genomic DNA was obtained from the S. aureus strain ISP3. S. aureus strain ISP3, has been deposited at the American Type Culture Collection, as a convenience to those of skill in the art. The S. aureus strain ISP3 was deposited on Apr. 7, 1998 at the ATCC, 10801 University Blvd. Manassas, Va. 20110-2209, and given accession number 202108. As discussed elsewhere herein, polynucleotides of the present invention readily may be obtained by routine application of well known and standard procedures for cloning and sequencing DNA. A wide variety of S. aureus strains can be used to prepare S. aureus genomic DNA for cloning and for obtaining polynucleotides and polypeptides of the present invention. A wide variety of S. aureus strains are available to the public from recognized depository institutions, such as the American Type Culture Collection (ATCC). It is recognized that minor variations is the nucleic acid and amino acid sequence may be expected from S. aureus strain to strain. The present invention provides for genes, including both polynucleotides and polypeptides, of the present invention from all the S. aureus strains.

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. By "nucleotide sequence" of a nucleic acid molecule or polynucleotide is intended to mean either a DNA or RNA sequence. Using the information provided herein, such as the nucleotide sequence in Table 1, a nucleic acid molecule of the present invention encoding a S. aureus polypeptide may be obtained using standard cloning and screening procedures, such as those for cloning DNAs using genomic DNA as starting material. See, e.g., Sambrook et al. MOLECULAR CLONING: A LABORATORY MANUAL (Cold Spring Harbor, N.Y. 2nd ed. 1989); Ausubel et al., CURRENT PROTOCOLS IN MOLECULAR BIOLOGY (John Wiley and Sons, N.Y. 1989). Illustrative of the invention, the nucleic acid molecule described in Table 1 was discovered in a DNA library derived from a S. aureus ISP3 genomic DNA.

TABLE 1

Nucleotide and Amino Acid Sequences of S. aureus Genes.

SEQ ID NO:1

>HGS001, fabH, 3-oxoacyl-acyl-carrier protein synthase,
ATTAACTAGTCAATATTCCTACCTCTGACTTGAGTTTAAAAAGTAATCTATGTTAAATTAATACCTGGTATTAAAAATTT

TATTAAGAAGGTGTTCAACTATGAACGTGGGTATTAAAGGTTTTGGTGCATATGCGCCAGAAAAGATTATTGACAATGCC

TATTTTGAGCAATTTTTAGATACATCTGATGAATGGATTTCTAAGATGACTGGAATTAAAGAAAGACATTGGGCAGATGA

TGATCAAGATACTTCAGATTTAGCATATGAAGCAAGTTTAAAAGCAATCGCTGACGCTGGTATTCAGCCCGAAGATATAG

ATATGATAATTGTTGCCACAGCAaCTGGaGATATGCCATTTCCAACTGTCGCAAATATGTTGCAAGAACGTTTAGGGACG

GGCAAAGTTGCCTCTATGGATCAACTTGCAGCATGTTCTGGATTTATGTATTCAATGATTACAGCTAAACAATATGTTCA

ATCTGGAGATTATCATAACATTTTAGTTGTCGGTGCAGATAAATTATCTAAAATAACAGATTTAACTGACCGTTCTACTG

CAGTTCTATTTGGAGATGGTGCAGGTGCGGTTATCATCGGTGAAGTTTCAGATGGCAGAGGTATTATAAGTTATGAAATG

GGTTCTGATGGCACAGGTGGTAAACATTTATATTTAGATAAAGATACTGGTAAACTGAAAATGAATGGTCGAGAAGTATT

TAAATTTGCTGTTAGAATTATGGGTGATGCATCAACACGTGTAGTTGAAAAAGCGAATTTAACATCAGATGATATAGATT

TATTTATTCCTCATCAAGCTAATATTAGAATTATGGAATCAGCTAGAGAACGCTTAGGTATTTCAAAAGACAAAATGAGT

GTTTCTGTAAATAAATATGGAAATACTTCAGCTGCGTCAATACCTTTAAGTATCGATCAAGAATTAAAAAATGGTAAAAT

CAAAGATGATGATACAATTGTTCTTGTCGGATTCGGTGGCGGCCTAACTTGGGGCGCAATGACAATAAAATGGGGAAAAT

AGGAGGATAACGAATGAGTCAAAATAAAAGAGTAGTTATTACAGGTATGGGA

SEQ ID NO:2

>HGS001, FabH, 3-oxoacyl-acyl-carrier protein synthase,
MNVGIKGFGAYAPEKIIDNAYFEQFLDTSDEWISKMTGIKERHWADDDQDTSDLAYEASLKAIADAGIQPEDIDMIIVAT

ATGDMPFPTVANMLQERLGTGKVASMDQLAACSGFMYSMITAKQYVQSGDYHNILVVGADKLSKITDLTDRSTAVLFGDG

AGAVIIGEVSDGRGIISYEMGSDGTGGKHLYLDKDTGKLKMNGREVFKFAVRIMGDASTRVVEKANLTSDDIDLFIPHQA

NIRIMESARERLGISKDKMSVSVNKYGNTSAASIPSIDQELKNGKIKDDDTIVLVGFGGGLTWGAMTIKWGK

TABLE 1-continued

SEQ ID NO:3
>HGS002, murB, UDP-N-acetylenolpyruvoylglucosamine reductase,
ATACTAATTCTAATACTTTCTTTTCAATTTTCGCAAATGAATTTTAAAATTGGTATAATACTATATGATATTAAAGACAT

GAGAAAGGATGTACTGAGAAGTGATAAATAAAGACATCTATCAAGCTTTACAACAACTTATCCCAAATGAAAAAATTAAA

GTTGATGAACCTTTAAAACGATACACTTATACTAAAACAGGTGGTAATGCCGACTTTTACATTACCCCTACTAAAAATGA

AGAAGTACAAGCAGTTGTTAAATATGCCTATCAAAATGAGATTCCTGTTACATATTTAGGAAATGGCTCAAATATTATTA

TCCGTGAAGGTGGTATTCGCGGTATTGTAATTAGTTTATTATCACTAGATCATATCGAAGTATCTGATGATGCGATAATA

GCCGGTAGCGGCGCTGCAATTATTGATGTCTCACGTGTTGCTCGTGATTACGCACTTACTGGCCTTGAATTTGCATGTGG

TATTCCAGGTTCAATTGGTGGTGCAGTGTATATGAATGCTGGCGCTTATGGTGGCGAAGTTAAAGATTGTATAGACTATG

CGCTTTGCGTAAACGAACAAGGCTCGTTAATTAAACTTACAACAAAAGAATTAGAGTTAGATTATCGTAATAGCATTATT

CAAAAAGAACACTTAGTTGTATTAGAAGCTGCATTTACTTTAGCTCCTGGTAAAATGACTGAAATACAAGCTAAAATGGA

TGATTTAACAGAACGTAGAGAATCTAAACAACCTTTAGAGTATCCTTCATGTGGTAGTGTATTCCAAAGACCGCCTGGTC

ATTTTGCAGGTAAATTGATACAAGATTCTAATTTGCAAGGTCACCGTATTGGCGGCGTTGAAGTTTCAACCAAACACGCT

GGTTTTATGGTAAATGTAGACAATGGAACTGCTACAGATTATGAAAACCTTATTCATTATGTACAAAAGACCGTCAAAGA

AAAATTTGGCATTGAATTAAATCGTGAAGTTCGCATTATTGGTGAACATCCAAAGGAATCGTAAGTTAAGGAGCTTTGTC

TATGCCTAAAGTTTATGGTTCATTAATCGATACT

SEQ ID NO:4
>HSGS002, MurB, UDP-N-acetylenolpyruvoylglucosamine reductase,
VINKDIYQALQQLIPNEKIKVDEPLKRYTYTKTGGNADFYITPTKNEEVQAVVKYAYQNEIPVTYLGNGSNIIIREGGIR

GIVISLLSLDHIEVSDDAIIAGSGAAIIDVSRVARDYALTGLEFACGIPGSIGGAVYMNAGAYGGEVKDCIDYALCVNEQ

GSLIKLTTKELELDYRNSIIQKEHLVVLEAAFTLAPGKMTEIQAKMDDLTERRESKQPLEYPSCGSVFQRPPGHFAGKLI

QDSNLQGHRIGGVEVSTKHAGFMVNVDNGTATDYENLIHYVQKTVKEKFGIELNREVRIIGEHPKES

SEQ ID NO:5
>HGS003, fabI, enoyl-acyl-carrier protein reductase,
AATAGTGTTAAAATGTATTGACGAATAAAAAGTTAGTTAAAACTGGGATTAGATATTCTATCCGTTAAATTAATTATTAT

AAGGAGTTATCTTACATGTTAAATCTTGAAAACAAAACATATGTCATCATGGGAATCGCTAATAAGCGTAGTATTGCTTT

TGGTGTCGCTAAAGTTTTAGATCAATTAGGTGCTAAATTAGTATTTACTTACCGTAAAGAACGTAGCCGTAAAGAGCTTG

AAAAATTATTAGAACAATTAAATCAACCAGAAGCGCACTTATATCAAATTGATGTTCAAAGCGATGAAGAGGTTATTAAT

GGTTTTGAGCAAATTGGTAAAGATGTTGGCAATATTGATGGTGTATATCATTCAATCGCATTTGCTAATATGGAAGACTT

ACGCGGACGCTTTTCTGAAACTTCACGTGAAGGCTTCTTGTTAGCTCAAGACATTAGTTCTTACTCATTAACAATTGTGG

CTCATGAAGCTAAAAAATTAATGCCAGAAGGTGGTAGCATTGTTGCAACAACATATTTAGGTGGCGAATTCGCAGTTCAA

AACTATAATGTGATGGGTGTTGCTAAAGCGAGCTTAGAAGCAAATGTTAAATATTTAGCATTAGACTTAGGTCCAGATAA

TATTCGCGTTAATGCAATTTCAGCTAGTCCAATCCGTACATTAAGTGCAAAAGGTGTGGGTGGTTTCAATACAATTCTTA

AAGAAATCGAAGAGCGTGCACCTTTAAAACGTAATGTTGATCAAGTAGAAGTAGGTAAAACTGCGGCTTACTTATTAAGT

GATTTATCAAGTGGCGTTACAGGTGAAAATATTCATGTAGATAGCGGATTCCACGCAATTAAATAATATCATTCAACAGC

TTTGTTCACGTTATTATATATGTGAGCAAAGCTTTT

SEQ ID NO:6
>HGS003, FabI, enonyl-acyl-carrier protein reductase,
MLNLENKTYVIMGIANKRSIAFGVAKVLDQLGAKLVFTYRKERSRKELEKLLEQLNQPEAHLYQIDVQSDEEVINGFEQI

GKDVGNIDGVYHSIAFANMEDLRGRFSETSREGFLLAQDISSYSLTIVAHEAKKLMPEGGSIVATTYLGGEFAVQNYNVM

GVAKASLEANVKYLALDLGPDNIRVNAISASPIRTLSAKGVGGFNTILKEIEERAPLKRNVDQVEVGKTAAYLLSDLSSG

VTGENIHVDSGFHAIK

SEQ ID NO:7
>HGS004, murA, UDP-N-acetylglucosamine 1-carboxyvinyltransferase,

TABLE 1-continued

```
TAAAATAATTTTAAAATAGGGAAATGTAAAGTAATAGGAGTTCTAAGTGGAGGATTTACGATGGATAAAATAGTAATCAA
AGGTGGAAATAAATTAACGGGTGAAGTTAAAGTAGAAGGTGCTAAAAATGCAGTATTACCAATATTGACAGCATCTTTAT
TAGCTTCTGATAAACCGAGCAAATTAGTTAATGTTCCAGCTTTAAGTGATGTAGAAACAATAAATAATGTATTAACAACT
TTAAATGCTGACGTTACATACAAAAAGGACGAAAATGCTGTTGTCGTTGATGCAACAAAGACTCTAAATGAAGAGGCACC
ATATGAATATGTTAGTAAAATGCGTGCAAGTATTTTAGTTATGGGACCTCTTTTAGCAAGACTAGGACATGCTATTGTTG
CATTGCCTGGTGGTTGTGCAATTGGAAGTAGACCGATTGAGCAACACATTAAAGGTTTTGAAGCTTTAGGCGCAGAAATT
CATCTTGAAAATGGTAATATTTATGCTAATGCTAAAGATGGATTAAAAGGTACATCAATTCATTTAGATTTTCCAAGTGT
AGGAGCAACACAAAATATTATTATGGCAGCATCATTAGCTAAGGGTAAGACTTTAATTGAAAATGCAGCTAAAGAACCTG
AAATTGTCGATTTAGCAAACTACATTAATGAAATGGGTGGTAGAATTACTGGTGCTGGTACAGACACAATTACAATCAAT
GGTGTAGAATCATTACATGGTGTAGAACATGCTATCATTCCAGATAGAATTGAAGCAGGCACATTACTAATCGCTGGTGC
TATAACGCGTGGTGATATTTTTGTACGTGGTGCAATCAAAGAACATATGGCGAGTTTAGTCTATAAACTAGAAGAAATGG
GCGTTGAATTGGACTATCAAGAAGATGGTATTCGTGTACGTGCTGAAGGGGAATTACAACCTGTAGACATCAAAACTCTA
CCACATCCTGGATTCCCGACTGATATGCAATCACAAATGATGGCATTGTTATTAACGGCAAATGGTCATAAAGTCGTAAC
CGAAACTGTTTTTGAAAACCGTTTTATGCATGTTGCAGAGTTCAAACGTATGAATGCTAATATCAATGTAGAAGGTCGTA
GTGCTAAACTTGAAGGTAAAAGTCAATTGCAAGGTGCACAAGTTAAAGCGACTGATTTAAGAGCAGCAGCCGCCTTAATT
TTAGCTGGATTAGTTGCTGATGGTAAAACAAGCGTTACTGAATTAACGCACCTAGATAGAGGCTATGTTGACTTACACGG
TAAATTGAAGCAATTAGGTGCAGACATTGAACGTATTAACGATTAATTCAGTAAATTAATATAATGGAGGATTTCAACCA
TGGAAACAATTTTTGA
```

SEQ ID NO:8
>HGS004, MurA, UDP-N-acetylglucosamine 1-carboxyvinyltransferase,
```
MDKIVIKGGNKLTGEVKVEGAKNAVLPILTASLLASDKPSKLVNVPALSDVETINNVLTTLNADVTYKKDENAVVVDATK
TLNEEAPYEYVSKMRASILVMGPLLARLGHAIVALPGGCAIGSRPIEQHIKGFEALGASIHLENGNIYANAKDGLKGTSI
HLDFPSVGATQNIIMAASLAKGKTLIENAAKEPEIVDLANYINEMGGRITGAGTDTITINGVESLHGVEHAIIPDRIEAG
TLLIAGAITRGDIFVRGAIKEHMASLVYKLEEMGVELDYQEDGIRVRAEGELQPVDIKTLPHPGFPTDMQSQMMALLLTA
NGHKVVTETVFENRFMHVAEFKRMNANINVEGRSAKLEGKSQLQGAQVKATDLRAAAALILAGLVADGKTSVTELTHLDR
GYVDLHGKLKQLGADIERIND
```

SEQ ID NO:9
>HGS005, rho, transcriptional terminator Rho,
```
TTCATGTATTTAAAAGGTTGGGGATTAGCATAATGGGATTGTGCTAGCACAGTTATTTATGCATTGTCATGCCTATCTAT
TACTTACTAACTAAAAAATAATGAAATGGGTGTAAACTATATGCCTGAAAGAGAACGTACATCTCCTCAGTATGAATCAT
TCCACGAATTGTACAAGAACTATACTACCAAGGAACTCACTCAAAAAGCTAAAACTCTTAAGTTGACGAACCATAGTAAA
TTAAATAAAAAAGAACTTCTTCTAGCTATTATGGAAGCACAAATGGAAAAAGATGGTAACTATTATATGGAAGGTATCTT
AGATGATATACAACCAGGTGGTTATGGTTTTTTAAGAACAGTGAACTATTCTAAAGGGGAAAAAGATATTTATATATCTG
CTAGCCAAATTCGTCGTTTTGAAATTAAACGTGGGGATAAAGTAACTGGGAAAGTTAGAAAACCTAAAGATAACGAAAAA
TATTATGGCTTATTACAAGTTGACTTTGTCAATGACCATAACGCAGAAGAAGTGAAGAAACGTCCGCATTTCCAAGCTTT
GACACCACTTTATCCAGATGAGCGTATTAAATTAGAGACAGAAATACAAAATTATTCAACGCGCATCATGGATTTAGTAA
CACCGATTGGTTTAGGTCAACGTGGTTTAATAGTGGCGCCACCTAAAGCAGGTAAAACATCGTTATTAAAAGAAATAGCG
AATGCAATCAGTACGAACAAACCAGATGCAAAGCTATTTATTTTGTTAGTTGGCGAGCGTCCTGAAGAGGTAACAGATTT
AGAACGCTCAGTAGAAGCTGCTGAAGTCGTTCATTCAACGTTTGACGAACCACCAGAACACCATGTTAAAGTAGCTGAAT
TATTACTTGAACGTGCAAAGCGTTTAGTAGAAATTGGGGAAGATGTCATTATTTTAATGGATTCTATAACGAGATTAGCA
CGCGCTTATAACTTAGTTATTCCACCAAGTGGTCGTACATTATCAGGTGGTTTAGATCCTGCATCTTTACACAAACCAAA
AGCATTCTTCGGTGCAGCGAGAAATATTGAAGCGGGTGGAAGTTTAACAATACTTGCAACTGCATTAGTTGATACGGGTT
```

TABLE 1-continued

```
CACGTATGGACGATATGATTTACGAAGAATTTAAAGGAACAGGTAACATGGAGTTACATTTAGATCGTAAATTGTCTGAA
CGTCGTATCTTCCCTGCAATTGATATTGGCAGAAGTTCAACGCGTAAAGAAGAATTGTTGATAAGTAAATCTGAATTAGA
CACATTATGGCAATTAAGAAATCTATTCACTGACTCAACTGACTTTACTGAAAGATTTATTCGCAAACTTAAAAGGTCTA
AGAATAATGAAGATTTCTTCAAGCAGCTACAAAAGTCTGCAGAAGAAAGTACTAAAACGGGTCGACCTATAATTTAATAA
ACATTATATAGGGGCTTGCGTTTTGAATTAATTACCTTTATAATTACACAGTATTGGGTAAAAACTCACAAATAACTCTG
TTCCAGATGGTTCAGGG
```

SEQ ID NO:10

>HGS005, Rho, transcriptional terminator Rho,
```
MPERERTSPQYESFHELYKNYTTKELTQKAKTLKLTNHSKLNKKELVLAIMEAQMEKDGNYYMEGILDDIQPGGYGFLRT
VNYSKGEKDIYISASQIRRFEIKRGDKVTGKVRKPKDNEKYYGLLQVDFVNDHNAEEVKKRPHPQALTPLYPDERIKLET
EIQNYSTRIMDLVTPIGLGQRGLIVAPPKAGKTSLLKEIANAISTNKPDAKLFILLVGERPEEVTDLERSVEAAEVVHST
FDEPPEHHVKVAELLLERAKRLVEIGEDVIILMDSITRLARAYNLVIPPSGRTLSGGLDPASLHKPKAFFGAARNIEAGG
SLTILATALVDTGSRMDDMIYEEFKGTGNMELHLDRKLSERRIFPAIDIGRSSTRKEELLISKSELDTLWQLRNLFTDST
DFTERFIRKLKRSKNNEDFFKQLQKSAEESTKTGRPII
```

SEQ ID NO:11

>HGS006, rnpA, ribonuclease P protein component,
```
GATCTTTTTTTTCGTTTAAATTAAGAATAAATAGAAATTTATGTTATAAGCTCAATAGAAGTTTAAATATAGCTTCAATA
AAAACGATAATAAGCGAGTGATGTTATTGGAAAAAGCTTACCGAATTAAAAAGAATGCAGATTTTCAGAGAATATATAAA
AAAGGTCATTCTGTAGCCAACAGACAATTTGTTGTATACACTTGTAATAATAAAGAAATAGACCATTTTCGCTTAGGTAT
TAGTGTTTCTAAAAAACTAGGTAATGCAGTGTTAAGAAACAAGATTAAAAGAGCAATACGTGAAAATTTCAAAGTACATA
AGTCGCATATATTGGCCAAAGATATTATTGTAATAGCAAGACAGCCAGCTAAAGATATGACGACTTTACAAATACAGAAT
AGTCTTGAGCACGTACTTAAAATTGCCAAAGTTTTTAATAAAAAGATTAAGTAAGGATAGGGTAGGGGAAGGAAAACATT
AACCACTCAACACATCCCGAAGTCTTACCTCAGACAAACGTAAGACTGACCTTAGGGTTATAATAACTTACTTT
```

SEQ ID NO:12

>HGSPP6, RnpA, ribonuclease P protein component,
```
MLLEKAYRIKKNADFQRIYKKGHSVANRQFVVYTCNNKEIDHFRLGISVSKKLGNAVLRNKIKRAIRENFKVHKSHILAD
DIIVIARQPAKDMTTLQIQNSLEHVLKIAKVFNKKIK
```

SEQ ID NO:13

>HGS007M, dnaB, replicative DNA helicase,
```
CAGCAAAAACTGGTGAAGGTGGTAAATTGTTTGGGTCAGTAAGTACAAAACAAATTGCCGAAGCACTAAAAGCACAACAT
GATATTAAAATTGATAAACGTAAAATGGATTTACCAAATGGAATTCATTCCCTAGGATATACGAATGTACCTGTTAAATT
AGATAAAGAAGTTGAAGGTACAATTCGCGTACACACAGTTGAACAATAAAGTTGGATTGAAATAAGAGGTGTAACCATTC
ATGGATAGAATGTATGAGCAAAATCAAATGCCGCATAACAATGAAGCTGAACAGTCTGTCTTAGGTTCAATTATTATAGA
TCCAGAATTGATTAATACTACTCAGGAAGTTTTGCTTCCTGAGTCGTTTTATAGGGGTGCCCATCAACATATTTTCCGTG
CAATGATGCACTTAAATGAAGATAATAAAGAAATTGATGTTGTAACATTGATGGATCAATTATCGACGGAAGGTACGTTG
AATgAAGCGGGTGGCCCGCAATATCTTGCAGAGTTATCTACAAATGTACCAACGACGCGAAATGTTCAGTATTATACTGA
TATCGTTTCTAAGCATGCATTAAAACGTAGATTGATTCAAACTGCAGATAGTATTGCCAATGATGGATATAATGATGAAC
TTGAACTAGATGCGATTTTAAGTGATGCAGAACGTCGAATTTTAGAGCTATCATCTTCTCGTGAAAGCGATGGCTTTAAA
GACATTCGAGACGTCTTAGGACAAGTGTATGAAACAGCTGAAGAGCTTGATCAAAATAGTGGTCAAACACCAGGTATACC
TACAGGATATCGAGATTTAGACCAAATGACAGCAGGGTTCAACCGAAATGATTTAATTATCCTTGCAGCGCGTCCATCTG
TAGGTAAGACTGCGTTCGCACTTAATATTGCACAAAAAGTTGCAACGCATGAAGATATGTATACAGTTGGTATTTTCTCG
CTAGAGATGGGTGCTGATCAGTTAGCCACACGTATGATTTGTAGTTCTGGAAATGTTGACTCAAACCGCTTAAGAACGGG
TACTATGACTGAGGAAGATTGGAGTCGTTTTACTATAGCGGTAGGTAAATTATCACGTACGAAGATTTTTATTGATGATA
```

TABLE 1-continued

```
CACCGGGTATTCGAATTAATGATTTACGTTCTAAATGTCGTCGATTAAAGCAAGAACATGGCTTAGACATGATTGTGATT
GACTACTTACAGTTGATTCAAGGTAGTGGTTCACGTGCGTCCGATAACAGACAACAGGAAGTTTCTGAAATCTCTCGTAC
ATTAAAAGCATTAGCCCGTGAATTAAAATGTCCAGTTATCGCATTAAGTCAGTTATCTCGTGGTGTTGAACAACGACAAG
ATAAACGTCCAATGATGAGTGATATTCGTGAATCTGGTTCGATTGAGCAAGATGCCGATATCGTTGCATTCTTATACCGT
GATGATTACTATAACCGTGGCGGCGATGAAGATGATGACGATGATGGTGGTTTCGAGCCACAAACGAATGATGAAAACGG
TGAAATTGAAATTATCATTGCTAAGCAACGTAACGGTCCAACAGGCACAGTTAAGTTACATTTTATGAAACAATATAATA
AATTTACCGATATCGATTATGCACATGCAGATATGATGTAAAAAAGTTTTTCCGTACAATAATCATTAAGATGATAAAAT
TGTACGGTTTTTATTTTGTTCTGAACGGGTTG
```

SEQ ID NO:14
>HGS007M, DnaB, replicative DNA helicase,
```
MDRMYEQNQMPHNNEAEQSVLGSIIIDPELINTTQEVLLPESFYRGAHQHIFRAMMHLNEDNKEIDVVTLMDQLSTEGTL
NEAGGPQYLAELSTNVPTTRNVQYYTDIVSKHALKRRLIQTADSIANDGYNDELELDAILSDAERRILELSSSRESDGFK
DIRDVLGQVYETAEELDQNSGQTPGIPTGYRDLDQMTAGFNRNDLIILAARPSVGKTAFALNIAQKVATHEDMYTVGIFS
LEMGADQLATRMICSSGNVDSNRLRTGTMTEEDWSRFTIAVGKLSRTKIFIDDTPGIRINDLRSKCRRLKQEHGLDMIVI
DYLQLIQGSGSRASDNRQQEVSEISRTLKALARELKCPVIALSQLSRGVEQRQDKRPMMSDIRESGSIEQDADIVAFLYR
DDYYNRGGDEDDDDDGGFEPQTNDENGEIEIIIAKQRNGPTGTVKLHFMKQYNKFTDIDYAHADMM
```

SEQ ID NO:15
>HGS008, fabD, malonyl CoA-acyl carrier protein transacylase,
```
GTGGTTCCGTATTATTAGGATTGGAAGGTACTGTAGTTAAAGCACACGGTAGTTCAAATGCTAAAGCTTTTTATTCTGCA
ATTAGACAAGCGAAAATCGCAGGAGAACAAAATATTGTACAAACAATGAAAGAGACTGTAGGTGAATCAAATGAGTAAAA
CAGCAATTATTTTTCCGGGACAAGGTGCCCAAAAAGTTGGTATGGCGCAAGATTTGTTTAACAACAATGATCAAGCAACT
GAAATTTTAACTTCAGCAGCGAACACATTAGACTTTGATATTTTAGAGACAATGTTTACTGATGAAGAAGGTAAATTGGG
TGAAACTGAAAACACACAACCAGCTTTATTGACGCATAGTTCGGCATTATTAGCAGCGCTAAAAAATTTGAATCCTGATT
TTACTATGGGGCATAGTTTAGGTGAATATTCAAGTTTAGTTGCAGCTGACGTATTATCATTTGAAGATGCAGTTAAAATT
GTTAGAAAACGTGGTCAATTAATGGCGCAAGCATTTCCTACTGGTGTAGGAAGCATGGCTGCAGTATTGGGATTAGATTT
TGATAAAGTCGATGAAATTTGTAAGTCATTATCATCTGATGACAAAATAATTGAACCAGCAAACATTAATTGCCCAGGTC
AAATTGTTGTTTCAGGTCACAAAGCTTTAATTGATGAGCTAGTAGAAAAAGGTAAATCATTAGGTGCAAAACGTGTCATG
CCTTTAGCAGTATCTGGACCATTCCATTCATCGCTAATGAAAGTGATTGAAGAAGATTTTTCAAGTTACATTAATCAATT
TGAATGGCGTGATGCTAAGTTTCCTGTAGTTCAAAATGTAAATGCGCAAGGTGAAACTGACAAAGAAGTAATTAAATCTA
ATATGGTCAAGCAATTATATTCACCAGTACAATTCATTAACTCAACAGAATGGCTAATAGACCAAGGTGTTGATCATTTT
ATTGAAATTGGTCCTGGAAAAGTTTTATCTGGCTTAATTAAAAAAATAAATAGAGATGTTAAGTTAACATCAATTCAAAC
TTTAGAAGATGTGAAAGGATGGAATGAAAATGACTAAGAGTGCTTTAGTAACAGGTGCATCAAGAGGAATTGGACGTAGT
ATTGCGTTACAATTAGCAGAAGAAGGATATAATGTAGCAGTAAACTATGC
```

SEQ ID NO:16
>HGS008, FabD, malonyl CoA-acyl carrier protein transacylase,
```
MSKTAIIFPGQGADKVGMAQDLFNNNDQATEILTSAANTLDFDILETMFTDEEGKLGETENTQPALLTHSSALLAALKNL
NPDFTMGHSLGEYSSLVAADVLSFEDAVKIVRKRGQLMAQAFPTGVGSMAAVLGLDFDKVDEICKSLSSDDKIIEPANIN
CPGQIVVSGHKALIDELVEKGKSLGAKRVMPLAVSGPFHSSLMKVIEEDFSSYINQFEWRDAKFPVVQNVNAQGETDKEV
IKSNMVKQLYSPVQFINSTEWLIDQGVDHFIEIGPGKVLSGLIKKINRDVKLTSIQTLEDVKGWNEND
```

SEQ ID NO:17
>HGS009, alf1, fructose-bisphosphate aldolase,
```
AAATACACATTTAATCTGCAGTATTTCAATGCATTGACGCTATTTTTTTGATATAATTACTTTGAAAAATACGTGCGTAA
GCACTCAAGGAGGAACTTTCATGCCTTTAGTTTCAATGAAAGAAATGTTAATTGATGCAAAAGAAATGGTTATGCGGTA
GGTCAATACAATATTAATAACCTAGAATTCACTCAAGCAATTTTAGAAGCGTCACAAGAAGAAATGCACCTGTAATTTT
```

TABLE 1-continued

```
AGGTGTTTCTGAAGGTGCTGCTCGTTACATGAGCGGTTTCTACACAATTGTTAAAATGGTTGAAGGGTTAATGCATGACT

TAAACATCACTATTCCTGTAGCAATCCATTTAGACCATGGTTCAAGCTTTGAAAAATGTAAAGAAGCTATCGATGCTGGT

TTCACATCAGTAATGATCGATGCTTCACACAGCCCATTCGAAGAAAACGTAGCAACAACTAAAAAAGTTGTTGAATACGC

TCATGAAAAAGGTGTTTCTGTAGAAGCTGAATTAGGTACTGTTGGTGGACAAGAAGATGATGTTGTAGCAGACGGCATCA

TTTATGCTGATCCTAAAGAATGTCAAGAACTAGTTGAAAAAACTGGTATTGATGCATTAGCGCCAGCATTAGGTTCAGTT

CATGGTCCATACAAAGGTGAACCAAAATTAGGATTTAAAGAAATGGAAGAAATCGGTTTATCTACAGGTTTACCATTAGT

ATTACACGGTGGTACTGGTATCCCGACTAAAGATATCCAAAAAGCAATTCCATTTGGTACAGCTAAAATTAACGTAAACA

CTGAAAACCAAATCGCTTCAGCAAAAGCAGTTCGTGACGTTTTAAATAACGACAAAGAAGTTTACGATCCTCGTAAATAC

TTAGGACCTGCACGTGAAGCCATCAAAGAAACAGTTAAAGGTAAAATTAAAGAGTTCGGTACTTCTAACCGCGCTAAATA

ATTAATATTTAGTCTTTAAGTTATTAATAACGTAGGGATATTAATTTTAAAAGAAGCAGACAAAATGGTGTTTGCTTCTT

TTTTATGTCGTATAAGTAATAAATAAAACAGTTTGATTTT
```

SEQ ID NO:18
>HGS009, alf1, fructose bisphosphate aldolase,
MPLVSMKEMLIDAKENGYAVGQYNINNLEFTQAILEASQEENAPVILGVSEGAARYMSGFYTIVKMVEGLMHDLNITIPV

AIHLDHGSSFEKCKEAIDAGFTSVMIDASHSPFEENVATTKKVVEYAHEKGVSVEAELGTVGGQEDDVVADGIIYADPKE

CQELVEKTGIDALAPALGSVHGPYKGEPKLGFKEMEEIGLSTGLPLVLHGGTGIPTKDIQKAIPFGTAKINVNTENQIAS

AKAVRDVLNNDKEVYDPRKYLGPAREAIKETVKGKIKEFGTSNRAK

SEQ ID NO:19
>HGS014,
```
GCTATAATAGGCATGGTTACAATGAGCTTGCTCATACATATTAATATAATTACAAAAACACGTCGGAGGTACGACATGAT

TAAAAATACAATTAAAAAATTGATAGAACATAGTATATATACGACTTTTAAATTACTATCAAAATTGCCAAACAAGAATC

TAATTTATTTTGAAAGCTTTCATGGTAAACAATACAGCGACAACCCCAAAGCATTATATGAATACTTAACTGAACATAGC

GATGCCCAATTAATATGGGGTGTGAAAAAAGGATATGAACACATATTCCAACAGCACAATGTACCATATGTTACAAAGTT

TTCAATGAAATGGTTTTTAGCGATGCCAAGAGCGAAAGCGTGGATGATTAACACACGTACACCAGATTGGTTATATAAAT

CACCGCGAACGACGTACTTACAAACATGGCATGGCACGCCATTAAAAAAGATTGGTTTGGATATTAGTAACGTTAAAATG

CTAGGAACAAATACTCAAAATTACCAAGATGGCTTTAAAAAAGAAAGCCAACGGTGGGATTATCTAGTGTCACCTAATCC

ATATTCGACATCGATATTTCAAAATGCATTTCATGTTAGTCGAGATAAGATTTTGGAAACAGGTTATCCAAGAAATGATA

AATTATCACATAAACGCAATGACTACTGAATATATTAATGGTATTAAGACAAGATTAAATATTCCATTAGATAAAAAGTG

ATTATGTACGCGCCAACTTGGCGTGACGATGAAGCGATTCGAGAAGGTTCATATCAATTTAATGTTAACTTTGATATAGA

AGCTTTGCGTCAAGCGCTGGATGATGATTATGTTATTTTATTACGCATGCATTATTTAGTTGTGACACGTATTGATGAAC

ATGATGATTTTGTGAAAGACGTTTCAGATTATGAAGACATTTCGGATTTATACTTAATCAGCGATGCGTTAGTTACCGAC

TACTCATCTGTCATGTTCGACTTCGGTGTATTAAAGCGTCCGCAAATTTTCTATGCATATGACTTAGATAAATATGGCGA

TGAGCTTAGAGGTTTTTACATGGATTATAAAAAAGAGTTGCCAGGTCCAATTGTTGAAAATCAAACAGCACTCATTGATG

CATTAAAACAAATCGATGAGACTGCAAATGAGTATATTGAAGCACGAACGGTATTTTATCAAAAATTCTGTTCATTAGAA

GATGGACAAGCGTCACAACGAATTTGCCAAACGATTTTTAAGTGATAACTTAAAAACAATAAAAAATTATAAATTAATTA

GTTAAGTGATATAAATAATAAACGAAATGTTTGCTTGTATGTTATTATTTGTGTATGAAA
```

SEQ ID NO:20
>HGS014,
MIKNTIDDLIEHSIYTTFKLLSKLPNKNLIYFESFHGKQYSDNPKALYEYLTEHSDAQLIWGVKKGYEHIFQQHNVPYVT

KFSMKWFLAMPRAKAWMINTRTPDWLYKSPRTTYLQTWHGTPLKKIGLDISNVKMLGTNTQNYQDGFKKESQRWDYLVSP

NPYSTSIFQNAFHVSRDKILETGYPRNDKLSHKRNDTEYINGIKTRLNIPLDKKVIMYAPTWRDDEAIREGSYQFNVNFD

IEALRQALDDDYVILLRMHYLVVTRIDEHDDFVKDVSDYEDISDLYLISDALVTDYSSVMFDFGVLKRPQIFYAYDLDKY

TABLE 1-continued

GDELRGFYMDYKKELPGPIVENQTALIDALKQIDETANEYIEARTVFYQKFCSLEDGQASQRICQTIFK

SEQ ID NO:21
>HGS016, murA, UDP-N-acetylglucosamine 1-carboxyvinyltransferase,
TGATTTGTAATCAAAACTAGATATAATTAAATAATGACTTAAAATAATTTTAAAATAGGGAAATGTAAAGTAATAGGAGT

TCTAAGTGGAGGATTTACGATGGATAAAATAGTAATCAAAGGTGGAAATAAATTAACGGGTGAAGTTAAAGTAGAAGGTG

CTAAAAATGCAGTATTACCAATATTGACAGCATCTTTATTAGCTTCTGATAAACCGAGCAAATTAGTTAATGTTCCAGCT

TTAAGTGATGTAGAAACAATAAATAATGTATTAACAACTTTAAATGCTGACGTTACATACAAAAAGGACGAAAATGCTGT

TGTCGTTGATGCAACAAAGACTCTAAATGAAGAGGCACCATATGAATATGTTAGTAAAATGCGTGCAAGTATTTTAGTTA

TGGGACCTCTTTTAGCAAGACTAGGACATGCTATTGTTGCATTGCCTGGTGGTTGTGCAATTGGAAGTAGACCGATTGAG

CAACACATTAAAGGTTTTGAAGCTTTAGGCGCAGAAATTCATCTTGAAAATGGTAATATTTATGCTAATGCTAAAGATGG

ATTAAAAGGTACATCAATTCATTTAGATTTTCCAAGTGTAGGAGCAACACAAAATATTATTATGGCAGCATCATTAGCTA

AGGGTAAGACTTTAATTGAAAATGCAGCTAAAGAACCTGAAATTGTCGATTTAGCAAACTACATTAATGAAATGGGTGGT

AGAATTACTGGTGCTGGTACAGACACAATTACAATCAATGGTGTAGAATCATTACATGGTGTAGAACATGCTATCATTCC

AGATAGAATTGAAGCAGGCACATTACTAATCGCTGGTGCTATAACGCGTGGTGATATTTTTGTACGTGGTGCAATCAAAG

AACATATGGCGAGTTTAGTCTATAAACTAGAAGAAATGGGCGTTGAATTGGACTATCAAGAAGATGGTATTCGTGTACGT

GCTGAAGGGGAATTACAACCTGTAGACATCAAAACTCTACCACATCCTGGATTCCCGACTGATATGCAATCACAAATGAT

GGCATTGTTATTAACGGCAAATGGTCATAAAGTCGTAACCGAAACTGTTTTTGAAAACCGTTTTATGCATGTTGCAGAGT

TCAAACGTATGAATGCTAATATCAATGTAGAAGGTCGTAGTGCTAAACTTGAAGGTAAAAGTCAATTGCAAGGTGCACAA

GTTAAAGCGACTGATTTAAGAGCAGCAGCCGCCTTAATTTTAGCTGGATTAGTTGCTGATGGTAAAACAAGCGTTACTGA

ATTAACGCACCTAGATAGAGGCTATGTTGACTTACACGGTAAATTGAAGCAATTAGGTGCAGACATTGAACGTATTAACG

ATTAATTCAGTAAATTAATATAATGGAGGATTTCAACCATGGAAACAATTTTTGATTATAACCAAATTAA

SEQ ID NO:22
>HGS016, MurA, UDP-N-acetylglucosamine 1-carboxyvinyltransferase,
MDKIVIKGGNKLTGEVKVEGAKNAVLPILTASLLASDKPSKLVNVPALSDVETINNVLTTLNADVTYKKDENAVVVDATK

TLNEEAPYEYVSKMRASILVMGPLLARLGHAIVALPGGCAIGSRPIEQHIKGFEALGAEIHLENGNIYANAKDGLKGTSI

HLDFPSVGATQNIIMAASLAKGKTLIENAAKEPEIVDLANYINEMGGRITGAGTDTITINGVESLHGVEHAIIPDRIEAG

TLLIAGAITRGDIFVRGAIKEHMASLVYKLEEMGVELDYQEDGIRVRAEGELQPVDIKTLPHPGFPTDMQSQMMALLLTA

NGHKVVTETVFENRFMHVAEFKRMNANINVEGRSAKLEGKSQLQGAQVKATDLRAAAALILAGLVADGKTSVTELTHLDR

GYVDLHGKLKQLGADIERIND

SEQ ID NO:22
>HGS018, DnaJ, DNA ligase,
MADLSSRVNELHDLLNQYSYEYYVEDNPSVPDSEYDKLLHELIKIEEEHPEYKTVDSPTVRVGGEAQASFNKVNHDTPML

SLGNAFNEDDLRKFDQRIREQIGNVEYMCELKIDGLAVSLKYVDGYFVQGLTRGDGTTGEDITENLKTIHAIPLKMKEPL

NVEVRGEAYMPRRSFLRLNEEKEKNDEQLFANPRNAAAGSLRQLDSKLTAKRKLSVFIYSVNDFTDFNARSQSEALDELD

KLGFTTNKNRARVNNIDGVLEYIEKWTSQRESLPYDIDGIVIKVNDLDQQDEMGFTQKSPRWAIAYKFPAEEVVTKLLDI

ELSIGRTGVVTPTAILEPVKVAGTTVSRASLHNEDLIHDRDIRIGDSVVVKKAGDIIPEVVRSIPERRPEDAVTYHMPTH

CPSCGHELVRIEGEVALRCINPKCQAQLVEGLIHFVSRQAMNIDGLGTKIIQQLYQSELIKDVADIFYLTEEDLLPLDRM

GQKKVDNLLAAIQQAKDNSLENLLFGLGIRHLGVKASQVLAEKYETIDRLLTVTEAELVEIHDIGDKVAQSVVTYLENED

IRALIQKLKDKHVNMIYKGIKTSDIEGHPEFSGKTIVLTGKLHQMTRNEASKWLASQGAKVTSSVTKNTDVVIAGEDAGS

KLTKAQSLGIEIWTEQQFVDKQNELNS

SEQ ID NO:25
>HGS019, mapM, methionine aminopeptidase,
TGTCTCACTCACTTTCCAAAATACTAAAGTAACATCTTTAGTATATCAAAGAATTTTTGCTATAATAAGTTATAATTATA

TAAAAAAGGAACGGGATAAAATGATTGTAAAAACAGAAGAAGAATTACAAGCGTTAAAAGAAATTGGATACATATGCGCT

TABLE 1-continued

```
AAAGTGCGCAATACAATGCAAGCTGCAACCAAACCAGGTATCACTACGAAAGAGCTTGATAATATTGCGAAAGAGTTATT

TGAAGAATACGGTGCTATTTCTGCGCCAATTCATGATGAAAATTTTCCTGGTCAAACGTGTATTAGTGTCAATGAAGAGG

TGGCACATGGGATTCCAAGTAAGCGTGTCATTCGTGAAGGAGATTTAGTAAATATTGATGTATCGGCTTTGAAGAATGGC

TATTATGCAGATACAGGCATTTCATTTGTCGTTGGAGAATCAGATGATCCAATGAAACAAAAAGTATGTGACGTAGCAAC

GATGGCATTTGAGAATGCAATTGCAAAAGTAAAACCGGGTACTAAGTTAAGTAACATTGGTAAAGCGGTGCATAATACAG

CTAGACAAAATGATTTGAAAGTCATTAAAAACTTAACAGGTCATGGTGTTGGTTTATCATTACATGAAGCACCAGCACAT

GTACTTAATTACTTTGATCCAAAAGACAAAACATTATTAACTGAAGGTATGGTATTAGCTATTGAACCGTTTATCTCATC

AAATGCATCATTTGTTACAGAAGGTAAAAATGAATGGGCTTTTGAAACGAGCGATAAAAGTTTTGTTGCTCAAATTGAGC

ATACGGTTATCGTGACTAAGGATGGTCCGATTTTAACGACAAAGATTGAAGAAGAATAGTTCAACATATACTAAGACTAA

AGTATGAACATCATTTAGTTCCGGAGCCTATTCATATTGGTTTCGGAACTGTTTTATAATAATTAAGAACACAATCAATD
```

SEQ ID NO:26
>HGS019, MapM, methionine aminopeptidase,
```
MIVKTEEELQALKEIGYICAKVRNTMQAATKPGITTKELDNIAKELFEEYGAISAPIHDENFPGQTCISVNEEVAHGIPS

KRVIREGDLVNIDVSALKNGYYADTGISFVVGESDDPMKQKVCDVATMAFENAIAKVKPGTKLSNIGKAVHNTARQNDLK

VIKNLTGHGVGLSLHEAPAHVLNYFDPKDKTLLTEGMVLAIEPFISSNASFVTEGKNEWAFETSDKSFVAQIEHTVIVTK

DGPILTTKIEEE
```

SEQ ID NO:27
>HGS022-23-24, adt, glutamyl-tRNA amidotransferase subunit a, b, and c,
(operon comprising three ORFs listed below)
```
TATACAGTTTATATGAAATTAAAGTAGCACCTCATAAATACTTAGATTTTTAATTGGAAATTTGATACAATTTAGTGATG

AATGACTTAAAGGAGGCTTTTATTAATGACAAAAGTAACACGTGAAGAAGTTGAGCATATCGCGAATCTTGCAAGACTTC

AAATTTCTCCTGAAGAAACGGAAGAAATGGCCAACACATTAGAAAGCATTTTAGATTTTGCAAAACAAAATGATAGCGCT

GATACAGAAGGCGTTGAACCTACATATCACGTTTTAGATTTACAAAACGTTTTACGTGAAGATAAAGCAATTAAAGGTAT

TCCACAAGAATTAGCTTTGAAAAATGCCAAAGAAACAGAAGATGGACAATTTAAAGTGCCTACAATCATGAATGAGGAGG

ACGCGTAAGATGAGCATTCGCTACGAATCGGTTGAGAATTTATTAACTTTAATAAAAGACAAAAAAATCAAACCATCTGA

TGTTGTTAAAGATATATATGATGCAATTGAAGAGACTGATCCAACAATTAAGTCTTTTCTAGCGCTGGATAAAGAAAATG

CAATCAAAAAAGCGCAAGAATTGGATGAATTACAAGCAAAAGATCAAATGGATGGCAAATTATTTGGTATTCCAATGGGT

ATAAAAGATAACATTATTACAAACGGATTAGAAACAACATGTGCAAGTAAAATGTTAGAAGGTTTTGTGCCAATTTACGA

ATCTACTGTAATGGAAAAACTACATAATGAAAATGCCGTTTTAATCGGTAAATTAAATATGGATGAGTTTGCAATGGGTG

GTTCAACAGAAACATCTTATTTCAAAAAAACAGTTAACCCATTTGACCATAAAGCAGTGCCAGGTGGTTCATCAGGTGGA

TCTGCAGCAGCAGTTGCAGCTGGCTTAGTACCATTTAGCTTAGGTTCAGACACAGGTGGTTCAATTAGACAACCGGCTGC

ATATTGTGGCGTTGTCGGTATGAAACCAACATACGGTCGTGTATCTCGATTTGGATTAGTTGCTTTTGCATCTTCATTAG

ACCAAATTGGTCCATTGACTCGAAATGTAAAAGATAATGCAATCGTATTAGAAGCTATTTCTGGTGCAGATGTTAATGAC

TCTACAAGTGCACCAGTTGATGATGTAGACTTTACATCTGAAATTGGTAAAGATATTAAAGGATTAAAAGTTGCATTACC

TAAAGAATACTTAGGTGAAGGTGTAGCTGATGACGTAAAAGAAGCAGTTCAAAACGCTGTAGAAACTTTAAAATCTTTAG

GTGCTGTCGTTGAGGAAGTATCATTGCCAAATACTAAATTTGGTATTCCATCATATTACGTGATTGCATCATCAGAAGCT

TCGTCAAACCTTTCTCGTTTTGACGGAATTCGTTATGGTTATCATTCTAAAGAAGCTCATTCATTAGAAGAATTATATAA

AATGTCAAGATCTGAAGGTTTCGGTAAAGAAGTAAAACGTCGTATTTTCTTAGGTACATTTGCATTAAGTTCAGGTTACT

ATGATGCTTACTATAAAAAATCTCAAAAAGTTAGAACATTGATTAAAAATGACTTTGATAAAGTATTCGAAAATTATGAT

GTAGTAGTTGGTCCAACAGCGCCTACAACTGCGTTTAATTTAGGTGAAGAAATTGATGATCCATTAACAATGTATGCCAA

TGATTTATTAACAACACCAGTAAACTTAGCTGGATTACCTGGTATTTCTGTTCCTTGTGGACAATCAAATGGCCGACCAA

TCGGTTTACAGTTCATTGGTAAACCATTCGATGAAAAAACGTTATATCGTGTCGCTTATCAATATGAAACACAATACAAT
```

TABLE 1-continued

```
TTACATGACGTTTATGAAAAATTATAAGGAGTGGAAATCATGCATTTTGAAACAGTTATAGGACTTGAAGTTCACGTAGA
GTTAAAAACGGACTCAAAAATGTTTTCTCCATCACCAGCGCATTTTGGAGCAGAACCTAACTCAAATACAAATGTTATCG
ACTTAGCATATCCAGGTGTCTTACCAGTTGTTAATAAGCGTGCAGTAGACTGGGCAATGCGTGCTGCAATGGCACTAAAT
ATGGAAATCGCAACAGAATCTAAGTTTGACCGTAAGAACTATTTCTATCCAGATAATCCAAAAGCATATCAAATTTCTCA
ATTTGATCAACCAATTGGTGAAAATGGATATATCGATATCGAAGTCGACGGTGAAACAAAACGAATCGGTATTACTCGTC
TTCACATGGAAGAAGATGCTGGTAAGTCAACACATAAAGGTGAGTATTCATTAGTTGACTTGAACCGTCAAGGTACACCG
CTAATTGAAATCGTATCTGAACCAGATATTCGTTCACCTAAAGAAGCATATGCATATTTAGAAAAATTGCGTTCAATTAT
TCAATACACTGGTGTATCAGACGTTAAGATGGAAGAGGGATCTTTACGTTGTGATGCTAACATCTCTTTACGTCCATATG
GTCAAGAAAAATTTGGTACTAAAGCCGAATTGAAAAACTTAAACTCATTTAACTATGTACGTAAAGGTTTAGAATATGAA
GAAAAACGCCAAGAAGAAGAATTGTTAAATGGTGGAGAAATCGGACAAGAAACACGTCGATTTGATGAATCTACAGGTAA
AACAATTTTAATGCGTGTTAAAGAAGGTTCTGATGATTACCGTTACTTCCCAGAGCCTGACATTGTACCTTTATATATTG
ATGATGCTTGGAAAGAGCGTGTTCGTCAGACAATTCCTGAATTACCAGATGAACGTAAAGCTAAGTATGTAAATGAATTA
GGTTTACCTGCATACGATGCACACGTATTAACATTGACTAAAGAAATGTCAGATTTCTTTGAATCAACAATTGAACACGG
TGCAGATGTTAAATTAACATCTAACTGGTTAATGGGTGGCGTAAACGAATATTTAAATAAAAATCAAGTAGAATTATTAG
ATACTAAATTAACACCAGAAAATTTAGCAGGTATGATTAAACTTATCGAAGACGGAACAATGAGCAGTAAAATTGCGAAG
AAAGTCTTCCCAGAGTTAGCAGCTAAAGGTGGTAATGCTAAACAGATTATGGAAGATAATGGCTTAGTTCAAATTTCTGA
TGAAGCAACACTTCTAAAATTTGTAAATGAAGCATTAGACAATAACGAACAATCAGTTGAAGATTACAAAAATGGTAAAG
GCAAAGCTATGGGCTTCTTAGTTGGTCAAATTATGAAAGCGTCTAAAGGTCAAGCTAATCCACAATTAGTAAATCAACTA
TTAAAACAAGAATTAGATAAAAGATAATTTAAATCATCAAACTATGAAGATTTAAAAAATAAACCCTTGATTGCTGACTT
AGATGCAATCGAGGGTTTATTTATATCTATAGAAGTCAAA
```

SEQ ID NO:28
>HGS022, Adt, glutamyl-tRNA amidotransferase subunit a,
MSIRYESVENLLTLIKDKKIKPSDVVKDIYDAIEETDPTIKSFLALDKENAIKKAQELDELQAKDQMDGKLFGIPMGIKD
NIITNGLETTCASKMLEGFVPIYESTVMEKLHNENAVLIGKLNMDEFAMGGSTETSYFKKTVNPFDHKAVPGGSSGGSAA
AVAAGLVPFSLGSDTGGSIRQPAAYCGVVGMKPTYGRVSRFGLVAFASSLDQIGPLTRNVKDNAIVLEAISGADVNDSTS
APVDDVDFTSEIGKDIKGLKVALPKEYLGEGVADDVKEAVQNAVETLKSLGAVVEEVSLPNTKFGIPSYYVIASSEASSN
LSRFDGIRYGYHSKEAHSLEELYKMSRSEGFGKEVKRRIFLGTFALSSGYYDAYYKKSQKVRTLIKNDFDKVFENYDVVV
GPTAPTTAFNLGEEIDDPLTMYANDLLTTPVNLAGLPGISVPCGQSNGRPIGLQFIGKPFDEKTLYRVAYQYETQYNLHD
VYEKL SEQ ID NO:29
>HGS023, Adt, glutamyl-tRNA amidotransferase subunit b,
MHFETVIGLEVHVELKTDSKMFSPSPAHFGAEPNSNTNVIDLAYPGVLPVVNKRAVDWAMRAAMALNMEIATESKFDRKN
YFYPDNPKAYQISQFDQPIGENGYIDIEVDGETKRIGITRLHMEEDAGKSTHKGEYSLVDLNRQGTPLIEIVSEPDIRSP
KEAYAYLEKLRSIIQYTGVSDVKMEEGSLRCDANISLRPYGQEKPGTKAELKNLNSFNYVRKGLEYEEKRQEEELLNGGE
IGQETRRFDESTGKTILMRVKEGSDDYRYFPEPDIVPLYIDDAWKERVRQTIPELPDERKAKYVNELGLPAYDAHVLTLT
KEMSDEFESTIEHGADVKLTSNWLMGGVNEYLNKNQVELLDTKLTPENLAGMIKLIEDGTMSSKIAKKVFPELAAKGGNA
KQIMEDNGLVQISDEATLLKFVNEALDNNEQSVEDYKNGKGKAMGFLVGQIMKASKGQANPQLVNQLLKQELDKR SEQ ID NO:30
>HGS024, Adt, glutamyl-tRNA amidotransferase subunit c,
MTKVTREEVEHIANLARLQISPEETEEMANTLESILDFAKQNDSADTEGVEPTYHVLDLQNVLREDKAIKGIPQELALKN
AKETEDGQFKVPTIMNEEDA SEQ ID NO:31
>HGS025, pth, peptidyl-tRNA hydrolase, TABLE 1-continued

```
CTTACTAAGCTAAAGAATAATGATAATTGATGGCAATGGCGGAAAATGGATGTTGTCATTATAATAATAAATGAAACAAT
TATGTTGGAGGTAAACACGCATGAAATGTATTGTAGGTCTAGGTAATATAGGTAAACGTTTTGAACTTACAAGACATAAT
ATCGGCTTTGAAGTCGTTGATTATATTTTAGAGAAAAATAATTTTTCATTAGATAAACAAAAGTTTAAAGGTGCATATAC
AATTGAACGAATGAACGGCGATAAAGTGTTATTTATCGAACCAATGACAATGATGAATTTGTCAGGTGAAGCAGTTGCAC
CGATTATGGATTATTACAATGTTAATCCAGAAGATTTAATTGTCTTATATGATGATTTAGATTTAGAACAAGGACAAGTT
CGCTTAAGACAAAAAGGAAGTGCGGGCGGTCACAATGGTATGAAATCAATTATTAAAATGCTTGGTACAGACCAATTTAA
ACGTATTCGTATTGGTGTGGGAAGACCAACGAATGGTATGACGGTACCTGATTATGTTTTACAACGCTTTTCAAATGATG
AAATGGTAACGATGGAAAAAGTTATCGAACACGCAGCACGCGCAATTGAAAAGTTTGTTGAAACATCACGATTTGACCAT
GTTATGAATGAATTTAATGGTGAAGTGAAATAATGACAATATTGACAACGCTTATAAAAGAAGATAATCATTTTCAAGAC
CTTAATCAGGTATTTGGACAAGCAAACACACTAGTAACTGGTCTTTCCCCGT
```

SEQ ID NO:32
>HGS025, Pth, peptidyl-tRNA hydrolase,
MKCIVGLGNIGKRFELTRHNIGFEVVDYILEKNNFSLDKQKFKGAYTIERMNGDKVLFIEPMTMMNLSGEAVAPIMDYYN
VNPEDLIVLYDDLDLEQGQVRLRQKGSAGGHNGMKSIIKMLGTDQFKRIRIGVGRPTNGMTVPDYVLQRFSNDEMVTMEK
VIEHAARAIEKFVETSRFDHVMNEFNGEVK SEQ ID NO:33
>HGS026,
```
TGATCCGATTATCTTAGTAGGTGCCAATGAAAGTTATGAGCCACGTTGTCGCGCGCACCATATCGTAGCACCTAGTGATA
ATAATAAGGAGGAATTATAAGTGTTTGATCAATTAGATATTGTAGAAGAAAGATACGAACAGTTAAATGAACTGTTAAGT
GACCCAGATGTTGTAAATGATTCAGATAAATTACGTAAATATTCTAAAGAGCAAGCTGATTTACAAAAAACTGTAGATGT
TTATCGTAACTATAAAGCTAAAAAAGAAGAATTAGCTGATATTGAAGAAATGTTAAGTGAGACTGATGATAAAGAAGAAG
TAGAAATGTTAAAAGAGGAGAGTAATGGTATTAAAGCTGAACTTCCAAATCTTGAAGAAGAGCTTAAAATATTATTGATT
CCTAAAGATCCTAATGATGACAAAGACGTTATTGTAGAAATAAGAGCAGCAGCAGGTGGTGATGAGGCTGCGATTTTTGC
TGGTGATTTAATGCGTATGTATTCAAAGTATGCTGAATCACAAGGATTCAAAACTGAAATAGTAGAAGCGTCTGAAAGTG
ACCATGGTGGTTACAAAGAAATTAGTTTCTCAGTTTCTGGTAATGGCGCGTATAGTAAATTGAAATTTGAAAATGGTGCG
CACCGCGTTCAACGTGTGCCTGAAACAGAATCAGGTGGACGTATTCATACTTCAACAGCTACAGTGGCAGTTTTACCAGA
AGTTGAAGATGTAGAAATTGAAATTAGAAATGAAGATTTAAAAATCGACACGTATCGTTCAAGTGGTGCAGGTGGTCAGC
ACGTAAACACAACTGACTCTGCAGTACGTATTACCCATTTACCAACTGGTGTCATTGCAACATCTTCTGAGAAGTCTCAA
ATTCAAAACCGTGAAAAAGCAATGAAAGTGTTAAAAGCACGTTTATACGATATGAAAGTTCAAGAAGAACAACAAAAGTA
TGCGTCACAACGTAAATCAGCAGTCGGTACTGGTGATCGTTCAGAACGTATTCGAACTTATAATTATCCACAAAGCCGTG
TAACAGACCATCGTATAGGTCTAACGCTTCAAAAATTAGGGCAAATTATGGAAGGCCATTTAGAAGAAATTATAGATGCA
CTGACTTTATCAGAGCAGACAGATAAAATTGAAAGAACTTAATAATGGTGAATTATAAAGAAAAGTTAGATGAAGCAATTC
ATTTAACACAACAAAAAGGGTTTGAACAAACACGAGCTGAATGGTTAATGTTAGATGTATTTCAATGGACGCGTACG
```

SEQ ID NO:34
>HGS026,
VFDQLDIVEERYEQLNELLSDPDVVNDSDKLRKYSKEQADLQKTVDVYRNYKAKKEELADIEEMLSETDDKEEVEMLKEE
SNGIKAELPNLEEELKILLIPKDPNDDKDVIVEIRAAAGGDEAAIFAGDLMRMYSKYAESQGFKTEIVEASESDHGGYKE
ISFSVSGNGAYSKLKFENGAHRVQRVPETESGGRIHTSTATVAVLPEVEDVEIEIRNEDLKIDTYRSSGAGGQHVNTTDS
AVRITHLPTGVIATSSEKSQIQNREKAMKVLKARLYDMKVQEEQQKYASQRKSAVGTGDRSERIRTYNYPQSRVTDHRIG
LTLQKLGQIMEGHLEEIIDALTLSEQTDKLKELNNGEL

SEQ ID NO:35
>HGS028,
```
ATTTCTTAACATTGTTATTTAACAAAATTATGTTAAAATTTAGCATTATAAAAGATGCAAATCAATGACTTGAATTGAAA
TATAAATAGGAGCGAATGCTATGGAATTATCAGAAATCAAACGAAATATAGATAAGTATAATCAAGATTTAACACAAATT
```

TABLE 1-continued

AGGGGGTCTCTTGACTTAGAGAACAAAGAAACTAATATTCAAGAATATGAAGAAATGATGGCAGAACCTAATTTTTGGGA

TAACCAAACGAAAGCGCAAGATATTATAGATAAAAATAATGCGTTAAAAGCAATAGTTAATGGTTATAAAACACTACAAG

CAGAAGTAGATGACATGGATGCTACTTGGGATTTATTACAAGAAGAATTTGATGAAGAAATGAAAGAAGACTTAGAGCAA

GAGGTCATTAATTTTAAGGCTAAAGTGGATGAATACGAATTGCAATTATTATTAGATGGGCCTCACGATGCCAATAACGC

AATTCTAGAGTTACATCCTGGTGCAGGTGGCACGGAGTCTCAAGATTGGGCTAATATGCTATTTAGAATGTATCAACGTT

ATTGTGAGAAGAAAGGCTTTAAAGTTGAAACTGTTGATTATCTACCTGGGGATGAAGCGGGGATTAAAAGTGTAACATTG

CTCATCAAAGGGCATAATGCTTATGGTTATTTAAAAGCTGAAAAAGGTGTACACCGACTAGTACGAATTTCTCCATTTGA

TTCATCAGGACGTCGTCATACATCATTTGCATCATGCGACGTTATTCCAGATTTTAATAATGATGAAATAGAGATTGAAA

TCAATCCGGATGATATTACAGTTGATACATTCAGAGCTTCTGGTGCAGGTGGTCAGCATATTAACAAAACTGAATCGGCA

ATACGAATTACCCACCACCCCTCAGGTATAGTTGTTAATAACCAAAATGAACGTTCTCAAATTAAAAACCGTGAAGCAGC

TATGAAAATGTTAAAGTCTAAATTATATCAATTAAAATTGGAAGAGCAGGCACGTGAAATGGCTGAAATTCGTGGCGAAC

AAAAAGAAATCGGCTGGGGAAGCCAAATTAGATCATATGTTTTCCATCCATACTCAATGGTGAAAGATCATCGTACGAAC

GAAGAAACAGGTAAGGTTGATGCAGTGATGGATGGAGACATTGGACCATTTATCGAATCATATTTAAGACAGACAATGTC

GCACGATTAATATATATTTTAAAACCGAGGCTCTAAAAGGGCGTCGGTTTTTGGTTTTTTTAAAGGTAGCTAAATAAATT

GTAAATTAGATTTTGGAATATGATTTGTTTATGAA

SEQ ID NO:36
>HGS028,
MELSEIKRNIDKYNQDLTQIRGSLDLENKETNIQEYEEMMAEPNFWDNQTKAQDIIDKNNALKAIVNGYKTLQAEVDDMD

ATWDLLQEEFDEEMKEDLEQEVINFKAKVDEYELQLLLDGPHDANNAILELHPGAGGTESQDWANMLFRMYQRYCEKKGF

KVETVDYLPGDEAGIKSVTLLIKGHNAYGYLKAEKGVHRLVRISPFDSSGRRHTSFASCDVIPDFNNDEIEIEINPDDIT

VDTFRASGAGGQHINKTESAIRITHHPSGIVVNNQNERSQIKNREAAMKMLKSKLYQLKLEEQAREMAEIRGEQKEIGWG

SQIRSYVFHPYSMVKDHRTNEETGKVDAVMDGDIGPFIESYLRQTMSHD

SEQ ID NO:37
>HGS030, Tmk, thymidylate kinase,
AATAACTGAAAATATGATAGAATTGGTAAATGAATATCTGGAAACTGGAATGATAGTTGAAGGAATTAAAAATAATAAAA

TTTTAGTTGAGGATGAATAAAATGTCAGCTTTTATAACTTTTGAGGGCCCAGAAGGCTCTGGAAAAACAACTGTAATTAA

TGAAGTTTACCATAGATTAGTAAAAGATTATGATGTCATTATGACTAGAGAACCAGGTGGTGTTCCTACTGGTGAAGAAA

TACGTAAAATTGTATTAGAAGGCAATGATATGGACATTAGAACTGAAGCAATGTTATTTGCTGCATCTAGAAGAGAACAT

CTTGTATTAAAGGTCATACCAGCTTTAAAAGAAGGTAAGGTTGTGTTGTGTGATCGCTATATCGATAGTTCATTAGCTTA

TCAAGGTTATGCTAGAGGGATTGGCGTTGAAGAAGTAAGAGCATTAAACGAATTTGCAATAAATGGATTATATCCAGACT

TGACGATTTATTTAAATGTTAGTGCTGAAGTAGGTCGCGAACGTATTATTAAAAATTCAAGAGATCAAAATAGATTAGAT

CAAGAAGATTTAAAGTTTCACGAAAAAGTAATTGAAGGTTACCAAGAAATCATTCATAATGAATCACAACGGTTCAAAAG

CGTTAATGCAGATCAACCTCTTGAAAATGTTGTTGAAGACACGTATCAAACTATCATCAAATATTTAGAAAAGATATGAT

ATAATTGTTAGAAGAGGTGTTATAAAATGAAAATGATTATAGCGATCGTACAAGATCAAGATAGTCAGGAACTTGCAGAT

CAACTTGTTAAAAATAACTTTAGAGCAACAAAATTGGCAA

SEQ ID NO:40
>HGS031, pyrH, uridylate kinase,
MAQISKYKRVVLKLSGEALAGEKGFGINPVIIKSVAEQVAEVAKMDCEIAVIVGGGNIWRGKTGSDLGMDRGTADYMGML

ATVMNALALQDSLEQLDCDTRVLTSIEMKQVAEPYIRRRAIRHLEKKRVVIFAAGIGNPYFSTDTTAALRAAEVEADVIL

MGKNNVDGVYSADPKVNKDAVKYEHLTHIQMLQEGLQVMDSTASSFCMDNNIPLTVFSIMEEGNIKRAVMGEKIGTLITK

SEQ ID NO:41
>HGS032,
GATAGCATCCATGTATAGTGATAGTATTTACAACAATTATTATAATACTATTTAGTTAAGTAGAGAAATAGTTAAACATT

TABLE 1-continued

```
TGAAAGTGTGGTTTAATGGAATGTCAGCAATAGGAACAGTTTTTAAAGAACATGTAAAGAACTTTTATTTAATTCAAAGA

CTGGCTCAGTTTCAAGTTAAAATTATCAATCATAGTAACTATTTAGGTGTGGCTTGGGAATTAATTAACCCTGTTATGCA

AATTATGGTTTACTGGATGGTTTTTGGATTAGGAATAAGAAGTAATGCACCAATTCATGGTGTACCTTTTGTTTATTGGT

TATTGGTTGGTATCAGTATGTGGTTCTTCATCAACCAAGGTATTTTAGAAGGTACTAAAGCAATTACACAAAAGTTTAAT

CAAGTATCGAAAATGAACTTCCCGTTATCGATAATACCGACATATATTGTGACAAGTAGATTTTATGGACATTTAGGCTT

ACTTTTACTTGTGATAATTGCATGTATGTTTACTGGTATTTATCCATCAATACATATCATTCAATTATTGATATATGTAC

CGTTTTGTTTTTTCTTAACTGCCTCGGTGACGTTATTAACATCAACACTCGGTGTGTTAGTTAGAGATACACAAATGTTA

ATGCAAGCAATATTAAGAATATTATTTTACTTTTCACCAATTTTGTGGCTACCAAAGAACCATGGTATCAGTGGTTTAAT

TCATGAAATGATGAAATATAATCCAGTTTACTTTATTGCTGAATCATACCGTGCAGCAATTTTATATCACGAATGGTATT

TCATGGATCATTGGAAATTAATGTTATACAATTTCGGTATTGTTGCCATTTTCTTTGCAATTGGTGCGTACTTACACATG

AAATATAGAGATCAATTTGCAGACTTCTTGTAATATATTTATATGACGAAACCCCGCTAACCATTAATAAATGGAAGTGG

GGTTCATTTTTGTTTATAATTTAAGTAAATAACATATTAAGTTGGTGTATTAT
```

SEQ ID NO:42
>HGS032,
```
MSAIGTVFKEHVKNFYLIQRLAQFQVKIINHSNYLGVAWELINPVMQIMVYWMVFGLGIRSNAPIHGVPFVYWLLVGISM

WFFINQGILEGTKAITQKFNQVSKMNFPLSIIPTYIVTSRFYGHLGLLLLVIIACMFTGIYPSIHIIQLLIYVPFCFFLT

ASVTLLTSTLGVLVRDTQMLMQAILRILFYFSPILWLPKNHGISGLIHEMMKYNPVYFIAESYRAAILYHEWYFMDHWKL

MLYNFGIVAIFFAIGAYLHMKYRDQFADFL
```

SEQ ID NO:43
>HGS033,
```
TAACAAAATCTTCTATACACTTTACAACAGGTTTTAAAATTTAACAACTGTTGAGTAGTATATTATAATCTAGATAAATG

TGAATAAGGAAGGTCTACAAATGAACGTTTCGGTAAACATTAAAAATGTAACAAAAGAATATCGTATTTATCGTACAAAT

AAAGAACGTATGAAAGATGCGCTCATTCCCAAACATAAAAACAAAACATTTTTCGCTTTAGATGACATTAGTTTAAAAGC

ATATGAAGGTGACGTCATAGGGCTTGTTGGCATCAATGGTTCCGGCAAATCAACGTTGAGCAATATCATTGGCGGTTCTT

TGTCGCCTACTGTTGGCAAAGTGGATCGTAATGGTGAAGTCAGCGTTATCGCAATTAGTGCTGGCTTGAGTGGACAACTT

ACAGGGATTGAAAATATCGAATTTAAAATGTTATGTATGGGCTTTAAGCGAAAAGAAATTAAAGCGATGACACCTAAGAT

TATTGAATTTAGTGAACTTGGTGAGTTTATTTATCAACCAGTTAAAAAGTATTCAAGTGGTATGCGTGCAAAACTTGGTT

TTTCAATTAATATCCACAGTTAATCCAGATATCTTAGTCATTGACGAAGCTTTATCTGTAGGTGACCAAACTTTTGCACAA

AAATGTTTAGATAAAATTTACGAGTTTAAAGAGCAAAACAAAACCATCTTTTTCGTTAGTCATAACTTAGGACAAGTGAG

ACAATTTTGTACTAAGATTGCTTGGATTGAAGGCGGAAAGTTAAAAGATTACGGTGAACTTGATGATGTATTACCTAAAT

ATGAAGCTTTCCTTAACGATTTTAAAAAGAAATCCAAAGCCGAACAAAAAGAATTTAGAAACAAACTCGATGAGTCCCGC

TTCGTTATTAAATAAACCGAAAAAACCGAGAATCTCCATTTAAGGATTTCCTCGGTTTTATTTTTGTCATCATGATTATT

TCGCCTTTTTTATTTTTCTTTTTGCTTTGGCTATT
```

SEQ ID NO:44
>HGS033,
```
MNVSVNIKNVTKEYRIYRTNKERMKDALIPKHKNKTFFALDDISLKAYEGDVIGLVGINGSGKSTLSNIIGGSLSPTVGK

VDRNGEVSVIAISAGLSGQLTGIENIEFKMLCMGFKRKEIKAMTPKIIEFSELGEFIYQPVKKYSSGMRAKLGFSINITV

NPDILVIDEALSVGDQTFAQKCLDKIYEFKEQNKTIFFVSHNLGQVRQFCTKIAWIEGGKLKDYGELDDVLPKYEAFLND

FKKKSKAEQKEFRNKLDESRFVIK
```

SEQ ID NO:45
>HGS034,
```
ATAAGGTGAAGACACATAAAACAATATATCTTAGTAAGCATGCAACACTCTTTTTTGTTTATTCATAACAACAAAAAGA

ATTAAAGGAGGAGTCTTATTATGGCTCGATTCAGAGGTTCAAACTGGAAAAAATCTCGTCGTTTAGGTATCTCTTTAAGC

GGTACTGGTAAAGAATTAGAAAAACGTCCTTACTCACCAGGACAACATGGTCCAAACCAACGTAAAAAATTATCAGAATA
```

TABLE 1-continued

```
TGGTTTACAATTACGTGAAAAACAAAAATTACGTTACTTATATGGAATGACTGAAAGACAATTCCGTAACACATTTGACA
TCGCTGGTAAAAAATTCGGTGTACACGGTGAAAACTTCATGATCTTATTAGCAAGTCGTTTAGACGCTGTTGTTTATTCA
TTAGGTTTAGCTCGTACTCGTCGTCAAGCACGTCAATTAGTTAACCACGGTCATATCTTAGTAGATGGTAAACGTGTTGA
TATTCCATCTTATTCTGTTAAACCTGGTCAAACAATTTCAGTTCGTGAAAAATCTCAAAAATTAAACATCATCGTTAAT
CAGTTGAAATCAACAATTTCGTACCTGAGTACTTAAACTTTGATGCTGACAGCTTAACTGGTACTTTCGTACGTTTACCA
GAACGTAGCGAATTACCTGCTGAAATTAACGAACAATTAATCCGTTGAGTACTACTCAAGATAATACGGTCAATACCAAC
ACCCACAATTGTGGGTGT
```

SEQ ID NO:46
>HGS034,
```
MARFRGSNWKKSRRLGISLSGTGKELEKRPYAPGQHGPNQRKKLSEYGLQLREKQKLRYLYGMTERQFRNTFDIAGKKFG
VHGENFMILLASRLDAVVYSLGLARTRRQARQLVNHGHILVDGKRVDIPSYSVKPGQTISVREKSQKLNIIVESVEINNF
VPEYLNFDADSLTGTFVRLPERSELPAEINEQLIR
```

SEQ ID NO:47
>HGS036,
```
TGTTGATTGCACCTGCTTCAGTCATTGCTATAACTATTTTAATTTTTAATTTAACCGGTGATGCACTAAGAGATAGATTG
CTGAAACAACGGGGTGAATATGATGAGTCTCATTGATATACAAAATTTAACAATAAAGAATACTAGTGAGAAATCTCTTA
TTAAAGGGATTGATTTGAAAATTTTTAGTCAACAGATTAATGCCTTGATTGGAGAGAGCGGCGCTGGAAAAAGTTTGATT
GCTAAAGCTTTACTTGAATATTTACCATTTGATTTAAGCTGCACGTATGATTCGTACCAATTTGATGGGAAAATGTTAG
TAGATTGAGTCAATATTATGGTCATACAATTGGCTATATTTCTCAAAATTATGCAGAAAGTTTTAACGACCATACTAAAT
TAGGTAAACAGTTAACTGCGATTTATCGTAAGCATTATAAAGGTAGTAAAGAAGAGGCTTTGTCCAAAGTTGATAAGGCT
TTGTCGTGGGTTAATTTACAAAGCAAAGATATATTAAATAAATATAGTTTCCAACTTTCTGGGGGCCAACTTGAACGCGT
ATACATAGCAAGCGTTCTCATGTTGGAGCCTAAATTAATCATTGCAGACGAACCAGTTGCATCATTGGATGCTTTGAACG
GTAATCAAGTGATGGATTTATTACAGCATATTGTATTAGAACATGGTCAAACATTATTTATTATCACACATAACTTAAGT
CATGTATTGAAATATTGTCAGTACATTTATGTTTTAAAAGAAGGTCAAATCATTGAACGAGGTAATATTAATCATTTCAA
GTATGAGCATTTGCATCCGTATACTGAACGTCTAATTAAATATAGAACACAATTAAAGAGGGATTACTATGATTGAGTTA
AAACATGTGACTTTTGGTTATAATAAAAAGCAGATGGTGCTACAAGATATCAATATTACTATACCTGATGGAGAAAATGT
TGGTATTTTAGGCGAAAGTG
```

SEQ ID NO:48
>HGS036,
```
MMSLIDIQNLTIKNTSEKSLIKGIDLKIFSQQINALIGESGAGKSLIAKALLEYLPFDLSCTYDSYQFDGENVSRLSQYY
GHTIGYISQNYAESFNDHTKLGKQLTAIYRKHYKGSKEEALSKVDKALSWVNLQSKDILNKYSFQLSGGQLERVYIASVL
MLEPKLIIADEPVASLDALNGNQVMDLLQHIVLEHGQTLFIITHNLSHVLKYCQYIYVLKEGQIIERGNINHFKYEHLHP
YTERLIKYRTQLKRDYYD
```

SEQ ID NO:49
HGS040,
```
GATGATATTTTAATTACAGAAAATGGTTGTCAAGTCTTTACTAAATGCACAAAAGACCTTATAGTTTTAACATAAGCGTG
TAAAATGAGGAGGAAACTGAATGATTTCGGTTAATGATTTTAAAACAGGTTTAACAATTTCTGTTGATAACGCTATTTGG
AAAGTTATAGACTTCCAACATGTAAAGCCTGGTAAAGGTTCAGCATTCGTTCGTTCAAAATTACGTAATTTAAGAACTGG
TGCAATTCAAGAGAAAACGTTTAGAGCTGGTGAAAAAGTTGAACCAGCAATGATTGAAAATCGTCGCATGCAATATTTAT
ATGCTGACGGRGATAATCATGTATTTATGGATAATGAAAGCTTTGAACAAACAGAACTTTCAAGTGATTACTTAAAAGAA
GAATTGAATTACTTAAAAGAAGGTATGGAAGTACAAATTCAAACATACGAAGGTGAAACTATCGGTGTTGAATTACCTAA
AACTGTTGAATTAACAGTAACTGAAACAGAACCTGGTATTAAAGGTGATACTGCAACTGGTGCCACTAAATCGGCAACTG
TTGAAACTGGTTATACATTAAATGTACCTTTATTTGTAAACGAAGGTGACGTTTTAATTATCAACACTGGTGATGGAAGC
```

TABLE 1-continued

TACATTTCAAGAGGATAATCTCTAATTTGTTAACAAATAGCTTGTATTCACTATACTGATTTAACGTAAGANATTCTAAA

TAAGTCTCATAAAGCTATTGCCTAAAATGATTATAGGTTA

SEQ ID NO:50
>HGS040,
MISVNDFKTGLTISVDNAIWKVIDFQHVKPGKGSAFVRSKLRNLRTGAIQEKTFRAGEKVEPAMIENRRMQYLYADGDNH

VFMDNESFEQTELSSDYLKEELNYLKEGMEVQIQTYEGETIGVELPKTVELTVTETEPGIKGDTATGATKSATVETGYTL

NVPLFVNEGDVLIINTGDGSYISRG

SEQ ID NO:51
>168153/168339, (operon comprising ORFs for five polypeptides listed below),
TTAGGATGTAAGAAAGTTCCAGTGCAAGAAATCCATGAAACACAATATTCAATTAGTACATGGCAACATAAAGTTCCATT

TGGTGTGTGGTGGGAAACGTTACAACAAGAACATCGCTTGCCATGGACTACTGAGAGAAGACAAGAAGCGCCATTTATTA

CAATGTGTCATGGTGATACAGAACAATATTTGTATACAAAAGATTTAGGCGAAGCACATTTTCAAGTATGGGAAAAGGTT

GTCGCAAGTTATAGTGGTTGTTGTTCTGTAGAGAATTGCACAAGGTACATATCCTTGTCTTTCTCAACAAGATGTACT

CATGAAGTATCAGCCATTGAGTTATAAGGAAATTGAAGCGGTTGTTCATAAAGGGGAAACTGTGCCAGCAGGTGTGACAC

GCTTTAATATTTCAGGACGATGTCTTAATCTTCAAGTACCACTGGCATTACTTAAACAAGATGATGATGTTGAACAATGC

GCAATTGGAAGCAGTTTTTAGCAGATAAGTTTGCCAATATGAGATGCTATACTGAAAAAGTATACTTGGTGGAGCAATAG

TTTTACTGTGATGTTGAGGGAAATATGATGATTTAGCGTATTGATAGCGAAAATATAATAAAACAATATAGTGTGGAGAA

CTTTTGATATTTTATAAATATTGAAGTTCTCCATTTTTGTATTTTGCATATAAAAATTAAATAAAATAAGGTATATTAAG

GTAAAGTATAAATTTTAAATAAATGGGGAATGAGTATGAGCTCAATTATAGGAAAAATAGCAATTTGGATAGGCATCGTA

GCTCAAATATATTTTAGTGTCGTTTTTGTTAGGATGATATCTATTAATATTGCTGGAGGATCTGATTACGAAACAATTTT

TTTATTAGGATTAATATTGGCTCTTTTCACTGTTTTACCAACCATCTTTACTGCGATTTATATGGAAAGTTACTCTGTAA

TCGGAGGTGCACTTTTTATTGTTTATGCTATTATTGCACTGTGTTTATATAATTTCCTTTCGTCAATTTTATGGCTGATT

GGTGGTATTTTGCTGATTTGGAATAAATACTCAAAAGATGAATCGACAGACGAAAATGAAAAGTTGATATTGAAAGTAC

AGAGAATCAATTTGAATCTAAAGATAAAATCACTAAAGAATAAAGAGAATATTTAAGGTAAAGTATAAATTTTAAATAAA

TGGGGAATAGACATGGAAAAAAATGTAGAAAAATCATTCATAAAGATAGGTTTATATTTTCAAATAGCTTATATAGTACT

CATGGCTATAACTTATGTGGGTTTGTAATTTGCTATGGACTAATTTTCGGCCTTTTCTATTTATTATCAGGTAGCAGAG

CTGATTATTAATAGTAACAATAGTTATATCGGCAATAATTTCTATATTTGTAATTATACTTTCAATCGTACCTGTCATC

GTATTGGCATCTGACTTATTTAAAGAAAGGATTTCAAAAGGTGTCATATTAATTGTATTGGCTATTATCGCTTTAGTATT

ATGCAACTTTGTATCTGCAATACTCTGGTTTGTTTCAGCCATATCTATTTTAGGTAGAAAAAAATTAGTAGCTGCAGCAG

ATACTACCACTATTCAAAAAAGTAAAGGGAACGCAAATCAAGCATCACATAAAGACACGTGTAAAAAGGAACTTGATAGT

CAAGACATGATGGAACATCCTGAGGTTAAAAATCCCACGACTAAAAACCTTGAAGGATTTAACGAAGAAATACATAAAGA

TGAAGCTACAACTAAAGTTGTCAGTGATAACACGGAACCGCCTATTGAATCAAAAGACCATGTCTCGAAAAAAGATTGAT

GACAAACTAATCGAGAGACTTAAAAAAATAATATTCAACATAAGAACTTTTAAAACGACATTTAAACGCATTGCCAATCA

CTAATGGTAGTGCGTTTAACTATACCTTAAATATCTGAATATTTTGTTAAATGGAGCTACCTTTGTTGTACTATTCAAAT

GAAGAGGAGTAAAATGTAATTAAAGGAAAGAAATTTGAGGAGTGATCTTTATGACAAACAACAAAGTAGCATTAGTAACT

GGCGGAGCACAAGGGATTGGTTTTAAAATTGCAGAACGTTTAGTGGAAGATGGTTTCAAAGTAGCAGTTGTTGATTTCAA

TGAAGAAGGGGCAAAAGCAGCTGCACTTAAATTATCAAGTGATGGTACAAAAGCTATTGCTATCAAAGCAGATGTATCAA

ACCGTGATGATGTATTTAACGCATAAGACAAACTGCCGCGCAATTTGGCGATTTCCATGTCATGGTTAACAATGCCGGCC

TTGGACCAACAACACCAATCGATACAATTACTGAAGAACAGTTTAAAACAGTATATGGCGTGAACGTTGCAGGTGTGCTA

TGGGGTATTCAAGCCGCACATGAACAATTTAAAAAATTCAATCATGGCGGTAAAATTATCAATGCAACATCTCAAGCAGG

CGTTGAGGGTAACCCAGGCTTGTCTTTATATTGCAGTACAAAATTCGCAGTGCGAGGTTTAACACAAGTAGCCGCACAAG

ATTTAGCGTCTGAAGGTATTACTGTGAATGCATTCGCACCTGGTATCGTTCAAACACCAATGATGGAAAGTATCGCAGTG

TABLE 1-continued

```
GCAACAGCCGAAGAAGCAGGTAAACCTGAAGCATGGGGTTGGGAACAATTTACAAGTCAGATTGCTTTGGGCAGAGTTTC
TCAACCAGAAGATGTTTCAAATGTAGTGAGCTTCTTAGCTGGTAAAGACTCTGATTACATTACTGGACAAACAATTATTG
TAGATGGTGGTATGAGATTCCGTTAATAATCATCCACTAATGATAAATAAATCCTTATTGTTAAGTTTAATCACTTAGCA
GTAAGGATTTTTTAGTGCACTTAGAAGGGAGTGTATTGGTAGAAAATTAATAAGCGAAGTTCTTAAGTGAGTTATGATGT
CACAGTCTAATGCATCAGTTGAAAGCATTATTAGTATTAACACACCCAAGATATTATAAAACATCACAAAAACACCACTA
TCTAATTTATCTCAATAAAAATTCACAAAGTTATCTCATTTTATTTTTATAAATAAAAAATATCGATAAAAAGCTTACAA
TACTTTATGTTTTTATGATATATTTTTAATGTATAAATGAGGTGGAAGATTTGGAAAGAGTTTTGATAACTGGTGGGGCT
GGTTTTATTGGGTCGCATTTAGTAGATGATTTACAACAAGATTATGATGTTTATGTTCTAGATAACTATAGAACAGGTAA
ACGAGAAAATATTAAAAGTTTGGCTGACGATCATGTGTTTGAATTAGATATTCGTGAATATGATGCAGTTGAACAAATCA
TGAAGACATATCAATTTGATTATGTTATTCATTTAGCAGCATTAGTTAGTGTTGCTGAGTCGGTTGAGAAACCTATCTTA
TCTCAAGAAATAAACGTCGTAGCAACATTAAGATTGTTAGAAATCATTAAAAAATATAATAATCATATAAAACGTTTTAT
CTTTGCTTCGTCAGCAGCTGTTTATGGTGATCTTCCTGATTTGCCTAAAAGTGATCAATCATTAATCTTACCATTATCAC
CATATGCAATAGATAAATATTACGGCGAACGGACGACATTAAATTATTGTTCGTTATATAACATACCAACAGCGGTTGTT
AAATTTTTTAATGTATTTGGGCCAAGACAGGATCCTAAGTCACAATATTCAGGTGTGATTTCAAAGATGTTCGATTCATT
TGAGCATAACAAGCCATTTACATTTTTTGGTGACGGACTGCAAACTAGAGATTTTGTATATGTATATGATGTTGTTCAAT
CTGTACGCTTAATTATGGAACACAAAGATGCAATTGGACACGGTTATAACATTGGTACAGGCACTTTTACTAATTTATTA
GAGGTTTATCGTATTATTGGTGAATTATATGGAAAATCAGTCGAGCATGAATTTAAAGAAGCACGAAAAGGAGATATTAA
GCATTCTTATGCAGATATTTCTAACTTAAAGGCATTAGGATTTGTTCCTAAATATACAGTAGAAACAGGTTTAAAGGATT
ACTTTAATTTTGAGGTAGATAATATTGAAGAAGTTACAGCTAAAGAAGTGGAAATGTCGTGAAAATGACATTGAAGCTGT
CCATAATAATAAGGGTTATGCCTATCAAAGAAAATTAGACAAACTAGAAGAAGTGAGAAAAAGCTATTACCCAATTAAAC
GTGCGATTGACTTAATTTTAAGCATTGTTTTATTATTTTTAACTTTACCGATTATGGTTATATTCGCCATTGCTATCGTC
ATAGATTCGCCAGGAAACCCTATTTATAGTCAGGTTAGAGTTGGGAAGATGGGTAAATTAATTAAAATATACAAATTACG
TTCGATGTGCAAAAACGCAGAGAAAAACGGTGCGCAATGGCTGATAAAGATGATGATCGTATAACAAATGTCGGGAAGT
TTATTCGTAAAACACGCATTGATGAATTACCACAACTAATTAATGTTGTTAAAGGGAAATGAGTTTTATTGGACCACGC
CCGGAACGTCCGGAATTTGTAGAATTATTTAGTTCAGAAGTGATAGGTTTCGAGCAAAGATGTCTTGTTACACCAGGGTT
AACAGGACTTGCGCAAATTCAAGGTGGATATGACTTAACACCGCAACAAAAACTGAAATATGACATGAAATATATACATA
AAGGTAGTTTAATGATGGAACTATATATATCAATTAGAACATTGATGGTTGTTATTACAGGGGAAGGCTCAAGGTAGTCT
TAATTTACTTAATAAGTTCAAATAAAAGTTATATTTTAAAGATTGTGACCAATTGTTACAGTATAACGAGGAATCCCTTG
AGACAGTATCAAATGGCATTAAGAAATATGTGCCATCATTGATTTGCATGGCTATAAATACTATTCATCTGATGAGATAG
CCATGTTAAGAAATTGAAAGTATAGCATTAAAGGGGTTTGTAACAGTTGAAAATTATATATTGTATTACTAAAGCAGACA
ATGGTGGTGCACAAACACATCTCATTCAACTCGCCAACCATTTTTGCGTACACAATGATGTTTATGTCATTGTAGGCAAT
CATGGACCAATGATTGAACAACTAGATGCAAGAGTTAATGTAATTATTATCGAACATTTAGTAGGTCCAATTGACTTTAA
ACAAGATATTTTAGCTGTCAAAGTGTTAGCACAGTTATTCTCGAAAATTAAACCTGATGTTATCCATTTACATTCTTCCA
AAGCTGGAACGGTCGGACGAATTGCGAAGTTCATTTCGAAATCGAAAGACACACGTATAGTTTTTACTGCACATGGATGG
GCTTTTACAGAGGGTGTTAAACCAGCTAAAAAATTTCTATATTTAGTTATCGAAAAATTAATGTCACTTATTACAGATAG
CATTATTTGTGTTTCAGATTATGCCCCGACAAAGCATCAATTTGTTATGATTGCAAGATTTGCTTATCCAAAATTGCCAC
AAAATCTAATCGCGGCAATAGAGATATTGAAATTACATAACAGTAATCATGCGCATTTTACATTTATAGGCGATGGACCT
ACATTAAATGATTGTCAGCAACAAGTTGTACAAGCTGGGTTAGAAAATGATGTCACATTTTTGGGCAATGTCATTAATGC
GAGTCATTTATTATCACAATACGATACGTTTATTTTAATAAGTAAGCATGAAGGTTTGCCAATTAGCATTATAGAAGCTA
```

TABLE 1-continued

```
TGGCTACAGGTTTGCCTGTTATAGCCAGTCATGTTGGCGGTATTTCAGAATTAGTAGCTGATAATGGTATATGTATGATG
AACAACCAACCCGAAACTATTGCTAAAGTCCTGGAAAAATATTTAATAGACAGTGATTACATCAAAATGAGTAATCAATC
TAGAAAACGTTATTTAGAATGTTTTACTGAGGAGAAAATGATTAAAGAAGTGGAAGACGTTTATAATGGAAAATCAACAC
AATAGTAAATTACTAACATTGTTACTTATCGGTTTAGCGGTTTTTATTCAGCAATCTTCGGTTATTGCCGGTGTGAATGT
TTCTATAGCTGACTTTATCACATTACTAATATTAGTTTATTTACTGTTTTTCGCTAACCATTTATTAAAGGCAAATCATT
TTTTACAGTTTTTCATTATTTTGTATACATATCGTATGATTATTACGCTTTGTTTGCTATTTTTTGATGATTTGATATTT
ATTACGGTTAAGGAAGTTCTTGCATCTACAGTTAAATATGCATTTGTAGTCATTTATTTCTATTTAGGGATGATCATCTT
TAAGTTAGGTAATAGCAAAAAAGTGATCGTTACCTCTTATATTATAAGCAGTGTGACTATAGGTACCTTTTATAATATCA
ACTACTATTTATTCCAATTAAGCGACCTTGATGCCTTACCGTCATTAGATCGAATGGCGTCTATTTTTGAAGAGGGCTTT
GCATCATTAAATGATAGTGGGTCTGAGCGAAGTGTTGTATGGATAAATGCCATTTCAGTAATTAAATATACACTAGGTTT
TGGTGTCGGATTAGTGGATTATGTACATATTGGCTCGCAAATTAATGGTATTTTACTTGTTGCCCATAATACATATTTGC
AGATCTTTGCGGAATGGGGCATTTTATTCGGTGCATTATTTATCATATTTATGCTTTATTTACTGTTTGAATTATTTAGA
TTTAACATTTCTGGGAAAAATGTAACAGCAATTGTTGTAATGTTGACGATGCTGATTTACTTTTTAACAGTATCATTTAA
TAACTCAAGATATGTCGCTTTTATTTTAGGAATTATCGTCTTTATTGTTCAATATGAAAAGATGGAAAGGGATCGTAATG
AAGAGTGATTCACTAAAAGAAAATATTATTTATCAAGGGCTATACCAATTGATTAGAACGATGACACCACTGATTACAAT
ACCCATTATTTCACGTGCATTTGGTCCCAGTGGTGTGGGTATTGTTTCATTTTCTTTCAATATCGTGCAATACTTTTTGA
TGATTGCAAGTGTTGGCGTTCAGTTATATTTTAATAGAGTTATCGCGAAGTCCGTTAACGACAAACGGCAATTGTCACAG
CAGTTTTGGGATATCTTTGTCAGTAAATTATTTTTAGCGTTAACAGTTTTTGCGATGTATATGGTCGTAATTACTATATT
TATTGATGATTACTATCTTATTTTCCTACTACAAGGAATCTATATTATAGGTGCAGCACTCGATATTTCATGGTTTTATG
CTGGAACTGAAAAGTTTAAAATTCCTAGCCTCAGTAATATTGTTGCGTCTGGTATTGTATTAAGTGTAGTTGTTATTTTT
GTCAAAGATCAATCAGATTTATCATTGTATGTATTTACTATTGCTATTGTGACGGTATTAAACCAATTACCTTTGTTTAT
CTATTTAAAACGATACATTAGCTTTGTTTCGGTTAATTGGATACACGTCTGGCAATTGTTTCGTTCGTCATTAGCATACT
TATTACCAAATGGACAGCTCAACTTATATACTAGTATTTCTTGCGTTGTTCTTGGTTTAGTAGGTACATACCAACAAGTT
GGTATCTTTTCTAACGCATTTAATATTTTAACGGTCGCAATCATAATGATTAATACATTTGATCTTGTAATGATTCCGCG
TATTACCAAAATGTCTATCCAGCAATCACATAGTTTAACTAAAACGTTAGCTAATAATATGAATATTCAATTGATATTAA
CAATACCTATGGTCTTTGGTTTAATTGCAATTATGCCATCATTTTATTTATGGTTCTTTGGTGAGGAATTCGCATCAACT
GTCCCATTGATGACCATTTTAGCGATACTTGTATTAATCATTCCTTTAAATATGTTGATAAGCAGGCAATATTTATTAAT
AGTGAATAAAATAAGATTATATAATGCGTCAATTACTATTGGTGCAGTGATAAACCTAGTATTATGTATTATTTTGATAT
ATTTTTATGGAATTTACGGTGCTGCTATTGCGCGTTTAATTACAGAGTTTTTCTTGCTCATTTGGCGATTTATTGATATT
ACTAAAATCAATGTGAAGTTGAATATTGTAAGTACGATTCAATGTGTCATTGCTGCTGTTATGATGTTTATTGTGCTTGG
TGTGGTCAATCATTATTTGCCCCCTACAATGTACGCTACGCTGCTATTAATTGCGATTGGTATAGTAGTTTATCTTTTAT
TAATGATGACTATGAAAAATCAATACGTATGGCAAATATTGAGGCATCTTCGACATAAAACAATTTAAGTACCGGTAATG
CTATACTTTAGAAAATTAAGATTAAGAAGAAAAGGCAATTTCTTATTGAAAAATGGAAGTTGTCTTTTTTAATTCTCTTT
AAAAGCGGGAAACAAAAGCAGTTAAATGCCTTTTTGCATTCAATATTAAATATTATATCAATTTCGAATATTTAAATTTT
ATATAATTGGATATAACAAATAAATAATAATTATTGCAAAACACACCCAAAATTAATTATTATAAAAGTATATTCATAAA
AGGAGGAATATACTTATGGCATTTAAATTACCAAATTTACCATATGCATATGATGCATTGGAACCATATATAGATCAAAG
AACAATGGAGTTTCATCACGACAAACATCACAATACGTACGTGACGAAATTAAACGCAACAGTTGAAGGAACAGAGTTAG
AGCATCAATCACTAGCGGATATGATTGCTAACTTAGACAAGGTACCGGAAGCGATGGGGTACCGAGCTCGAATTCGTAAT
CATGTCATAGCTGTTTCCTGTG
```

TABLE 1-continued

SEQ ID NO:52
>168153_3,
GTGGAAGATTTGGAAAGAGTTTTGATAACTGGTGGGGCTGGTTTTATTGGGTCGCATTTAGTAGATGATTTACAACAAGA
TTATGATGTTTATGTTCTAGATAACTATAGAACAGGTAAACGAGAAAATATTAAAAGTTTGGCTGACGATCATGTGTTTG
AATTAGATATTCGTGAATATGATGCAGTTGAACAAATCATGAAGACATATCAATTTGATTATGTTATTCATTTAGCAGCA
TTAGTTAGTGTTGCTGAGTCGGTTGAGAAACCTATCTTATCTCAAGAAATAAACGTCGTAGCAACATTAAGATTGTTAGA
AATCATTAAAAAATATAATAATCATATAAAACGTTTTATCTTTGCTTCGTCAGCAGCTGTTTATGGTGATCTTCCTGATT
TGCCTAAAAGTGATCAATCATTAATCTTACCATTATCACCATATGCAATAGATAAATATTACGGCGAACGGACGACATTA
AATTATTGTTCGTTATATAACATACCAACAGCGGTTGTTAAATTTTTAATGTATTTGGGCCAAGACAGGATCCTAAGTC
ACAATATTCAGGTGTGATTTCAAAGATGTTCGATTCATTTGAGCATAACAAGCCATTTACATTTTTTGGTGACGGACTGC
AAACTAGAGATTTTGTATATGTATATGATGTTGTTCAATCTGTACGCTTAATTATGGAACACAAAGATGCAATTGGACAC
GGTTATAACATTGGTACAGGCACTTTTACTAATTTATTAGAGGTTTATCGTATTATTGGTGAATTATATGGAAAATCAGT
CGAGCATGAATTTAAAGAAGCACGAAAAGGAGATATTAAGCATTCTTATGCAGATATTTCTAACTTAAAGGCATTAGGAT
TTGTTCCTAAATATACAGTAGAAACAGGTTTAAAGGATTACTTTAATTTTGAGGTAGATAATATTGAAGAAGTTACAGCT
AAAGAAGTGGAAATGTCGTGA

SEQ ID NO:53
>168153_3,
VEDLERVLITGGAGFIGSHLVDDLQQDYDVYVLDNYRTGKRENIKSLADDHVFELDIREYDAVEQIMKTYQFDYVIHLAA
LVSVAESVEKPILSQEINVVATLRLLEIIKKYNNHIKRFIFASSAAVYGDLPDLPKSDQSLILPLSPYAIDKYYGERTTL
NYCSLYNIPTAVVKFFNVFGPRQDPKSQYSGVISKMFDSFEHNKPFTFFGDGLQTRDFVYVYDVVQSVRLIMEHKDAIGH
GYNIGTGTFTNLLEVYRIIGELYGKSVEHEFKEARKGDIKHSYADISNLKALGFVPKYTVETGLKDYFNFEVDNIEEVTA
KEVEMS

SEQ ID NO:54
>168153_2,
ATGGTTATATTCGCCATTGCTATCGTCATAGATTCGCCAGGAAACCCTATTTATAGTCAGGTTAGAGTTGGGAAGATGGG
TAAATTAATTAAAATATACAAATTACGTTCGATGTGCAAAAACGCAGAGAAAAACGGTGCGCAATGGGCTGATAAAGATG
ATGATCGTATAACAAATGTCGGGAAGTTTATTCGTAAAACACGCATTGATGAATTACCACAACTAATTAATGTTGTTAAA
GGGGAAATGAGTTTTATTGGACCACGCCCGGAACGTCCGGAATTTGTAGAATTATTTAGTTCAGAAGTGATAGGTTTCGA
GCAAAGATGTCTTGTTACACCAGGGTTAACAGGACTTGCGCAAATTCAAGGTGGATATGACTTAACACCGCAACAAAAAC
TGAAATATGACATGAAATATATACATAAAGGTAGTTTAATGATGGAACTATATATATCAATTAGAACATTGATGGTTGTT
ATTACAGGGGAAGGCTCAAGGTAG

SEQ ID NO:55
>168153_2,
LDKLEEVRKSYYPIKRAIDLILSIVLLFLTLPIMVIFAIAIVIDSPGNPIYSQVRVGKMGKLIKIYKLRSMCKNAEKNGA
QWADKDDDRITNVGKFIRKTRIDELPQLINVVKGEMSFIGPRPERPEFVELFSSEVIGFEQRCLVTPGLTGLAQIQGGYD
LTPQQKLKYDMKYIHKGSLMMELYISIRTLMVVITGEGSR

SEQ ID NO:54
>168153_1,
ATGATTGAACAACTAGATGCAAGAGTTAATGTAATTATTATCGAACATTTAGTAGGTCCAATTGACTTTAAACAAGATAT
TTTAGCTGTCAAAGTGTTAGCACAGTTATTCTCGAAAATTAAACCTGATGTTATCCATTTACATTCTTCCAAAGCTGGAA
CGGTCGGACGAATTGCGAAGTTCATTTCGAAATCGAAAGACACACGTATAGTTTTTACTGCACATGGATGGCTTTTACA
GAGGGTGTTAAACCAGCTAAAAAATTTCTATATTTAGTTATCGAAAAATTAATGTCACTTATTACAGATAGCATTATTTG
TGTTTCAGATTTCGATAAACAGTTAGCGTTAAAATATCGATTTAATCGATTGAAATTAACCACAATACATAATGGTATTG
CAGATGTTCCCGCTGTTAAGCAAACGCTAAAAAGCCAATCACATAACAATATTGGCGAAGTAGTTGGAATGTTGCCTAAT

TABLE 1-continued

```
AAACAAGATTTACAGATTAATGCCCCGACAAAGCATCAATTTGTTATGATTGCAAGATTTGCTTATCCAAAATTGCCACA

AAATCTAATCGCGGCAATAGAGATATTGAAATTACATAACAGTAATCATGCGCATTTTACATTTATAGGCGATGGACCTA

CATTAAATGATTGTCAGCAACAAGTTGTACAAGCTGGGTTAGAAAATGATGTCACATTTTTGGGCAATGTCATTAATGCG

AGTCATTTATTATCACAATACGATACGTTTATTTTAATAAGTAAGCATGAAGGTTTGCCAATTAGCATTATAGAAGCTAT

GGCTACAGGTTTGCCTGTTATAGCCAGTCATGTTGGCGGTATTTCAGAATTAGTAGCTGATAATGGTATATGTATGATGA

ACAACCAACCCGAAACTATTGCTAAAGTCCTGGAAAAATATTTAATAGACAGTGATTACATCAAAATGAGTAATCAATCT

AGAAAACGTTATTTAGAATGTTTTACTGAGGAGAAAATGATTAAAGAAGTGGAAGACGTTTATAATGGAAAATCAACACA

ATAG
```

SEQ ID NO:57
>168153_1,
LKIIYCITKADNGGAQTHLIQLANHFCVHNDVYVIVGNHGPMIEQLDARVNVIIIEHLVGPIDFKQDILAVKVLAQLFSK

IKPDVIHLHSSKAGTVGRIAKFISKSKDTRIVFTAHGWAFTEGVKPAKKFLYLVIEKLMSLITDSIICVSDFDKQLALKY

RFNRLKLTTIHNGIADVPAVKQTLKSQSHNNIGEVVGMLPNKQDLQINAPTKHQFVMIARFAYPKLPQNLIAAIEILKLH

NSNHAHFTFIGDGPTLNDCQQQVVQAGLENDVTFLGNVINASHLLSQYDTFILISKHEGLPISIIEAMATGLPVIASHVG

GISELVADNGICMMNNQPETIAKVLEKYLIDSDYIKMSNQSRKRYLECFTEEKMIKEVEDVYNGKSTQ

SEQ ID NO:58
>168339_1, (ORF overlaps the 3' end of 168153_1 by 20 nucleotides),
```
ATGGAAAATCAACACAATAGTAAATTACTAACATTGTTACTTATCGGTTTAGCGGTTTTTATTCAGCAATCTTCGGTTAT

TGCCGGTGTGAATGTTTCTATAGCTGACTTTATCACATTACTAATATTAGTTTATTTACTGTTTTTCGCTAACCATTTAT

TAAAGGCAAATCATTTTTTACAGTTTTTCATTATTTTGTATACATATCGTATGATTATTACGCTTTGTTTGCTATTTTTT

GATGATTTGATATTTATTACGGTTAAGGAAGTTCTTGCATCTACAGTTAAATATGCATTTGTAGTCATTTATTTCTATTT

AGGGATGATCATCTTTAAGTTAGGTAATAGCAAAAAAGTGATCGTTACCTCTTATATTATAAGCAGTGTGACTATAGGTC

TATTTTGTATTATAGCTGGTTTGAACAAGTCCCCTTTACTAATGAAATTGTTATATTTTGATGAAATACGTTCAAAAGGA

TTAATGAATGACCCTAACTATTTCGCGATGACACAGATTATTACATTGGTACTTGCTTACAAGTATATTCATAATTACAT

ATTCAAGGTCCTTGCATGTGGTATTTTGCTATGGTCTTTAACTACAACGGGGTCTAAGACTGCGTTTATCATATTAATCG

TCTTAGCCATTTATTTCTTTATTAAAAAGTTATTTAGTAGAAATGCGGTAAGTGTTGTGAGTATGTCAGTGATTATGCTG

ATATTACTTTGTTTTACCTTTTATAATATCAACTACTATTTATTCCAATTAAGCGACCTTGATGCCTTACCGTCATTAGA

TCGAATGGCGTCTATTTTTGAAGAGGGCTTTGCATCATTAAATGATAGTGGGTCTGAGCGAAGTGTTGTATGGATAAATG

CCATTTCAGTAATTAAATATACACTAGGTTTTGGTGTCGGATTAGTGGATTATGTACATATTGGCTCGCAAATTAATGGT

ATTTTACTTGTTGCCCATAATACATATTTGCAGATCTTTGCGGAATGGGCATTTTATTCGGTGCATTATTTATCATATT

TATGCTTTATTTACTGTTTGAATTATTTAGATTTAACATTTCTGGGAAAAATGTAACAGCAATTGTTGTAATGTTGACGA

TGCTGATTTACTTTTTAACAGTATCATTTAATAACTCAAGATATGTCGCTTTTATTTTAGGAATTATCGTCTTTATTGTT

CAATATGAAAAGATGGAAAGGGATCGTAATGAAGAGTGA
```

SEQ ID NO:59
>168339_1,
MENQHNSKLLTLLLIGLAVFIQQSSVIAGVNVSIADFITLLILVYLLFFANHLLKANHFLQFFIILYTYRMIITLCLLFF

DDLIFITVKEVLASTVKYAFVVIYFYLGMIIFKLGNSKKVIVTSYIISSVTIGLFCIIAGLNKSPLIMKLLYFDEIRSKG

LMNDPNYFAMTQIITLVLAYKYIHNYIFKVLACGILLWSLTTTGSKTAFIILIVLAIYFFIKKLFSRNAVSVVSMSVIML

ILLCFTFYNINYYLFQLSDLDALPSLDRMASIFEEGFASLNDSGSERSVVWINAISVIKYTLGFGVGLVDYVHIGSQING

ILLVAHNTYLQIFAEWGILFGALFIIFMLYLLFELFRFNISGKNVTAIVVMLTMLIYFLTVSFNNSRYVAFILGIIVFIV

QYEKMERDRNEE

SEQ ID NO:60
>168339_2, (ORF overlaps the 3' end of 168339_1 by 35 nucleotides),
ATGAAAAGATGGAAAGGGATCGTAATGAAGAGTGATTCACTAAAAGAAAATATTATTTATCAAGGGCTATACCAATTGAT

TABLE 1-continued

```
TAGAACGATGACACCACTGATTACAATACCCATTATTTCACGTGCATTTGGTCCCAGTGGTGTGGGTATTGTTTCATTTT

CTTTCAATATCGTGCAATACTTTTTGATGATTGCAAGTGTTGGCGTTCAGTTATATTTTAATAGAGTTATCGCGAAGTCC

GTTAACGACAAACGGCAATTGTCACAGCAGTTTTGGGATATCTTTGTCAGTAAATTATTTTTAGCGTTAACAGTTTTTGC

GATGTATATGGTCGTAATTACTATATTTATTGATGATTACTATCTTATTTTCCTACTACAAGGAATCTATATTATAGGTG

CAGCACTCGATATTTCATGGTTTTATGCTGGAACTGAAAAGTTTAAAATTCCTAGCCTCAGTAATATTGTTGCGTCTGGT

ATTGTATTAAGTGTAGTTGTTATTTTTGTCAAAGATCAATCAGATTTATCATTGTATGTATTTACTATTGCTATTGTGAC

GGTATTAAACCAATTACCTTTGTTTATCTATTTAAAACGATACATTAGCTTTGTTTCGGTTAATTGGATACACGTCTGGC

AATTGTTTCGTTCGTCATTAGCATACTTATTACCAAATGGACAGCTCAACTTATATACTAGTATTTCTTGCGTTGTTCTT

GGTTTAGTAGGTACATACCAACAAGTTGGTATCTTTTCTAACGCATTTAATATTTTAACGGTCGCAATCATAATGATTAA

TACATTTGATCTTGTAATGATTCCGCGTATTACCAAAATGTCTATCCAGCAATCACATAGTTTAACTAAAACGTTAGCTA

ATAATATGAATATTCAATTGATATTAACAATACCTATGGTCTTTGGTTTAATTGCAATTATGCCATCATTTTATTTATGG

TTCTTTGGTGAGGAATTCGCATCAACTGTCCCATTGATGACCATTTTAGCGATACTTGTATTAATCATTCCTTTAAATAT

GTTGATAAGCAGGCAATATTTATTAATAGTGAATAAAATAAGATTATATAATGCGTCAATTACTATTGGTGCAGTGATAA

ACCTAGTATTATGTATTATTTTGATATATTTTTATGGAATTTACGGTGCTGCTATTGCGCGTTTAATTACAGAGTTTTTC

TTGCTCATTTGGCGATTTATTGATATTACTAAAATCAATGTGAAGTTGAATATTGTAAGTACGATTCAATGTGTCATTGC

TGCTGTTATGATGTTTATTGTGCTTGGTGTGGTCAATCATTATTTGCCCCCTACAATGTACGCTACGCTGCTATTAATTG

CGATTGGTATAGTAGTTTATCTTTTATTAATGATGACTATGAAAAATCAATACGTATGGCAAATATTGAGGCATCTTCGA

CATAAAACAATTTAA

SEQ ID NO:61
>168339_2,
MKSDSLKENIIYQGLYQLIRTMTPLITIPIISRAFGPSGVGIVSFSFNIVQYFLMIASVGVQLYFNRVIAKSVNDKRQLS

QQFWDIFVSKLFLALTVFAMYMVVITIFIDDYYLIFLLQGIYIIGAALDISWFYAGTEKFKIPSLSNIVASGIVLSVVVI

FVKDQSDLSLYVFTIAIVTVLNQLPLFIYLKRYISFVSVNWIHVWQLFRSSLAYLLPNGQLNLYTSISCVVLGLVGTYQQ

VGIFSNAFNILTVAIIMINTFDLVMIPRITKMSIQQSHSLTKTLANNMNIQLILTIPMVFGLIAIMPSFYLWFFGEEFAS

TVPLMTILAILVLIIPLNMLISRQYLLIVNKIRLYNASITIGAVINLVLCIILIYFYGIYGAAIARLITEFFLLIWRFID

ITKINVKLNIVSTIQCVIAAVMMFIVLGVVNHYLPPTMYATLLLIAIGIVVYLLLMMTMKNQYVWQILRHLRHKTI
```

Nucleic acid molecules of the present invention may be in the form of RNA, such as mRNA, or in the form of DNA, including, for instance, DNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

The present invention further encompasses nucleic acid molecules of the present invention that are chemically synthesized, or reproduced as peptide nucleic acids (PNA), or according to other methods known in the art. The use of PNAs would serve as the preferred form if the nucleic acid molecules of the invention are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, a PNA binds more strongly to DNA than does DNA itself. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T^{sub\ m}$) by 8°–20° C., vs. 4°–16° C. for the DNA/DNA 15-mer duplex. Also, the absence-of charge groups in PNA means that hybridization can be done at low ionic strengths and reduce possible interference by salt during the analysis.

By "isolated" polynucleotide sequence is intended a nucleic acid molecule, DNA or RNA, which has been removed from its native environment. This includes segments of DNA comprising the *S. aureus* polynucleotides of the present invention isolated from the native chromosome. These fragments include both isolated fragments consisting only of *S. aureus* DNA and fragments comprising heterologous sequences such as vector sequences or other foreign DNA. For example, recombinant DNA molecules contained in a vector are considered isolated for the purposes of the present invention which may be partially or substantially purified. Further examples of isolated DNA molecules include recombinant DNA molecules introduced and maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically which may be partially or substantially purified the excluded RNA or heterologous DNA. Isolated nucleic acid molecules at least 10%, 20%, 30%, 40%, 50%, 60%, 70%, 80%, 90%, 95%, 96%, 96%, 98%, 99%, or 100% pure relative to heterologous (Staphylococcus or other) (DNA or RNA) or relative to all materials and compounds other than the carrier solution. The term "isolated" does not refer to genomic or cDNA libraries, whole cell mRNA preparations, genomic DNA digests (including those gel separated by electrophoresis), whole chromosome or sheared whole cell genomic DNA preparations or other compositions where the art demonstrates no distinguishing features of the polynucleotides sequences of the present invention.

In addition, isolated nucleic acid molecules of the invention include DNA molecules which comprise a sequence substantially different from those described above but which, due to the degeneracy of the genetic code, still encode a *S. aureus* polypeptides and peptides of the present invention (e.g., polypeptides of Table 1). That is, all possible DNA sequences that encode the *S. aureus* polypeptides of the present invention. This includes the genetic code and species-specific codon preferences known in the art. Thus, it would be routine for one skilled in the art to generate the degenerate variants described above, for instance, to optimize codon expression for a particular host (e.g., change codons in the bacteria mRNA to those preferred by a mammalian or other bacterial host such as *E. coli*).

The invention further provides isolated nucleic acid molecules having the nucleotide sequence shown in Table 1 or a nucleic acid molecule having a sequence complementary to one of the above sequences. Such isolated molecules, particularly DNA molecules, are useful as probes for gene mapping and for identifying *S. aureus* in a biological sample, for instance, by PCR or hybridization analysis (e.g., including but not limited to, Northern blot analysis). In specific embodiments, the polynucleotides of the present invention are less than 300 kb, 200 kb, 100 kb, 50 kb, 10,kb, 7.5 kb, 5 kb, 2.5 kb, and 1 kb. In another embodiment, the polynucleotides comprising the coding sequence for polypeptides of the present invention do not contain genomic flanking gene sequences or contain only genomic flanking gene sequences having regulatory control sequences for the said polynucleotides.

The present invention is further directed to nucleic acid molecules encoding portions or fragments of the nucleotide sequences described herein. Uses for the polynucleotide fragments of the present invention include probes, primers, molecular weight markers and for expressing the polypeptide fragments of the present invention. Fragments include portions of the nucleotide sequences of Table 1, at least 10 contiguous nucleotides in length selected from any two integers, one of which representing a 5' nucleotide position and a second of which representing a 3' nucleotide position, where the first nucleotide for each nucleotide sequence in Table 1 is position 1. That is, every combination of a 5' and 3' nucleotide position that a fragment at least 10 contiguous nucleotides in length could occupy is included in the invention as an individual species. "At least" means a fragment may be 10 contiguous nucleotide bases in length or any integer between 10 and the length of an entire nucleotide sequence minus 1. Therefore, included in the invention are contiguous fragments specified by any 5' and 3' nucleotide base positions of a nucleotide sequences of Table 1 wherein the contiguous fragment is any integer between 10 and the length of an entire nucleotide sequence minus 1.

The polynucleotide fragment specified by 5' and 3' positions can be immediately envisaged using the clone description and are therefore not individually listed solely for the purpose of not unnecessarily lengthening the specifications.

Although it is particularly pointed out that each of the above described species may be included in or excluded from the present invention. The above species of polynucleotides fragments of the present invention may alternatively be described by the formula "a to b"; where "a" equals the 5' nucleotide position and "b" equals 3' nucleotide position of the polynucleotide fragment, where "a" equals an integer between 1 and the number of nucleotides of the polynucleotide sequence of the present invention minus 10, where "b" equals an integer between 10 and the number of nucleotides of the polynucleotide sequence of the present invention; and where "a" is an integer smaller then "b" by at least 10.

Again, it is particularly pointed out that each species of the above formula may be specifically included in, or excluded from, the present invention. Further, the invention includes polynucleotides comprising sub-genuses of fragments specified by size, in nucleotides, rather than by nucleotide positions. The invention includes any fragment size, in contiguous nucleotides, selected from integers between 10 and the length of an entire nucleotide sequence minus 1. Preferred size of contiguous nucleotide fragments include at least 20 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 175 nucleotides, at least 200 nucleotides, at least 250 nucleotides, at least 300 nucleotides, at least 350 nucleotides, at least 400 nucleotides, at least 450 nucleotides, at least 500 nucleotides, at least 550 nucleotides, at least 600 nucleotides, at least 650 nucleotides, at least 700 nucleotides, at least 750 nucleotides, at least 800 nucleotides, at least 850 nucleotides, at least 900 nucleotides, at least 950 nucleotides, at least 1000 nucleotides, at least 1050 nucleotides, at least 1100 nucleotides, and at least 1150 nucleotides. Other preferred sizes of contiguous polynucleotide fragments, which may be useful as diagnostic probes and primers, include fragment sizes representing each integer between 50–300. Larger fragments are also useful according to the present invention corresponding to most, if not all, of the polynucleotide sequences of the sequence listing or Table 1. The preferred sizes are, of course, meant to exemplify not limit to present invention as all size fragments, representing any integer-between 10 and the length of an entire nucleotide sequence minus 1 of the sequence listing or deposited clones, may be specifically included from the invention. Additional preferred nucleic acid fragment of the present invention include nucleic acid molecules encoding epitope-bearing portions of the polynucleotides (e.g., including but not limited to, nucleic acid molecules encoding epitope-bearing portions of the polynucleotides which are shown in Table 4).

In another aspect, the invention provides an isolated nucleic acid molecule comprising a polynucleotide which hybridizes under stringent hybridization conditions to a portion of a polynucleotide in a nucleic acid molecules of the invention described above, for instance, nucleotide sequences of Table 1. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1× SSC at about 65° C. Hybridizing polynucleotides are useful as diagnostic probes and primers as discussed above. Portions of a polynucleotide which hybridize to a nucleotide sequence in Table 1, which can be used as probes and primers, may be precisely specified by 5' and 3' base positions or by size in nucleotide bases as described above or precisely excluded in the same manner. Preferred hybridizing polynucleotdies of the present invention are those that, when labeled and used in a hybridization assay known in the art (e.g. Southern and Northern blot analysis), display the greatest signal strength with the polynucleotides of Table 1 regardless of other heterologous sequences present in equamolar amounts The nucleic acid molecules of the present invention, which encode a S. aureus polypeptide, may include, but are not limited to, nucleic acid molecules encoding the full length S. aureus polypeptides of Table 1. Also included in the present invention are nucleic acids encoding the above full length sequences and further comprise additional sequences, such as those encoding an added secretory leader sequence, such as a pre-, or pro- or prepro-protein sequence. Further included in the present invention are nucleic acids encoding the above full length sequences and portions thereof and further comprise additional heterologous amino acid sequences encoded by nucleic acid sequences from a different source.

Also included in the present invention are nucleic acids encoding the above protein sequences together with additional, non-coding sequences, including for example, but not limited to non-coding 5' and 3' sequences. These sequences include transcribed, non-translated sequences that may play a role in transcription, and mRNA processing, for example, ribosome binding and stability of mRNA. Also included in the present invention are additional coding sequences which provide additional functionalities.

Thus, a nucleotide sequence encoding a polypeptide may be fused-to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. For instance, hexa-histidine provides for convenient purification of the fusion protein. See Gentz et al. (1989) Proc. Natl. Acad. Sci. 86:821–24. The "HA" tag is another peptide useful for purification which corresponds to an epitope derived from the influenza hemagglutinin protein. See Wilson et al., (1984) Cell 37:767. As discussed below, other such fusion proteins include the S. aureus fused to Fc at the N- or C-terminus.

Variant and Mutant Polynucleotides

The present invention further relates to variants of the nucleic acid molecules which encode portions, analogs or derivatives of a S. aureus polypeptides of Table 1, and variant polypeptides thereof including portions, analogs, and derivatives of the S. aureus polypeptides. Variants may occur naturally, such as a natural allelic variant. By an "allelic variant" is intended one of several alternate forms of a gene occupying a given locus on a chromosome of an organism. See, e.g., B. Lewin, Genes IV (1990). Non-naturally occurring variants may be produced using art-known mutagenesis techniques.

Such nucleic acid variants include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of a S. aureus protein of the present invention or portions thereof. Also preferred in this regard are conservative substitutions.

Such polypeptide variants include those produced by amino acid substitutions, deletions or additions. The substitutions, deletions, or additions may involve one or more residues. Alterations may produce conservative or non-conservative amino acid substitutions, deletions, or additions. Especially preferred among these are silent substitutions, additions and deletions, which do not alter the properties and activities of a S. aureus protein of the present invention or portions thereof. Also especially preferred in this regard are conservative substitutions.

The present invention also relates to recombinant vectors, which include the isolated nucleic acid molecules of the present invention, and to host cells containing the recombinant vectors, as well as to methods of making such vectors and host cells and for using them for production of S. aureus polypeptides or peptides by recombinant techniques.

The present application is directed to nucleic acid molecules at least 90%, 95%, 96%, 97%, 98% or 99% identical to a nucleic acid sequence shown in Table 1. The above nucleic acid sequences are included irrespective of whether they encode a polypeptide having S. aureus activity. This is because even where a particular nucleic acid molecule does not encode a polypeptide having S. aureus activity, one of skill in the art would still know how to use the nucleic acid molecule, for instance, as a hybridization probe or primer. Uses of the nucleic acid molecules of the present invention that do not encode a polypeptide having S. aureus activity include, inter alia, isolating an S. aureus gene or allelic variants thereof from a DNA library, and detecting S. aureus mRNA expression in biological or environmental samples, suspected of containing S. aureus by Northern Blot analysis or PCR.

For example, one such method involves assaying for the expression of a polynucleotide encoding S. aureus polypeptides in a sample from an animal host (e.g, including, but not limited to, human, bovine, rabbit, porcine, murine, chicken, and/or avian species). The expression of polynucleotides can be assayed by detecting the nucleic acids of Table 1. An example of such a method involves the use of the polymerase chain reaction (PCR) to amplify and detect Staphylococcus nucleic acid sequences in a biological or environmental sample.

The present invention also relates to nucleic acid probes having all or part of a nucleotide sequence described in Table 1 which are capable of hybridizing under stringent conditions to Staphylococcus nucleic acids. The invention further relates to a method of detecting one or more Staphylococcus nucleic acids in a biological sample obtained from an animal, said one or more nucleic acids encoding Staphylococcus polypeptides, comprising: (a) contacting the sample with one or more of the above-described nucleic acid probes, under conditions such that hybridization occurs, and (b) detecting hybridization of said one or more probes to the Staphylococcus nucleic acid present in the biological sample.

The invention also includes a kit for analyzing samples for the presence of members of the Staphylococcus genus in a biological or environmental sample. In a general embodiment, the kit includes at least one polynucleotide probe containing a nucleotide sequence that will specifically hybridize with a S. aureus nucleic acid molecule of Table 1 and a suitable container. In a specific embodiment, the kit includes two polynucleotide probes defining an internal region of the S. aureus nucleic acid molecule of Table 1, where each probe has one strand containing a 31'mer-end internal to the region. In a further embodiment, the probes may be useful as primers for polymerase chain reaction amplification.

The method(s) provided above may preferably be applied in a diagnostic method and/or kits in which S. aureus polynucleotides of Table 1 are attached to a solid support. In one exemplary method, the support may be a "gene chip" or a "biological chip" as described in U.S. Pat. Nos. 5,837,832, 5,874,219, and 5,856,174. Further, such a gene chip with S. aureus polynucleotides of Table 1 attached may be used to diagnose S. aureus infection in an animal host, preferably a human. The US Patents referenced above are incorporated herein by reference in their entirety.

The present invention is further directed to nucleic acid molecules having sequences at least 90%, 95%, 96%, 97%, 98% or 99% identical to the nucleic acid sequence shown in Table 1, which do, in fact, encode a polypeptide having S. aureus protein activity. By "a polypeptide having S. aureus activity" is intended polypeptides exhibiting activity similar, but not necessarily identical, to an activity of the S. aureus protein of the invention, as measured in a particular biological assay suitable for measuring activity of the specified protein. The biological activity of some of the polypeptides of the presents invention are listed in Table 1, after the name of the closest homolog with similar activity. The biological activities were determined using methods known in the art for the particular biological activity listed. For the remaining polypeptides of Table 1, the assays known in the art to measure the activity of the polypeptides of Table 2, sharing a high degree of identity, may be used to measure the activity of the corresponding polypeptides of Table 1.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequences shown in Table 1 will encode a polypeptide having biological activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having biological activity. This is because the skilled artisan is fully aware of amino acid substitutions that are either less likely or not likely to significantly effect protein function (e.g., replacing one aliphatic amino acid with a second aliphatic amino acid), as further described below.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the S. aureus polypeptide. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be an entire sequence shown in Table 1, the ORF (open reading frame), or any fragment specified as described herein.

Other methods of determining and defining whether any particular nucleic acid molecule or polypeptide is at least 90%, 95%, 96%, 97%, 98% or 99% identical to a nucleotide sequence of the presence invention can be done by using known computer programs. A preferred method for determining the best overall match between a query sequence (a sequence of the present invention) and a subject sequence, also referred to as a global sequence alignment, can be determined using the FASTDB computer program based on the algorithm of Brutlag et al. See Brutlag et al. (1990) Comp. App. Biosci. 6:237–245. In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

TABLE 2

Closest matching sequence between the polypeptides of the present invention and GenSeq and GenBank sequences in databases

| Sequence ID | Antigen Accession No. | Match Gene Name | High Score | Smallest Sum Probability P (N) |
|---|---|---|---|---|
| GenSeq | | | | |
| HGS001 | W34207 | Streptomyces fabH homologue (frenolicin gene I pro . . . | 285 | 3.50E−65 |
| HGS001 | W55808 | Streptomyces roseofulvus frenolicin gene cluster p . . . | 285 | 3.50E−65 |
| HGS002 | W20949 | H. pylori cytoplasmic protein, 29zp10241orf7. | 81 | 5.10E−12 |
| HGS003 | W48300 | Staphylococcus aureus Fab I enoyl-ACP reductase. | 1271 | 1.90E−170 |

TABLE 2-continued

Closest matching sequence between the polypeptides of the present invention and GenSeq and GenBank sequences in databases

| Sequence ID | Antigen Accession No. | Match Gene Name | High Score | Smallest Sum Probability P (N) |
|---|---|---|---|---|
| HGS003 | W40806 | *M. bovis* InhA protein. | 95 | 1.00E−29 |
| HGS003 | R23793 | Stearoyl-ACP-desaturase (from clone pDES7). | 157 | 1.60E−28 |
| HGS003 | R66290 | *M. tuberculosis* inhA gene. | 94 | 7.40E−28 |
| HGS003 | R66901 | *M. tuberculosis* InhA. | 94 | 7.40E−28 |
| HGS003 | R66292 | *Mycobacterium bovis* InhA. | 92 | 4.70E−19 |
| HGS003 | R63900 | *M. bovis* InhA. | 92 | 4.70E−19 |
| HGS003 | W16684 | *Lawsonia intracellularis* enoyl-(acyl carrier prote . . . | 114 | 1.80E−09 |
| HGS003 | W40805 | *M. tuberculosis* InhA protein. | 96 | 2.60E−09 |
| HGS003 | W40807 | *M. smegmatis* InhA protein, mc2155 inhA-1. | 101 | 9.70E−09 |
| HGS004 | W32287 | *Streptococcus pneumoniae* MurA protein. | 643 | 4.00E−89 |
| HGS004 | W26786 | *Streptococcus pneumoniae* Mur A-1. | 643 | 4.10E−89 |
| HGS004 | W27782 | UDP-N-acetylglucosamine 1-carboxyvinyltransferase. | 163 | 1.80E−15 |
| HGS004 | W27783 | UDP-N-acetylglucosamine 1-carboxyvinyltransferase. | 120 | 1.90E−12 |
| HGS006 | W36168 | *Staphylococcus aureus* SP protein. | 584 | 4.30E−78 |
| HGS006 | W37468 | *Staphylococcus aureus* RNase P. | 581 | 1.10E−77 |
| HGS007M | W27798 | Amino acid sequence of a replicative DNA heli case | 5524 | 6e−83.2 |
| HGS007M | R29636 | pCTD ORF 1. | 241 | 7e−34.3 |
| HGS008 | W27814 | A malonyl coenzymeA-acyl carrier protein transacyl . . . | 365 | 4.70E−46 |
| HGS008 | W19629 | *Streptomyces venezuelae* polyketide synthase. | 96 | 2.30E−19 |
| HGS008 | W22602 | Tylactone synthase ORF2 protein. | 83 | 2.90E−18 |
| HGS008 | W22605 | Tylactone synthase ORF5 protein. | 95 | 8.90E−17 |
| HGS008 | R44431 | eryA region polypeptide module #2. | 88 | 2.30E−14 |
| HGS008 | R42452 | Enzyme involved in eicosapentaenoic acid (EPA) syn . . . | 94 | 5.30E−14 |
| HGS008 | R99462 | Biosynthetic enzyme of icosapentaenoic acid synthase. | 94 | 4.60E−13 |
| HGS008 | W37050 | *S. putrefaciens* EPO biosynthesis gene cluster ORF6 . . . | 94 | 4.60E−13 |
| HGS008 | R44432 | eryA region polypeptide module #3. | 83 | 6.20E−13 |
| HGS008 | W22607 | Platenolide synthase ORF2 protein. | 80 | 2.20E−12 |
| HGS014 | W34454 | *Racillus subtilis* teichoic acid polymerase. | 597 | 2.70E−87 |
| HGS014 | W34455 | *Racillus subtilis* teichoic acid polymerase. | 597 | 3.10E−87 |
| HGS014 | W27744 | Amino acid sequence of techoic acid biosynthesis p . . . | 425 | 2.50E−53 |
| HGS016 | W32287 | *Streptococcus pneumoniae* MurA protein. | 643 | 4.00E−89 |
| HGS016 | W26786 | *Streptococcus pneumoniae* Mur A-1. | 643 | 4.10E−89 |
| HGS016 | W27782 | UDP-N-acetylglucosamine 1-carboxyvinyltransferase. | 163 | 1. 80E−15 |
| HGS016 | W27783 | UDP-N-acetylglucosamine 1-carboxyvinyltransferase. | 120 | 1 .90E−12 |
| HGS018 | R95648 | Thermostable DNA-ligase. | 833 | 3.00E−205 |
| HGS018 | R81473 | *Thermus aquaticus* DNA ligase protein. | 428 | 2.00E−201 |
| HGS018 | R15299 | Thermostable *T. aquaticus* ligase (I). | 428 | 7.40E−199 |
| HGS018 | R15694 | Thermostable *T. aquaticus* ligase (II). | 428 | 4.80E−196 |
| HGS019 | P70096 | Met-aminopeptidase. | 143 | 2.90E−35 |
| HGS019 | R90027 | *Methionine aminopeptidase* sequence. | 138 | 1.60E−20 |
| HGS022 | R12401 | *Enantioselective amidase* of Rhodococcus. | 405 | 4.70E−102 |
| HGS022 | R25320 | *Enantioselective amidase.* | 405 | 4.70E−102 |
| HGS022 | W14159 | *Rhodococcus rhodochrous* amidase. | 352 | 6.10E−63 |
| HGS022 | W17820 | *Pseudomonas putida* amidase. | 208 | 1.20E−62 |
| HGS022 | R12400 | *Enantioselective amidase* of Brevibacterium. | 353 | 2.90E−62 |
| HGS022 | R24529 | *Enantioselective amidase.* | 353 | 2.90E−62 |
| HGS022 | W10882 | *Comamonas acidovorans* derived amidase enzyme. | 261 | 4.00E−61 |
| HGS022 | R60155 | *Comamonas testosteroni* NI 1 amidase. | 306 | 5.30E−47 |
| HGS022 | R42839 | *Urea amidolyase.* | 243 | 1.40E−31 |
| HGS022 | R44504 | *Urea amide* lyase. | 224 | 8.60E−30 |
| HGS026 | W29380 | *S. pneumoniae* peptide releasing factor RF-1. | 593 | 3.30E−142 |
| HGS028 | W29380 | *S. pneumoniae* peptide releasing factor RF-1. | 218 | 1.70E−49 |
| HGS031 | W20646 | *H. pylori* cytoplasmic protein, 02cp11822orf26. | 291 | 5.70E−47 |
| HGS031 | W20147 | *H. pylori* cytoplasmic protein, 14574201.aa. | 75 | 1.50E−08 |
| HGS033 | W20861 | *H. pylori* cell envelope transporter protein, 12gel . . . | 100 | 2.30E−18 |
| HGS033 | W20101 | *H. pylori* transporter protein 11132778.aa. | 100 | 6.10E−17 |
| HGS033 | W25671 | hABC3 protein. | 111 | 4.20E−15 |
| HGS033 | W46761 | Amino acid sequence of human ATP binding cassette . . . | 111 | 4.20E−15 |
| HGS033 | W46771 | Amino acid sequence of human ATP binding cassette . . . | 111 | 4.30E−15 |
| HGS033 | W42393 | *Bacillus thermoleovorans* phosphatase (68FY5). | 96 | 1.90E−13 |
| HGS033 | W34202 | *Streptomyces efflux* pump protein (frenolicin gene . . . | 92 | 5.50E−12 |
| HGS033 | W55803 | *Streptomyces roseofulvus* frenolicin gene cluster p . . . | 92 | 5.50E−12 |
| HGS033 | W20224 | *H. pylori* transporter protein, 22265691.aa. | 88 | 7.40E−12 |
| HGS033 | W20668 | *H. pylori* transporter protein O3ee11215orf29. | 88 | 8.90E−12 |
| HGS036 | W20640 | *H. pylori* transporter protein, 02ce11022orf8. | 264 | 2.20E−33 |
| HGS036 | W34202 | *Streptomyces efflux* pump protein (frenolicin gene . . . | 184 | 1.30E−29 |
| HGS036 | W55803 | *Streptomyces roseofulvus* frenolicin gene cluster p . . . | 184 | 1.30E−29 |
| HGS036 | W20289 | *H. pylori* transporter protein, 24218968.aa. | 201 | 5.50E−21 |
| HGS036 | W20711 | *H. pylori* transporter protein, 05cp11911orf41. | 148 | 2.10E−19 |
| HGS036 | W20101 | *H. pylori* transporter protein 11132778.aa. | 164 | 3.50E−19 |
| HGS036 | W20861 | *H. pylori* cell envelope transporter protein, 12gel . . . | 164 | 4.20E−19 |
| HGS036 | W20492 | *H. pylori* cell envelope transporter protein 433843 . . . | 148 | 1.60E−18 |

TABLE 2-continued

Closest matching sequence between the polypeptides of the present invention and GenSeq and GenBank sequences in databases

| Sequence ID | Antigen Accession No. | Match Gene Name | High Score | Smallest Sum Probability P (N) |
|---|---|---|---|---|
| HGS036 | W21019 | H. pylori cell envelope transporter protein, hp5el . . . | 144 | 8.30E−16 |
| HGS036 | R71091 | C. jejuni PEB1A antigen from ORF3. | 136 | 7.90E−14 |
| 168153_3 | W01619 | Human uridine diphosphate galactose-4-epimerase. | 128 | 9.80E−29 |
| 168153_3 | W40383 | S. glaucescens acbD protein. | 105 | 1.10E−15 |
| 168153_3 | R98529 | dTDP-glucose dehydratase encoded by the acbB gene. | 108 | 4.50E−15 |
| 168153_3 | R80287 | galE gene of S. lividans gal operon. | 88 | 2.60E−13 |
| 168153_3 | P70275 | Sequence encoded by S. lividans gal operon galE gene. | 86 | 5.10E−13 |
| 168153_3 | R41529 | S. lividans UDP-4-epimerase. | 86 | 5.10E−13 |
| 168153_3 | R32195 | ADP-L-glycero-D-mannoheptose-6-epimerase protein. | 82 | 3.40E−10 |
| 168153_2 | W03997 | Glucosyl IP-transferase (SpsB protein). | 168 | 8.30E−36 |
| 168153_2 | W32794 | Sphingomonas genus microbe isolated SpsB protein. | 168 | 8.30E−36 |
| 168153_2 | W22173 | S. thermophilus exopolysaccharide synthesis operon . . . | 141 | 2.20E−31 |
| 168153_2 | W14074 | S. thermophilus exopolysaccharide biosynthesis enzy . . . | 141 | 2.20E−31 |
| 168153_2 | P70458 | Sequence of gpD encoded by segment of Xanthomonas . . . | 183 | 2.30E−30 |
| 168153_1 | W22175 | S. thermophilus exopolysaccharide synthesis operon . . . | 141 | 6.40E−35 |
| 168153_1 | W14076 | S. thermophilus exopolysaccharide biosynthesis enzy . . . | 141 | 9.50E−35 |
| 168153_1 | W22174 | S. thermophilus exopolysaccharide synthesis operon . . . | 162 | 9.50E−30 |
| 168153_1 | W14075 | S. thermophilus exopolysaccharide biosynthesis enzy . . . | 162 | 9.50E−30 |
| 168339_2 | W27736 | Putative O-antigen transporter protein. | 820 | 5.70E−11.5 |
| GenBank | | | | |
| HGS001 | gnl|PID|e1183136 | similar to 3-oxoacyl-acyl-carrier protein | 569 | 2.20E−129 |
| HGS001 | gi|151943 | ORF3; putative [Rhodobacter capsulatus] | 404 | 1.40E−92 |
| HGS001 | gi|2983572 | (AE000723) 3-oxoacyl-[acyl-carrier-protein] | 311 | 5.10E−92 |
| HGS001 | gi|1276662 | beta-ketoacyl-acyl carrier protein synthase | 292 | 3.90E−90 |
| HGS001 | gi|2313291 | (AE000540) beta-ketoacyl-acyl carrier protein | 269 | 3.50E−89 |
| HGS001 | gnl|PID|e1183019 | similar to 3-oxoacyl-acyl-carrier protein | 373 | 2.00E−86 |
| HGS001 | gi|1143069 | 3-ketoacyl carrier protein synthase III | 287 | 3.60E−86 |
| HGS001 | gi|22744 | beta-ketoacyl-acyl carrier protein synthase | 292 | 1.20E−85 |
| HGS001 | gi|311686 | 3-ketoacyl-acyl carrier protein synthase | 322 | 3.40E−85 |
| HGS001 | gi|145898 | beta-ketoacyl-acyl carrier protein synthase | 366 | 7.30E−84 |
| HGS002 | gi|142833 | ORF2 [Bacillus subtilis] > gnl|PID|e11851 . . . | 215 | 2.50E−70 |
| HGS002 | gnl|PID|d1019368 | hypothetical protein [Synechocystis sp.] | 235 | 8.50E−67 |
| HGS002 | gi|2983165 | (AE000694) UDP-N-acetylenolpyruvoylgluco . . . | 207 | 1.10E−58 |
| HGS002 | gi|404010 | ORF2 [Bacillus licheniformis] > pir|I4022 . . . | 251 | 1.10E−50 |
| HGS002 | gi|2688520 | (AE001161) UDP-N-acetylmuramate dehydrog . . . | 197 | 1.80E−42 |
| HGS002 | gi|1841789 | UDP-N-acetylenolpyruvylglucosamine reduc . . . | 249 | 7.10E−40 |
| HGS002 | gi|2983149 | (AE000693) UDP-acetoenolpyruvoylglucos . . . | 212 | 3.80E−36 |
| HGS002 | gi|431730 | UDP-N-acetylenolpyruvoylglucosamine redu . . . | 119 | 4.50E−22 |
| HGS002 | gi|1573234 | UDP-N-acetylenolpyruvoylglucosamine redu . . . | 139 | 6.20E−22 |
| HGS002 | gi|290456 | UDP-N-acetylpyruvoylglucosamine reductas . . . | 123 | 2.90E−20 |
| HGS003 | gnl|PID|e1183192 | similar to enoyl-acyl-carrier protein r . . . | 743 | 1.80E−97 |
| HGS003 | gi|142010 | Shows 70.2% similarity and 48.6% identit . . . | 519 | 8.90E−80 |
| HGS003 | gnl|PID|d1017769 | enoyl-[acyl-carrier-protein] reductase [ . . . | 482 | 2.10E−73 |
| HGS003 | gi|2313282 | (AE000539) enoyl-(acyl-carrier-protein) . . . | 449 | 1.70E−71 |
| HGS003 | gi|145851 | envM [Escherichia coli] > gi|587106 enoyl . . . | 388 | 3.70E−71 |
| HGS003 | gi|153955 | envM protein [Salmonella typhimurium] > p . . . | 386 | 2.10E−69 |
| HGS003 | gi|1574591 | short chain alcohol dehydrogenase homolo . . . | 362 | 3.10E−68 |
| HGS003 | gi|2983915 | (AE000745) enoyl-[acyl-carrier-protein] . . . | 268 | 1.10E−64 |
| HGS003 | gi|1053075 | orf1; similar to E. coli EnvM [Proteus mi . . . | 259 | 2.60E−29 |
| HGS003 | gnl|PID|e1188732 | (AJ003124) enoyl-ACP reductase [Petunia . . . | 154 | 2.20E−28 |
| HGS004 | gnl|PID|e276830 | UDP-N-acetylglucosamine 1-carboxyvinyltr . . . | 1251 | 2.50E−195 |
| HGS004 | gi|415662 | UDP-N-acetylglucosamine 1-carboxyvinyl t . . . | 534 | 1.40E−139 |
| HGS004 | gnl|PID|d1010850 | UDP-N-acetylglucosamine 1-carboxyvinyltr . . . | 732 | 7.50E−138 |
| HGS004 | gi|41344 | UDP-N-acetylglucosamine 1-carboxyvinyltr . . . | 537 | 2.90E−137 |
| HGS004 | gi|1574635 | UDP-N-acetylglucosamine enolpyruvyl tran . . . | 536 | 4.70E−136 |
| HGS004 | gi|146902 | UDP-N-acetylglucosamine enolpyruvyl tran . . . | 509 | 5.10E−134 |
| HGS004 | gi|2983705 | (AE000732) UDP-N-acetylglucosamine 1-car . . . | 492 | 6.20E−121 |
| HGS004 | gnl|PID|e229797 | UDP-N-acetylglucosamine enolpyruvyl tran . . . | 606 | 3.00E−119 |
| HGS004 | gi|699337 | UDP-N-acetyglucosamine 1-carboxyvinyl tr . . . | 605 | 1.10E−118 |
| HGS004 | gi|2313767 | (AE000578) UDP-N-acetylglucosamine enolp . . . | 440 | 1.90E−117 |
| HGS005 | gi|143434 | Rho Factor [Bacillus subtilis] | 755 | 1.10E−190 |
| HGS005 | gi|853769 | transcriptional terminator Rho [Bacillus . . . | 746 | 1.80E−189 |
| HGS005 | gi|2983405 | (AE000711) transcriptional terminator Rho . . . | 580 | 2.10E−154 |
| HGS005 | gi|454859 | The first ATG in the open reading frame . . . | 543 | 7.90E−150 |
| HGS005 | gi|147607 | transcription termination factor [Escheri . . . | 592 | 9.40E−149 |
| HGS005 | gi|49363 | ho Factor [Salmonella typhimurium] > pir| . . . | 592 | 1.70E−148 |
| HGS005 | gnl|PID|e220353 | Rho gene product [Streptomyces lividans] . . . | 575 | 4.90E−148 |
| HGS005 | gi|1573263 | transcription termination factor rho (rho . . . | 575 | 5.40E−147 |
| HGS005 | gi|49365 | Rho factor [Neisseria gonorrhoeae] > pir| . . . | 590 | 1.40E−146 |
| HGS005 | gi|2313666 | (AE000569) transcription termination fact . . . | 547 | 8.10E−146 |
| HGS006 | gi|580904 | homologous to E. coli rnpA [Bacillus subt . . . | 295 | 8.10E−37 |

TABLE 2-continued

Closest matching sequence between the polypeptides of the present invention and
GenSeq and GenBank sequences in databases

| Sequence ID | Antigen Accession No. | Match Gene Name | High Score | Smallest Sum Probability P (N) |
|---|---|---|---|---|
| HGS006 | gnl\|PID\|d1005777 | protein component of ribonuclease P [Bac . . . | 293 | 1.60E−36 |
| HGS006 | gnl\|PID\|d1004132 | RNaseP C5 subunit [*Mycoplasma capricolum* . . . | 99 | 3.60E−22 |
| HGS006 | gi\|144147 | rnpA [*Buchnera aphidicola*] > gi\|2827012 ( . . . | 97 | 3.90E−10 |
| HGS006 | gi\|511457 | RNase P protein component [Coxiella burn . . . | 117 | 2.30E−09 |
| HGS007M | gnl\|PID\|d1005718 | replicative DNA helicase [Bacillus subti . . . | 579 | 6.20E−169 |
| HGS007M | gi\|3282821 | (AF045058) DnaC replicative helicase [Ba . . . | 536 | 3.60E−156 |
| HGS007M | gnl\|PID\|e321938 | helicase [*Rhodothermus marinus*] | 433 | 1.50E−123 |
| HGS007M | gi\|2335167 | (AF006675) DNA helicase [Rhodothermus ma . . . | 271 | 2.90E−109 |
| HGS007M | gnl\|PID\|e211889 | DNA-replication helicase [Odontella sine . . . | 395 | 1.60E−108 |
| HGS007M | gnl\|PID\|e1263993 | (AL022118) replicative DNA helicase DnaB . . . | 235 | 3.20E−103 |
| HGS007M | gnl\|PID\|e244747 | gene 40 [Bacteriophage SPP1] > gi\|529650 . . . | 477 | 4.40E−103 |
| HGS007M | gi\|2983861 | (AE000742) replicative DNA helicase [Aqu . . . | 244 | 1.10E−102 |
| HGS007M | gi\|2314528 | (AE000636) replicative DNA helicase (dna . . . | 246 | 7.70E−101 |
| HGS007M | gnl\|PID\|d1011167 | replicative DNA helicase [Synechocystis . . . | 209 | 1.50E−100 |
| HGS008 | gnl\|PID\|e1185181 | malonyl CoA-acyl carrier protein transac . . . | 560 | 4.30E−90 |
| HGS008 | gi\|1502420 | malonyl-CoA:Acyl carrier protein transac . . . | 391 | 1.40E−86 |
| HGS008 | gi\|3282803 | (AF044668) malonyl CoA-acyl carrier prot . . . | 308 | 2.50E−75 |
| HGS008 | gi\|2738154 | malonyl-CoA:acyl carrier protein transac . . . | 283 | 3.40E−75 |
| HGS008 | gi\|145887 | malonyl coenzyme A-acyl carrier protein . . . | 304 | 6.30E−75 |
| HGS008 | gi\|1573113 | malonyl coenzyme A-acyl carrier protein . . . | 270 | 7.60E−74 |
| HGS008 | gi\|2983416 | (AE000712) malonyl-CoA:Acyl carrier prot . . . | 213 | 2.70E−73 |
| HGS008 | gi\|840626 | transacylase [*Bacillus subtilis*] | 221 | 1.20E−66 |
| HGS008 | gi\|3150402 | (AC004165) putative malonyl-CoA:Acyl car . . . | 235 | 1.60E−57 |
| HGS008 | gnl\|PID\|e1185300 | pksC [*Bacillus subtilis*] > gnl\|PID\|e11833 . . . | 145 | 4.40E−38 |
| HGS009 | gi\|460911 | fructose-bisphosphate aldolase [Bacillus . . . | 1169 | 2.10E−154 |
| HGS009 | gi\|PID\|e1251871 | fructose-1,6-bisphosphate aldolase type . . . | 1121 | 6.70E−148 |
| HGS009 | gnl\|PID\|d1003809 | hypothetical protein [*Bacillus subtilis*] . . . | 467 | 1.50E−110 |
| HGS009 | gi\|2313265 | (AE000538) fructose-bisphosphate aldolas . . . | 252 | 6.40E−91 |
| HGS009 | gi\|1673788 | (AE000015) *Mycoplasma pneumoniae*, fructo . . . | 238 | 4.60E−81 |
| HGS009 | gnl\|PID\|d1045692 | fructose-bisphosphate aldolase [Mycoplas . . . | 226 | 6.40E−77 |
| HGS009 | gnl\|PID\|d1016691 | Tagatose-bisphosphate aldolase GatY (EC . . . | 279 | 2.30E−75 |
| HGS009 | gi\|599738 | unknown function [*Escherichia coli*] > pir . . . | 274 | 2.00E−74 |
| HGS009 | gi\|1732204 | putative aldolase [*Vibro furnissii*] | 277 | 5.00E−74 |
| HGS009 | gi\|606077 | ORF_o286 [*Escherichia coli*] > gi\|1789526 . . . | 264 | 1.30E−73 |
| HGS014 | gi\|40100 | rodC (tag3) polypeptide (AA 1–746) [Baci . . . | 597 | 1.70E−86 |
| HGS014 | gnl\|PID\|e1169895 | tasA [*Streptococcus pneumoniae*] | 108 | 4.90E−27 |
| HGS014 | gi\|2621425 | (AE000822) teichoic acid biosynthesis pr . . . | 142 | 2.00E−23 |
| HGS014 | gi\|2621421 | (AE000822) teichoic acid biosynthesis pr . . . | 147 | 5.90E−22 |
| HGS014 | gi\|143725 | putative [*Bacillus subtilis*] > gnl\|PID\|e1 . . . | 114 | 4.60E−19 |
| HGS014 | gi\|547513 | orf3 [*Haemophilus influenzae*] > pir\|S4924 . . . | 106 | 5.60E−14 |
| HGS014 | gnl\|PID\|d1027517 | (AB009477) 395aa long hypothetical prote . . . | 79 | 4.20E−12 |
| HGS014 | gi\|2072447 | EpsJ [*Lactococcus lactis cremoris*] | 106 | 5.20E−10 |
| HGS014 | gi\|915199 | ggaB [*Bacillus subtilis*] > gnl\|PID\|e11844 . . . | 89 | 8.10E−08 |
| HGS016 | gnl\|PID\|e276830 | UDP-N-acetylglucosamine 1-carboxyvinyltr . . . | 1251 | 2.50E−195 |
| HGS016 | gi\|415662 | UDP-N-acetylglucosamine 1-carboxyvinyl t . . . | 534 | 1.40E−139 |
| HGS016 | gnl\|PID\|d1010850 | UDP-N-acetylglucosamine 1-carboxyvinyltr . . . | 732 | 7.50E−138 |
| HGS016 | gi\|41344 | UDP-N-acetylglucosamine 1-carboxyvinyltr . . . | 537 | 2.90E−137 |
| HGS016 | gi\|1574635 | UDP-N-acetylglucosamine enolpyruvyl tran . . . | 536 | 4.70E−136 |
| HGS016 | gi\|146902 | UDP-N-acetylglucosamine enolpyruvyl tran . . . | 509 | 5.10E−134 |
| HGS016 | gi\|2983705 | (AE000732) UDP-N-acetylglucosamine 1-car . . . | 492 | 6.20E−121 |
| HGS016 | gnl\|PID\|e229797 | UDP-N-acetylglucosamine enolpyruvyl tran . . . | 606 | 3.00E−119 |
| HGS016 | gi\|699337 | UDP-N-acetyglucosamine 1-carboxyvinyl tr . . . | 605 | 1.10E−118 |
| HGS016 | gi\|2313767 | (AE000578) UDP-N-acetylglucosamine enolp . . . | 440 | 1.90E−117 |
| HGS018 | gnl\|PID\|e1182642 | similar to DNA ligase [*Bacillus subtilis* . . . | 1574 | 9.60E−287 |
| HGS018 | gnl\|PID\|d1017321 | DNA ligase [Synechocystis sp.] > pir\|S744 . . . | 830 | 5.70E−209 |
| HGS018 | gi\|1574651 | DNA ligase (lig) [*Haemophilus influenzae* . . . | 484 | 1.30E−204 |
| HGS018 | gi\|607820 | DNA ligase [*Rhodothermus marinus*] > sp\|P4 . . . | 833 | 1.60E−204 |
| HGS018 | gi\|155088 | DNA ligase [*Thermus aquaticus* thermophil . . . | 428 | 3.10E−201 |
| HGS018 | gi\|609276 | DNA ligase [*Thermus scotoductus*] > pir\|S5 . . . | 436 | 1.10E−200 |
| HGS018 | gi\|2983242 | (AE000699) DNA ligase (NAD dependent) [A . . . | 724 | 1.00E−179 |
| HGS018 | gi\|49284 | DNA ligase [*Zymomonas mobilis*] > pir\|S206 . . . | 523 | 1.60E−170 |
| HGS018 | gnl\|PID\|e1237759 | (AL021287) DNA ligase [Mycobacterium tub . . . | 529 | 1.80E−161 |
| HGS018 | gnl\|PID\|e349403 | DNA ligase [*Mycobacterium leprae*] | 527 | 7.30E−160 |
| HGS019 | dbj\|D86417_12 | YflG [*Bacillus subtilis*] > gnl\|PID\|e11827 . . . | 559 | 8.00E−72 |
| HGS019 | gi\|1044986 | methionine aminopeptidase [Bacillus subt . . . | 254 | 4.50E−58 |
| HGS019 | gi\|1574578 | methionine aminopeptidase (map) [Haemoph . . . | 185 | 5.10E−56 |
| HGS019 | gnl\|PID\|e1172953 | (AL008883) methionine aminopeptidase [My . . . | 214 | 1.10E−51 |
| HGS019 | gi\|2982825 | (AE000672) methionyl aminopeptidase [Aqu . . . | 192 | 3.70E−48 |
| HGS019 | gnl\|PID\|e1253272 | (AL021958) methionine aminopeptidase [My . . . | 130 | 5.20E−48 |
| HGS019 | gi\|2687996 | (AE001123) methionine aminopeptidase (ma . . . | 195 | 9.00E−48 |
| HGS019 | gnl\|PID\|e1254451 | methionine aminopeptidase [Streptomyces . . . | 151 | 2.10E−43 |
| HGS019 | gi\|975723 | methionine aminopeptidase I [Saccharomyc . . . | 294 | 3.60E−43 |

TABLE 2-continued

Closest matching sequence between the polypeptides of the present invention and
GenSeq and GenBank sequences in databases

| Sequence ID | Antigen Accession No. | Match Gene Name | High Score | Smallest Sum Probability P (N) |
|---|---|---|---|---|
| HGS019 | gi|2583129 | (AC002387) putative methionine aminopept . . . | 211 | 2.10E−41 |
| HGS022 | gnl|PID|e1182648 | alternate gene name: yedB; similar to am . . . | 1586 | 2.80E−212 |
| HGS022 | gi|2589195 | (AF008553) Glu-tRNAGln amidotransferase . . . | 1436 | 1.70E−198 |
| HGS022 | gnl|PID|d1018331 | amidase [Synechocystis sp.] > pir|S77264| . . . | 867 | 2.30E−178 |
| HGS022 | gi|2982954 | (AE000680) glutamyl-tRNA (gln) amidotran . . . | 1247 | 6.50E−176 |
| HGS022 | gi|1224069 | amidase [Moraxella catarrhalis] > sp|Q490 . . . | 522 | 4.40E−158 |
| HGS022 | gi|2648182 | (AE000943) Glu-tRNA amidotransferase, su . . . | 548 | 1.30E−145 |
| HGS022 | gnl|PID|e349405 | probable amidase [Mycobacterium leprae] | 465 | 6.30E−143 |
| HGS022 | gnl|PID|e1237756 | (AL021287) putative Glu-tRNA-Gln amidotr . . . | 470 | 1.90E−141 |
| HGS022 | gi|2313964 | (AE000594) amidase [Helicobacter pylori] . . . | 550 | 7.30E−123 |
| HGS022 | gi|2622613 | (AE000910) amidase [Methanobacterium the . . . | 524 | 5.80E−116 |
| HGS023 | gi|1354211 | PET112-like protein [Bacillus subtilis] . . . | 2291 | 2.90E−307 |
| HGS023 | gi|2653657 | Bacillus subtilis PET112-like protein [B . . . | 1313 | 1.20E−250 |
| HGS023 | gi|2589196 | (AF008553) Glu-tRNAGln amidotransferase . . . | 1315 | 4.20E−250 |
| HGS023 | gnl|PID|e1182649 | similar to pet112-like protein [Bacillus . . . | 1346 | 7.10E−224 |
| HGS023 | gi|2983123 | (AE000691) glutamyl-tRNA (Gln) amidotran . . . | 931 | 2.30E−165 |
| HGS023 | gnl|PID|d1019042 | PET112 [Synechocystis sp.] > pir|S75850|S . . . | 859 | 4.10E−161 |
| HGS023 | gi|1224071 | unknown [Moraxella catarrhalis] > sp|Q490 . . . | 323 | 3.90E−132 |
| HGS023 | gi|2313783 | (AE000579) PET112-like protein [Helicoba . . . | 664 | 6.80E−132 |
| HGS023 | gi|2688237 | (AE001140) glu-tRNA amidotransferase, su . . . | 318 | 4.00E−131 |
| HGS023 | gi|1590917 | Glu-tRNA amidotransferase (gatB) [Methan . . . | 263 | 8.60E−125 |
| HGS024 | gi|2465557 | (AF011545) YedA [Bacillus subtilis] > gi| . . . | 237 | 6.30E−27 |
| HGS024 | gnl|PID|d1011444 | hypothetical protein [Synechocystis sp.] . . . | 153 | 8.60E−22 |
| HGS024 | gi|2648183 | (AE000943) Glu-tRNA amidotransferase, su . . . | 126 | 1.80E−21 |
| HGS024 | gnl|PID|e1237757 | (AL021287) putative Glu-tRNA-Gln amidotr . . . | 166 | 1.80E−17 |
| HGS024 | gi|2984354 | (AE000775) glutamyl-tRNA (Gln) amidotran . . . | 102 | 2.70E−17 |
| HGS024 | gnl|PID|e349616 | hypothetical protein MLCB637.12 [Mycobac . . . | 154 | 7.10E−16 |
| HGS025 | gnl|PID|d1005830 | stage V sporulation [Bacillus subtilis] . . . | 496 | 4.90E−69 |
| HGS025 | gnl|PID|d1011124 | peptidyl-tRNA hydrolase [Synechocystis s . . . | 307 | 2.10E−49 |
| HGS025 | gi|2983032 | (AE000685) peptidyl-tRNA hydrolase [Aqui . . . | 386 | 2.20E−49 |
| HGS025 | gnl|PID|e304565 | Pth [Mycobacterium tuberculosis] > gnl|PI . . . | 266 | 2.60E−43 |
| HGS025 | gi|1045760 | peptidyl-tRNA hydrolase homolog [Mycopla . . . | 211 | 1.40E−39 |
| HGS025 | gi|2314676 | (AE000648) peptidyl-tRNA hydrolase (pth) . . . | 102 | 3.30E−39 |
| HGS025 | gi|1674312 | (AE000058) Mycoplasma pneumoniae, peptid . . . | 208 | 9.50E−39 |
| HGS025 | gi|1127571 | peptidyl-tRNA hydrolase [Chlamydia trach . . . | 187 | 7.00E−37 |
| HGS025 | gi|1573366 | peptidyl-tRNA hydrolase (pth) [Haemophil . . . | 201 | 8.50E−34 |
| HGS025 | gi|581202 | peptidyl-tRNA hydrolase [Escherichia col . . . | 186 | 2.50E−27 |
| HGS026 | gi|853776 | peptide chain release factor 1 [Bacillus . . . | 889 | 6.10E−160 |
| HGS026 | gnl|PID|d1009421 | Peptide Termination Factor [Mycoplasma c . . . | 715 | 1.10E−126 |
| HGS026 | gnl|PID|d1019559 | peptide chain release factor [Synechocys . . . | 539 | 2.70E−121 |
| HGS026 | gi|2688096 | (AE001130) peptide chain release factor . . . | 627 | 1.80E−115 |
| HGS026 | gnl|PID|d1015453 | Peptide chain release factor 1 (RF-1) [E . . . | 467 | 3.90E−113 |
| HGS026 | gi|968930 | peptide chain release factor 1 [Escheric . . . | 463 | 1.30E−112 |
| HGS026 | gi|147567 | peptide chain release factor 1 [Escheric . . . | 467 | 3.40E−112 |
| HGS026 | gi|154104 | release factor 1 [Salmonella typhimurium . . . | 460 | 2.90E−111 |
| HGS026 | gi|1574404 | polypeptide chain release factor 1 (prfA . . . | 449 | 1.50E−109 |
| HGS026 | gi|2313158 | (AE000529) peptide chain release factor . . . | 576 | 1.20E−104 |
| HGS028 | gi|2331287 | (AF013188) release factor 2 [Bacillus . . . | 769 | 2.50E−173 |
| HGS028 | sp|P28367|RF2_BACSU | PEPTIDE CHAIN RELEASE FACTOR 2 (RF-2) . . . | 742 | 3.00E−157 |
| HGS028 | gi|2984119 | (AE000758) peptide chain release fact . . . | 442 | 2.20E−128 |
| HGS028 | gnl|PID|e254636 | peptide release factor 2 [Bacillus fi . . . | 718 | 2.90E−125 |
| HGS028 | pir|S76448|S76448 | translation releasing factor RF-2 - S . . . | 883 | 3.30E−116 |
| HGS028 | pir|A64190|A64190 | translation releasing factor RF-2 - H . . . | 444 | 1.70E−110 |
| HGS028 | gi|154276 | peptide chain release factor 2 [Salmo . . . | 444 | 1.80E−108 |
| HGS028 | gi|2687953 | (AE001120) peptide chain release fact . . . | 408 | 3.90E−108 |
| HGS028 | gi|2367172 | (AE000372) peptide chain release fact . . . | 437 | 1.60E−107 |
| HGS028 | gi|147569 | peptide chain release factor 2 [Esche . . . | 434 | 4.00E−107 |
| HGS030 | gnl|PID|d1005806 | unknown [Bacillus subtilis] > gnl|PID|e11 . . . | 283 | 2.60E−64 |
| HGS030 | gi|3176887 | (AF065312) thymidylate kinase [Yersinia . . . | 124 | 3.00E−43 |
| HGS030 | gi|2983484 | (AE000716) thymidylate kinase [Aquifex a . . . | 272 | 2.40E−37 |
| HGS030 | gi|1244710 | thymidylate kinase [Escherichia coli] > g . . . | 136 | 7.20E−34 |
| HGS030 | gi|2650584 | (AE001102) thymidylate kinase (tmk) [Arc . . . | 71 | 2.60E−30 |
| HGS030 | gi|1045674 | thymidylate kinase [Mycoplasma genitaliu . . . | 173 | 8.20E−28 |
| HGS030 | gi|1673808 | (AE000016) Mycoplasma pneumoniae, thymid . . . | 171 | 1.70E−27 |
| HGS030 | gi|1246364 | thymidylate:zeocin resistance protein:ND . . . | 136 | 2.20E−27 |
| HGS030 | gi|1246361 | thymidine:thymidylate kinase:zeocin resi . . . | 136 | 4.30E−27 |
| HGS030 | gi|950071 | ATP-bind. pyrimidine kinase [Mycoplasma . . . | 80 | 8.70E−21 |
| HGS031 | gnl|PID|e1185242 | uridylate kinase [Bacillus subtilis] > pi . . . | 920 | 8.40E−123 |
| HGS031 | gnl|PID|d1019291 | uridine monophosphate kinase [Synechocys . . . | 530 | 1.70E−96 |
| HGS031 | gnl|PID|e1296663 | (AL023797) uridylate kinase [Streptomyce . . . | 678 | 2.10E−89 |
| HGS031 | gnl|PID|e248883 | hypothetical protein MTCY274.14c [Mycoba . . . | 416 | 6.00E−89 |
| HGS031 | gnl|PID|e327783 | uridylate kinase [Mycobacterium leprae] | 403 | 7.90E−86 |

TABLE 2-continued

Closest matching sequence between the polypeptides of the present invention and GenSeq and GenBank sequences in databases

| Sequence ID | Antigen Accession No. | Match Gene Name | High Score | Smallest Sum Probability P (N) |
|---|---|---|---|---|
| HGS031 | gi\|473234 | uridine 5'-monophosphate (UMP) kinase [E . . . | 384 | 2.10E−72 |
| HGS031 | gi\|1552748 | uridine 5'-monophosphate (UMP) kinase [E . . . | 375 | 3.60E−71 |
| HGS031 | gi\|1574616 | mukB suppressor protein (smbA) [Haemophi . . . | 409 | 3.70E−71 |
| HGS031 | gi\|2983290 | (AE000703) UMP kinase [*Aquifex aeolicus*] | 452 | 3.70E−58 |
| HGS031 | gi\|1518662 | UMP kinase [*Chlamydia trachomatis*] > sp\|P . . . | 323 | 9.10E−55 |
| HGS032 | gi\|755152 | highly hydrophobic integral membrane pro . . . | 297 | 2.40E−81 |
| HGS032 | gi\|1235660 | RfbA [*Myxococcus xanthus*] > sp\|Q50862\|RFB . . . | 173 | 4.90E−24 |
| HGS032 | gnl\|PID\|d1017629 | ABC transporter [Synechocystis sp.] > pir . . . | 149 | 1.50E−19 |
| HGS032 | gnl\|PID\|d1029275 | (AB010294) integral membrane component o . . . | 126 | 6.40E−19 |
| HGS032 | gnl\|PID\|d1008332 | putative integral membrane component of . . . | 125 | 9.10E−19 |
| HGS032 | gnl\|PID\|d1029271 | (AB010293) integral membrane component o . . . | 125 | 9.10E−19 |
| HGS032 | gnl\|PID\|d1029279 | (AB010295) integral membrane component o . . . | 125 | 9.10E−19 |
| HGS032 | gnl\|PID\|d1029264 | (AB010150) integral membrane component o . . . | 109 | 3.00E−15 |
| HGS032 | gi\|2983575 | (AE000723) ABC transporter (ABC-2 subfam . . . | 71 | 9.60E−13 |
| HGS032 | gi\|609595 | homologous to kpsM (*E. coli*), bexB (H.inf . . . | 78 | 2.60E−12 |
| HGS033 | gi\|755153 | ATP-binding protein [*Bacillus subtilis*]. . . | 655 | 9.30E−94 |
| HGS033 | gi\|609596 | ATP-binding protein [*Serratia marcescens*] | 387 | 3.70E−69 |
| HGS033 | gi\|765059 | ABC-transporter protein [Klebsiella pneu . . . | 371 | 3.70E−69 |
| HGS033 | gi\|567183 | ATP-binding protein [Klebsiella pneumoni . . . | 367 | 1.20E−67 |
| HGS033 | gi\|304013 | abcA [*Aeromonas salmonicida*] > pir\|A36918 . . . | 294 | 7.20E−59 |
| HGS033 | gnl\|PID\|d1020415 | (AB002668) ABC transport protein [Actino . . . | 323 | 4.00E−57 |
| HGS033 | gi\|1123030 | CpxA [*Actinobacillus pleuropneumoniae*] | 190 | 2.40E−56 |
| HGS033 | gi\|3135679 | (AF064070) putative ABC-2 transporter hy . . . | 219 | 2.10E−53 |
| HGS033 | gi\|2983576 | (AE000723) ABC transporter [Aquifex aeol . . . | 294 | 2.10E−53 |
| HGS033 | gi\|1235661 | RfbB [*Myxococcus xanthus*] > sp\|Q50863\|RFB . . . | 336 | 6.70E−53 |
| HGS034 | gi\|143647 | ribosomal protein S4 [*Bacillus subtilis*] . . . | 798 | 4.50E−106 |
| HGS034 | gi\|2314460 | (AE000633) ribosomal protein S4 (rps4) [ . . . | 322 | 1.50E−62 |
| HGS034 | gi\|2982819 | (AE000672) ribosomal protein S04 [Aquife . . . | 253 | 2.00E−62 |
| HGS034 | gi\|606231 | 30S ribosomal subunit protein S4 [Escher . . . | 292 | 2.40E−58 |
| HGS034 | gnl\|PID\|e1234848 | (AJ223236) ribosomal protein S4 [Salmone . . . | 292 | 6.10E−58 |
| HGS034 | gi\|1573812 | ribosomal protein S4 (rpS4) [Haemophilus . . . | 292 | 1.60E−57 |
| HGS034 | gi\|639791 | ribosomal protein S4 [Mycoplasma pneumon . . . | 260 | 1.90E−56 |
| HGS034 | gi\|1046011 | ribosomal protein S4 [Mycoplasma genital . . . | 245 | 2.10E−54 |
| HGS034 | gnl\|PID\|e316061 | RpsD [*Mycobacterium tuberculosis*] > gnl\|P . . . | 270 | 1.40E−52 |
| HGS034 | gi\|144143 | ribosomal protein S4 [Buchnera aphidicol . . . | 255 | 2.00E−51 |
| HGS036 | gi\|2648781 | (AE000980) dipeptide ABC transporter, AT . . . | 136 | 1.90E−40 |
| HGS036 | gnl\|PID\|e1264523 | (AL022121) putative peptide ABC transpor . . . | 185 | 5.50E−35 |
| HGS036 | gi\|143686 | sporulation protein [*Bacillus subtilis*] | 191 | 7.70E−34 |
| HGS036 | gnl\|PID\|e1183166 | oligopeptide ABC transporter (ATP-bindin . . . | 191 | 7.70E−34 |
| HGS036 | gnl\|PID\|e1253461 | oligopeptide transport ATP-binding prote . . . | 213 | 5.50E−33 |
| HGS036 | gi\|2313342 | (AE000544) oligopeptide ABC transporter, . . . | 258 | 7.60E−32 |
| HGS036 | gnl\|PID\|d1015858 | Dipeptide transport ATP-binding protein . . . | 205 | 1.10E−31 |
| HGS036 | gi\|47346 | AmiE protein [*Streptococcus pneumoniae*] . . . | 202 | 7.40E−31 |
| HGS036 | gi\|972897 | DppD [*Haemophilus influenzae*] > gi\|157411 . . . | 204 | 1.40E−30 |
| HGS036 | gi\|677943 | AppD [*Bacillus subtilis*] > gnl\|PID\|e11831 . . . | 205 | 9.70E−30 |
| HGS040 | gnl\|PID\|e1185713 | elongation factor P [*Bacillus subtilis*] . . . | 702 | 7.00E−91 |
| HGS040 | gi\|1399276 | elongation factor P [Synechococcus PCC79 . . . | 541 | 4.90E−69 |
| HGS040 | gnl\|PID\|d1010902 | elongation factor P [Synechocystis sp.] . . . | 535 | 3.20E−68 |
| HGS040 | gi\|951349 | ORF1; putative [Anabaena sp.] > sp\|Q44247 . . . | 505 | 3.80E−64 |
| HGS040 | gnl\|PID\|e290977 | unknown [*Mycobacterium tuberculosis*] > gn . . . | 480 | 9.20E−61 |
| HGS040 | gnl\|PID\|e1169516 | elongation factor P [Corynebacterium glu . . . | 460 | 4.80E−58 |
| HGS040 | gi\|2983772 | (AE000736) elongation factor P [Aquifex . . . | 435 | 1.10E−54 |
| HGS040 | gi\|1658506 | elongation factor P homologue; EF-P [Bac . . . | 203 | 7.20E−52 |
| HGS040 | gi\|2313266 | (AE000538) translation elongation factor . . . | 409 | 4.00E−51 |
| HGS040 | gi\|536991 | elongation factor P [*Escherichia coli*] > . . . | 362 | 9.40E−45 |
| 168153_3 | gnl\|PID\|d1028815 | (AB009524) Vi polysaccharide biosynthes . . . | 237 | 5.80E−72 |
| 168153_3 | gi\|47961 | wcdB; ORF3 in citation [1] [Salmonella . . . | 234 | 1.80E−71 |
| 168153_3 | gi\|1590951 | UDP-glucose 4-epimerase (galE) [Methano . . . | 148 | 3.20E−60 |
| 168153_3 | pir\|C69149\|C69149 | conserved hypothetical protein MTH380- . . . | 151 | 1.90E−50 |
| 168153_3 | gi\|1143204 | ORF2; Method: conceptual translation s . . . | 227 | 4.50E−47 |
| 168153_3 | gnl\|PID\|e316552 | unknown [*Mycobacterium tuberculosis*] > g . . . | 109 | 4.70E−45 |
| 168153_3 | gnl\|PID\|e1185960 | similar to NDP-sugar epimerase [Bacillu . . . | 155 | 1.80E−39 |
| 168153_3 | gnl\|PID\|e1289548 | (AL023093) putative sugar dehyratase [M . . . | 86 | 1.80E−36 |
| 168153_3 | gnl\|PID\|e288124 | glucose epimerase [Bacillus thuringiensis] | 95 | 2.70E−35 |
| 168153_3 | gi\|1591707 | capsular polysaccharide biosynthesis pr . . . | 85 | 1.60E−34 |
| 168153_2 | gnl\|PID\|e1184467 | alternate gene name: yvhA [Bacillus subt . . . | 354 | 4.90E−45 |
| 168153_2 | gi\|1657652 | Cap8M [*Staphylococcus aureus*] | 138 | 9.00E−42 |
| 168153_2 | gi\|1773352 | Cap5M [*Staphylococcus aureus*] | 138 | 9.00E−42 |
| 168153_2 | gnl\|PID\|e238668 | hypothetical protein [*Bacillus subtilis*] . . . | 139 | 6.10E−39 |
| 168153_2 | gi\|1199573 | spsB [Sphingomonas sp.] > gi\|1314578 gluc . . . | 168 | 4.40E−35 |
| 168153_2 | gnl\|PID\|d1005318 | ORF14 [*Klebsiella pneumoniae*] > sp\|Q48460 . . . | 260 | 5.50E−33 |
| 168153_2 | gnl\|PID\|d1020425 | (AB002668) galactosyltransferase [Actino . . . | 155 | 5.60E−33 |

TABLE 2-continued

Closest matching sequence between the polypeptides of the present invention and GenSeq and GenBank sequences in databases

| Sequence ID | Antigen Accession No. | Match Gene Name | High Score | Smallest Sum Probability P (N) |
|---|---|---|---|---|
| 168153_2 | gnl\|PID\|d1029082 | (AB010415) glycosyltransferase [Actinoba . . . | 155 | 2.00E−32 |
| 168153_2 | gnl\|PID\|d1019174 | galactosyl-1-phosphate transferase [Syne . . . | 139 | 2.30E−32 |
| 168153_2 | gnl\|PID\|e220381 | structural gene [Agrobacterium radiobacter] | 138 | 2.40E−32 |
| 168153_1 | gi\|1276880 | EpsG [Streptococcus thermophilus] | 141 | 3.40E−34 |
| 168153_1 | gi\|1276879 | EpsF [Streptococcus thermophilus] | 162 | 1.70E−29 |
| 168153_1 | gi\|633699 | WbcQ [Yersinia enterocolitica ] > pir\|S512 . . . | 134 | 9.10E−26 |
| 168153_1 | gnl\|PID\|e238704 | hypothetical protein [Bacillus subtilis] . . . | 131 | 1.90E−18 |
| 168153_1 | gi\|2983976 | (AE000749) capsular polysaccharide biosy . . . | 134 | 1.50E−15 |
| 168153_1 | gnl\|PID\|d1005311 | ORF7 [Klebsiella pneumoniae] > sp\|Q48453\| . . . | 94 | 2.10E−12 |
| 168153_1 | gi\|633696 | WbcN [Yersinia enterocolitica] > pir\|S512 . . . | 123 | 2.50E−12 |
| 168153_1 | gi\|755606 | unknown [Bacillus subtilis] | 144 | 5.40E−12 |
| 168153_1 | gi\|1146237 | 21.4% of identity to trans-acting transc . . . | 144 | 6.00E−12 |
| 168153_1 | gnl\|PID\|e238664 | hypothetical protein [Bacillus subtilis] . . . | 141 | 3.20E−11 |
| 168339_2 | gnl\|PID\|e1169894 | putative repeating unit transporter . . . | 234 | 5.70E−57 |
| 168339_2 | gi\|2209215 | (AF004325) putative oligosaccharide . . . | 139 | 4.90E−37 |
| 168339_2 | gi\|633692 | Wzx [Yersinia enterocolitica] > pir\|S . . . | 141 | 3.00E−31 |
| 168339_2 | gi\|2621404 | (AE000819) O-antigen transporter [Me . . . | 129 | 8.90E−29 |
| 168339_2 | gi\|2072448 | EpsK [Lactococcus lactis cremoris] | 199 | 4.00E−27 |
| 168339_2 | sp\|P37746\|RFBX_ECOLI | PUTATIVE O-ANTIGEN TRANSPORTER. | 140 | 2.10E−23 |
| 168339_2 | gnl\|PID\|d1016603 | Putative O-antigen transporter. [Esc . . . | 140 | 2.90E−23 |
| 168339_2 | gi\|510252 | membrane protein [Escherichia coli] | 140 | 8.10E−23 |
| 168339_2 | gi\|2621427 | (AE000822) O-antigen transporter [Me . . . | 122 | 3.10E−20 |
| 168339_2 | gi\|152778 | RFBX [Shigella dysenteriae] > pir\|S34 . . . | 114 | 8.50E−19 |

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score.

For example, a 90 nucleotide subject sequence is aligned to a 100 nucleotide query sequence to determine percent identity. The deletions occur at the 5' end of the subject sequence and therefore, the FASTDB alignment does not show a matched/alignment of the first 10 nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%. In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are made for the purposes of the present invention.

Vectors and Host Cell

The present invention also relates to vectors which include the isolated DNA molecules of the present invention, host cells comprising the recombinant vectors, and the production of S. aureus polypeptides and peptides of the present invention expressed by the host cells.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The S. aureus polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, tip, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin, or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE9, pQE10 available from Qiagen; pBS vectors, Phagescript vectors, Bluescript vectors, pNH8A, pNH16a, pNH18A, pNH46A available from Stratagene Cloning Systems, Inc.; pET series of vectors available from Novagen; and ptrc99a, pKK223–3, pKK233–3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.-5K, pPIC9K, and PAO815 (all available from Invitrogen, Carlbad, Calif.). Other suitable vectors will be readily apparent to the skilled artisan.

Among known bacterial promoters suitable for use in the present invention include the *E. coli* lacI and lacZ promoters, the T3, T5 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma Virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)). It is specifically contemplated that the polypeptides of the present invention may in fact be expressed by a host cell lacking a recombinant vector.

Transcription of DNA encoding the polypeptides of the present invention by higher eukaryotes may be increased by inserting an enhancer sequence into the vector. Enhancers are cis-acting elements of DNA, usually about from 10 to 300 nucleotides that act to increase transcriptional activity of a promoter in a given host cell-type. Examples of enhancers include the SV40 enhancer, which is located on the late side of the replication origin at nucleotides 100 to 270, the cytomegalovirus early promoter enhancer, the polyoma enhancer on the late side of the replication origin, and adenovirus enhancers.

For secretion of the translated polypeptide into the lumen of the endoplasmic reticulum, into the periplasmic space or into the extracellular environment, appropriate secretion signals may be incorporated into the expressed polypeptide, for example, the amino acid sequence KDEL. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0 232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See Bennett, D. et al. (1995) J. Molec. Recogn. 8:52–58 and Johanson, K. et al. (1995) J. Biol. Chem. 270 (16) :9459–9471.

The *S. aureus* polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography and high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells.

Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast Pichia pastoris is used to express any plasma membrane associated protein of the invention in a eukaryotic system. Pichia pastoris is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, Pichia pastoris must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a plasma membrane associated polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a plasma membrane associated polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a plasma membrane associated protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a plasma membrane associated polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses host cells that have been engineered to delete or replace endogenous genetic material (e.g. coding sequences for the polypeptides of the present invention), and/or to include genetic material (e.g. heterologous polynucleotide sequences) that is operably associated with polynucleotides of the present invention, and which activates, alters, and/or amplifies endogenous polynucleotides of the present invention. For example, techniques known in the art may be used to operably associate heterologous control regions (e.g. promoter and/or enhancer) and endogenous polynucleotide sequences via homologous recombination (see, e.g. U.S. Pat. No. 5,641,670, issued Jun. 24, 1997; Internation Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra, et al., Nature 342:435–438 (1989), the disclosures of each of which are hereby incorporated by reference in their entireties).

In addition, polypeptides of the invention can he chemically synthesized using techniques known in the art (e.g., see Creighton, 1983, Proteins: Structures and Molecular Principles, W. H. Freeman & Co., N.Y., and Hunkapiller et al., Nature, 310:105–111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., Nucl. Acids Res. 13:4331 (1986); and Zoller et al., Nucl. Acids Res. 10:6487 (1982)), cassette mutagenesis (see, e.g., Wells et al., Gene 34:315 (1985)), restriction selection mutagenesis (see, e.g., Wells et al., Philos. Trans. R. Soc. London SerA 317:415 (1986)).

The invention additionally, encompasses polypeptides of the present invention which are differentially modified during or after translation, such as for example, by glycosylation, acetylation, phosphorylation, amidation, derivatization by known protecting/blocking groups, proteolytic cleavage, linkage to an, antibody molecule or other cellular ligand, etc. Any of numerous chemical modifications may be carried out by known techniques, including but not limited to: specific chemical cleavage by cyanogen bromide; trypsin; chymotrypsin; papain; V8 protease; $NaBH_4$; acetylation; formylation; oxidation; reduction; and metabolic synthesis in the presence of tunicamycin, etc.

Additional post-translational modifications encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile, which can include, for example, the duration of sustained release desired; the effects, if any, on biological activity; the ease in handling; the degree or lack of antigenicity; and other known effects of the polyethylene glycol on a therapeutic protein or analog. For example, the polyethylene glycol may have an average molecular weight of about 200, 500, 1000, 1500, 2000, 2500, 3000, 3500, 4000, 4506, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference in their entireties.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'- carbonyldiimidazole, MPEG-2,4,5-trichlorophenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of Table 1 (including fragments, variants, splice variants, and fusion proteins, corresponding to these as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., the polypeptide sequences shown in Table 1). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein.

In one example, covalent associations are between the heterologous sequence contained in a fusion protein of the invention (see, e.g., U.S. Pat. No. 5,478,925). In a specific example, the covalent associations are between the heterologous sequence contained in a Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, International Publication NO: WO 98/49305, the contents of which is incorporated herein by reference in its entirety). In another embodiment, two or more polypeptides of the invention are joined through peptide linkers. Examples include those peptide linkers described in U.S. Pat. No. 5,073,627 (incorporated herein by reference in its entirety). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is incorporated herein by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is incorporated herein by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is incorporated herein by reference in its entirety). Additionally, techniques known in the art may be applied to generate liposomes containing the polypeptide components desired to be contained in the multimer of the invention (see, e.g., U.S. Pat. No. 5,478,925, which is incorporated herein by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is incorporated herein by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is incorporated herein by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is incorporated herein by reference in its entirety).

Polypeptides and Fragments

The invention further provides an isolated *S. aureus* polypeptide having an amino acid sequence in Table 1 or SEQ ID NO:1 through 61, or a peptide or polypeptide comprising a portion, fragment, variant or analog of the above polypeptides.

Variant and Mutant Polypeptides

To improve or alter the characteristics of *S. aureus* polypeptides of the present invention, protein engineering may be employed. Recombinant DNA technology known to those skilled in the art can be used to create novel mutant proteins or muteins including single or multiple amino acid substitutions, deletions, additions, or fusion proteins. Such modified polypeptides can show, e.g., increased/decreased activity or increased/decreased stability. In addition, they may be purified in higher yields and show better solubility than the corresponding natural polypeptide, at least under certain purification and storage conditions. Further, the polypeptides of the present invention may be produced as multimers including dimers, trimers and tetramers. Multimerization may be facilitated by linkers or recombinantly though heterologous polypeptides such as Fc regions.

N-Terminal and C-Terminal Deletion Mutants

It is known in the art that one or more amino acids may be deleted from the N-terminus or C-terminus without substantial loss of biological function. For instance, Ron et al. J. Biol. Chem., 268:2984–2988 (1993), reported modified KGF proteins that had heparin binding activity even if 3, 8, or 27 N-terminal amino acid residues were missing. Accordingly, the present invention provides polypeptides having one or more residues deleted from the amino terminus of the polypeptides shown in Table 1.

Similarly, many examples of biologically functional C-terminal deletion mutants are known. For instance, Interferon gamma shows up to ten times higher activities by deleting 8–10 amino acid residues from the carboxy-terminus of the protein See, e.g., Dobeli, et al. (1988) J. Biotechnology 7:199–216. Accordingly, the present invention provides polypeptides having one or more residues from the carboxy terminus of the polypeptides shown in Table 1. The invention also provides polypeptides having one or more amino acids deleted from both the amino and the carboxyl termini as described below.

The present invention is further directed to polynucleotide encoding portions or fragments of the amino acid sequences described herein as well as to portions or fragments of the isolated amino acid sequences described herein. Fragments include portions of the amino acid sequences of Table 1, at least 7 contiguous amino acid in length, selected from any two integers, one of which representing a N-terminal position. The first codon of the polypeptides of Table 1 is position 1. Every combination of a N-terminal and C-terminal position that a fragment at least 7 contiguous amino acid residues in length could occupy, on any given amino acid sequence of Table 1 is included in the invention. At least means a fragment may be 7 contiguous amino acid residues in length or any integer between 7 and the number of residues in a full length amino acid sequence minus 1. Therefore, included in the invention are contiguous fragments specified by any N-terminal and C-terminal positions of amino acid sequence set forth in Table 1 wherein the contiguous fragment is any integer between 7 and the number of residues in a full length sequence minus 1.

Further, the invention includes polypeptides comprising fragments specified by size, in amino acid residues, rather than by N-terminal and C-terminal positions. The invention includes any fragment size, in contiguous amino acid residues, selected from integers between 7 and the number of residues in a full length sequence minus 1. Preferred sizes of contiguous polypeptide fragments include about 7 amino acid residues, about 10 amino acid residues, about 20 amino acid residues, about 30 amino acid residues, about 40 amino acid residues, about 50 amino acid residues, about 100 amino acid residues, about 200 amino acid residues, about 300 amino acid residues, and about 400 amino acid residues. The preferred sizes are, of course, meant to exemplify, not limit, the present invention as all size fragments representing any integer between 7 and the number of residues in a full length sequence minus 1 are included in the invention. The present invention also provides for the exclusion of any fragments specified by N-terminal and C-terminal positions or by size in amino acid residues as described above. Any number of fragments specified by N-terminal and C-terminal positions or by size in amino acid residues as described above may be excluded.

The present invention further provides polypeptides having one or more residues deleted from the amino terminus of the amino acid sequence of a polypeptide disclosed herein (e.g., any polypeptide of Table 1). In particular, N-terminal deletions may be described by the general formula m-q, where q is a whole integer representing the total number of amino acid residues in a polypeptide of the invention (e.g., a polypeptide disclosed in Table 1), and m is defined as any integer ranging from 2 to q-6. Polynucleotides encoding these polypeptides are also encompassed by the invention.

The present invention further provides polypeptides having one or more residues from the carboxy-terminus of the amino acid sequence of a polypeptide disclosed herein (e.g., a polypeptide disclosed in Table 1) In particular, C-terminal deletions may be described by the general formula 1-n, where n is any whole integer ranging from 6 to q-1, and where n corresponds to the position of amino acid residue in a polypeptide of the invention. Polynucleotides encoding these polypeptides are also encompassed by the invention.

In addition, any of the above described N- or C-terminal deletions can be combined to produce a N- and C-terminal deleted polypeptide. The invention also provides polypeptides having one or more amino acids deleted from both the amino and the carboxyl termini, which may be described generally as having residues m-n of a polypeptide encoded by a nucleotide sequence (e.g., including, but not limited to the preferred polypeptide disclosed in Table 1), or the cDNA contained in a deposited clone, and/or the complement thereof, where n and m are integers as described above. Polynucleotides encoding these polypeptides are also encompassed by the invention.

The polypeptide fragments of the present invention can be immediately envisaged using the above description and are therefore not individually listed solely for the purpose of not unnecessarily lengthening the specification.

The above fragments need not be active since they would be useful, for example, in immunoassays, in epitope mapping, epitope tagging, to generate antibodies to a particular portion of the polypeptide, as vaccines, and as molecular weight markers.

In addition to N- and C-terminal deletion forms of the protein discussed above, it also will be recognized by one of ordinary skill in the art that some amino acid sequences of the S. aureus polypeptides of the present invention can be varied without significant effect of the structure or function of the protein. If such differences in sequence are contemplated, it should be remembered that there will be critical areas on the protein which determine activity.

Thus, the invention further includes variations of the S. aureus polypeptides which show substantial S. aureus polypeptide activity or which include regions of S. aureus protein such as the protein portions discussed below. Such mutants include deletions, insertions, inversions, repeats, and substitutions selected according to general rules known in the art so as to have little effect on activity. For example, guidance concerning how to make phenotypically silent amino acid substitutions is provided. There are two main approaches for studying the tolerance of an amino acid sequence to change. See, Bowie, J. U. et al. (1990), Science 247:1306–1310. The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions. The studies indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative, analog, or homolog of the polypeptide of Table 1 may be, for example: (i) one in which one or more of the amino acid residues are substituted with a conserved or non-conserved amino acid residue (preferably a conserved amino acid residue) and such substituted amino acid residue may or may not be one encoded by the genetic code: or (ii) one in which one or more of the amino acid residues includes a substituent group: or (iii) one in which the S. aureus polypeptide is fused with another compound, such as a compound to increase the half-life of the polypeptide (for example, polyethylene glycol): or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the S. aureus polypeptides of the present invention may include one or more amino acid substitutions, deletions, or additions, either from natural mutations or human manipulation. As indicated, changes are preferably of a minor nature, such as conservative amino acid substitutions that do not significantly affect the folding or activity of the protein (see Table 3).

TABLE 3

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the S. aureus proteins of the present invention that are essential for function can be identified by methods known in the art, such as site-directed mutagenesis or alanine-scanning mutagenesis. See, e.g., Cunningham et al. (1989) Science 244:1081–1085. The latter procedure introduces single alanine mutations at every residue in the molecule. The resulting mutant molecules are then tested for biological activity using assays appropriate for measuring the function of the particular protein.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic. See, e.g., Pinckard et al., (1967) Clin. Exp. Immunol. 2:331–340; Robbins, et al., (1987) Diabetes 36:838–845; Cleland, et al., (1993) Crit. Rev. Therapeutic Drug Carrier Systems 10:307–377.

The polypeptides of the present invention are preferably provided in an isolated form, and may partially or substantially purified. A recombinantly produced version of the S. aureus polypeptide can be substantially purified by the one-step method described by Smith et al., (1988) Gene 67:31–40. Polypeptides of the invention also can be purified from natural or recombinant sources using antibodies directed against the polypeptides of the invention in methods which are well known in the art of protein purification. The purity of the polypeptide of the present invention may also specified in percent purity as relative to heterologous containing polypeptides. Preferred purities include at least 25%, 50%, 75%, 80%, 85%, 90%, 91%, 92%, 93%, 94%, 95%, 96%, 97%, 98%, 99%, 99.5%, 99.75%, and 100% pure, as relative to heretologous containing polypeptides.

The invention provides for isolated S. aureus polypeptides comprising an the amino acid sequence of a full-length S. aureus polypeptide having the complete amino acid sequence shown in Table 1 and the amino acid sequence of a full-length S. aureus polypeptide having the complete amino acid sequence shown in Table 1 excepting the N-terminal codon (e.g. including, but not limited to, methionine, leucine, and/or valine) The polypeptides of the present invention also include polypeptides having an amino acid sequence at least 80% identical, more preferably at least 90% identical, and still more preferably 95%, 96%, 97%, 98% or 99% identical to a member of the group consisting of (a) a polypeptide encoded by any of the polynucleotide sequences shown in Table 1, (b) any of the polypeptide sequences shown in Table 1 and (c) the complement of a polynucleotide sequence encoding the polypeptide of (a) or (b) above. Further polypeptides of the present invention include polypeptides which have at least 90% similarity, more preferably at least 95% similarity, and still more preferably at least 96%, 97%, 98% or 99% similarity to those described above.

A further embodiment of the invention relates to a polypeptide which comprises the amino acid sequence of a S. aureus polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a S. aureus polypeptide, having at least one, but not more than 10, 9, 8, 7, 6, 5, 4, 3, 2 or 1 conservative amino acid substitutions.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequences shown in Table 1, or a fragment thereof can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, the results, in percent identity, must be manually corrected. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not match/align with the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are to made for the purposes of the present invention.

The above polypeptide sequences are included irrespective of whether they have their normal biological activity. This is because even where a particular polypeptide molecule does not have biological activity, one of skill in the art would still know how to use the polypeptide, for instance, as a vaccine or to generate antibodies. Other uses of the polypeptides of the present invention that do not have S. aureus activity include, inter alia, as epitope tags, in epitope mapping, and as molecular weight markers on SDS-PAGE gels or on molecular sieve gel filtration columns using methods known to those of skill in the art.

As described below, the polypeptides of the present invention can also be used to raise polyclonal and monoclonal antibodies, which are useful in assays for detecting S. aureus protein expression or as agonists and antagonists capable of enhancing or inhibiting S. aureus protein function. Further, such polypeptides can be used in the yeast two-hybrid system to "capture" S. aureus protein binding proteins which are also candidate agonists and antagonists according to the present invention. See, e.g., Fields et al. (1989) Nature 340:245–246.

Epitopes and Antibodies

The present invention encompasses polypeptides comprising, or alternatively consisting of, an epitope of the polypeptide having an amino acid sequence in Table 1, or encoded by a polynucleotide that hybridizes to the complement of a nucleotide sequence shown in Table 1 under stringent hybridization conditions or alternatively, lower stringency hybridization conditions as defined supra. The present invention further encompasses polynucleotide sequences encoding an epitope of a polypeptide sequence of the invention (such as, for example, a nucleotide sequence disclosed in Table 1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are incorporated herein by reference in its entirety). In one embodiment, alteration of polynucleotides corresponding to those shown in Table 1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Predicted antigenic epitopes are shown in Table 4, below. It is pointed out that Table 4 only lists amino acid residues comprising epitopes predicted to have the highest degree of antigenicity by a particular algorithm. The polypeptides not listed in Table 4 and portions of polypeptides not listed in Table 4 are not considered non-antigenic. This is because they may still be antigenic in vivo but merely not recognized as such by the particular algorithm used. Thus, Table 4 lists the amino acids residues comprising only preferred antigenic epitopes, not a complete list. In fact, all fragments of the polypeptide sequence of Table 1, at least 7 amino acid residues in length, are included in the present invention as being useful in epitope mapping and in making antibodies to particular portions of the polypeptides. Moreover, Table 4 lists only the critical residues of the epitopes determined by the Jameson-Wolf analysis. Thus, additional flanking residues on either the N-terminal, C-terminal, or both N- and C-terminal ends may be added to the sequences of Table 4 to generate an epitope-bearing protion a least 7 residues in length. Amino acid residues comprising other antigenic epitopes may be determined by algorithms similar to the Jameson-Wolf analysis or by in vivo testing for an antigenic response using the methods described herein or those known in the art.

TABLE 4

Residues Comprising Antigenic Epitoes

| | |
|---|---|
| HGS001 | from about Asp-47 to about Asp-50, from about Ser-128 to about Asp-130, from about Lys-265 to about Gly-267. |
| HGS005 | from about Arg-104 to about Asp-106, from about Lys-116 to about Lys-120. |
| HGS007m | from about Glu-155 to about Gly-158, from about Gln-178 to about Gly-181, from about Ser-304 to about Cys-306, from about Asp-401 to about Tyr-403, from about Asn-405 to about Gly-408, from about Asp-411 to about Gly-416. |
| HGS009 | from about Pro-257 to about Lys-259. |
| HGS014 | from about Arg-186 to about Asp-188. |
| HGS019 | from about Lys-98 to about Gly-100, from about Pro-187 to about Asp-189. |
| HGS023 | from about Ser-251 to about Gly-253, from about Lys-437 to about Lys-440. |
| HGS025 | from about Met-51 to about Gly-53. |
| HGS026 | from about Asn-105 to about Lys-108, from about Glu-190 to about Gly-193, from about Arg-226 to about Ala-230. |
| HGS028 | from about Ile-10 to about Tyr-13. |
| HGS030 | from about Glu-11 to about Gly-14, from about Arg-147 to about Gln-149. |
| HGS033 | from about Lys-143 to about Ser-145. |
| HGS034 | from about Pro-33 to about Gln-35. |
| HGS036 | from about Asp-64 to about Tyr-66, from about Asp-255 to about Tyr-257. |
| HGS040 | from about Pro-30 to about Lys-32, from about Asp-76 to about Asp-78. |

TABLE 4-continued

Residues Comprising Antigenic Epitoes

| | |
|---|---|
| 168153_3 | from about Asn-35 to about Arg-37, from about Pro-135 to about Asp-138, from about Pro-185 to about Gln-188. |
| 168153_2 | from about Asp-54 to about Arg-56. |
| 168153_1 | from about Lys-64 to about Asp-67, from about Gln-319 to about Lys-322, from about Asn-342 to about Lys-344. |
| 168339_2 | from about Asn-82 to about Arg-85. |

Non-limiting examples of antigenic polypeptides or peptides that can be used to generate an Staphylococcal-specific immune response or antibodies include fragments of the amino acid sequences of Table 1 as discussed above. Table 4 discloses a list of non-limiting residues that are involved in the antigenicity of the epitope-bearing fragments of the present invention. Therefore, also included in the present inventions are isolated and purified antigenic epitope-bearing fragments of the polypeptides of the present invention comprising a peptide sequences of Table 4. The antigenic epitope-bearing fragments comprising a peptide sequence of Table 4 preferably contain between 7 to 50 amino acids (i.e. any integer between 7 and 50) of a polypeptide of the present invention. Also, included in the present invention are antigenic polypeptides between the integers of 7 and the full length sequence of a polypeptide of Table 1 comprising 1 or more amino acid sequences of Table 4. Therefore, in most cases, the polypeptides of Table 4 make up only a portion of the antigenic polypeptide. All combinations of sequences between the integers of 7 and the full sequence of a polypeptide sequence of Table 1 are included. The antigenic epitope-bearing fragments may be specified by either the number of contiguous amino acid residues or by specific N-terminal and C-terminal positions as described above for the polypeptide fragments of the present invention, wherein the first codon of each polypeptide sequence of Table 1 is position 1. Any number of the described antigenic epitope-bearing fragments of the present invention may also be excluded from the present invention in the same manner.

Antibodies

Further polypeptides of the invention relate to antibodies and T-cell antigen receptors (TCR) which immunospecifically bind a polypeptide, polypeptide fragment, or variant of a polypeptide sequence shown in Table 1, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and sequence listing. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15):3209–3214 (1998); Yoon et al., J. Immunol. 160(7) :3170–3179 (1998); Prat et al., J. Cell. Sci. 111(Pt2) :237–247 (1998); Pitard et al., J. Immunol. Methods 205(2) :177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP-396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 16). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 1879–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885, 793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing antiidiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having an amino acid sequence in Table 1.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, for example, a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described above. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule-of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5) :155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of a polypeptide sequence shown in Table 1 may be fused or conjugated to the above antibody portions to increase the in vivo half life of the polypeptides or for use in immunoassays using methods known in the art. Further, any one of the polypeptides shown in Table 1 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fe portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993), Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Millet et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. Diagnosis and Imaging Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods-known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($125I$, $121I$), carbon ($14C$), sulfur ($35S$), tritium ($3H$), indium ($112In$), and technetium ($99Tc$); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody; and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Diagnostic Assays

The present invention further relates to methods for assaying staphylococcal infection in an animal (e.g., a mammal, including but not limited to a human) by detecting the expression of genes encoding staphylococcal polypeptides of the present invention. The methods comprise analyzing tissue or body fluid from the animal for Staphylococcus-specific antibodies, nucleic acids, or proteins. Analysis of nucleic acid specific to Staphylococcus is assayed by PCR or hybridization techniques using nucleic acid sequences of the present invention as either hybridization probes or primers. See, e.g., Sambrook et al. Molecular cloning: A Laboratory Manual (Cold Spring Harbor Laboratory Press, 2nd ed., 1989, page 54 reference); Eremeeva et al. (1994) J. Clin. Microbiol. 32:803–810 (describing differentiation among spotted fever group Rickettsiae species by analysis of restriction fragment length polymorphism of PCR-amplified DNA) and Chen et al. 1994 J. Clin. Microbiol. 32:589–595 (detecting bacterial nucleic acids via PCR).

Where diagnosis of a disease state related to infection with Staphylococcus has already been made, the present invention is useful for monitoring progression or regression of the disease state by measuring the amount of Staphylococcus cells present in a patient or whereby patients exhibiting enhanced Staphylococcus gene expression will experience a worse clinical outcome relative to patients expressing these gene(s) at a lower level.

By "biological sample" is intended any biological sample obtained from an animal, cell line, tissue culture, or other source which contains Staphylococcus polypeptide, mRNA, or DNA. Biological samples include body fluids (such as saliva, blood, plasma, urine, mucus, synovial fluid, etc.) tissues (such as muscle, skin, and cartilage) and any other biological source suspected of containing Staphylococcus polypeptides or nucleic acids. Methods for obtaining biological samples such as tissue are well known in the art.

The present invention is useful for detecting diseases related to Staphylococcus infections in animals. Preferred animals include monkeys, apes, cats, dogs, birds, cows, pigs, mice, horses, rabbits and humans. Particularly preferred are humans.

Total RNA can be isolated from a biological sample using any suitable technique such as the single-step guanidinium-thiocyanate-phenol-chloroform method described in Chomczynski et al. (1987) Anal. Biochem. 162:156–159. mRNA encoding Staphylococcus polypeptides having sufficient homology to the nucleic acid sequences identified in Table 1 to allow for hybridization between complementary sequences are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al. (1990) Cell 63:303–312. Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. A S. aureus polynucleotide sequence shown in Table 1 labeled according to any appropriate method (such as the $^{32}$P-multiprimed DNA labeling system (Amersham)) is used as probe. After hybridization overnight, the filter is washed and exposed to x-ray film. DNA for use as probe according to the present invention is described in the sections above and will preferably at least 15 nucleotides in length.

S1 mapping can be performed as described in Fujita et al. (1987) Cell 49:357–367. To prepare probe DNA for use in S1 mapping, the sense strand of an above-described S. aureus DNA sequence of the present invention is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding polypeptides of the present invention).

Levels of mRNA encoding Staphylococcus polypeptides are assayed, for e.g., using the RT-PCR method described in Makino et al. (1990) Technique 2:295–301. By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the Staphylococcus polypeptides of the present invention) are quantified using an imaging analyzer. RT and PCR reaction ingredients and conditions, reagent and gel concentrations, and labeling methods are well known in the art. Variations on the RT-PCR method will be apparent to the skilled artisan. Other PCR methods that can detect the nucleic acid of the present invention can be found in PCR PRIMER: A LABORATORY MANUAL (C. W. Dieffenbach et al. eds., Cold Spring Harbor Lab Press, 1995).

The polynucleotides of the present invention, including both DNA and RNA, may be used to detect polynucleotides of the present invention or Staphylococcus species including S. aureus using bio chip technology. The present invention includes both high density chip arrays (>1000 oligonucleotides per cm$^2$) and low density chip arrays (<1000 oligonucleotides per cm$^2$). Bio chips comprising arrays of polynucleotides of the present invention may be used to detect Staphylococcus species, including S. aureus, in biological and environmental samples and to diagnose an animal, including humans, with an S. aureus or other Staphylococcus infection. The bio chips of the present invention may comprise polynucleotide sequences of other pathogens including bacteria, viral, parasitic, and fungal polynucleotide sequences, in addition to the polynucleotide sequences of the present invention, for use in rapid differential pathogenic detection and diagnosis. The bio chips can also be used to monitor an S. aureus or other Staphylococcus infections and to monitor the genetic changes (deletions, insertions, mismatches, etc.) in response to drug therapy in the clinic and drug development in the laboratory. The bio chip technology comprising arrays of polynucleotides of the present invention may also be used to simultaneously monitor the expression of a multiplicity of genes, including those of the present invention. The polynucleotides used to comprise a selected array may be specified in the same manner as for the fragments, i.e, by their 5' and 3' positions or length in contigious base pairs and include from. Methods and particular uses of the polynucleotides of the present invention to detect Staphylococcus species, including S. aureus, using bio chip technology include those known in the art and those of: U.S. Pat. Nos. 5,510,270, 5,545,531, 5,445,934, 5,677,195, 5,532,128, 5,556,752, 5,527,681, 5,4516,83, 5,424,186, 5,607,646, 5,658,732 and World Patent Nos. WO/9710365, WO/9511995, WO/9743447, WO/9535505, each incorporated herein in their entireties.

Biosensors using the polynucleotides of the present invention may also be used to detect, diagnose, and monitor S. aureus or other Staphylococcus species and infections thereof. Biosensors using the polynucleotides of the present invention may also be used to detect particular polynucleotides of the present invention. Biosensors using the polynucleotides of the present invention may also be used to monitor the genetic changes (deletions, insertions, mismatches, etc.) in response to drug therapy in the clinic and drug development in the laboratory. Methods and particular uses of the polynucleotides of the present invention to detect Staphylococcus species, including S. aureus, using biosenors include those known in the art and those of: U.S. Pat. Nos. 5,721,102, 5,658,732, 5,631,170, and World Patent Nos. WO97/35011, WO/9720203, each incorporated herein in their entireties.

Thus, the present invention includes both bio chips and biosensors comprising polynucleotides of the present invention and methods of their use.

A preferred composition of matter comprises isolated nucleic acid molecules wherein the nucleotide sequences of said nucleic acid molecules comprise a bio chip or biosensor of at least 1, 2, 3, 4, 5, 6, 7, 8, 9, 10, 15, 20, 25, 30, 40, 50, 100, 150, 200, 250, 300, 500, 1000, 2000, 3000 or 4000 nucleotide sequences, wherein at least one sequence in said DNA bio chip or biosensor is at least 95% identical to a sequence of at least 50 contiguous nucleotides in a S. aureus polynucleotide shown in Table 1. The nucleic acid molecules can comprise DNA molecules or RNA molecules.

Assaying Staphylococcus polypeptide levels in a biological sample can occur using any art-known method, such as antibody-based techniques. For example, Staphylococcus polypeptide expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of Staphylococcus polypeptides for Western-blot or dot/slot assay. See, e.g., Jalkanen, M. et al. (1985) J. Cell. Biol. 101:976–985; Jalkanen, M. et al.

(1987) J. Cell. Biol. 105:3087–3096. In this technique, which is based on the use of cationic solid phases, quantitation of a Staphylococcus polypeptide can be accomplished using an isolated Staphylococcus polypeptide as a standard. This technique can also be applied to body fluids.

Other antibody-based methods useful for detecting Staphylococcus polypeptide gene expression include immunoassays, such as the ELISA and the radioimmunoassay (RIA). For example, a Staphylococcus polypeptide-specific monoclonal antibodies can be used both as an immunoabsorbent and as an enzyme-labeled probe to detect and quantify a Staphylococcus polypeptide. The amount of a Staphylococcus polypeptide present in the sample can be calculated by reference to the amount present in a standard preparation using a linear regression computer algorithm. Such an ELISA is described in Iacobelli et al. (1988) Breast Cancer Research and Treatment 11:19–30. In another ELISA assay, two distinct specific monoclonal antibodies can be used to detect Staphylococcus polypeptides in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting the Staphylococcus polypeptide with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample. Variations of the above and other immunological methods included in the present invention can also be found in Harlow et al., ANTIBODIES: A LABORATORY MANUAL, (Cold Spring Harbor Laboratory Press, 2nd ed. 1988).

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Further suitable labels for the Staphylococcus polypeptide-specific antibodies of the present invention are provided below. Examples of suitable enzyme labels include malate dehydrogenase, Staphylococcus nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$E, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging. See, e.g., Perkins et al. (1985) Eur. J. Nucl. Med. 10:296–301; Carasquillo et al. (1987) J. Nucl. Med. 28:281–287. For example, $^{111}$In coupled to monoclonal antibodies with 1-(P-isothiocyanatobenzyl)-DPTA has shown little uptake in non-tumors tissues, particularly the liver, and therefore enhances specificity of tumor localization. See, Esteban et al. (1987) J. Nucl. Med. 28:861–870.

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, Pseudomonas toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al. (1976) Clin. Chim. Acta 70:1–31, and Schurs et al. (1977) Clin. Chim. Acta 81:1–40. Coupling techniques mentioned in the latter are the glutaraldehyde method, the periodate method, the dimaleimide method, the m-maleimidobenzyl-N-hydroxysuccinimide ester method, all of which methods are incorporated by reference herein.

In a related aspect, the invention includes a diagnostic kit for use in screening serum containing antibodies specific against S. aureus infection. Such a kit may include an isolated S. aureus antigen comprising an epitope which is specifically immunoreactive with at least one anti-S. aureus antibody. Such a kit also includes means for detecting the binding of said antibody to the antigen. In specific embodiments, the kit may include a recombinantly produced or chemically synthesized peptide or polypeptide antigen. The peptide or polypeptide antigen may be attached to a solid support.

In a more specific embodiment, the detecting means of the above-described kit includes a solid support to which said peptide or polypeptide antigen is attached. Such a kit may also include a non-attached reporter-labeled anti-human antibody. In this embodiment, binding of the antibody to the S. aureus antigen can be detected by binding of the reporter labeled antibody to the anti-S. aureus polypeptide antibody.

In a related aspect, the invention includes a method of detecting S. aureus infection in a subject. This detection method includes reacting a body fluid, preferably serum, from the subject with an isolated S. aureus antigen, and examining the antigen for the presence of bound antibody. In a specific embodiment, the method includes a polypeptide antigen attached to a solid support, and serum is reacted with the support. Subsequently, the support is reacted with a reporter-labeled anti-human antibody. The support is then examined for the presence of reporter-labeled antibody.

The solid surface reagent employed in the above assays and kits is prepared by known techniques for attaching protein material to solid support material, such as polymeric beads, dip sticks, 96-well plates or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group.

Alternatively, streptavidin coated plates can be used in conjunction with biotinylated antigen(s).

The polypeptides and antibodies of the present invention, including fragments thereof, may be used to detect Staphylococcus species including S. aureus using bio chip and biosensor technology. Bio chip and biosensors of the present invention may comprise the polypeptides of the present invention to detect antibodies, which specifically recognize Staphylococcus species, including S. aureus. Bio chip and biosensors of the present invention may also comprise antibodies which specifically recognize the polypeptides of the present invention to detect Staphylococcus species, including S. aureus or specific polypeptides of the present invention. Bio chips or biosensors comprising polypeptides or antibodies of the present invention may be used to detect Staphylococcus species, including S. aureus, in biological and environmental samples and to diagnose an animal, including humans, with an S. aureus or other Staphylococcus infection. Thus, the present invention includes both bio chips and biosensors comprising polypeptides or antibodies of the present invention and methods of their use.

The bio chips of the present invention may further comprise polypeptide sequences of other pathogens including bacteria, viral, parasitic, and fungal polypeptide sequences, in addition to the polypeptide sequences of the present invention, for use in rapid diffenertial pathogenic detection and diagnosis. The bio chips of the present invention may further comprise antibodies or fragements thereof specific for other pathogens including bacteria, viral, parasitic, and fungal polypeptide sequences, in addition to the antibodies or fragements thereof of the present invention, for use in rapid diffenertial pathogenic detection and diagnosis. The bio chips and biosensors of the present invention may also be used to monitor an S. aureus or other Staphylococcus infection and to monitor the genetic changes (amio acid deletions, insertions, substitutions, etc.) in response to drug therapy in the clinic and drug development in the laboratory. The bio chip and biosensors comprising polypeptides or antibodies of the present invention may also be used to simultaneously monitor the expression of a multiplicity of polypeptides, including those of the present invention. The polypeptides used to comprise a bio chip or biosensor of the present invention may be specified in the same manner as for the fragments, i.e, by their N-terminal and C-terminal positions or length in contiguous amino acid residue. Methods and particular uses of the polypeptides and antibodies of the present invention to detect Staphylococcus species, including S. aureus, or specific polypeptides using bio chip and biosensor technology include those known in the art, those of the U.S. Patent Nos. and World Patent Nos. listed above for bio chips and biosensors using polynucleotides of the present invention, and those of: U.S. Pat. Nos. 5,658,732, 5,135,852, 5,567,301, 5,677,196, 5,690,894 and World Patent Nos. WO9729366, WO9612957, each incorporated herein in their entireties.

Treatment
Agonists and Antagonists—Assays and Molecules

The invention also provides a method of screening compounds to identify those which enhance or block the biological activity of the S. aureus polypeptides of the present invention. The present invention further provides where the compounds kill or slow the growth of S. aureus. The ability of S. aureus antagonists, including S. aureus ligands, to prophylactically or therapeutically block antibiotic resistance may be easily tested by the skilled artisan. See, e.g., Straden et al. (1997) J Bacteriol. 179(1):9–16.

An agonist is a compound which increases the natural biological function or which functions in a manner similar to the polypeptides of the present invention, while antagonists decrease or eliminate such functions. Potential antagonists include small organic molecules, peptides, polypeptides, and antibodies that bind to a polypeptide of the invention and thereby inhibit or extinguish its activity.

The antagonists may be employed for instance to inhibit peptidoglycan cross bridge formation. Antibodies against S. aureus may be employed to bind to and inhibit S. aureus activity to treat antibiotic resistance. Any of the above antagonists may be employed in a composition with a pharmaceutically acceptable carrier.

Vaccines

The present invention also provides vaccines comprising one or more polypeptides of the present invention. Heterogeneity in the composition of a vaccine may be provided by combining S. aureus polypeptides of the present invention. Multi-component vaccines of this type are desirable because they are likely to be more effective in eliciting protective immune responses against multiple species and strains of the Staphylococcus genus than single polypeptide vaccines.

Multi-component vaccines are known in the art to elicit antibody production to numerous immunogenic components. See, e.g., Decker et al. (1996) J. Infect. Dis. 174:S270–275. In addition, a hepatitis B, diphtheria, tetanus, pertussis tetravalent vaccine has recently been demonstrated to elicit protective levels of antibodies in human infants against all four pathogenic agents. See, e.g., Aristegui, J. et al. (1997) Vaccine 15:7–9.

The present invention in addition to single-component vaccines includes multi-component vaccines. These vaccines comprise more than one polypeptide, immunogen or antigen. Thus, a multi-component vaccine would be a vaccine comprising more than one of the S. aureus polypeptides of the present invention.

Further within the scope of the invention are whole cell and whole viral vaccines. Such vaccines may be produced recombinantly and involve the expression of one or more of the S. aureus polypeptides described in Table 1. For example, the S. aureus polypeptides of the present invention may be either secreted or localized intracellular, on the cell surface, or in the periplasmic space. Further, when a recombinant virus is used, the S. aureus polypeptides of the present invention may, for example, be localized in the viral envelope, on the surface of the capsid, or internally within the capsid. Whole cells vaccines which employ cells expressing heterologous proteins are known in the art. See, e.g., Robinson, K. et al. (1997) Nature Biotech. 15:653–657; Sirard, J. et al. (1997) Infect. Immun. 65:2029–2033; Chabalgoity, J. et al. (1997) Infect. Immun. 65:2402–2412 These cells may be administered live or may be killed prior to administration. Chabalgoity, J. et al., supra, for example, report the successful use in mice of a live attenuated Salmonella vaccine strain which expresses a portion of a platyhelminth fatty acid-binding protein as a fusion protein on its cells surface.

A multi-component vaccine can also be prepared using techniques known in the art by combining one or more S. aureus polypeptides of the present invention, or fragments thereof, with additional non-staphylococcal components (e.g., diphtheria toxin or tetanus toxin, and/or other compounds known to elicit an immune response). Such vaccines are useful for eliciting protective immune responses to both members of the Staphylococcus genus and non-staphylococcal pathogenic agents.

The vaccines of the present invention also include DNA vaccines. DNA vaccines are currently being developed for a number of infectious diseases. See, et al., Boyer, et al. (1997)

Nat. Med. 3:526–532; reviewed in Spier, R. (1996) Vaccine 14:1285–1288. Such DNA vaccines contain a nucleotide sequence encoding one or more *S. aureus* polypeptides of the present invention oriented in a manner that allows for expression of the subject polypeptide. For example, the direct administration of plasmid DNA encoding *B. burgdorgeri* OspA has been shown to elicit protective immunity in mice against borrelial challenge. See, Luke et al. (1997) J. Infect. Dis. 175:91–97.

The present invention also relates to the administration of a vaccine which is co-administered with a molecule capable of modulating immune responses. Kim et al. (1997) Nature Biotech. 15:641–646, for example, report the enhancement of immune responses produced by DNA immunizations when DNA sequences encoding molecules which stimulate the immune response are co-administered. In a similar fashion, the vaccines of the present invention may be co-administered with either nucleic acids encoding immune modulators or the immune modulators themselves. These immune modulators include granulocyte macrophage colony stimulating factor (GM-CSF) and CD86.

The vaccines of the present invention may be used to confer resistance to staphylococcal infection by either passive or active immunization. When the vaccines of the present invention are used to confer resistance to staphylococcal infection through active immunization, a vaccine of the present invention is administered to an animal to elicit a protective immune response which either prevents or attenuates a staphylococcal infection. When the vaccines of the present invention are used to confer resistance to staphylococcal infection through passive immunization, the vaccine is provided to a host animal (e.g., human, dog, or mouse), and the antisera elicited by this antisera is recovered and directly provided to a recipient suspected of having an infection caused by a member of the Staphylococcus genus.

The ability to label antibodies, or fragments of antibodies, with toxin molecules provides an additional method for treating staphylococcal infections when passive immunization is conducted. In this embodiment, antibodies, or fragments of antibodies, capable of recognizing the *S. aureus* polypeptides disclosed herein, or fragments thereof, as well as other Staphylococcus proteins, are labeled with toxin molecules prior to their administration to the patient. When such toxin derivatized antibodies bind to Staphylococcus cells, toxin moieties will be localized to these cells and will cause their death.

The present invention thus concerns and provides a means for preventing or attenuating a staphylococcal infection resulting from organisms which have antigens that are recognized and bound by antisera produced in response to the polypeptides of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the compound(s) are provided in advance of any symptoms of staphylococcal infection. The prophylactic administration of the compound (s) serves to prevent or attenuate any subsequent infection. When provided therapeutically, the compound(s) is provided upon or after the detection of symptoms which indicate that an animal may be infected with a member of the Staphylococcus genus. The therapeutic administration of the compound(s) serves to attenuate any actual infection. Thus, the *S. aureus* polypeptides, and fragments thereof, of the present invention may be provided either prior to the onset of infection (so as to prevent or attenuate an anticipated infection) or after the initiation of an actual infection.

The polypeptides of the invention, whether encoding a portion of a native protein or a functional derivative thereof, may be administered in pure form or may be coupled to a macromolecular carrier. Example of such carriers are proteins and carbohydrates. Suitable proteins which may act as macromolecular carrier for enhancing the immunogenicity of the polypeptides of the present invention include keyhole limpet hemacyanin (KLH) tetanus toxoid, pertussis toxin, bovine serum albumin, and ovalbumin. Methods for coupling the polypeptides of the present invention to such macromolecular carriers are disclosed in Harlow et al., ANTIBODIES: A LABORATORY MANUAL, (Cold Spring Harbor Laboratory Press, 2nd ed. 1988).

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

While in all instances the vaccine of the present invention is administered as a pharmacologically acceptable compound, one skilled in the art would recognize that the composition of a pharmacologically acceptable compound varies with the animal to which it is administered. For example, a vaccine intended for human use will generally not be co-administered with Freund's adjuvant. Further, the level of purity of the *S. aureus* polypeptides of the present invention will normally be higher when administered to a human than when administered to a non-human animal.

As would be understood by one of ordinary skill in the art, when the vaccine of the present invention is provided to an animal, it may be in a composition which may contain salts, buffers, adjuvants, or other substances which are desirable for improving the efficacy of the composition. Adjuvants are substances that can be used to specifically augment a specific immune response. These substances generally perform two functions: (1) they protect the antigen(s) from being rapidly catabolized after administration and (2) they nonspecifically stimulate immune responses.

Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus Brucella. Other substances useful as adjuvants are the saponins such as, for example, Quil A. (Superfos A/S, Denmark). Preferred adjuvants for use in the present invention include aluminum salts, such as $AlK(SO_4)_2$, $AlNa(SO_4)_2$, and $AlNH_4(SO_4)$. Examples of materials suitable for use in vaccine compositions are provided in REMINGTON'S PHARMACEUTICAL SCIENCES-1324–1341 (A. Osol, ed, Mack Publishing Co, Easton, Pa., (1980) (incorporated herein by reference).

The therapeutic compositions of the present invention can be administered parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Therapeutic compositions of the present invention can also be administered in encapsulated form. For example, intranasal immunization using vaccines encapsulated in biodegradable microsphere composed of poly(DL-lactide-coglycolide). See, Shahin, R. et al. (1995) Infect. Immun. 63:1195–1200. Similarly, orally administered encapsulated Salmonella typhimurium antigens can also be used. Allaoui-Attarki, K. et al. (1997) Infect. Immun. 65:853–857. Encapsulated vaccines of the present invention can be administered by a variety of routes including those involving contacting the vaccine with mucous membranes (e.g., intranasally, intracolonicly, intraduodenally).

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage needed to provide an effective amount of the composition will vary depending upon such factors as the animal's or human's age, condition, sex, and extent of disease, if any, and other variables which can be adjusted by one of ordinary skill in the art.

The antigenic preparations of the invention can be administered by either single or multiple dosages of an effective amount. Effective amounts of the compositions of the invention can vary from 0.01–1,000 µg/ml per dose, more preferably 0.1–500 µg/ml per dose, and most preferably 10–300 µg/ml per dose.

EXAMPLES

Example 1

Isolation of a Selected DNA Clone from the Deposited Sample

Three approaches can be used to isolate a S. aureus clone comprising a polynucleotide of the present invention from any S. aureus genomic DNA library. The S. aureus strain ISP3 has been deposited as a convienent source for obtaining a S. aureus strain although a wide varity of strains S. aureus strains can be used which are known in the art.

S. aureus genomic DNA is prepared using the following method. A 20 ml overnight bacterial culture grown in a rich medium (e.g., Trypticase Soy Broth, Brain Heart Infusion broth or Super broth), pelleted, washed two times with TES (30 mM Tris-pH 8.0, 25 mM EDTA, 50 mM NaCl), and resuspended in 5 ml high salt TES (2.5M NaCl). Lysostaphin is added to final concentration of approx 50 ug/ml and the mixture is rotated slowly 1 hour at 37 C. to make protoplast cells. The solution is then placed in incubator (or place in a shaking water bath) and warmed to 55 C. Five hundred micro liter of 20% sarcosyl in TES (final concentration 2%) is then added to lyse the cells. Next, guanidine HCl is added to a final concentration of 7M (3.69 g in 5.5 ml). The mixture is swirled slowly at 55 C. for 60–90 min (solution should clear). A CsCl gradient is then set up in SW41 ultra clear tubes using 2.0 ml 5.7M CsCl and overlaying with 2.85M CsCl. The gradient is carefully overlayed with the DNA-containing GuHCl solution. The gradient is spun at 30,000 rpm, 20 C. for 24 hr and the lower DNA band is collected. The volume is increased to 5 ml with TE buffer. The DNA is then treated with protease K (10 ug/ml) overnight at 37 C., and precipitated with ethanol. The precipitated DNA is resuspended in a desired buffer.

In the first method, a plasmid is directly isolated by screening a plasmid S. aureus genomic DNA library using a polynucleotide probe corresponding to a polynucleotide of the present invention. Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (See, e.g., Maniatis et al., Molecular Cloning: A Laboratory Manual, Cold Spring Harbor Press, Cold Spring, N.Y. (1982).) The library is transformed into a suitable host, as indicated above (such as XL-1 Blue (Stratagene)) using techniques known to those of skill in the art. See, e.g., Sambrook et al. MOLECULAR CLONING: A LABORATORY MANUAL (Cold Spring Harbor, N.Y. 2nd ed. 1989); Ausubel et al., CURRENT PROTOCOLS IN MOLECULAR BIOLOGY (John Wiley and Sons, N.Y. 1989). The transformants are plated on 1.5% agar plates (containing the appropriate selection agent, e.g., ampicillin) to a density of about 150 transformants (colonies) per plate. These plates are screened using Nylon membranes according to routine methods for bacterial colony screening. See, e.g., Sambrook et al. MOLECULAR CLONING: A LABORATORY MANUAL (Cold Spring Harbor, N.Y. 2nd ed. 1989); Ausubel et al., CURRENT PROTOCALS IN MOLECULAR BIOLOGY (John Wiley and Sons, N.Y. 1989) or other techniques known to those of skill in the alt.

Alternatively, two primers of 15–25 nucleotides derived from the 5' and 3' ends of a polynucleotide of Table 1 are synthesized and used to amplify the desired DNA by PCR using a S. aureus genomic DNA prep (e.g., the deposited S. aureus ISP3) as a template. PCR is carried out under routine conditions, for instance, in 25 µl of reaction mixture with 0.5 ug of the above DNA template. A convenient reaction mixture is 1.5–5 mM MgCl$_2$, 0.01% (w/v) gelatin, 20 µM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Finally, overlapping oligos of the DNA sequences of Table 1 can be synthesized and used to generate a nucleotide sequence of desired length using PCR methods known in the art.

Example 2(a)

Expression and Purification Staphylococcal Polypeptides in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin (QIAGEN, Inc., supra) and suitable single restriction enzyme cleavage sites. These elements are arranged such that an inserted DNA fragment encoding a polypeptide expresses that polypeptide with the six His residues (i.e., a "6xHis tag") covalently linked to the carboxyl terminus of that polypeptide.

The NA sequence encoding the desired portion of a *S. aureus* protein of the present invention is amplified from *S. aureus* genomic DNA or from the deposited DNA clone using PCR oligonucleotide primers which anneal to the 5' and 3' sequences coding for the portion of the *S. aureus* polynucleotide. Additional nucleotides containing restriction sites to facilitate cloning in the pQE60 vector are added to the 5' and 3' sequences, respectively.

For cloning the mature protein, the 5' primer has a sequence containing an appropriate restriction site followed by nucleotides of the amino terminal coding sequence of the desired *S. aureus* polynucleotide sequence in Table 1. One of ordinary skill in the art would appreciate that the point in the protein coding sequence where the 5' and 3' primers begin may be varied to amplify a DNA segment encoding any desired portion of the complete protein shorter or longer than the mature form. The 3' primer has a sequence containing an appropriate restriction site followed by nucleotides complementary to the 3' end of the desired coding sequence of Table 1, excluding a stop codon, with the coding sequence aligned with the restriction site so as to maintain its reading frame with that of the six His codons in the pQE60 vector.

The amplified *S. aureus* DNA fragment and the vector pQE60 are digested with restriction enzymes which recognize the sites in the primers and the digested DNAs are then ligated together. The *S. aureus* DNA is inserted into the restricted pQE60 vector in a manner which places the *S. aureus* protein coding region downstream from the IPTG-inducible promoter and in-frame with an initiating AUG and the six histidine codons.

The ligation mixture is transformed into competent *E. coli* cells using standard procedures such as those described by Sambrook et al., supra. *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing a *S. aureus* polypeptide, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the *S. aureus* polypeptide is loaded onto a nickel-nitrilo-tri-acetic acid ("Ni-NTA") affinity resin column (QIAGEN, Inc., supra). Proteins with a 6xHis tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the *S. aureus* polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

Alternatively, the polypeptides of the present invention can be produced by a non-denaturing method. In this method, after the cells are harvested by centrifugation, the cell pellet from each liter of culture is resuspended in 25 ml of Lysis Buffer A at 4° C. (Lysis Buffer A=50 mM Na-phosphate, 300 mM NaCl, 10 mM 2-mercaptoethanol, 10% Glycerol, pH 7.5 with 1 tablet of Complete EDTA-free protease inhibitor cocktail (Boehringer Mannheim #1873580) per 50 ml of buffer). Absorbance at 550 nm is approximately 10–20 O.D./ml. The suspension is then put through three freeze/thaw cycles from −70° C. (using a ethanol-dry ice bath) up to room temperature. The cells are lysed via sonication in short 10 sec bursts over 3 minutes at approximately 80W while kept on ice. The sonicated sample is then centrifuged at 15,000 RPM for 30 minutes at 4° C. The supernatant is passed through a column containing 1.0 ml of CL-4B resin to pre-clear the sample of any proteins that may bind to agarose non-specifically, and the flow-through fraction is collected.

The pre-cleared flow-through is applied to a nickel-nitrilo-tri-acetic acid ("Ni-NTA") affinity resin column (Quiagen, Inc., supra). Proteins with a 6xHis tag bind to the Ni-NTA resin with high affinity and can be purified in a simple one-step procedure. Briefly, the supernatant is loaded onto the column in Lysis Buffer A at 4° C., the column is first washed with 10 volumes of Lysis Buffer A until the A280 of the eluate returns to the baseline. Then, the column is washed with 5 volumes of 40 mM Imidazole (92% Lysis Buffer A/8% Buffer B) (Buffer B=50 mM Na-Phosphate, 300 mM NaCl, 10% Glycerol, 10 mM 2-mercaptoethanol, 500 mM Imidazole, pH of the final buffer should be 7.5).

The protein is eluted off of the column with a series of increasing Imidazole solutions made by adjusting the ratios of Lysis Buffer A to Buffer B. Three different concentrations are used: 3 volumes of 75 mM Imidazole, 3 volumes of 150 mM Imidazole, 5 volumes of 500 mM Imidazole. The fractions containing the purified protein are analyzed using 8%, 10% or 14% SDS-PAGE depending on the protein size. The purified protein is then dialyzed 2×against phosphate-buffered saline (PBS) in order to place it into an easily workable buffer. The purified protein is stored at 4° C. or frozen at −80°

The following is another alternative method may be used to purify S. aureus expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the S. aureus polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded S. aureus polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the S. aureus polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 n1M sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the S. aureus polypeptide (determined, for instance, by 16% SDS-PAGE) are then pooled.

The resultant S. aureus polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2(b)

Expression and Purification Staphylococcal Polypeptides in E coli

Alternatively, the vector pQE10 can be used to clone and express polypeptides of the present invention. The difference being such that an inserted DNA fragment encoding a polypeptide expresses that polypeptide with the six His residues (i.e., a "6× His tag") covalently linked to the amino terminus of that polypeptide. The bacterial expression vector pQE10 (QIAGEN, Inc., 9259 Eton Avenue, Chatsworth, Calif., 91311) is used in this example. The components of the pQE10 plasmid are arranged such that the inserted DNA sequence encoding a polypeptide of the present invention expresses the polypeptide with the six His residues (i.e., a "6× His tag")) covalently linked to the amino terminus.

The DNA sequences encoding the desired portions of a polypeptide of Table 1 are amplified using PCR oligonucleotide primers from either genomic S. aureus DNA or DNA from the plasmid clones listed in Table 1 clones of the present invention. The PCR primers anneal to the nucleotide sequences encoding the desired amino acid sequence of a polypeptide of the present invention. Additional nucleotides containing restriction sites to facilitate cloning in the pQE10 vector are added to the 5' and 3' primer sequences, respectively.

For cloning a polypeptide of the present invention, the 5' and 3' primers are selected to amplify their respective nucleotide coding sequences. One of ordinary skill in the art would appreciate that the point in the protein coding sequence where the 5' and 3' primers begins may be varied to amplify a DNA segment encoding any desired portion of a polypeptide of the present invention. The 5' primer is designed so the coding sequence of the 6× His tag is aligned with the restriction site so as to maintain its reading frame with that of S. aureus polypeptide. The 3' is designed to include an stop codon. The amplified DNA fragment is then cloned, and the protein expressed, as described above for the pQE60 plasmid.

The DNA sequences encoding the amino acid sequences of Table 1 may also be cloned and expressed as fusion proteins by a protocol similar to that described directly above, wherein the pET-32b(+) vector (Novagen, 601 Science Drive, Madison, Wis. 53711) is preferentially used in place of pQE10.

Example 2(c)

Expression and Purification of Staphylococcus Polypeptides in E. coli

The bacterial expression vector pQE60 is used for bacterial expression in this example (QIAGEN, Inc., 9259 Eton Avenue, Chatsworth, Calif., 91311). However, in this example, the polypeptide coding sequence is inserted such that translation of the six His codons is prevented and, therefore, the polypeptide is produced with no 6×His tag.

The DNA sequence encoding the desired portion of the *S. aureus* amino acid sequence is amplified from a *S. aureus* genomic DNA prep using PCR oligonucleotide primers which anneal to the 5' and 3' nucleotide sequences corresponding to the desired portion of the *S. aureus* polypeptides. Additional nucleotides containing restriction sites to facilitate cloning in the pQE60 vector are added to the 5' and 3' primer sequences.

For cloning a *S. aureus* polypeptides of the present invention, 5' and 3' primers are selected to amplify their respective nucleotide coding sequences. One of ordinary skill in the art would appreciate that the point in the protein coding sequence where the 5' and 3' primers begin may be varied to amplify a DNA segment encoding any desired portion of a polypeptide of the present invention. The 3' and 5' primers contain appropriate restriction sites followed by nucleotides complementary to the 5' and 3' ends of the coding sequence respectively. The 3' primer is additionally designed to include an in-frame stop codon.

The amplified *S. aureus* DNA fragments and the vector pQE60 are digested with restriction enzymes recognizing the sites in the primers and the digested DNAs are then ligated together. Insertion of the *S. aureus* DNA into the restricted pQE60 vector places the *S. aureus* protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described by Sambrook et al. *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing *S. aureus* polypeptide, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

To purify the *S. aureus* polypeptide, the cells are then stirred for 3–4 hours at 4° C. in 6M guanidine-HCl, pH 8. The cell debris is removed by centrifugation, and the supernatant containing the *S. aureus* polypeptide is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure *S. aureus* polypeptide. The purified protein is stored at 4° C. or frozen at −80° C.

The following alternative method may be used to purify *S. aureus* polypeptides expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 nM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the *S. aureus* polypeptide-containing supernatant is incubated at 4° C. overnight to allow further GLuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded *S. aureus* polypeptide solution, a previously prepared tangential filtration unit equipped with 0.16 µm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the *S. aureus* polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the *S. aureus* polypeptide (determined, for instance, by 16% SDS-PAGE) are then pooled.

The resultant *S. aureus* polypeptide exhibits greater than 95% purity after the above refolding and purification steps. No major contaminant bands are observed from Commassie blue stained 16% SDS-PAGE gel when 5 µg of purified protein is loaded. The purified protein is also tested for endotoxin/LPS contamination, and typically the LPS content is less than 0.1 ng/ml according to LAL assays.

Example 2(d)

Cloning and Expression of S. aureus in Other Bacteria

S. aureus polypeptides also can be produced in: S. aureus using the methods of S. Skinner et al., (1988) Mol. Microbiol. 2:289–297 or J. I. Moreno (1996) Protein Expr. Purif. 8(3):332–340; Lactobacillus using the methods of C. Rush et al., 1997 Appl. Microbiol. Biotechnol. 47(5):537–542, or in Bacillus subtilis using the methods Chang et al., U.S. Pat. No. 4,952,508.

Example 3

Cloning and Expression in COS Cells

A S. aureus expression plasmid is made by cloning a portion of the DNA encoding a S. aureus polypeptide into the expression vector pDNAI/Amp or pDNAIII (which can be obtained from Invitrogen, Inc.). The expression vector pDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a DNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al. 1984 Cell 37:767. The fusion of the HA tag to the target protein allows easy detection and recovery of the recombinant protein with an antibody that recognizes the HA epitope. pDNAIII contains, in addition, the selectable neomycin marker.

A DNA fragment encoding a S. aureus polypeptide is cloned into the polylinker region of the vector so that recombinant protein expression is directed by the CMV promoter. The plasmid construction strategy is as follows. The DNA from a S. aureus genomic DNA prep is amplified using primers that contain convenient restriction sites, much as described above for construction of vectors for expression of S. aureus in E. coli. The 5' primer contains a Kozak sequence, an AUG start codon, and nucleotides of the 5' coding region of the S. aureus polypeptide. The 3' primer, contains nucleotides complementary to the 3' coding sequence of the S. aureus DNA, a stop codon, and a convenient restriction site.

The PCR amplified DNA fragment and the vector, pDNAI/Amp, are digested with appropriate restriction enzymes and then ligated. The ligation mixture is transformed into an appropriate E. coli strain such as SURE™ (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the S. aureus polypeptide For expression of a recombinant S. aureus polypeptide, COS cells are transfected with an expression vector, as described above, using DEAE-dextran, as described, for instance, by Sambrook et al. (supra). Cells are incubated under conditions for expression of S. aureus by the vector.

Expression of the S. aureus-HA fusion protein is detected by radiolabeling and immunoprecipitation, using methods described in, for example Harlow et al., supra. To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 4

Cloning and Expression in CHO Cells

The vector pC4 is used for the expression of S. aureus polypeptide in this example. Plasmid pC4 is a derivative of the plasmid pSV2-dhfr (ATCC Accession No. 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented. See, e.g., Alt et al., 1978, J. Biol. Chem. 253:1357–1370; Hamlin et al., 1990, Biochem. et Biophys. Acta, 1097:107–143; Page et al., 1991, Biotechnology 9:64–68. Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains the strong promoter of the long terminal repeat (LTR) of the Rouse Sarcoma Virus, for expressing a polypeptide of interest, Cullen, et al. (1985) Mol. Cell. Biol. 5:438–447; plus a fragment isolated from the enhancer of the immediate early gene of human cytomegalovirus (CMV), Boshart, et al., 1985, Cell 41:521–530. Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the S. aureus polypeptide in a regulated way in mammalian cells (Gossen et al., 1992, Proc. Natl. Acad. Sci. USA 89:5547–5551. For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes and then dephosphorylated using calf intestinal phosphates by procedures known in the art. The vector is then isolated from a 1% agarose gel. The DNA sequence encoding the S. aureus polypeptide is amplified using PCR oligonucleotide primers corresponding to the 5' and 3' sequences of the desired portion of the gene. A 5' primer containing a restriction site, a Kozak sequence, an AUG start codon, and nucleotides of the 5' coding region of the S. aureus polypeptide is synthesized and used. A 3' primer, containing a restriction site, stop codon, and nucleotides complementary to the 3' coding sequence of the S. aureus polypeptides is synthesized and used. The amplified fragment is digested with the restriction endonucleases and then purified again on a 1% agarose gel. The isolated fragment and the dephosphorylated vector are then ligated with T4 DNA ligase. E. coli HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five µg of the expression plasmid pC4 is cotransfected with 0.5 µg of the plasmid pSVneo using a lipid-mediated transfection agent such as Lipofectin™ or LipofectAMINE.™ (LifeTechnologies Gaithersburg, Md.). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

Example 5

Quantitative Murine Soft Tissue Infection Model for S. aureus

Compositions of the present invention, including polypeptides and peptides, are assayed for their ability to function as vaccines or to enhance/stimulate an immune response to a bacterial species (e.g., S. aureus) using the following quantitative murine soft tissue infection model. Mice (e.g., NIH Swiss female mice, approximately 7 weeks old) are first treated with a biologically protective effective amount, or immune enhancing/stimulating effective amount of a composition of the present invention using methods known in the art, such as those discussed above. See, e.g., Harlow et al., ANTIBODIES: A LABORATORY MANUAL, (Cold Spring Harbor Laboratory Press, 2nd ed. 1988). An example of an appropriate starting dose is 20 ug per animal.

The desired bacterial species used to challenge the mice, such as S. aureus, is grown as an overnight culture. The culture is diluted to a concentration of $5 \times 10^8$ cfu/ml, in an appropriate media, mixed well, serially diluted, and titered. The desired doses are further diluted 1:2 with sterilized Cytodex 3 microcarrier beads preswollen in sterile PBS (3 g/100 ml). Mice are anesthetize briefly until docile, but still mobile and injected with 0.2 ml of the Cytodex 3 bead/bacterial mixture into each animal subcutaneously in the inguinal region. After four days, counting the day of injection as day one, mice are sacrificed and the contents of the abscess is excised and placed in a 15 ml conical tube containing 1.0 ml of sterile PBS. The contents of the abscess is then enzymatically treated and plated as follows.

The abscess is first disrupted by vortexing with sterilized glass beads placed in the tubes. 3.0 mls of prepared enzyme mixture (1.0 ml Collagenase D (4.0 mg/ml), 1.0 ml Trypsin (6.0 mg/ml) and 8.0 ml PBS) is then added to each tube followed by a 20 min. incubation at 37 C. The solution is then centrifuged and the supernatant drawn off. 0.5 ml dH20 is then added and the tubes are vortexed and then incubated for 10 min. at room temperature. 0.5 ml media is then added and samples are serially diluted and plated onto agar plates, and grown overnight at 37 C. Plates with distinct and separate colonies are then counted, compared to positive and negative control samples, and quantified. The method can be used to identify composition and determine appropriate and effective doses for humans and other animals by comparing the effective doses of compositions of the present invention with compositions known in the art to be effective in both mice and humans. Doses for the effective treatment of humans and other animals, using compositions of the present invention, are extrapolated using the data from the above experiments of mice. It is appreciated that further studies in humans and other animals may be needed to determine the most effective doses using methods of clinical practice known in the art.

Example 6

Murine Systemic Neutropenic Model for S. aureus Infection

Compositions of the present invention, including polypeptides and peptides, are assayed for their ability to function as vaccines or to enhance/stimulate an immune response to a bacterial species (e.g., S. aureus) using the following qualitative murine systemic neutropenic model. In addition, antibodies of the present invention are employed to provide passive immune or immunophylatic therapy prior to or post S. aureus infection. Mice (e.g., NIH Swiss female mice, approximately 7 weeks old) are first treated with a biologically protective effective amount, or immune enhancing/stimulating effective amount of a composition of the present invention using methods known in the art, such as those discussed above. See, e.g., Harlow et al., ANTIBODIES: A LABORATORY MANUAL, (Cold Spring Harbor Laboratory Press, 2nd ed. 1988). An example of an appropriate starting dose is 20 ug of protein per animal. Mice are then injected with 250–300 mg/kg cyclophosphamide intraperitonially. Counting the day of C.P. injection as day one, the mice are left untreated for 5 days to begin recovery of PMINL'S.

The desired bacterial species used to challenge the mice, such as S. aureus, is grown as an overnight culture. The culture is diluted to a concentration of $5 \times 10^8$ cfu/ml, in an appropriate media, mixed well, serially diluted, and titered. The desired doses are further diluted 1:2 in 4% Brewer's yeast in media.

Mice are injected with the bacteria/brewer's yeast challenge intraperitonially. The Brewer's yeast solution alone is used as a control. The mice are then monitored twice daily for the first week following challenge, and once a day for the next week to ascertain morbidity and mortality. Mice remaining at the end of the experiment are sacrificed. The method can be used to identify compositions and determine appropriate and effective doses for humans and other animals by comparing the effective doses of compositions of the present invention with compositions known in the art to be effective in both mice and humans. Doses for the effective treatment of humans and other animals, using compositions of the present invention, are extrapolated using the data from the above experiments of mice. It is appreciated that further studies in humans and other animals may be needed to determine the most effective doses using methods of clinical practice known in the art.

Example 7

Murine Lethal Sepsis Model

S. aureus polypeptides of the present invention can be evaluated for potential vaccine efficacy using the murine lethal sepsis model. In this model, mice are challenged with low lethal doses (for example, between $10^6$ and $10^7$ colony forming units [cfu]) of virulent strains of S. aureus. Initial studies are conducted to determine a less virulent yet lethal strain of S. aureus to determine its $LD_{50}$. Polypeptides of the present invention (e.g., the polypeptides described in Table 1, fragments thereof and fragments that comprise the epitopes shown in Table 4), produced as Examples 2a–d, 3 and 4, and optionally conjugated with another immunogen, are tested as vaccine candidates. Vaccine candidates are selected as protective antigens if they can protect against death when approximately 100 times the $LD_{50}$ of the strain is employed. Immunized mice are then challenged with a lethal dose of S. aureus.

More specifically, female C2H/HeJ mices are immunized subcutaneously in groups of 10 with 15 ug of the protein of the present invention formulated in complete Freund's adjuvant (CFA). Twenty one days later, mice are boosted in the same way with protein formulated in incomplete Freund's adjuvant. Twenty-eight days following the boost, animals are bled and immune titers against S. aureus proteins are determined by ELISA. 35 days following the boost, a freshly prepared culture of S. aureus in BHI (Brain Heart Infusion) both is diluted to approximately 35 to $100\times LD_{50}$ in sterile PBS. A lethal dose is then injected intraperitoneally into mice in a volume of 100 ul. Mice are monitored for 14 days for mortality. Survival rate is compared with a sham group immunized with PBS and adjuvant alone.

Example 8

Identifying Vaccine Antigens Prevalent in S. aureus Strains

It is further determined whether the majority of the most prevalent S. aureus strains express the vaccine antigen(s) and polypeptide(s) identified by the lethal model of Example 7 or the models of Examples 5 or 6. Immunoblot analysis is performed with cell lysates prepared from Staphylococcus strains representative of the major capsular serotypes and probed with polyclonal antisera specific for the protective antigens. A preferred vaccine is comprised of a serological epitope of the polypeptide of the present invention that is well conserved among the majority of infective Staphyloccus serotypes.

Example 9

Production of an Antibody a) Hybridoma Technology

The antibodies of the present invention can be prepared by a variety of methods. (See, Current Protocols, Chapter 2.) As one example of such methods, cells expressing polypeptide(s) of the invention are administered to an animal to induce the production of sera containing polyclonal antibodies. In a preferred method, a preparation of polypeptide(s) of the invention is prepared and purified to render it substantially free of natural contaminants. Such a preparation is then introduced into an animal in order to produce polyclonal antisera of greater specific activity.

Monoclonal antibodies specific for polypeptide(s) of the invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with polypeptide(s) of the invention or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the polypeptide(s) of the invention.

Alternatively, additional antibodies capable of binding to polypeptide(s) of the invention can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by polypeptide(s) of the invention. Such antibodies comprise anti-idiotypic antibodies to the protein-specific antibody and are used to immunize an animal to induce formation of further protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed Against Polypeptide(s) from a Library of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library

A library of scFvs is constructed from the RNA of human PBLs as described in PCT publication WO 92/01047. To rescue phage displaying antibody fragments, approximately 10⁹ E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×10⁸ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 10¹³ transducing units/ml (ampicillin-resistant clones).

Panning of the Library

Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 10¹³ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

The disclosure of all publications (including patents, patent applications, journal articles, laboratory manuals, books, or other documents) cited herein and the sequence listings are hereby incorporated by reference in their entireties.

The present invention is not to be limited in scope by the specific embodiments described herein, which are intended as single illustrations of individual aspects of the invention. Functionally equivalent methods and components are within the scope of the invention, in addition to those shown and described herein and will become apparent to those skilled in the art from the foregoing description and accompanying drawings Such modifications are intended to fall within the scope of the appended claims.

What is claimed is:

1. An isolated polynucleotide encoding an amino acid sequence at least 95% identical to the full length amino acid sequence of SEQ ID NO:38.

2. The isolated polynucleotide of claim 1 which is fused to a heterologous polynucleotide sequence.

3. The isolated polynucleotide of claim 2, wherein said heterologous polynucleotide sequence encodes a heterologous polypeptide.

4. The isolated polynucleotide which is fully complimentary to the polynucleotide of claim 1.

5. A method for making a recombinant vector comprising inserting the isolated polynucleotide of claim 1 into a vector.

6. A recombinant vector comprising the isolated polynucleotide of claim 1.

7. The recombinant vector of claim 6, wherein said isolated polynucleotide is operably associated with a heterologous regulatory sequence that controls gene expression.

8. An isolated recombinant host cell comprising the isolated polynucleotide of claim 1.

9. The isolated recombinant host cell of claim 8, wherein said polynucleotide is operably associated with a heterologous regulatory sequence that controls gene expression.

10. A method for producing a polypeptide, comprising culturing the host cell of claim 8 under conditions suitable to produce the polypeptide encoded by said polynucleotide.

11. An isolated polynucleotide which encodes at least 30 contiguous amino acid residues of SEQ ID NO:38.

12. The isolated polynucleotide which is fully complimentary to the polynucleotide of claim 11.

13. The isolated polynucleotide of claim 11 which encodes at least 50 continuous amino acid residues of SEQ ID NO:38.

14. The isolated polynucleotide which is fully complimentary to the polynucleotide of claim 13.

15. An isolated polynucleotide consisting of at least 250 contiguous nucleotides selected from nucleotides 102–719 of SEQ ID NO:37.

16. The isolated polynucleotide which is fully complimentary to the polynucleotide of claim 15.

17. An isolated polynucleotide of claim 15 consisting of at least 400 contiguous nucleotides selected from nucleotides 102–719 of SEQ ID NO:37.

18. The isolated polynucleotide which is fully complimentary to the polynucleotide of claim 17.

19. An isolated polynucleotide claim 17 consisting of nucleotides 102–719 of SEQ ID NO:37.

20. An isolated polynucleotide comprising a nucleic acid encoding an epitope-bearing portion of the acid sequence of SEQ ID NO:38.

21. An isolated polynucleotide of claim 20 wherein the epitope-bearing portion of the amino acid sequence of SEQ ID NO:38 is selected from the group consisting of:

(a) from about Gln-11 about Gly-14; and (b) from about Arg-147 to about Gln-149.

22. A method of detecting Staphylococcus nucleic acids in a biological sample comprising:

(a) contacting the sample with one or more nucleic acids of claims 1, 4 or 11–21, under conditions such that hybridization occurs; and (b) detecting hybridization of said nucleic acids to the one or more Staphylococcus nucleic acid sequences present in the biological sample.

* * * * *